(12) United States Patent
Boyden et al.

(10) Patent No.: US 9,474,831 B2
(45) Date of Patent: Oct. 25, 2016

(54) SYSTEMS, DEVICES, AND METHODS INCLUDING IMPLANTABLE DEVICES WITH ANTI-MICROBIAL PROPERTIES

(75) Inventors: Edward S. Boyden, Chestnut Hill, MA (US); Roy P. Diaz, Seattle, WA (US); Roderick A. Hyde, Redmond, WA (US); Jordin T. Kare, Seattle, WA (US); Elizabeth A. Sweeney, Seattle, WA (US); Lowell L. Wood, Jr., Bellevue, WA (US)

(73) Assignee: GEARBOX, LLC, Bellevue, WA (US)

( * ) Notice: Subject to any disclaimer, the term of this patent is extended or adjusted under 35 U.S.C. 154(b) by 247 days.

(21) Appl. No.: 12/931,926

(22) Filed: Feb. 14, 2011

(65) Prior Publication Data

US 2011/0275912 A1 Nov. 10, 2011

Related U.S. Application Data

(63) Continuation-in-part of application No. 12/315,880, filed on Dec. 4, 2008, now Pat. No. 8,162,924, and a continuation-in-part of application No. 12/315,881, filed on Dec. 4, 2008, now abandoned, and a (Continued)

(51) Int. Cl.
*A61L 2/00* (2006.01)
*A61L 29/08* (2006.01)
*A61L 2/232* (2006.01)

(Continued)

(52) U.S. Cl.
CPC .............. *A61L 29/08* (2013.01); *A61L 2/0011* (2013.01); *A61L 2/08* (2013.01); *A61L 2/14* (2013.01); *A61L 2/232* (2013.01); *A61L 2/24* (2013.01); *A61L 2/26* (2013.01); *A61L 17/145* (2013.01); *A61L 27/28* (2013.01); *A61L 27/306* (2013.01); *A61L 27/54* (2013.01); *A61L 29/00* (2013.01); *A61L 29/16* (2013.01); *A61L 31/08* (2013.01); *B82Y 5/00* (2013.01); *B82Y 30/00* (2013.01); *A61L 2300/606* (2013.01); *B82Y 40/00* (2013.01)

(58) Field of Classification Search
CPC ..................................... A61L 2/0011
USPC .............. 424/423; 600/365; 607/88–94
See application file for complete search history.

(56) References Cited

U.S. PATENT DOCUMENTS 3,274,406 A 9/1966 Sommers, Jr.
3,825,016 A 7/1974 Lale et al.

(Continued)

FOREIGN PATENT DOCUMENTS

EP 1 614 442 A2 1/2006
JP H11117194 4/1999

(Continued)

OTHER PUBLICATIONS

European Patent Office; Extended Supplementary European Search Report; Application No. EP 09 83 0731; Dec. 18, 2012; (Received by our associate Dec. 19, 2012) ; pp. 1-3.

(Continued)

*Primary Examiner* — William Thomson
*Assistant Examiner* — John R Downey
(74) *Attorney, Agent, or Firm* — Daniel J. Honz; Advent, LLP

(57) ABSTRACT

Systems, devices, methods, and compositions are described for providing an actively controllable implant configured to, for example, monitor, treat, or prevent microbial growth or adherence to the implant.

45 Claims, 30 Drawing Sheets

Related U.S. Application Data continuation-in-part of application No. 12/315,882, filed on Dec. 4, 2008, now abandoned, and a continuation-in-part of application No. 12/315,883, filed on Dec. 4, 2008, now abandoned, and a continuation-in-part of application No. 12/315,884, filed on Dec. 4, 2008, now abandoned, and a continuation-in-part of application No. 12/315,885, filed on Dec. 4, 2008, now abandoned, and a continuation-in-part of application No. 12/380,553, filed on Feb. 27, 2009, now abandoned, and a continuation-in-part of application No. 12/592,976, filed on Dec. 3, 2009, now Pat. No. 9,005,263, and a continuation-in-part of application No. 12/660,156, filed on Feb. 19, 2010, now Pat. No. 8,366,652, and a continuation-in-part of application No. 12/800,766, filed on May 21, 2010, now Pat. No. 8,216,173, and a continuation-in-part of application No. 12/800,774, filed on May 21, 2010, now abandoned, and a continuation-in-part of application No. 12/800,778, filed on May 21, 2010, now abandoned, and a continuation-in-part of application No. 12/800,779, filed on May 21, 2010, now abandoned, and a continuation-in-part of application No. 12/800,780, filed on May 21, 2010, now abandoned, and a continuation-in-part of application No. 12/800,781, filed on May 21, 2010, now abandoned, and a continuation-in-part of application No. 12/800,786, filed on May 21, 2010, now abandoned, and a continuation-in-part of application No. 12/800,790, filed on May 21, 2010, now Pat. No. 8,343,086, and a continuation-in-part of application No. 12/800,791, filed on May 21, 2010, now Pat. No. 8,282,593, and a continuation-in-part of application No. 12/800,792, filed on May 21, 2010, now Pat. No. 8,888,731, and a continuation-in-part of application No. 12/800,793, filed on May 21, 2010, now Pat. No. 8,414,517, and a continuation-in-part of application No. 12/800,798, filed on May 21, 2010, and a continuation-in-part of application No. 12/931,921, filed on Feb. 14, 2011, now abandoned, and a continuation-in-part of application No. 12/931,924, filed on Feb. 14, 2011, now abandoned, and a continuation-in-part of application No. 12/931,928, filed on Feb. 14, 2011, and a continuation-in-part of application No. 12/931,929, filed on Feb. 14, 2011, and a continuation-in-part of application No. 12/931,923, filed on Feb. 14, 2011, now abandoned, and a continuation-in-part of application No. 12/931,925, filed on Feb. 14, 2011, now abandoned, and a continuation-in-part of application No. 12/931,931, filed on Feb. 14, 2011, now abandoned, and a continuation-in-part of application No. 12/931,930, filed on Feb. 14, 2011, now abandoned, and a continuation-in-part of application No. 12/931,920, filed on Feb. 14, 2011, now abandoned, and a continuation-in-part of application No. 12/931,927, filed on Feb. 14, 2011, now abandoned, and a continuation-in-part of application No. 12/931,922, filed on Feb. 14, 2011, and a continuation-in-part of application No. 12/927,297, filed on Nov. 10, 2010, now Pat. No. 8,460,229, and a continuation-in-part of application No. 12/927,284, filed on Nov. 10, 2010, now Pat. No. 8,647,292, and a continuation-in-part of application No. 12/927,288, filed on Nov. 10, 2010, now Pat. No. 8,734,718, and a continuation-in-part of application No. 12/927,296, filed on Nov. 10, 2010, now abandoned, and a continuation-in-part of application No. 12/927,287, filed on Nov. 10, 2010, now Pat. No. 8,706,211, and a continuation-in-part of application No. 12/927,294, filed on Nov. 10, 2010, now Pat. No. 8,585,627, and a continuation-in-part of application No. 12/927,285, filed on Nov. 10, 2010, now Pat. No. 8,753,304, and a continuation-in-part of application No. 12/927,290, filed on Nov. 10, 2010, now Pat. No. 8,702,640, and a continuation-in-part of application No. 12/927,291, filed on Nov. 10, 2010, now abandoned, and a continuation-in-part of application No. 12/927,295, filed on Nov. 10, 2010.

(51) Int. Cl.

| | | |
|---|---|---|
| *A61L 2/24* | (2006.01) |
| *A61L 2/26* | (2006.01) |
| *A61L 27/54* | (2006.01) |
| *A61L 31/08* | (2006.01) |
| *A61L 17/14* | (2006.01) |
| *A61L 27/28* | (2006.01) |
| *A61L 27/30* | (2006.01) |
| *A61L 29/00* | (2006.01) |
| *A61L 29/16* | (2006.01) |
| *B82Y 5/00* | (2011.01) |
| *B82Y 30/00* | (2011.01) |
| *A61L 2/08* | (2006.01) |
| *A61L 2/14* | (2006.01) |
| *B82Y 40/00* | (2011.01) |

(56) References Cited

U.S. PATENT DOCUMENTS

| | | |
|---|---|---|
| 4,081,764 A | 3/1978 | Christmann et al. |
| 4,598,579 A | 7/1986 | Cummings et al. |
| 4,698,058 A | 10/1987 | Greenfeld et al. |
| 4,718,417 A | 1/1988 | Kittrell et al. |
| 4,788,975 A | 12/1988 | Shturman et al. |
| 4,863,849 A | 9/1989 | Melamede |
| 4,900,553 A | 2/1990 | Silver et al. |
| 5,000,731 A | 3/1991 | Wong et al. |
| 5,127,735 A | 7/1992 | Pitt |
| 5,155,707 A | 10/1992 | Fisher |
| 5,156,839 A | 10/1992 | Pennell et al. |
| 5,226,902 A | 7/1993 | Bae et al. |
| 5,240,675 A | 8/1993 | Wilk et al. |
| 5,260,020 A | 11/1993 | Wilk et al. |
| 5,281,199 A | 1/1994 | Ensminger et al. |
| 5,302,345 A | 4/1994 | Oksman et al. |
| 5,324,275 A | 6/1994 | Raad et al. |
| 5,326,567 A | 7/1994 | Capelli |
| 5,431,694 A | 7/1995 | Snaper et al. |
| 5,445,608 A | 8/1995 | Chen et al. |
| 5,594,544 A | 1/1997 | Horiuchi et al. |
| 5,607,683 A | 3/1997 | Capelli |
| 5,622,848 A | 4/1997 | Morrow |
| 5,651,767 A | 7/1997 | Schulman et al. |
| 5,681,260 A | 10/1997 | Ueda et al. |
| 5,704,352 A | 1/1998 | Tremblay et al. |
| 5,733,270 A | 3/1998 | Ling et al. |
| 5,735,276 A | 4/1998 | Lemelson |
| 5,750,093 A | 5/1998 | Menon et al. |
| 5,766,934 A | 6/1998 | Guiseppi-Elie |
| 5,797,898 A | 8/1998 | Santini, Jr. et al. |
| 5,804,563 A | 9/1998 | Still et al. |
| 5,810,015 A | 9/1998 | Flaherty |
| 5,830,207 A | 11/1998 | Leeb et al. |
| 5,831,012 A | 11/1998 | Nilsson et al. |
| 5,855,203 A | 1/1999 | Matter |
| 5,865,744 A | 2/1999 | Lemelson |
| 5,961,923 A | 10/1999 | Nova et al. |
| 5,978,713 A | 11/1999 | Prutchi et al. |
| 5,993,378 A | 11/1999 | Lemelson |

(56) References Cited

U.S. PATENT DOCUMENTS

| | | |
|---|---|---|
| 5,993,382 A | 11/1999 | Pruitt, Sr. |
| 6,008,896 A | 12/1999 | Sabsabi et al. |
| 6,057,561 A | 5/2000 | Kawasaki et al. |
| 6,086,851 A | 7/2000 | Boni et al. |
| 6,135,990 A | 10/2000 | Heller et al. |
| 6,143,035 A | 11/2000 | McDowell |
| 6,146,409 A | 11/2000 | Overholt et al. |
| 6,162,242 A | 12/2000 | Peyman |
| 6,222,953 B1 | 4/2001 | Hoekstra et al. |
| 6,255,461 B1 | 7/2001 | Mosbach et al. |
| 6,266,551 B1 | 7/2001 | Osadchy et al. |
| 6,280,604 B1 | 8/2001 | Allen et al. |
| 6,282,444 B1 | 8/2001 | Kroll et al. |
| 6,304,786 B1 | 10/2001 | Heil, Jr. et al. |
| 6,312,770 B1 | 11/2001 | Sage et al. |
| 6,348,042 B1 | 2/2002 | Warren, Jr. |
| 6,350,263 B1 | 2/2002 | Wetzig et al. |
| 6,403,337 B1 | 6/2002 | Bailey et al. |
| 6,416,495 B1 | 7/2002 | Kriesel et al. |
| 6,418,342 B1 | 7/2002 | Owen et al. |
| 6,426,066 B1 | 7/2002 | Najafi et al. |
| 6,428,491 B1 | 8/2002 | Weiss |
| 6,440,097 B1 | 8/2002 | Kupiecki |
| 6,443,147 B1 | 9/2002 | Matter |
| 6,451,003 B1 | 9/2002 | Prosl et al. |
| 6,451,429 B2 | 9/2002 | Mumick et al. |
| 6,461,569 B1 | 10/2002 | Boudreaux |
| 6,470,212 B1 | 10/2002 | Weijand et al. |
| 6,470,888 B1 | 10/2002 | Matter |
| 6,478,778 B1 | 11/2002 | Jacobsen et al. |
| 6,488,704 B1 | 12/2002 | Connelly et al. |
| 6,491,666 B1 | 12/2002 | Santini, Jr. et al. |
| 6,506,416 B1 | 1/2003 | Okauchi et al. |
| 6,533,733 B1 | 3/2003 | Ericson et al. |
| 6,542,767 B1 | 4/2003 | McNichols et al. |
| 6,551,346 B2 | 4/2003 | Crossley |
| 6,562,295 B1 | 5/2003 | Neuberger |
| 6,571,125 B2 | 5/2003 | Thompson |
| 6,585,677 B2 | 7/2003 | Cowan, Jr. et al. |
| 6,599,274 B1 | 7/2003 | Kucharczyk et al. |
| 6,612,535 B1 | 9/2003 | Tai et al. |
| 6,626,902 B1 | 9/2003 | Kucharczyk et al. |
| 6,667,807 B2 | 12/2003 | Lieberman |
| 6,669,683 B2 | 12/2003 | Santini, Jr. et al. |
| 6,670,427 B1 | 12/2003 | Ulbricht et al. |
| 6,720,402 B2 | 4/2004 | Langer et al. |
| 6,730,113 B2 | 5/2004 | Eckhardt et al. |
| 6,743,190 B2 | 6/2004 | Connelly et al. |
| 6,750,055 B1 | 6/2004 | Connelly et al. |
| 6,755,621 B2 | 6/2004 | Lopez et al. |
| 6,764,501 B2 | 7/2004 | Ganz |
| 6,789,183 B1 | 9/2004 | Smith et al. |
| 6,793,642 B2 | 9/2004 | Connelly et al. |
| 6,793,880 B2 | 9/2004 | Kippenhan, Jr. |
| 6,797,522 B1 | 9/2004 | Still et al. |
| 6,802,811 B1 | 10/2004 | Slepian |
| 6,808,522 B2 | 10/2004 | Richards et al. |
| 6,831,748 B2 | 12/2004 | Tittel et al. |
| 6,838,292 B1 | 1/2005 | Rajan et al. |
| 6,844,028 B2 | 1/2005 | Mao et al. |
| 6,849,463 B2 | 2/2005 | Santini, Jr. et al. |
| 6,853,765 B1 | 2/2005 | Cochran |
| 6,866,859 B2 | 3/2005 | Trogolo et al. |
| 6,887,202 B2 | 5/2005 | Currie et al. |
| 6,908,460 B2 | 6/2005 | DiStefano |
| 6,913,589 B2 | 7/2005 | Dextradeur et al. |
| 6,914,279 B2 | 7/2005 | Lu et al. |
| 6,918,869 B2 | 7/2005 | Shaw et al. |
| 6,932,787 B2 | 8/2005 | Cowan et al. |
| 6,939,290 B2 | 9/2005 | Iddan |
| 6,960,201 B2 | 11/2005 | Cumbie |
| 6,969,382 B2 | 11/2005 | Richter |
| 6,980,716 B1 | 12/2005 | Diaz et al. |
| 7,020,355 B2 | 3/2006 | Lahann et al. |
| 7,030,989 B2 | 4/2006 | Yager et al. |
| 7,033,571 B2 | 4/2006 | Gutowska et al. |
| 7,041,130 B2 | 5/2006 | Santini, Jr. et al. |
| 7,052,488 B2 | 5/2006 | Uhland |
| 7,070,590 B1 | 7/2006 | Santini, Jr. et al. |
| 7,070,592 B2 | 7/2006 | Santini, Jr. et al. |
| 7,078,903 B2 | 7/2006 | Paliwal et al. |
| 7,097,662 B2 | 8/2006 | Evans, III et al. |
| 7,116,857 B2 | 10/2006 | Faris |
| 7,117,807 B2 | 10/2006 | Bohn, Jr. et al. |
| 7,118,548 B2 | 10/2006 | Børgesen |
| 7,124,773 B2 | 10/2006 | Midtgård et al. |
| 7,130,459 B2 | 10/2006 | Anderson et al. |
| 7,134,999 B2 | 11/2006 | Brauker et al. |
| 7,143,709 B2 | 12/2006 | Brennan et al. |
| 7,151,139 B2 | 12/2006 | Tiller et al. |
| 7,159,590 B2 | 1/2007 | Rife |
| 7,160,931 B2 | 1/2007 | Cheng et al. |
| 7,167,734 B2 | 1/2007 | Khalil et al. |
| 7,167,755 B2 | 1/2007 | Seeberger et al. |
| 7,183,048 B2 | 2/2007 | Felkner et al. |
| 7,195,608 B2 | 3/2007 | Burnett |
| 7,217,425 B2 | 5/2007 | Serhan et al. |
| 7,221,456 B2 | 5/2007 | Kanai et al. |
| 7,226,441 B2 | 6/2007 | Kulessa |
| 7,232,429 B2 | 6/2007 | Moreci |
| 7,236,821 B2 | 6/2007 | Cates et al. |
| 7,238,363 B2 | 7/2007 | Mansouri et al. |
| 7,244,232 B2 | 7/2007 | Connelly et al. |
| 7,250,615 B1 | 7/2007 | Soong et al. |
| 7,253,152 B2 | 8/2007 | Panero et al. |
| 7,276,255 B2 | 10/2007 | Selkon |
| 7,288,232 B2 | 10/2007 | Morrow et al. |
| 7,303,875 B1 | 12/2007 | Bock et al. |
| 7,306,620 B2 | 12/2007 | Cumbie |
| 7,309,330 B2 | 12/2007 | Bertrand et al. |
| 7,310,459 B1 | 12/2007 | Rahman |
| 7,319,038 B2 | 1/2008 | Southard |
| 7,322,965 B2 | 1/2008 | Gibson et al. |
| 7,334,594 B2 | 2/2008 | Ludin |
| 7,345,372 B2 | 3/2008 | Roberts et al. |
| 7,348,021 B2 | 3/2008 | Klein |
| 7,354,575 B2 | 4/2008 | Shachar et al. |
| 7,365,859 B2 | 4/2008 | Yun et al. |
| 7,367,342 B2 | 5/2008 | Butler |
| 7,390,310 B2 | 6/2008 | McCusker et al. |
| 7,396,676 B2 | 7/2008 | Robotti et al. |
| 7,425,581 B2 | 9/2008 | Hennink et al. |
| 7,442,372 B2 | 10/2008 | Kakkis |
| 7,455,667 B2 | 11/2008 | Uhland et al. |
| 7,504,702 B2 | 3/2009 | Mazur et al. |
| 7,524,298 B2 | 4/2009 | Gharib et al. |
| 7,531,120 B2 | 5/2009 | Van Rijn et al. |
| 7,535,692 B2 | 5/2009 | Krupenkin et al. |
| 7,572,669 B2 | 8/2009 | Tuominen et al. |
| 7,575,593 B2 | 8/2009 | Rea et al. |
| 7,621,905 B2 | 11/2009 | Penner et al. |
| 7,650,848 B2 | 1/2010 | Brennan et al. |
| 7,691,684 B2 | 4/2010 | Breitwisch et al. |
| 7,691,894 B2 | 4/2010 | Ono et al. |
| 7,706,178 B2 | 4/2010 | Parkinson |
| 7,714,326 B2 | 5/2010 | Kim et al. |
| 7,837,719 B2 | 11/2010 | Brogan et al. |
| 8,197,452 B2 | 6/2012 | Harding et al. |
| 8,496,610 B2 | 7/2013 | Levenson et al. |
| 2002/0030196 A1 | 3/2002 | Iwata et al. |
| 2002/0068093 A1 | 6/2002 | Trogolo et al. |
| 2002/0090388 A1 | 7/2002 | Humes et al. |
| 2002/0123787 A1 | 9/2002 | Weiss |
| 2002/0182262 A1 | 12/2002 | Selkon |
| 2002/0188323 A1 | 12/2002 | Penner et al. |
| 2002/0192366 A1 | 12/2002 | Cramer et al. |
| 2002/0192680 A1 | 12/2002 | Chan et al. |
| 2003/0012688 A1 | 1/2003 | Kippenhan, Jr. |
| 2003/0014091 A1 | 1/2003 | Rastegar et al. |
| 2003/0017073 A1 | 1/2003 | Eckhardt et al. |
| 2003/0092996 A1 | 5/2003 | Lowe et al. |
| 2003/0097121 A1 | 5/2003 | Jolly et al. |
| 2003/0109907 A1 | 6/2003 | Shadduck |
| 2003/0163079 A1 | 8/2003 | Burnett |

(56) References Cited

U.S. PATENT DOCUMENTS

| | | |
|---|---|---|
| 2003/0165702 A1 | 9/2003 | Disse et al. |
| 2003/0180319 A1 | 9/2003 | Rapson et al. |
| 2003/0195415 A1 | 10/2003 | Iddan |
| 2003/0199806 A1 | 10/2003 | Kieval |
| 2003/0204163 A1 | 10/2003 | Marchitto et al. |
| 2003/0214579 A1 | 11/2003 | Iddan |
| 2003/0225331 A1 | 12/2003 | Diederich et al. |
| 2004/0018508 A1 | 1/2004 | Friedman |
| 2004/0022669 A1 | 2/2004 | Ruan et al. |
| 2004/0073278 A1 | 4/2004 | Pachys |
| 2004/0081646 A1 | 4/2004 | Engler et al. |
| 2004/0098005 A1 | 5/2004 | Mirza et al. |
| 2004/0098055 A1 | 5/2004 | Kroll et al. |
| 2004/0149582 A1 | 8/2004 | Kovacs |
| 2004/0186546 A1 | 9/2004 | Mandrusov et al. |
| 2004/0208940 A1 | 10/2004 | Selkon |
| 2004/0253138 A1 | 12/2004 | Malak |
| 2004/0260249 A1 | 12/2004 | Kulessa |
| 2005/0008285 A1 | 1/2005 | Kim et al. |
| 2005/0042743 A1 | 2/2005 | Kawai et al. |
| 2005/0043894 A1 | 2/2005 | Fernandez |
| 2005/0045183 A1 | 3/2005 | Callister et al. |
| 2005/0049181 A1 | 3/2005 | Madhyastha |
| 2005/0063647 A1 | 3/2005 | Thornton et al. |
| 2005/0089890 A1* | 4/2005 | Cubicciotti ............... 435/6 |
| 2005/0095351 A1 | 5/2005 | Zumeris et al. |
| 2005/0100937 A1 | 5/2005 | Holmes |
| 2005/0105077 A1 | 5/2005 | Padmanabhan et al. |
| 2005/0107289 A1 | 5/2005 | Ghadiri et al. |
| 2005/0142157 A1 | 6/2005 | Alimi |
| 2005/0149000 A1 | 7/2005 | Santini, Jr. et al. |
| 2005/0164169 A1 | 7/2005 | Malak |
| 2005/0171434 A1 | 8/2005 | Madden et al. |
| 2005/0171437 A1 | 8/2005 | Carberry |
| 2005/0175658 A1* | 8/2005 | DiMauro et al. ............ 424/423 |
| 2005/0180678 A1 | 8/2005 | Panepucci et al. |
| 2005/0192478 A1 | 9/2005 | Williams et al. |
| 2005/0196375 A1 | 9/2005 | Phaneuf et al. |
| 2005/0196421 A1 | 9/2005 | Hunter et al. |
| 2005/0203495 A1 | 9/2005 | Malak |
| 2005/0203582 A1 | 9/2005 | Healy et al. |
| 2005/0209665 A1 | 9/2005 | Hunter et al. |
| 2005/0245557 A1 | 11/2005 | Schoenhard et al. |
| 2005/0255604 A1 | 11/2005 | Gjerde et al. |
| 2005/0256554 A1 | 11/2005 | Malak |
| 2005/0263386 A9 | 12/2005 | Pitts, Jr. et al. |
| 2005/0266081 A1 | 12/2005 | Rogozinski |
| 2005/0266582 A1 | 12/2005 | Modlin et al. |
| 2005/0268921 A1 | 12/2005 | Zumeris et al. |
| 2005/0272974 A1 | 12/2005 | Iddan |
| 2005/0288654 A1 | 12/2005 | Nieman et al. |
| 2006/0004317 A1 | 1/2006 | Mauge et al. |
| 2006/0004431 A1 | 1/2006 | Fuller et al. |
| 2006/0009805 A1 | 1/2006 | Jensen et al. |
| 2006/0020186 A1 | 1/2006 | Brister et al. |
| 2006/0020239 A1 | 1/2006 | Geiger et al. |
| 2006/0047283 A1 | 3/2006 | Evans, III et al. |
| 2006/0047329 A1 | 3/2006 | Krespi et al. |
| 2006/0052782 A1 | 3/2006 | Morgan et al. |
| 2006/0074479 A1 | 4/2006 | Bailey et al. |
| 2006/0079740 A1 | 4/2006 | Silver et al. |
| 2006/0079762 A1 | 4/2006 | Norris et al. |
| 2006/0105275 A1 | 5/2006 | Maloney et al. |
| 2006/0121087 A1 | 6/2006 | Williams et al. |
| 2006/0122543 A1 | 6/2006 | Mayer et al. |
| 2006/0139667 A1 | 6/2006 | Morimoto et al. |
| 2006/0140911 A1 | 6/2006 | Sharp et al. |
| 2006/0147492 A1 | 7/2006 | Hunter et al. |
| 2006/0159671 A1 | 7/2006 | Fischetti |
| 2006/0159916 A1* | 7/2006 | Dubrow et al. ............ 428/357 |
| 2006/0210602 A1 | 9/2006 | Sehl et al. |
| 2006/0219143 A1 | 10/2006 | Brennan et al. |
| 2006/0247525 A1 | 11/2006 | Huo et al. |
| 2006/0253259 A1 | 11/2006 | Fernandez |
| 2006/0263033 A1 | 11/2006 | Lahann et al. |
| 2006/0271112 A1 | 11/2006 | Martinson et al. |
| 2006/0276713 A1 | 12/2006 | Maier |
| 2006/0287660 A1 | 12/2006 | Syed et al. |
| 2006/0289761 A1 | 12/2006 | Nabet et al. |
| 2007/0005024 A1 | 1/2007 | Weber et al. |
| 2007/0016163 A1 | 1/2007 | Santini, Jr. et al. |
| 2007/0020240 A1 | 1/2007 | Jayasheela et al. |
| 2007/0031777 A1 | 2/2007 | Wang et al. |
| 2007/0073135 A1 | 3/2007 | Lee et al. |
| 2007/0087445 A1 | 4/2007 | Tearney et al. |
| 2007/0106333 A1 | 5/2007 | Fernandez |
| 2007/0111201 A1 | 5/2007 | Doranz |
| 2007/0134287 A1 | 6/2007 | Troxel et al. |
| 2007/0142874 A1 | 6/2007 | John |
| 2007/0150019 A1 | 6/2007 | Youker et al. |
| 2007/0156039 A1 | 7/2007 | Casciani et al. |
| 2007/0156211 A1 | 7/2007 | Ferren et al. |
| 2007/0173755 A1 | 7/2007 | Alimi et al. |
| 2007/0176117 A1 | 8/2007 | Redmond et al. |
| 2007/0187626 A1 | 8/2007 | Gaska et al. |
| 2007/0196357 A1 | 8/2007 | Alimi et al. |
| 2007/0197890 A1 | 8/2007 | Boock et al. |
| 2007/0205382 A1 | 9/2007 | Gaska et al. |
| 2007/0208245 A1* | 9/2007 | Brauker et al. ............ 600/365 |
| 2007/0209143 A1 | 9/2007 | Choi et al. |
| 2007/0225634 A1 | 9/2007 | Ferren et al. |
| 2007/0225800 A1 | 9/2007 | Sahatjian et al. |
| 2007/0227428 A1 | 10/2007 | Brennan et al. |
| 2007/0244423 A1 | 10/2007 | Zumeris et al. |
| 2007/0249969 A1 | 10/2007 | Shields, Jr. |
| 2007/0259017 A1 | 11/2007 | Francis |
| 2007/0274909 A1 | 11/2007 | Justel et al. |
| 2007/0275068 A1 | 11/2007 | Martens et al. |
| 2007/0276208 A1 | 11/2007 | Connelly et al. |
| 2007/0280852 A1 | 12/2007 | Skubal et al. |
| 2007/0299384 A1 | 12/2007 | Faul et al. |
| 2008/0007885 A1 | 1/2008 | Mehrl et al. |
| 2008/0014632 A1 | 1/2008 | Cunningham et al. |
| 2008/0033519 A1 | 2/2008 | Burwell et al. |
| 2008/0039678 A1 | 2/2008 | Montpetit et al. |
| 2008/0039768 A1 | 2/2008 | Francis |
| 2008/0051691 A1 | 2/2008 | Dragoon et al. |
| 2008/0051736 A1 | 2/2008 | Rioux et al. |
| 2008/0058798 A1 | 3/2008 | Wallace et al. |
| 2008/0064980 A1 | 3/2008 | Lee et al. |
| 2008/0095977 A1 | 4/2008 | Aizenberg et al. |
| 2008/0118546 A1 | 5/2008 | Thatcher et al. |
| 2008/0119421 A1 | 5/2008 | Tuszynski et al. |
| 2008/0125838 A1 | 5/2008 | Francis |
| 2008/0195170 A1 | 8/2008 | Asgari |
| 2008/0214909 A1 | 9/2008 | Fuerst et al. |
| 2008/0223717 A1 | 9/2008 | Isaksson et al. |
| 2008/0234786 A1 | 9/2008 | Cumbie |
| 2008/0243231 A1* | 10/2008 | Flanagan et al. ........... 623/1.16 |
| 2008/0248993 A1 | 10/2008 | Hannappel et al. |
| 2008/0253712 A1 | 10/2008 | Allen et al. |
| 2008/0257355 A1 | 10/2008 | Rao et al. |
| 2008/0265179 A1 | 10/2008 | Havens et al. |
| 2009/0012610 A1 | 1/2009 | Olson et al. |
| 2009/0012626 A1 | 1/2009 | Thompson et al. |
| 2009/0015841 A1 | 1/2009 | Downey |
| 2009/0018424 A1 | 1/2009 | Kamath et al. |
| 2009/0048542 A1 | 2/2009 | Varadan et al. |
| 2009/0048648 A1 | 2/2009 | Dacey, Jr. et al. |
| 2009/0054824 A1 | 2/2009 | Melsheimer et al. |
| 2009/0054827 A1 | 2/2009 | Eide |
| 2009/0066195 A1 | 3/2009 | Wang et al. |
| 2009/0093713 A1 | 4/2009 | Hyde et al. |
| 2009/0093728 A1 | 4/2009 | Hyde et al. |
| 2009/0093807 A1 | 4/2009 | Hyde et al. |
| 2009/0110711 A1 | 4/2009 | Trollsas et al. |
| 2009/0117001 A1 | 5/2009 | Hyde et al. |
| 2009/0118661 A1 | 5/2009 | Moehle et al. |
| 2009/0118813 A1 | 5/2009 | Scheuermann et al. |
| 2009/0155215 A1 | 6/2009 | Collins et al. |
| 2009/0156460 A1* | 6/2009 | Jiang et al. ............... 514/2 |
| 2009/0177254 A1 | 7/2009 | Boyden et al. |
| 2009/0185988 A1 | 7/2009 | Maleski et al. |
| 2009/0195120 A1 | 8/2009 | Knospe |

(56) References Cited

U.S. PATENT DOCUMENTS

| | | | |
|---|---|---|---|
| 2009/0209897 | A1 | 8/2009 | Limaye et al. |
| 2009/0209904 | A1* | 8/2009 | Peeters .......................... 604/66 |
| 2009/0214617 | A1 | 8/2009 | Scott et al. |
| 2009/0259089 | A1 | 10/2009 | Gelbart et al. |
| 2009/0281412 | A1 | 11/2009 | Boyden et al. |
| 2009/0281635 | A1 | 11/2009 | Li et al. |
| 2009/0294732 | A1 | 12/2009 | Atanasoska et al. |
| 2009/0297574 | A1 | 12/2009 | Ahn et al. |
| 2009/0299153 | A1 | 12/2009 | Gerber et al. |
| 2009/0316195 | A1 | 12/2009 | Tseng et al. |
| 2010/0008822 | A1 | 1/2010 | Hyde et al. |
| 2010/0010327 | A1 | 1/2010 | Merz et al. |
| 2010/0046902 | A1 | 2/2010 | Kaplan et al. |
| 2010/0049422 | A1 | 2/2010 | Moriya |
| 2010/0063404 | A1 | 3/2010 | Kaplan et al. |
| 2010/0065784 | A1 | 3/2010 | Kaplan et al. |
| 2010/0068740 | A1 | 3/2010 | Kaplan et al. |
| 2010/0070068 | A1 | 3/2010 | Kaplan et al. |
| 2010/0096763 | A1 | 4/2010 | Kaplan et al. |
| 2010/0100160 | A1 | 4/2010 | Edman et al. |
| 2010/0104652 | A1 | 4/2010 | Biris et al. |
| 2010/0145286 | A1 | 6/2010 | Zhang et al. |
| 2010/0174346 | A1 | 7/2010 | Boyden et al. |
| 2010/0198357 | A1 | 8/2010 | Fuller et al. |
| 2010/0204802 | A1 | 8/2010 | Wilson et al. |
| 2010/0234792 | A1 | 9/2010 | Dacey, Jr. et al. |
| 2010/0249692 | A1 | 9/2010 | Dacey, Jr. et al. |
| 2010/0256607 | A1 | 10/2010 | Burnett |
| 2011/0116967 | A1 | 5/2011 | Roy et al. |
| 2011/0117582 | A1 | 5/2011 | Malima et al. |
| 2011/0160643 | A1 | 6/2011 | Dacey, Jr. et al. |
| 2013/0273564 | A1 | 10/2013 | Quinn |

FOREIGN PATENT DOCUMENTS

| | | |
|---|---|---|
| WO | WO 91/6855 A2 | 5/1991 |
| WO | WO/92/01222 | 1/1992 |
| WO | WO 97/00586 | 1/1997 |
| WO | WO 00/09733 | 2/2000 |
| WO | WO 00/29613 | 5/2000 |
| WO | WO 00/56185 | 9/2000 |
| WO | WO 01/13926 A2 | 3/2001 |
| WO | WO 01/54704 | 8/2001 |
| WO | WO 02/068049 A1 | 9/2002 |
| WO | WO 02/102421 A1 | 12/2002 |
| WO | WO 2004/027116 A2 | 4/2004 |
| WO | WO 2004/031077 A2 | 4/2004 |
| WO | WO 2005/100100 | 10/2005 |
| WO | WO 2005/117914 A2 | 12/2005 |
| WO | WO 2006/000764 A1 | 1/2006 |
| WO | WO 2006/044324 | 4/2006 |
| WO | WO 2007/070801 A3 | 6/2007 |
| WO | WO 2007/085021 | 7/2007 |
| WO | WO 2007/140544 A1 | 12/2007 |
| WO | WO 2008/020770 A1 | 2/2008 |
| WO | WO 2008/073774 A1 | 6/2008 |
| WO | WO 2008/083390 A2 | 7/2008 |
| WO | WO 2008/118211 A2 | 10/2008 |
| WO | WO 2009/067682 A2 | 5/2009 |
| WO | WO 2009/148728 A2 | 12/2009 |

OTHER PUBLICATIONS

Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.

Abdollahi et al.; "Apoptosis Signals in Lymphoblasts Induced by Focused Ultrasound"; The FASEB Journal-FJ Express; Sep. 2004; pp. 1413-1414; vol. 18; FASEB.

Agvald-Öhman et al.; "Multiresistant coagulase-negative staphylococci disseminate frequently between intubated patients in a multidisciplinary intensive care unit"; Critical Care; Feb. 2004; pp. R42-R47; vol. 8, No. 1; BioMed Central Ltd.

Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.

Alexander et al.; "Molecular imprinting science and technology: a survey of the literature for the years up to and including 2003"; Journal of Molecular Recognition; 2006; pp. 106-180; vol. 19; John Wiley & Sons Ltd.

Ammor, Mohammed Salim; "Recent Advances in the Use of Intrinsic Fluorescence for Bacterial Identification and Characterization"; J. Fluoresc.; 2007; pp. 1-5; Springer Science+Business Media LLC.

Apple et al.; "Review: Future Biomarkers for Detection of Ischemia and Risk Stratification in Acute Coronary Syndrome"; Clinical Chemistry; bearing a date of 2005; pp. 810-824; vol. 51, No. 5; American Association for Clinical Chemistry.

"Arglaes® Controlled-Release Silver Technology"; Medline; 2003; 6 pages; Medline Industries, Inc.; located at: www.medline.com.

Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.

Baddour et al.; "High Frequency Ultrasound Imaging of Changes in Cell Structure Including Apoptosis"; Ultrasonics Symposium; 2002; pp. 1639-1644; IEEE.

Barlen et al.; "Detection of *Salmonella* by Surface Plasmon Resonance"; Sensors; 2007; pp. 1427-1446; vol. 7; MDPI.

Barnes et al.; "Novel Biomarkers Associated with Deep Venous Thrombosis: A Comprehensive Review"; Biomarker Insights; bearing a date of 2008; pp. 93-100; vol. 3; Creative Commons Attribution.

Beebe et al.; "Nanosecond, High-Intensity Pulsed Electric Fields Induce Apoptosis in Huthan Cells"; The FASEB Journal; bearing a date of Jun. 17, 2003; pp. 1-23.

Bouchard et al.; "Optical characterization of *Pseudomonas fluorescens* on meat surfaces using time-resolved fluorescence"; Journal of Biomedical Optics; Jan./Feb. 2006; pp. 014011-1 to 014011-7; vol. 11, No. 1; Society of Photo-Optical Instrumentation Engineers.

Bozhevolnyi, Sergey I. et al.; "Photonic bandgap structures for long-range surface plasmon polaritons"; Optics Communications; bearing a date of 2005; pp. 328-333; vol. 250; Elsevier B.V.

Brogden, Kim A.; "Antimicrobial Peptides: Pore Formers or Metabolic Inhibitors in Bacteria?"; Nature Reviews, Microbiology; Mar. 2005; pp. 238-250; vol. 3.

Burton et al.; "Molecular Grandients of Bioinertness Reveal a Mechanistic Difference between Mammalian Cell Adhesion and Bacterial Biofilm Formation"; Langmuir; 2009; pp. 1547-1553; vol. 25, No. 3; American Chemical Society.

Byrne et al.; "Molecular imprinting within hydrogels"; Advanced Drug Delivery Reviews; 2002; pp. 149-161; vol. 54; Elsevier Science B.V.

Cao et al.; "Combining use of a panel of ssDNA aptamers in the detection of *Staphylococcus aureus*"; Nucleic Acids Research; 2009; pp. 1-8.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Carcillo, Joseph A. et al.; "Early Markers of Infection and Sepsis in Newborns and Children"; Leading Article, Advances in Sepsis; 2006; pp. 118-125; vol. 5, No. 4.

Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunologists, Inc.

Chen et al.; "Aptamer from whole-bacterium SELEX as new therapeutic reagent against virulent *Mycobacterium tubercolosis*"; Biochemical and Biophysical Communications; 2007; pp. 743-748; vol. 357; Elsevier Inc.

(56) References Cited

OTHER PUBLICATIONS

Chen, Ting-Hsuan et al.; "A Wettability Switchable Surface Driven by Electrostatic Induced Surface Morphology Change Without Energy Interference on Reagents in Droplets"; MEMS; Jan. 2006; pp. 178-181; IEEE.

Chen, Ting-Hsuan et al.; "A Wettability Switchable Surface by microscale surface morphology change"; Journal of Micromechanics and Microengineering; 2007; pp. 489-495; vol. 17, No. 3; IOP Publishing Ltd.

Cheng et al.; "Electrically Switchable and Optically Rewritable Reflective Fresnel Zone Plate in Dye-Doped Cholesteric Liquid Crystals"; Optics Express; bearing a date of Oct. 17, 2007; pp. 14078-14085; vol. 15, No. 21; OSA.

Cheng, Gang et al.; "Switchable Polymer Surfaces: A Switchable Biocompatible Polymer Surface with Self-Sterilizing and Nonfouling Capabilities"; Angewandte Chemie Int. Ed.; 2008; pp. 8831-8834; vol. 47; Wiley-VCH Verlag GmbH & Co.

Chung et al.; "Size Comparisons among Integral Membrane Transport Protein Homologues in Bacteria, *Archaea*, and *Eucarya*"; Journal of Bacteriology; Feb. 2001; pp. 1012-1021; vol. 183, No. 3; American Society for Microbiology.

Chung et al.; "Impact of Engineered surface microtopography on biofilm formation of *Staphylococcus aureus*"; Biointerphases; Jun. 2007; pp. 89-94; vol. 2, No. 2; American Vacuum Society.

Cohen et al.; "Whole Cell Imprinting in Sol-Gel Thin Films for Bacterial Recognition in Liquids: Macromolecular Fingerprinting"; In. J. Mol. Sci.; 2010; pp. 1236-1252; vol. 11.

Coppola et al.; "Visualization of Optical Deflection and Switching Operations by a Domain-Engineered-Based $LiNbO_3$ Electro-Optic Device"; Optics Express; bearing a date of May 19, 2003; vol. 11, No. 10; OSA.

Crawford et al.; "Peptide aptamers: Tools for biology and drug discovery"; Briefings in Functional Genomics and Proteomics; Apr. 2003; pp. 72-79; vol. 2, No. 1; Henry Stewart Publications.

Davis et al.; "A New Electro-Optic Waveguide Architecture and the Unprecedented Devices it Enables"; Proc. of SPIE; bearing a date of 2008; pp. 697503-1-697503-12; vol. 6975.

De Fabo, Edward C.; "Advances in Brief: Ultraviolet B but not Ultraviolet A Radiation-Initiates Melanoma"; Cancer Research; bearing a date of Sep. 15, 2004; pp. 6372-6376; vol. 64; American Association for Cancer Research.

Donlan, R. M. et al.; "Model System for Growing and Quantifying *Streptococcus pneumoniae* Biofilms in Situ and in Real Time"; Applied and Environmental Microbiology; Aug. 2004; pp. 4980-4988; vol. 70, No. 8; American Society for Microbiology.

Donlan; Rodney M.; "Biofilms and Device-Associated Infections"; Emerging Infectious Diseases; Mar.-Apr. 2001; pp. 277-281; vol. 7, No. 2.

Doornbos et al.; "White Blood Cell Differentiation Using a Solid State Flow Cytometer"; Cytometry; 1993; pp. 589-594; vol. 14; Wiley-Liss, Inc.

Dubinsky et al.; "High-Intensity Focused Ultrasound: Current Potential and Oncologic Applications"; Ultrasound Imaging-Review, AJR; bearing a date of Jan. 2008; pp. 191-199; vol. 190; American Roentgen Ray Society.

Elman et al.; "An Implantable MEMS Drug Delivery Device for Rapid Delivery in Ambulatory Emergency Care"; Biomedical Microdevices; Jun. 2009; pp. 625-631; vol. 11; Springer Netherlands.

European Search Report; European App. No. EP 08 25 1153; Jul. 10, 2009; pp. 1-2.

European Search Report; European App. No. EP 08 83 4851; Dec. 2, 2010 (received by our Agent on Dec. 14, 2010); pp. 1-6.

"Fact Sheet: Cerebrospinal Fluid Shunt Systems for the Management of Hydrocephalus"; Hydrocephalus Association; 2000; 7 pages; Hydrocephalus Association; located at: www.hydroassoc.org.

Fan et al.; "Sensitive optical biosensors for unlabeled targets: A review"; Analyticca Chimica Acta; 2008; pp. 8-26; vol. 620; Elsevier B.V.

Fenelon et al.; "Production of Specific Monoclonal Antibodies to *Aspergillus* Species and Their Use in Immunohistochemical Identification of Aspergillosis"; Journal of Clinical Microbiology; Apr. 1999; pp. 1221-1223; vol. 37, No. 4; American Society for Microbiology.

Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.

Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.

Feng et al.; "Plasmonic Effects in Dynamic Tunable Metal-Dielectric Composites"; PIERS Online; bearing a date of 2008; pp. 625-630; vol. 4, No. 6.

Fogh-Andersen, Niels et al.; "Composition of Interstitial Fluid"; General Clinical Chemistry; 1995; pp. 1522-1525; vol. 41, No. 10.

Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.

Frasca et al.; "Review: Prevention of Central Venous Catheter-Related Infection in the Intensive Care Unit"; Critical Care; bearing a date of 2010; pp. 1-8; vol. 14, No. 212; Springer-Verlag Berlin Heidelberg.

Gao et al.; "A Micro Sensing Probe for Detecting Individual Biological Cells"; Proceedings of the $25^{th}$ Annual International Conference of the IEEE EMBS; Cancun, Mexico, Sep. 17-21, 2003; pp. 3348-3351; IEEE.

Gavrieli et al.; "Identification of Programmed Cell Death in situ via Specific Labeling of Nuclear DNA Fragmentation"; The Journal of Cell Biology; bearing a date of Nov. 1992; pp. 493-501; vol. 119, No. 3; The Rockefeller University Press; located at: http://jcb.rupress.org/.

Giannitsis et al.; "Risk Stratification in Pulmonary Embolism Based on Biomarkers and Echocardiography"; Circulation: Journal of the American Heart Association; bearing a date of 2005; pp. 1520-1521; American Heart Association, Inc.; located at: http://circ.ahajournals.org/cgi/content/full/112/11/1520.

Givrad et al.; "Implantable Minipump with MEMS Electrothermal Valve for Bolus Injection in Mice"; Proceedings of BIOMed; $3^{rd}$ Frontiers in Biomedical Devices Conference; Jun. 18-20, 2008; pp. 1-2; ASME.

Gjerde et al.; "Carbon nanotube forests: a non-stick workbench for nanomanipulation"; Institute of Physics Publishing; 2006; pp. 4917-4922; vol. 17; IOP Publishing Ltd.

Goclawski, Jaroslaw et al.; "The Measurement of Wetting Angle by Applying an ADSA Model of Sessile Drop on Selected Textile Surfaces"; Fibres and Textiles in Eastern Europe; Apr./Jun. 2008; pp. 84-88; vol. 16, No. 2(67).

Gras et al.; "Intelligent control of surface hydrophobicity"; Chemphyschem.; Oct. 8, 2007; pp. 2036-2050; Abstract; one page; vol. 8, No. 14.

Greene, Mark E.; "Light switches surface hydrophobicity: Optical materials"; Materialstoday; Nov. 2006; p. 15; vol. 9, No. 11.

Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.

Gu et al.; "Precise engineering of targeted nanoparticles by using self-assembled biointegrated block copolymers"; PNAS; Feb. 19, 2008; pp. 2586-2591; vol. 105, No. 7; The National Academy of Sciences of the USA.

Hall et al.; "Nanosecond Pulsed Electric Fields Induce Apoptosis in p53-wildtype and p53-null HCT 116 Colon Carcinoma Cells"; Apoptosis; bearing a date of May 23, 2007; pp. 1721-1731; vol. 12; Springer Science+Business Media, LLC.

Harmon et al.; "Cell Death Induced in a Murine Mastocytoma by 42-47°C Heating in vitro: Evidence that the Form of Death Changes From Apoptosis to Necrosis Above a Critical Heat Load"; Int. J. Radiat. Biol., Rights Links; 1990; pp. 845-858; vol. 58, No. 5; Taylor & Francis Ltd.

(56) References Cited

OTHER PUBLICATIONS

Harlow & Lane; "Antibodies: A Laboratory Manual"; Jan. 1988; 1st edition; one page; Cold Spring Harbor Laboratory Press.

Heo et al.; "An Overview of Recent Strategies in Pathogen Sensing"; Sensors; 2009; pp. 4483-4502; vol. 9.

Herchline, Thomas; "Staphylococcal Infections"; eMedicine; pp. 1-22; located at http://emedicine.medscape.com/article/228816-print; accessed May 24, 2010.

Horng et al.; "Tunable Optical Switch Using Magnetic Fluids"; Applied Physics Letters; bearing a date of Dec. 6, 2004; pp. 5592-5594; vol. 85, No. 23; American Institute of Physics.

Hsu et al.; "Artificial Hairy Surfaces with a Nearly Perfect Hydrophobic Response"; Langmuir; 2010; pp. 1504-1506; Abstract; one page; vol. 26, No. 3; American Chemical Society.

Imam, S.K. et al.; "Radiotracers for Imaging of Infection and Inflammation—A Review"; World Journal Nuclear Medicine.; Jan. 2006; pp. 40-55; vol. 5, No. 1.

Ivanova et al.; "Impact of Nanoscale Roughness of Titanium Thin Film Surfaces on Bacterial Retention"; Langmuir; 2010; pp. 1973-1982; vol. 26, No. 3; American Chemical Society.

Jaffer et al.; "In Vivo Imaging of Thrombin Activity in Experimental Thrombi with Thrombin-Sensitive Near-Infrared Molecular Probe"; Arteriosclerosis, Thrombosis, and Vascular Biology: Journal of the American Heart Association; bearing a date of Nov. 2002; pp. 1929-1935; American Heart Association, Inc.; located at: http://atvb.ahajournals.org/cgi/content/full/22/11/1929.

Jaiswal et al.; "Long-Term Multiple Color Imaging of Live Cells Using Quantum Dot Bioconjugates"; Nature Biotechnology; bearing a date of Jan. 2003; pp. 47-51; vol. 21; Nature Publishing Group.

Jayasena et al.; "Aptamers: An Emerging Class of Molecules That Rival Antibodies in Diagnostics"; Clinical Chemistry; 1999; pp. 1628-1650; vol. 45, No. 9; American Association for Clinical Chemistry.

Kalchenko et al.; "Use of lipophilic near-infrared dye in whole-body optical imaging of hematopoietic cell homing"; Journal of Biomedical Optics; Sep./Oct. 2006; pp. 050507-1-050507-3; vol. 11, No. 5; SPIE.

Kamphuisen et al.; "Can Anticoagulant Treatment be Tailored with Biomarkers in Patients with Venous Thromboembolism?"; Journal of Thrombosis and Haemostasis; bearing a date of 2006; pp. 1206-1207; vol. 4; International Society on Thrombosis and Haemostasis.

Kashyap et al.; "Surface Plasmon Resonance Based Fiber and Planar Waveguide Sensors"; pp. 1-15; printed on Jan. 25, 2011.

Khan et al.; "The Effect of Hyperthermia on the Induction of Cell Death in Brain, Testis, and Thymus of the Adult and Developing Rat"; Cell Stress & Chaperones; 2002; pp. 73-90; vol. 7, No. 1; Cell Stress Society International.

Killer, H. E. et al.; "The Optic Nerve: A New Window into Cerebrospinal Fluid Composition?"; Brain; 2006; pp. 1027-1030; vol. 129.

Kim et al.; "Shape-Tunable Polymer Nanofibrillar Structures by Oblique Electron Beam Irradiation"; Langmuir; 2009; pp. 8879-8882; Abstract; one page; vol. 25, No. 16; American Chemical Society.

Knappik et al.; "Fully Synthetic Human Combinatorial Antibody Libraries (HuCAL) (Based on Modular Consensus Frameworks and CDRs Randomized with Trinucleotides"; J. Mol. Biol.; 2000; pp. 57-86; vol. 296; Academic Press.

Koenig et al.; "Laser-Induced Autofluorescence for Medical Diagnosis"; Journal of Fluorescence; 1994; pp. 17-40; vol. 4, No. 1; Plenum Publishing Corporation.

Kolodkin-Gal et al.; "$_D$-Amino Acids Trigger Biofilm Disassembly"; Science; Apr. 30, 2010; pp. 627-629; vol. 328.

Krupenkin et al.; "Electrically Tunable Superhydrophobic Nanostructured Surfaces"; Bell Labs Technical Journal; bearing a date of 2005; pp. 161-170; vol. 10, No. 3; Lucent Technologies Inc.

Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.

Lahann et al.; "A Reversibly Switching Surface"; Reports, Science; bearing a date of Jan. 17, 2003; pp. 371-374 (plus Erratum); vol. 299; located at: www.sciencemag.org.

Lau et al.; "Superhydrophobic Carbon Nanotube Forests"; Nano Letters; pp. 1-21; printed on Jan. 20, 2011.

Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; vol. 19, No. 3; Taylor & Francis Ltd.

Li et al.; "Muscle-Driven in Vivo Nanogenerator"; Advanced Materials; 2010; pp. 1-4; vol. 22; Wiley-VCH Verlag GmbH & Co. KGaA, Weinheim.

Li et al.; "Feasibility of Interstitial Doppler Optical Coherence Tomography for In Vivo Detection of Microvascular Changes During Photodynamic Therapy"; Lasers in Surgery and Medicine; bearing a date of Jul. 2, 2006; pp. 754-761; vol. 38; Wiley-Liss Inc.

Liou et al.; "An ASIC Control Circuit for Thermal Actuated Large Optical Packet Switch Array"; Proceedings of the World Congress of Engineering; bearing a date of Jul. 2-4, 2008; pp. 1-6; vol. I; WCE.

Lin, Yi-Hsin; "Electrically Tunable Wettability of Liquid Crystal/Polymer Composite Films"; Optics Express; bearing a date of Oct. 27, 2008; pp. 17591-17598; vol. 16, No. 22; OSA.

Liu et al.; "Fabricating Super-Hydrophobic Lotus-Leaf-Like Surfaces through Soft-Lithographic Imprinting"; Macromolecular Rapid Communications; Nov. 2, 2006; pp. 1859-1864; Abstract; one page; vol. 27, No. 21; Wiley-VCH Verlag GmbH & Co. KGaA, Weinheim.

Liu et al.; "Thermally sensitive micelles self-assembled from poly(N- isopropylacrylamide-co-N, N-dimethylacrylamide)b-poly(D,L-lactide-co-glycolide) for controlled delivery of paclitaxel"; Molecular BioSystems; 2005; pp. 158-165; vol. 1; The Royal Society of Chemistry.

Lockhart et al.; "Antimicrobial Resistance among Gram-Negative Bacilli Causing Infections in Intensive Care Unit Patients in the United States between 1993 and 2004"; Journal of Clinical Microbiology; Oct. 2007; pp. 3352-3359; vol. 45, No. 10; American Society for Microbiology.

Long et al.; "A model that predicts the attachment behavior of *Ulva linza* zoospores on surface topography"; Biofouling; May 2010; pp. 411-419; vol. 26, No. 4; Taylor & Francis.

Long et al.; "Potential for tunable static and dynamic contact angle anisotropy on gradient microscale patterned topographies"; Langmuir; Nov. 17, 2009; pp. 12982-12989; Abstract; one page; vol. 25, No. 22.

Low et al.; "DNA Aptamers Bind Specifically and Selectively to $(1 \rightarrow 3)$-β-D-glucans"; Biochem. Biophys. Res. Commun.; Jan. 23, 2009; pp. 701-705; vol. 378, No. 4.

Luckevich, Mark; "MEMS microvalves: the new valve world"; Valve World; May 2007; pp. 79-83.

Masteikova, Ruta et al.; "Stimuli-Sensitive Hydrogels in Controlled and Sustained Drug Delivery"; Medicina; 2003; pp. 19-24; vol. 39, No. 2.

Masuoka, James; "Surface Glycans of *Candida albicans* and Other Pathogenic Fungi: Physiological Roles, Clinical Uses, and Experimental Challenges"; Clinical Microbiology Reviews; Apr. 2004; pp. 281-310; vol. 17, No. 2; American Society for Microbiology.

Mateus et al.; "Adherence of *Candida albicans* to Silicone Induces Immediate Enhanced Tolerance to Fluconazole"; Antimicrobial Agents and Chemotherapy; Sep. 2004; pp. 3358-3366; vol. 48, No. 9; American Society for Microbiology.

McDannold et al.; "Microbubble Contrast Agent with Focused Ultrasound to Create Brain Lesions at Low Power Levels: MR Imaging and Histologic Study in Rabbits[1]": Original Research, Experimental Studies, Radiology; bearing a date of Oct. 2006; pp. 95-106; vol. 241, No. 1; RSNA.

Mckenna, Susan M. et al.; "The Inhibition of Bacterial Growth by Hypochlorous Acid"; Biochemistry; 1988; pp. 685-692; vol. 254.

(56) References Cited

OTHER PUBLICATIONS

Miyata et al.; "Tumor marker-responsive behavior of gels prepared by biomolecular imprinting"; PNAS; Jan. 31, 2006; pp. 1190-1193; vol. 103, No. 5; The National Academy of Sciences of the USA.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

Ng, P C; "Review: Diagnostic Markers of Infection in Neonates"; Arch Dis Child Fetal Neonatal Ed; 2004; pp. F229-F235; vol. 89; located at: www.archdischild.com.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.

O'Grady et al.; "Guidelines for the Prevention of Intravascular Catheter-Related Infections"; MMWR Morbidity and Mortality Weekly Report; Aug. 9, 2002; 32 pgs.; vol. 51, No. RR-10.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

Olcum et al.; "Tunable Surface Plasmon Resonance on an Elastomeric Substrate"; Optics Express; bearing a date of May 11, 2009; pp. 8542-8547; vol. 17, No. 10; OSA.

PCT International Search Report; International App. No. PCT/US10/00579; May 3, 2010; pp. 1-2.

PCT International Search Report; International App. No. PCT/US09/06393; May 13, 2010; pp. 1-4.

Peleg et al.; "Hospital-Acquired Infections Due to Gram-Negative Bacteria"; N. Engl. J. Med.; May 13, 2010; pp. 1804-1813; vol. 362, No. 19; Massachusetts Medical Society.

Peppas et al.; "Polymers and Gels as Molecular Recognition Agents"; Pharmaceutical Research; May 2002; pp. 578-587; vol. 19, No. 5; Plenum Publishing Corporation.

Piccolo et al.; "Antifuse Injectors for SOI LEDs"; printed in 2009; pp. 573-575.

Piper, Kerryl E. et al.; "MIST Ultrasound Therapy Device Removal of In Vitro Bacterial Biofilms"; one page; Mayo Clinic; printed on Jan. 25, 2011.

Prescott et al.; "Chronic, programmed polypeptide delivery from an implanted, multireservoir microchip device"; Nature Biotechnology; Apr. 2006; pp. 437-438; vol. 24, No. 4; Nature Publishing Group.

Pronovost et al.; "Sustaining reductions in catheter related bloodstream infections in Michigan intensive care units: observational study"; BMJ; 2010; pp. 1-6.

Proske et al.; "Aptamers-basic research, drug development, and clinical applications"; Appl. Microbiol. Biotechnol.; 2005; pp. 367-374; vol. 69; Springer-Verlag.

Rafiee et al.; "Superhydrophobic to Superhydrophillic Wetting Control in Graphene Films"; Advanced Materials; 2010; pp. 1-4; vol. 22; Wiley-VCH Verlag GmbH & Co., KGaA, Weinheim.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Remington: The Science and Practice of Pharmacy; 20$^{th}$ Edition; 2000; 2 pgs.; Lippincott Williams & Wilkins, Baltimore, Maryland.

Reynolds et al.; "Early Biomarkers of Stroke"; Clinical Chemistry: Oak Ridge Conference; bearing a date of Apr. 7, 2003; pp. 1733-1739; vol. 49, No. 10; American Association for Clinical Chemistry.

Richards Grayson, Amy C. et al.; "A BioMEMS Review: MEMS Technology for Physiolocially Integrated Devices"; Proceedings of the IEEE; Jan. 2004; pp. 6-21; vol. 92, No. 1; IEEE.

Rosalki et al.; "Cardiac Biomarkers for Detection of Myocardial Infarction: Perspectives from Past to Present"; Clinical Chemistry; bearing a date of Aug. 17, 2004; pp. 2205-2213; vol. 50, No. 11; American Association for Clinical Chemistry.

Roti Roti, Joseph L.; "Review: Cellular Responses to Hyperthermia (40-46°C): Cell Killing and Molecular Events"; Int. J. Hyperthermia; Feb. 2008; pp. 3-15; vol. 24, No. 1; Informa UK Ltd.

Sage et al.; "A Rapid and Nondestructive Method for Microbiological Testing in Pharmaceutical Manufacturing"; American Biotechnology Laboratory; Nov./Dec. 2006; pp. 1-5.

Sahly et al.; "Recognition of Bacterial Surface Polysaccharides by Lectins of the Innate Immune System and Its Contribution to Defense against Infection: the Case of Pulmonary Pathogens"; Infection and Immunity; Apr. 2008; pp. 1322-1332; vol. 76, No. 4; American Society for Microbiology.

Seehusen, Dean A. et al.; "Cerebrospinal Fluid Analysis"; American Family Physician; bearing a date of Sep. 15, 2003; pp. 1103-1108; vol. 68, No. 6; located at: www.aafp.org/afp.

Sendid et al.; "Antibodies against Glucan, Chitin, and *Saccharomyces cerevisiae* Mannan as New Biomarkers of *Candida albicans* Infection That Complement Tests Based on *C. albicans* Mannan"; Clinical and Vaccine Immunology; Dec. 2008; pp. 1868-1877; vol. 15, No. 12; American Society for Microbiology.

Serra et al.; "Lectin-modified piezoelectric biosensors for bacteria recognition and quantification"; Anal. Bioanal. Chem.; 2008; pp. 1853-1860; vol. 391; Springer-Verlag.

Setroikromo, R.; "Heat Shock Proteins and Bcl-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

Shackleford et al.; "Integrated Plasmonic Lens Photodetector"; Applied Physics Letters; bearing a date of Nov. 24, 2008; pp. 1-3; vol. 94, No. 083501; American Institute of Physics.

Shangguan et al.; "Aptamers evolved from live cells as effective molecular probes for cancer study"; PNAS; Aug. 8, 2006; pp. 11838-11843; vol. 103, No. 32; The National Academy of Sciences of the USA.

Sharklet Technologies Awarded NIH SBIR (Small Business Innovation Research) Grant for Development of Urinary Catheter with Sharklet™ Pattern; Sharklet Technologies; Nov. 16, 2009; pp. 1-3; located at www.sharklet.com/2009/11/sharklet-technologies-awarded-nih.

Shellman et al.; "Hyperthermia Induces Endoplasmic Reticulum-Mediated Apoptosis in Melanoma and Non-Melanoma Skin Cancer Cells"; Original Article, Journal of Investigative Dermatology; 2008; pp. 949-956; vol. 128; The Society for Investigative Dermatology; located at: www.jidonline.org.

"SilvaSorb® Targeted Antimicrobial Protection"; Medline; 2005; 16 pages; Medline Industries Inc.; located at www.medline.com.

Smith et al.; "Evanescent Wave Imaging in Optical Lithography"; printed on Dec. 10, 2010; pp. 1-9.

Sodja et al.; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Somwaru et al.; "Heat Induced Apoptosis of Mouse Meiotic Cells is Suppressed by Ectopic Expression of Testis-Specific Calpastatin"; Journal of Andrology; bearing a date of Jul./Aug. 2004; pp. 506-513; vol. 25, No. 4; American Society of Anthology.

Spori et al.; "Cassie-State Wetting Investigated by Means of a Hole-to-Pillar Density Gradient"; Langmuir Article; bearing a date Dec. 15, 2009; pp. 9465-9473; vol. 26, No. 12; American Chemical Society.

Stankiewicz et al.; "Hsp70 Inhibits Heat-Induced Apoptosis Upstream of Mitochondria by Preventing Bax Translocation"; The Journal of Biological Chemistry; Bearing a date of Nov. 18, 2005;

(56) References Cited

OTHER PUBLICATIONS pp. 38729-38739; vol. 280, No. 46; The American Society for Biochemistry and Molecular Biology, Inc.

Stubbe et al.; "'Programmed Polymeric Devices' for Pulsed Drug Delivery"; Pharmaceutical Research; Oct. 2004; pp. 1732-1740; vol. 21, No. 10; Springer Science+Business Media, Inc.

"Study E: Comparison of the Moisture Uptake and Retention Properties of Biopatch® and SilvaSorb Site®"; 2 pages.

Suslow, Trevor V.; "Introduction to ORP as the Standard of Post-harvest Water Disinfection Monitoring"; UC Davis, Vegetable Research and Information Center; pp. 1-4.

"Switchable Lotus Effect: Material Becomes Super Water-Repellent With the Flick of a Light"; Science Daily; Sep. 17, 2006; one page; printed on May 11, 2010; located at www.sciencedaily.com/releases/2006/09/060915204838.htm.

Tamura et al.; "One-chip sensing device (biomedial photonic LSI) enabled to assess hippocampal steep and gradual up-regulated proteolytic activities"; Journal of Neuroscience Methods; 2008; pp. 114-120; vol. 173; Elsevier B.V.

Taylor et al.; "Surface Plasmon Resonance (SPR) Sensors for the Detection of Bacterial Pathogens"; Principles of Bacterial Detection: Biosensors, Recognition Receptors and Microsystems; 2008; pp. 83-108; Springer Science+Business Media, LLC.

Thai et al.; "Development of a Fully-Integrated Ultrasensitive Wireless Sensor Utilizing Carbon Nanotubes and Surface Plasmon Theory"; Electronic Components and Technology Conference; bearing a date of 2008; pp. 436-439; IEEE.

Timko et al.; "Remotely Triggerable Drug Delivery Systems"; Advanced Materials; bearing a date of Jun. 4, 2010; pp. 4925-4943; vol. 22; Wiley-VCH Verlag GmbH&Co.

Tsutsui et al.; "Research: The use of Microbubbles to Target Drug Delivery"; BioMed Central-Open Access; bearing a date of Aug. 17, 2004; pp. 1-7; vol. 2, No. 23; BioMed Central Ltd.

Tuteja et al.; "Robust Omniphobic Surfaces"; PNAS; bearing a date of Nov. 25, 2008; pp. 18200-18205; vol. 105, No. 47; The National Academy of Sciences of the USA.

Ulrich et al.; "In Vitro Selection of RNA Aptamers That Bind to Cell Adhesion Receptors of *Trypanosoma cruzi* and Inhibit Cell Invasion"; The Journal of Biological Chemistry; Jun. 7, 2002; pp. 20756-20762; vol. 277, No. 23; The American Society for Biochemistry and Molecular Biology, Inc.

Vashist, Sandeep Kumar; "A Review of Microcantilevers for Sensing Applications"; Open Access Rewards System; Jun. 2007; pp. 1-15; vol. 3.

Vazquez et al.; "Optical Router for Optical Fiber Sensor Networks Based on a Liquid Crystal Cell"; IEEE Sensors Journal; bearing a date of Aug. 2003; pp. 513-518; vol. 3, No. 4; IEEE.

Vogel et al.; "Capillarity-based switchable adhesion"; PNAS; Feb. 23, 2010; pp. 3377-3381; vol. 107, No. 8.

Vykhodtseva et al.; "Induction of Apoptosis in vivo in the Rabbit Brain Focused Ultrasound and Optison®"; Original Contribution, Ultrasound in Med. & Biol.; 2006; pp. 1923-1929; vol. 32, No. 12; World Federation for Ultrasound in Medicine & Biology.

Wang et al.; "Review: Photoresponsive Surfaces with Controllable Wettability"; Journal of Photochemistry and Photobiology C: Photochemistry Review, Science Direct; 2007; pp. 18-29; vol. 8; Elsevier B.V.

Wang et al.; "Effective in Plane Launching and Focusing Surface Plasmons by a Plasmonic Lens"; OSA; bearing a date of 2009; pp. 1-2; IEEE.

Wang et al.; "APD: The Antimicrobial Peptide Database"; Nucleic Acids Research; 2004; pp. D590-D592; vol. 32; Oxford University Press.

Watson et al.; "Review: Clinical Utility of Biochemical Analysis of Cerebrospinal Fluid"; Clinical Chemistry; 1995; pp. 343-360; vol. 41, No. 3.

Wentworth et al.; "Reports: Evidence for Antibody-Catalyzed Ozone Formation in Bacterial Killing and Inflammation"; Science; 2002; pp. 2195-2199; vol. 298; downloaded on Jul. 14, 2009; located at: www.sciencemag.org.

Wissing et al.; "Illumination of the Malaria *Parasite Plasmodium falciparum* Alters Intracellular pH"; The Journal of Biological Chemistry; Oct. 4, 2002; pp. 37747-37755; vol. 277, No. 40; The American Society for Biochemistry and Molecular Biology, Inc.

Xanthos, Marino; "Polymers and Fillers, Part One"; Functional Fillers for Plastics; Second, updated and enlarged edition; 2010; cover page; pp. 3-18; Wiley-Vch Verlag GmbH & Co. KGaA, Weinheim.

Yang et al.; "Engineering Target-Responsive Hydrogels Based on Aptamer-Target Interactions"; J. Am. Chem. Soc.; 2008; pp. 6320-6321; vol. 130; American Chemical Society.

Yang et al.; "On-Chip Electrochemical Impedance Spectroscopy for Biosensor Arrays"; IEEE Sensors; Oct. 22-25, 2006; pp. 93-96; IEEE.

Yang et al.; "Polyimide-Waveguide-Based Thermal Optical Switch Using Total-Internal-Reflection Effect"; Applied Physics Letters; bearing a date of Oct. 14, 2002; pp. 2947-2949; vol. 81, No. 16; American Institute of Physics.

Ye et al.; "Molecularly imprinted polymers as antibody and receptor mimics for assays, sensors and drug discovery"; Anal. Bioanal. Chem.; 2004; pp. 1887-1897; vol. 378; Springer-Verlag.

Zelada-Guillén et al.; "Immediate Detection of Living Bacteria at Ultralow Concentrations Using a Carbon Nanotube Based Potentiometric Aptasensor"; Angew. Chem. Int. Ed.; 2009; pp. 1-4; vol. 48; Wiley-VCH Verlag GmbH & Co. KGaA, Weinheim.

Zharov et al.; "In vivo high-speed imaging of individual cells in fast blood flow"; Journal of Biomedical Optics; Sep./Oct. 2006; pp. 054034-1 to 054034-4; vol. 11, No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Design and Fabrication of a Micro Coulter Counter with Thin Film Electrodes"; Proceedings of 2006 International Conference on Microtechnologies in Medicine and Biology; May 9-12, 2006; pp. 16-19; IEEE.

Zhong et al.; "Review: Biomaterials for the Central Nervous System"; Journal of the Royal Society Interface; 2008; pp. 957-975; vol. 5; The Royal Society.

European Patent Office; Extended European Search Report; App. No. EP 10 74 6554; Apr. 5, 2013 (received by our agent on Apr. 8, 2013); 8 pages (1 cover page, 1 supplementary European search report, 6 European search opinion pages).

PCT International Search Report; International App. No. PCT/US2010/003088; Apr. 1, 2011; pp. 1-4.

PCT International Search Report; International App. No. PCT/US11/01883; May 3, 2012; pp. 1-5.

McCarthy et al.; "Steroid Modulation of Astrocytes in the Neonatal Brain: Implications for Adult Reproductive Function"; Biology of Reproduction; bearing a date of Apr. 5, 2002; pp. 691-698; vol. 67; Society for the Study of Reproduction, Inc.

Dienel et al.; Astrocyte activation in vivo during graded photic stimulation ; Journal of Neurochemistry; bearing a date of 2007; pp. 1506-1522; vol. 103; International Society for Neurochemistry.

Elmore, Susan; "Apoptosis: A Review of Programmed Cell Death"; Toxicol Pathology; Dec. 6, 2007; pp. 495-516 (pp. 1-40 as provided); vol. 35, No. 4; National Institute of Health.

Hashimoto et al.; "$TiO_2$ Photocatalysis: A Historical Overview and Future Prospects"; Japanese Journal of Applied Physics; bearing a date of 2005, published Dec. 8, 2005; pp. 8269-8285; vol. 44, No. 12; The Japan Society of Applied Physics.

Gal'China et al.; "Electroluminescence Spectra of Ultraviolet Light-Emitting Diodes Based *p-n*-Heterostructures Coated with Phosphors"; Semiconductors; bearing a date of 2007; pp. 1126-1131; vol. 41, No. 9; Pleiades Publishing Ltd.; ISSN 1063-7826.

Kim et al.; "Realization of p-type ZnO thin films via phosphorus doping and thermal activation of the dopant"; Applied Physics Letters; bearing a date of Jul. 7, 2003; pp. 63-65; vol. 83, No. 1; American Institute of Physics.

Könenkamp et al.; "Ultraviolet Electroluminescence from ZnO/Polymer Heterojunction Light-Emitting Diodes"; Nano Letters; bearing a date of 2005; pp. 2005-2008; vol. 5, No. 10; American Chemical Society.

(56) References Cited

OTHER PUBLICATIONS

Li et al.; "Ultraviolet nanophosphors"; Journal of Luminescence; bearing a date of 2007; pp. 345-347; vol. 122-123; Elsevier B.V.

Lim et al.; "UV Electroluminescence Emission from ZnO Light-Emitting Diodes Grown by High-Temperature Radiofrequency Sputtering"; Advanced Materials; bearing a date of 2006; pp. 2720-2724; vol. 18; Wiley-VCH Verlag GmbH & Co.

Sun et al.; "Realization of ultraviolet electroluminescence from ZnO homojunction with n-ZnO/p-ZnO:As/GaAs structure"; Applied Physics Letters; bearing a date of 2007; pp. 121128-1-121128-3; vol. 90; American Institute of Physics.

Tang et al.; "Cerium Phosphate Nanotubes: Synthesis, Valence State, and Optical Properties"; Angew. Chem. Int. Ed.; bearing a date of 2005; pp. 576-579; vol. 44; Wiley-VCH Verlag GmbH & Co. KGaA, Weinheim.

Zhang et al.; "Milliwatt power deep ultraviolet light-emitting diodes over sapphire with emission at 278 nm"; Applied Physics Letters; bearing a date of Dec. 23, 2002; pp. 4910-4912; vol. 81, No. 26; American Institute of Physics.

Gjerde, Kjetil, "Carbon nanotube forests: a non-stick workbench for nanomanipulation," Institute of Physics Publishing, 2006, pp. 4917-4922, Nanotechnology 17, IOP Publishing Ltd, UK.

Dostálek et al.; "Multichannel surface plasmon resonance biosensor with wavelength division multiplexing"; Sensors and Actuators B 108 Chemical; Feb. 5, 2005; pp. 758-764; Elsevier B.V.

Nugaeva et al.; Micromechanical cantilever array sensors for selective fungal immobilization and fast growth detection; Biosensors & Bioelectronics 21; Mar. 2, 2005; pp. 849-856; Elsevier B.V.

* cited by examiner

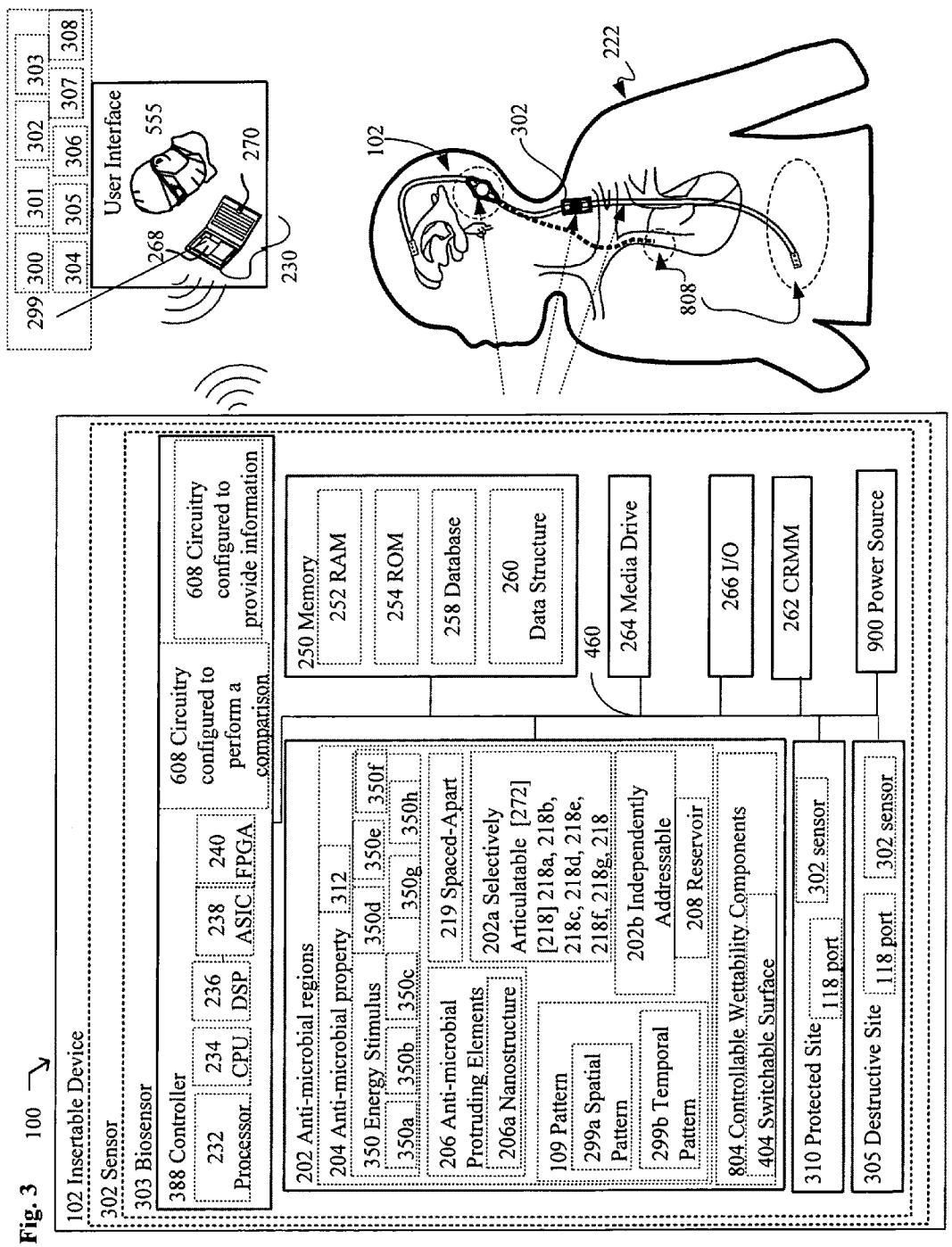

Fig. 8    100
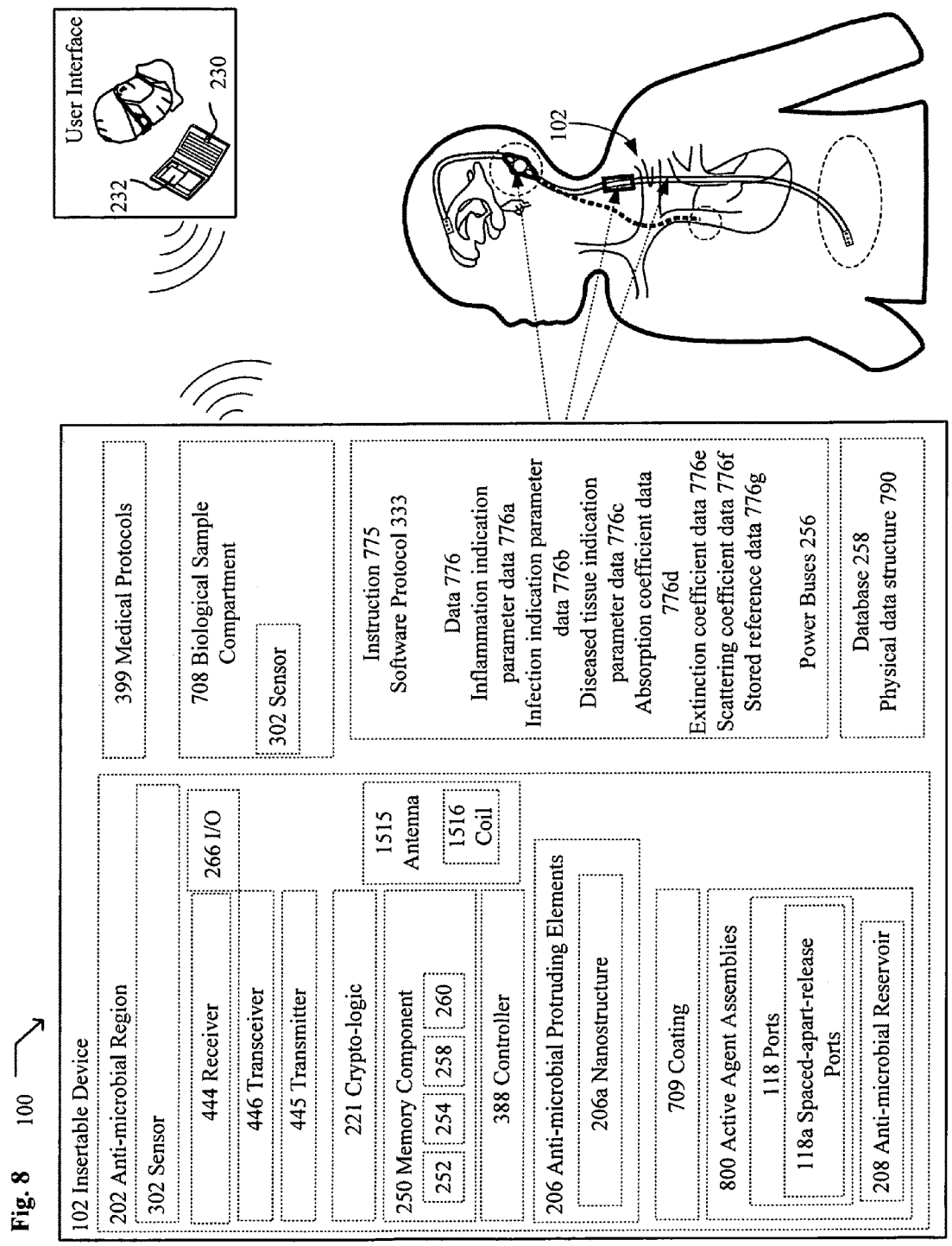

Fig. 9 1500

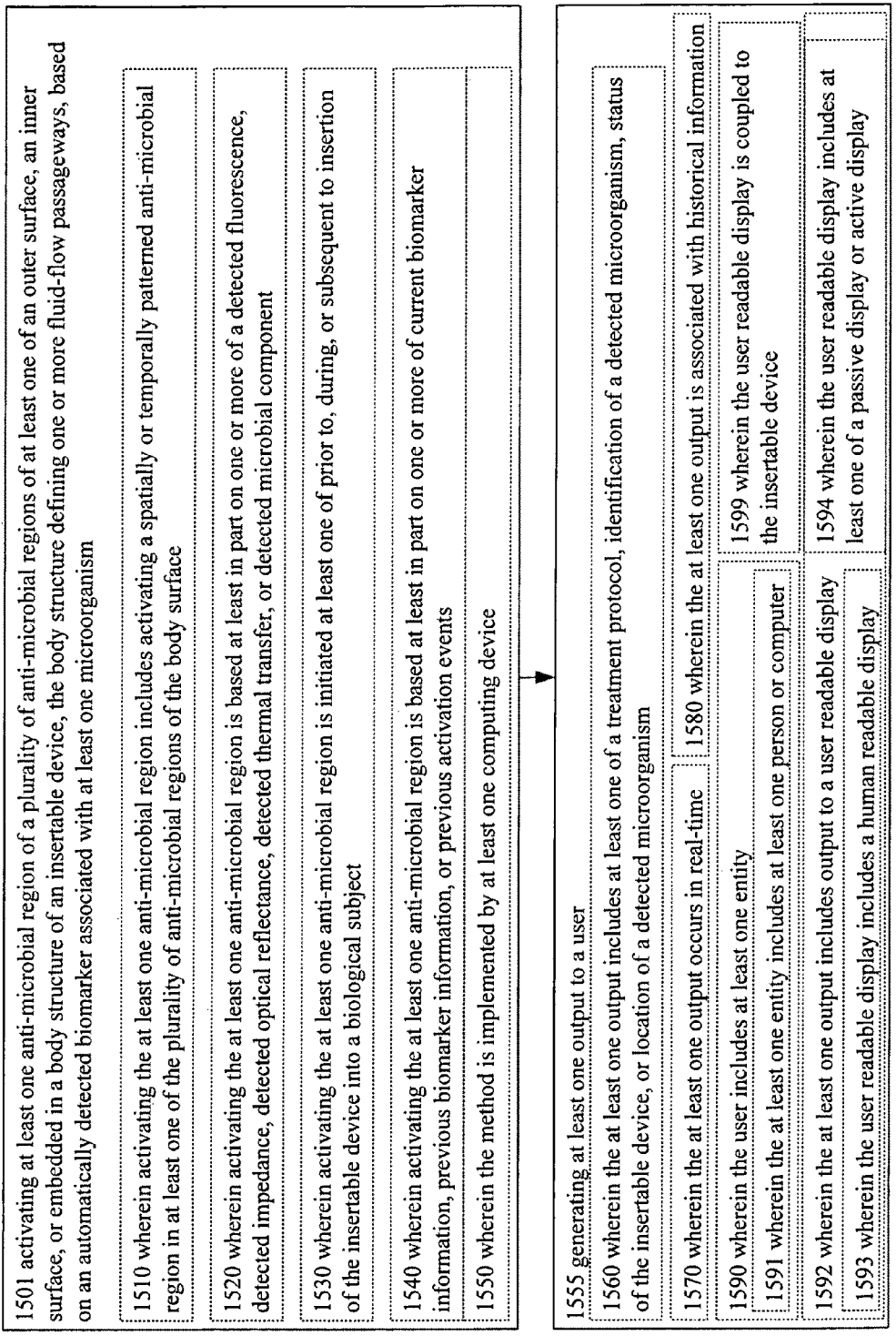

1501 activating at least one anti-microbial region of a plurality of anti-microbial regions of at least one of an outer surface, an inner surface, or embedded in a body structure of an insertable device, the body structure defining one or more fluid-flow passageways, based on an automatically detected biomarker associated with at least one microorganism 1510 wherein activating the at least one anti-microbial region includes activating a spatially or temporally patterned anti-microbial region in at least one of the plurality of anti-microbial regions of the body surface 1520 wherein activating the at least one anti-microbial region is based at least in part on one or more of a detected fluorescence, detected impedance, detected optical reflectance, detected thermal transfer, or detected microbial component 1530 wherein activating the at least one anti-microbial region is initiated at least one of prior to, during, or subsequent to insertion of the insertable device into a biological subject 1540 wherein activating the at least one anti-microbial region is based at least in part on one or more of current biomarker information, previous biomarker information, or previous activation events 1550 wherein the method is implemented by at least one computing device 1555 generating at least one output to a user 1560 wherein the at least one output includes at least one of a treatment protocol, identification of a detected microorganism, status of the insertable device, or location of a detected microorganism 1570 wherein the at least one output occurs in real-time 1580 wherein the at least one output is associated with historical information 1590 wherein the user includes at least one entity 1599 wherein the user readable display is coupled to the insertable device 1591 wherein the at least one entity includes at least one person or computer 1592 wherein the at least one output includes output to a user readable display 1594 wherein the user readable display includes at least one of a passive display or active display 1593 wherein the user readable display includes a human readable display

Fig. 10   1600

1610 actuating at least one anti-microbial region of a plurality of anti-microbial regions configured to direct at least one anti-microbial agent to one or more areas of at least one of an outer surface, an inner surface, or internally embedded in a body structure of an insertable device, the body structure defining one or more fluid-flow passageways, in response to an in vivo detected microbial component associated with a biological sample proximate to one or more areas of the body structure

Fig. 11 1700

1705 automatically comparing one or more characteristics communicated from an inserted insertable device to stored reference data, the one or more characteristics including at least one of information associated with microbial marker information; and information associated with at least one microbial component detected proximate to at least one of an outer surface or inner surface of the insertable device, or information associated with a fluid received within one or more fluid-flow passageways of the inserted insertable device; and initiating a treatment protocol based at least in part on the comparison 1710 wherein automatically comparing the one or more characteristics communicated from an inserted insertable device to stored reference data includes comparing, via circuitry forming part of the inserted insertable device, one or more characteristics communicated from the inserted insertable device to stored reference data 1720 wherein initiating the treatment protocol includes generating a spatially patterned distribution of at least one anti-microbial agent released from at least one anti-microbial region of the device 1730 wherein initiating the treatment protocol includes delivering a dose of at least one anti-microbial agent based at least in part on the comparison 1740 wherein initiating the treatment protocol includes concurrently or sequentially delivering two or more anti-microbial agents to at least one of the outer surface, or the inner surface of the body structure of the insertable device, based at least in part on the comparison 1750 wherein initiating the treatment protocol includes activating at least one of an authorization protocol, authentication protocol, or anti-microbial agent delivery protocol based at least in part on the comparison

Fig. 12   1800 → activating at least one activatable anti-microbial region including at least one anti-microbial reservoir configured to actively elute at least one anti-microbial agent proximate at least one of the outer surface or the inner surface of the body structure of the device, based at least in part on detecting the presence of at least one microorganism proximate to one or more areas of the body structure.

Fig. 13  1900 →

1905 selectively releasing at least one anti-microbial agent from an anti-microbial agent reservoir operably coupled to one or more anti-microbial regions proximate at least one of an outer surface, inner surface, or embedded in the internal body structure of an insertable device, the insertable device including a body structure having an outer surface and an inner surface defining one or more fluid-flow passageways, in response to an automatically detected signal associated with the at least one microbial component proximate at least one of the outer surface or inner surface of the insertable device, or present in the fluid-flow passageway 1910 wherein selectively releasing at least one anti-microbial agent from an anti-microbial agent reservoir operably coupled to one or more anti-microbial regions includes concurrently or sequentially releasing at least one first anti-microbial agent from an anti-microbial agent reservoir operably coupled to a first anti-microbial region, and releasing at least one second anti-microbial agent from an anti-microbial agent reservoir operably coupled to a second anti-microbial agent reservoir 1920 wherein releasing the at least one anti-microbial agent includes releasing the anti-microbial agent at a dose sufficient to modulate an activity of the detected microorganism in response to the automatically detected signal associated with at least one microbial component 1930 further comprising initiating a treatment protocol in response to the automatically detected signal associated with at least one microbial component proximate at least one of the outer surface or inner surface of the insertable device 1940 wherein initiating the treatment protocol includes activating at least one of an authorization protocol, authentication protocol, or anti-microbial agent delivery protocol, based at least in part on the automatically detected signal associated with at least one microbial component

Fig. 14 2000 →

2005 wherein the method is implemented by at least one computing device 2010 further comprising generating at least one output to a user 2020 wherein the at least one output includes at least one output to a user readable display 2030 wherein the at least one output includes at least one of a treatment protocol, identification of a detected microorganism, status of the insertable device, or location of a detected microorganism 2040 wherein the user includes at least one entity 2050 wherein the at least one entity includes at least one person or computer 2060 wherein the at least one output includes at least one output to a user readable display 2070 wherein the user readable display includes a human readable display 2080 wherein the user readable display includes one or more active displays 2090 wherein the user readable display includes one or more passive displays 2094 wherein the at least one output occurs in real-time 2095 wherein the user readable display includes one or more of a numeric format, graphical format, or audio format 2096 wherein the signal includes at least one of a fluorescent signal, impedance signal, optical signal, thermal signal, biochemical signal, or electrochemical signal 2097 wherein selectively releasing the at least one anti-microbial agent is initiated at least one of prior to, during, or subsequent to insertion of the insertable device into a biological subject 2098 wherein the at least one output is associated with historical information 2099 wherein the user readable display is coupled to the insertable device

Fig. 15  2100 ⟶

2110 selectively actuating one or more anti-microbial regions so as to partially release at least one anti-microbial agent through at least one of an outer surface or an inner surface of the catheter assembly in response to real-time detected information associated with the presence of a microbial component proximate one or more regions of at least one of an outer surface or inner surface of the catheter assembly

Fig. 16  2200 →

2210 activating via control circuitry at least one actively controllable anti-microbial nanostructure of at least one of the outer surface or the inner surface in a body structure of an insertable device 2215 wherein the body structure defines one or more fluid-flow passageways, based on at least one of an automatically detected biomarker, temporal randomness, or a heuristically determined parameter associated with at least one microorganism 2220 wherein activating the at least one actively controllable anti-microbial nanostructure includes electrically activating a spatially patterned anti-microbial nanostructure 2230 wherein activating the at least one actively controllable anti-microbial nanostructure includes electrically activating a temporally patterned anti-microbial nanostructure 2240 wherein the actuation is based at least in part on detection of at least one microorganism 2250 wherein the actuation is based at least in part on a schedule 2260 wherein the actuation is based at least in part on a command from an implant 2270 wherein the actuation is based at least in part on a command from one or more sensors 2280 wherein the actuation is based at least in part on an external command

Fig. 17  2300

2305 wherein activating the at least one actively controllable anti-microbial nanostructure includes activating a spatially patterned anti-microbial nanostructure based on at least one characteristic 2310 wherein the at least one characteristic includes at least one detected characteristic including one or more of detected fluorescence, detected impedance, detected optical reflectance, detected thermal transfer, detected change in conductance, detected change in index of refraction, detected pH, or detected microbial component of at least one microorganism 2320 wherein activating the at least one actively controllable anti-microbial nanostructure is initiated at least one of prior to, during, or subsequent to insertion of the insertable device into a biological subject 2330 wherein the method includes electrically activating a computing device to execute the method 2340 further comprising generating at least one output to a user 2350 wherein generating at least one output to the user includes electrically activating at least one of a treatment protocol, identification of a detected microorganism, status of the insertable device, or location of a detected microorganism 2360 wherein generating at least one output to the user includes generating at least one output to at least one entity 2365 wherein the at least one entity includes at least one person or computer 2370 wherein the at least one output includes at least one output to a user readable display 2380 wherein the user readable display includes one or more active displays 2390 wherein the user readable display includes one or more passive displays 2395 wherein the user readable display includes one or more of a numeric format, graphical format, or audio format

Fig. 18 2400 →

| 2405 wherein the heuristically determined parameter includes at least one of a threshold level or target parameter |
|---|

| 2410 wherein the heuristically determined parameter includes at least one heuristic protocol determined parameter or heuristic algorithm determined parameter |
|---|

Fig. 19  2500

2505 activating via control circuitry at least one independently addressable and actively controllable anti-microbial nanostructure projecting from at least one of the outer surface or the inner surface of a body structure of an insertable device, the body structure defining one or more fluid-flow passageways, based on at least one of an automatically detected biomarker or a heuristically determined parameter associated with at least one microorganism 2506 wherein activating the at least one actively controllable anti-microbial nanostructure includes activating a spatially patterned anti-microbial nanostructure 2507 wherein activating the at least one actively controllable anti-microbial nanostructure includes activating a temporally patterned anti-microbial nanostructure

Fig. 20  2600

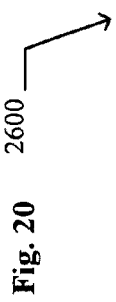

2605 actuating at least one anti-microbial region between a first anti-microbial state and a second anti-microbial state, the at least one anti-microbial region included in at least one of the outer surface or the inner surface of a body structure of an insertable device, the body structure defining one or more fluid-flow passageways, based at least in part on an automatically detected biomarker or a heuristically determined parameter associated with at least one microorganism 2610 wherein actuating includes reversibly actuating between the first actuatable anti-microbial state and the second actuatable anti-microbial state in response to a detected presence of at least one microbial component 2620 wherein the first actuatable anti-microbial state includes a first adsorption affinity, and the second actuatable anti-microbial state includes a second adsorption affinity 2630 wherein actuating between the at least one of the first actuatable anti-microbial state or the second actuatable anti-microbial state includes at least one of a change in at least one of hydrophilicity, hydrophobicity, electrical charge, chemical composition, polarizability, transparance, condictivity, light absorption, osmotic potential, zeta potential, surface energy, coefficient of friction, or tackiness 2640 wherein actuating the at least one actively controllable anti-microbial nanostructure includes actuating a spatially patterned anti-microbial nanostructure based on at least one of detected fluorescence, detected impedance, detected optical reflectance, detected thermal transfer, detected change in conductance, detected change in index of refraction, detected pH, or detected microbial component 2650 wherein the actuation is based at least in part on a schedule, command from an implant, command from one or more sensors, or external command 2660 further comprising generating at least one output to a user

Fig. 21   2700

2705 actuating at least one independently addressable and actuatable anti-microbial region, the at least one independently addressable and actuatable anti-microbial region included in at least one of the outer surface or the inner surface of a body structure of an insertable device, the body structure defining one or more fluid-flow passageways, based at least in part on an automatically detected biomarker or a heuristically determined parameter associated with at least one microorganism Fig. 22  2800 

2805 actuating one or more anti-microbial regions of an insertable device between at least a first actuatable anti-microbial state and a second actuatable anti-microbial state in response to a detected presence of at least one microbial component proximate at least one of the one or more anti-microbial regions of an insertable device 2810 wherein actuating includes reversibly actuating between the first actuatable anti-microbial state and the second actuatable anti-microbial state in response to a detected presence of at least one microbial component 2820 wherein the first actuatable anti-microbial state includes a first adsorption affinity, and the second actuatable anti-microbial state includes a second adsorption affinity 2830 wherein actuating between the at least one of the first actuatable anti-microbial state or the second actuatable anti-microbial state includes at least one of a change in at least one of hydrophilicity, hydrophobicity, electrical charge, chemical composition, polarizability, transparence, conductivity, light absorption, osmotic potential, zeta potential, surface energy, coefficient of friction, or tackiness

Fig. 23  2900

2904 actuating at least one anti-microbial region of a plurality of anti-microbial regions configured to direct at least one anti-microbial agent to one or more areas of at least one of an outer surface, an inner surface, or internally embedded in a body structure of an insertable device, the body structure defining one or more fluid-flow passageways, in response to an in vivo detected microbial component associated with a biological sample proximate to one or more areas of the body structure 2905 wherein actuating the at least one anti-microbial region including actuating at least one spatially patterned or temporally patterned anti-microbial region in at least one of the plurality of anti-microbial regions of the body surface 2906 wherein actuating the at least one anti-microbial region is based at least in part on at least one of a detected fluorescence, detected impedance, detected optical reflectance, detected thermal transfer, or detected microbial component 2907 wherein actuating the at least one anti-microbial region is initiated at least one of prior to, during, or subsequent to insertion of the insertable device into a biological subject 2908 wherein actuating the at least one anti-microbial region is based at least in part on one or more of current biomarker information, previous biomarker information, or previous actuation events

Fig. 24    3000

3010 wherein activating the at least one actively controllable anti-microbial nanostructure is based at least in part on detection of at least one microorganism 3020 wherein activating the at least one actively controllable anti-microbial nanostructure is based at least in part on a schedule 3030 wherein activating the at least one actively controllable anti-microbial nanostructure is based at least on part on a command from an implant 3040 wherein activating the at least one actively controllable anti-microbial nanostructure is based at least in part on a command from one or more sensors 3050 wherein activating the at least one actively controllable anti-microbial nanostructure is based at least in part on an external command 3060 wherein activating the at least one actively controllable anti-microbial nanostructure includes activating a spatially patterned anti-microbial nanostructure based on a detected fluorescence 3070 wherein activating the at least one actively controllable anti-microbial nanostructure includes activating a spatially patterned anti-microbial nanostructure based on a detected impedance 3080 wherein activating the at least one actively controllable anti-microbial nanostructure includes activating a spatially patterned anti-microbial nanostructure based on a detected optical reflectance

Fig. 25   3100

3110 wherein activating the at least one actively controllable anti-microbial nanostructure includes activating a spatially patterned anti-microbial nanostructure based on a detected thermal transfer 3120 wherein activating the at least one actively controllable anti-microbial nanostructure includes activating a spatially patterned anti-microbial nanostructure based on a detected change in conductance 3130 wherein activating the at least one actively controllable anti-microbial nanostructure includes activating a spatially patterned anti-microbial nanostructure based on a detected change in index of refraction 3140 wherein activating the at least one actively controllable anti-microbial nanostructure includes activating a spatially patterned anti-microbial nanostructure based on a detected pH 3150 wherein activating the at least one actively controllable anti-microbial nanostructure includes activating a spatially patterned anti-microbial nanostructure based on a detected microbial component of at least one microorganism 3160 wherein activating the at least one actively controllable anti-microbial nanostructure includes electrically activating a computing device to execute the method 3170 wherein activating the at least one actively controllable anti-microbial nanostructure is initiated at least one of prior to, during, or subsequent to insertion of the insertable device into a biological subject

Fig. 26

3200 

3210 wherein actuating the one or more anti-microbial regions is based at least in part on detection of at least one microorganism 3220 wherein actuating the one or more anti-microbial regions is based at least in part on a schedule 3230 wherein actuating the one or more anti-microbial regions is based at least in part on a command from an implant 3240 wherein actuating the one or more anti-microbial regions is based at least in part on a command from one or more sensors 3250 wherein actuating the one or more anti-microbial regions is based at least in part on an external command 3260 wherein actuating the one or more anti-microbial regions includes actuating a spatially patterned anti-microbial region based on a detected fluorescence 3270 wherein actuating the one or more anti-microbial regions includes activating a spatially patterned anti-microbial region based on a detected impedance 3280 wherein actuating the one or more anti-microbial regions includes actuating a spatially patterned anti-microbial region based on a detected optical reflectance

Fig. 27  3300

3310 wherein actuating the one or more anti-microbial regions includes actuating a spatially patterned anti-microbial region based on a detected thermal transfer 3320 wherein actuating the one or more anti-microbial regions includes actuating a spatially patterned anti-microbial region based on a detected change in conductance 3330 wherein actuating the one or more anti-microbial regions includes actuating a spatially patterned anti-microbial region based on a detected change in index of refraction 3340 wherein actuating the one or more anti-microbial regions includes actuating a spatially patterned anti-microbial region based on a detected pH 3350 wherein actuating the one or more anti-microbial regions includes actuating a spatially patterned anti-microbial region based on a detected microbial component of at least one microorganism 3360 wherein actuating the one or more anti-microbial regions includes electrically activating a computing device to execute the method 3370 wherein actuating the one or more anti-microbial regions is initiated at least one of prior to, during, or subsequent to insertion of the insertable device into a biological subject

Fig. 28

3400 

3401 actuating at least one actuatable anti-microbial region including at least one anti-microbial reservoir configured to actively elute at least one anti-microbial agent proximate at least one of the outer surface or the inner surface of the body structure of the device, based at least in part on detecting the presence of at least one microorganism proximate to one or more areas of the body structure

Fig. 29

3500

3510 wherein the at least one anti-microbial region includes one or more of an anti-microbial agent, or anti-microbial nanostructure 3520 wherein the anti-microbial agent includes at least one surfactant or amino acid 3530 wherein the amino acid includes at least one D-amino acid 3540 wherein the anti-microbial agent includes at least one of an anti-fungal agent, anti-parasitic agent, bacteriophage, or antibiotic 3550 wherein the anti-microbial agent includes at least one enzymatically active bacteriophage 3560 wherein the antibiotic includes at least one of azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, sulfadizine, sulfacetamide, sulfadiazine, sulfamethoxazole, sulfasalazine, sulfisoxazole, trimethoprim-sulfamethoxazole, sulfamethizole, linezolid, quinopristin+dalfopristin, bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, colistin, cycloserine, capreomycin, ethionamide, pyrazinamide, para-aminosalicyclic acid, erythromycin ethylsuccinate+sulfisoxazole, penicillin, beta- lactamase inhibitor, methicillin, cefaclor, cefamandole nafate, cefazolin, cefixime, cefinetazole, cefonioid, cefoperazone, cefornide, cefotanme, cefotaxime, cefotetan, cefoxitin, cefpodoxime proxetil, ceftazidime, ceftizoxime, ceftriaxone, ceftriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate, Amphotericin B, Carbol-Fuchsin, Ciclopirox, Clotrimzole, Econazole, Haloprogin, Ketoconazole, Mafenide, Miconazole, Naftifine, Nystatin, Oxiconazole Silver, Sulfadiazine, Sulconazole, Terbinatine, Tioconazole, Tolnaftate, Undecylenic acid, flucytosine, miconazole or cephalosporin

Fig. 30

3600 

3610 wherein the anti-microbial agent includes at least one of a macrolide, lincosamine, quinolone, fluoroquinolone, carbepenem, monobactam, aminoglycoside, glycopeptide, enzyme, tetracycline, sulfonamide, rifampin, oxazolidonone, streptogramin, or a synthetic moiety thereof 3620 wherein the anti-microbial agent includes at least one of a metal, ceramic, super-oxide forming compound, or polymer 3630 wherein the anti-microbial agent includes at least one of polyvinyl chloride, polyester, polyethylene, polypropylene, ethylene, polyolefin, homopolymers or copolymers thereof 3640 wherein the anti-microbial agent includes polytetrafluoroethylene 3650 wherein at least one of the plurality of anti-microbial regions includes at least one of silver, copper, zirconium, diamond, rubidium, platinum, gold, nickel, lead, cobalt, potassium, zinc, bismuth, tin, cadmium, chromium, aluminum, calcium, mercury, thallium, gallium, strontium, barium, lithium, magnesium, oxides, hydroxides, or salts thereof 3660 wherein at least one of the plurality of anti-microbial regions includes at least one of an electroactive polymer, hydrogenated diamond, or black silica

SYSTEMS, DEVICES, AND METHODS INCLUDING IMPLANTABLE DEVICES WITH ANTI-MICROBIAL PROPERTIES

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications or claims benefits under 35 U.S.C. §116(e) for provisional patent applications, for any and all parent, grandparent, great-grandparent, etc. applications of the Related Applications). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the United States Patent and Trademark Office (USPTO) extra-statutory requirements, the present application constitutes a continuation-in-part of U.S. patent application Ser. No. 12/931,921, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,924, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,928, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011.

For purposes of the United States Patent and Trademark Office (USPTO) extra-statutory requirements, the present application constitutes a continuation-in-part of U.S. patent application Ser. No. 12/931,929, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011.

For purposes of the United States Patent and Trademark Office (USPTO) extra-statutory requirements, the present application constitutes a continuation-in-part of U.S. patent application Ser. No. 12/931,923, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,925, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,931, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 February 2011 now abandoned.

For purposes of the United States Patent and Trademark Office (USPTO) extra-statutory requirements, the present application constitutes a continuation-in-part of U.S. patent application Ser. No. 12/931,930, titled SYSTEMS, DEVICES, AND METHODS INCLUDING IMPLANTABLE DEVICES WITH ANTI-MICROBIAL PROPERTIES, naming ELEANOR V. GOODALL, RODERICK A. HYDE, ELIZABETH A. SWEENEY, LOWELL L. WOOD, JR. as inventors, filed 14 February 2011 now abandoned.

For purposes of the United States Patent and Trademark Office (USPTO) extra-statutory requirements, the present application constitutes a continuation-in-part of U.S. patent application Ser. No. 12/931,920, titled SYSTEMS, DEVICES, AND METHODS INCLUDING IMPLANTABLE DEVICES WITH ANTI-MICROBIAL PROPERTIES, naming EDWARD S. BOYDEN, ROY P. DIAZ, RODERICK A. HYDE, JORDIN T. KARE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,927, titled SYSTEMS, DEVICES, AND METHODS INCLUDING IMPLANTABLE DEVICES WITH ANTI-MICROBIAL PROPERTIES, naming EDWARD S. BOYDEN, ROY P. DIAZ, RODERICK A. HYDE, JORDIN T. KARE, ELIZABETH A. SWEENEY, LOWELL L. WOOD, JR. as inventors, filed 14 Feb. 2011 now abandoned.

For purposes of the United States Patent and Trademark Office (USPTO) extra-statutory requirements, the present application constitutes a continuation-in-part of U.S. patent application Ser. No. 12/931,922, titled SYSTEMS, DEVICES, AND METHODS INCLUDING IMPLANTABLE DEVICES WITH ANTI-MICROBIAL PROPERTIES, naming EDWARD S. BOYDEN, ROY P. DIAZ, RODERICK A. HYDE, JORDIN T. KARE, ELIZABETH A. SWEENEY, LOWELL L. WOOD, JR. as inventors, filed 14 Feb. 2011.

For purposes of the United States Patent and Trademark Office (USPTO) extra-statutory requirements, the present application constitutes a continuation-in-part of U.S. patent application Ser. No. 12/315,880, titled SYSTEM, DEVICES, AND METHODS INCLUDING ACTIVELY-CONTROLLABLE SUPEROXIDE WATER GENERATING SYSTEMS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 4 Dec. 2008 now U.S. Pat. No. 8,162,924.

For purposes of the United States Patent and Trademark Office (USPTO) extra-statutory requirements, the present application constitutes a continuation-in-part of U.S. patent application Ser. No. 12/315,881, titled SYSTEM, DEVICES, AND METHODS INCLUDING STERILIZING EXCITATION DELIVERY IMPLANTS WITH CRYPTOGRAPHIC LOGIC COMPONENTS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR, VICTORIA Y. H. WOOD as inventors, filed 4 Dec. 2008 now abandoned.

For purposes of the United States Patent and Trademark Office (USPTO) extra-statutory requirements, the present application constitutes a continuation-in-part of U.S. patent application Ser. No. 12/315,882, titled SYSTEM, DEVICES, AND METHODS INCLUDING STERILIZING EXCITATION DELIVERY IMPLANTS WITH GENERAL CONTROLLERS AND ONBOARD POWER, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 4 Dec. 2008 now abandoned.

For purposes of the United States Patent and Trademark Office (USPTO) extra-statutory requirements, the present application constitutes a continuation-in-part of U.S. patent application Ser. No. 12/315,883, titled SYSTEM, DEVICES, AND METHODS INCLUDING STERILIZING EXCITATION DELIVERY IMPLANTS WITH GENERAL CONTROLLERS AND ONBOARD POWER, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR, VICTORIA Y. H. WOOD as inventors, filed 4 Dec. 2008 now abandoned.

For purposes of the United States Patent and Trademark Office (USPTO) extra-statutory requirements, the present application constitutes a continuation-in-part of U.S. patent application Ser. No. 12/315,884, titled SYSTEM, DEVICES, AND METHODS INCLUDING ACTIVELY CONTROLLABLE STERILIZING EXCITATION DELIVERY IMPLANTS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 4 Dec. 2008 now abandoned.

For purposes of the United States Patent and Trademark Office (USPTO) extra-statutory requirements, the present application constitutes a continuation-in-part of U.S. patent application Ser. No. 12/315,885, titled CONTROLLABLE ELECTROSTATIC AND ELECTROMAGNETIC STERILIZING EXCITATION DELIVERY SYSTEMS, DEVICE, AND METHODS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 4 Dec. 2008 now abandoned.

For purposes of the United States Patent and Trademark Office (USPTO) extra-statutory requirements, the present application constitutes a continuation-in-part of U.S. patent application Ser. No. 12/380,553, titled SYSTEM, DEVICES, AND METHODS INCLUDING ACTIVELY CONTROLLABLE STERILIZING EXCITATION DELIVERY IMPLANTS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 27 Feb. 2009 now abandoned.

For purposes of the United States Patent and Trademark Office (USPTO) extra-statutory requirements, the present application constitutes a continuation-in-part of U.S. patent application Ser. No. 12/592,976, titled SYSTEM, DEVICES, AND METHODS INCLUDING ACTIVELY-CONTROLLABLE STERILIZING EXCITATION DELIVERY IMPLANTS, naming EDWARD S. BOYDEN, RALPH G. DACEY, JR., GREGORY J. DELLA ROCCA, JOSHUA L. DOWLING, RODERICK A. HYDE, MURIEL Y. ISHIKAWA, JORDIN T. KARE, ERIC C. LEUTHARDT, NATHAN P. MYHRVOLD, DENNIS J. RIVET, PAUL SANTIAGO, MICHAEL A. SMITH, TODD J. STEWART, ELIZABETH A. SWEENEY, CLARENCE T. TEGREENE, LOWELL L. WOOD, JR., VICTORIA Y. H. WOOD as inventors, filed 3 Dec. 2009 now U.S. Pat. No. 9,005,263.

For purposes of the United States Patent and Trademark Office (USPTO) extra-statutory requirements, the present application constitutes a continuation-in-part of U.S. patent application Ser. No. 12/660,156, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 19 Feb. 2010 now U.S. Pat. No. 8,366,652.

For purposes of the United States Patent and Trademark Office (USPTO) extra-statutory requirements, the present application constitutes a continuation-in-part of U.S. patent application Ser. No. 12/800,766, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C.

LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now U.S. Pat. No. 8,216,173.

For purposes of the United States Patent and Trademark Office (USPTO) extra-statutory requirements, the present application constitutes a continuation-in-part of U.S. patent application Ser. No. 12/800,774, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,778, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,779, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,780, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,781, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,786, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now abandoned.

For purposes of the United States Patent and Trademark Office (USPTO) extra-statutory requirements, the present application constitutes a continuation-in-part of U.S. patent application Ser. No. 12/800,790, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now U.S. Pat No. 8,343,086.

For purposes of the United States Patent and Trademark Office (USPTO) extra-statutory requirements, the present application constitutes a continuation-in-part of U.S. patent application Ser. No. 12/800,791, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now U.S. Pat. No. 8,282,593.

For purposes of the United States Patent and Trademark Office (USPTO) extra-statutory requirements, the present application constitutes a continuation-in-part of U.S. patent application Ser. No. 12/800,792, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010 now U.S. Pat No. 8,888,731.

For purposes of the United States Patent and Trademark Office (USPTO) extra-statutory requirements, the present application constitutes a continuation-in-part of U.S. patent application Ser. No. 12/800,793, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L.

WOOD, JR., VICTORIA Y. H. WOOD as inventors, filed 21 May 2010 now U.S. Pat No. 8,414,517.

For purposes of the United States Patent and Trademark Office (USPTO) extra-statutory requirements, the present application constitutes a continuation-in-part of U.S. patent application Ser. No. 12/800,798, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21 May 2010, which is currently co-pending or is an application of which a currently co-pending application is entitled to the benefit of the filing date.

For purposes of the USPTO extra-statutory requirements, the present application is related to U.S. patent application Ser. No. 12/927,297, titled SYSTEMS, DEVICES, AND METHODS INCLUDING CATHETERS HAVING COMPONENTS THAT ARE ACTIVELY CONTROLLABLE BETWEEN TRANSMISSIVE AND REFLECTIVE STATES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,460,229.

For purposes of the USPTO extra-statutory requirements, the present application is related to U.S. patent application Ser. No. 12/927,284, titled SYSTEMS, DEVICES, AND METHODS INCLUDING CATHETERS HAVING COMPONENTS THAT ARE ACTIVELY CONTROLLABLE BETWEEN TWO OR MORE WETTABILITY STATES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,647,292.

For purposes of the USPTO extra-statutory requirements, the present application is related to U.S. patent application Ser. No. 12/927,288, titled SYSTEMS, DEVICES, AND METHODS INCLUDING CATHETERS HAVING AN ACTIVELY CONTROLLABLE THERAPEUTIC AGENT DELIVERY COMPONENT, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,734,718.

For purposes of the USPTO extra-statutory requirements, the present application is related to U.S. patent application Ser. No. 12/927,296, titled SYSTEMS, DEVICES, AND METHODS INCLUDING CATHETERS HAVING UV-ENERGY EMITTING COATINGS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now abandoned.

For purposes of the USPTO extra-statutory requirements, the present application is related to U.S. patent application Ser. No. 12/927,287, titled SYSTEMS, DEVICES, AND METHODS INCLUDING CATHETERS HAVING SELF-CLEANING SURFACES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,706,211.

For purposes of the USPTO extra-statutory requirements, the present application is related to U.S. patent application Ser. No. 12/927,294, titled SYSTEMS, DEVICES, AND METHODS INCLUDING CATHETERS CONFIGURED TO MONITOR BIOFILM FORMATION HAVING BIOFILM SPECTRAL INFORMATION CONFIGURED AS A DATA STRUCTURE, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,585,627.

For purposes of the USPTO extra-statutory requirements, the present application is related to U.S. patent application Ser. No. 12/927,285, titled SYSTEMS, DEVICES, AND METHODS INCLUDING CATHETERS HAVING ACOUSTICALLY ACTUATABLE WAVEGUIDE COMPONENTS FOR DELIVERING A STERILIZING STIMULUS TO A REGION PROXIMATE A SURFACE OF THE CATHETER, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,753,304.

For purposes of the USPTO extra-statutory requirements, the present application is related to U.S. patent application Ser. No. 12/927,290, titled SYSTEMS, DEVICES, AND METHODS INCLUDING CATHETERS HAVING LIGHT REMOVABLE COATINGS BASED ON A SENSED CONDITION, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now U.S. Pat No. 8,702,640.

For purposes of the USPTO extra-statutory requirements, the present application is related to U.S. patent application Ser. No. 12/927,291, titled SYSTEMS, DEVICES, AND METHODS INCLUDING CATHETERS HAVING LIGHT REMOVABLE COATINGS BASED ON A SENSED CONDITION, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010 now abandoned.

For purposes of the USPTO extra-statutory requirements, the present application is related to U.S. patent application Ser. No. 12/927,295, titled SYSTEMS, DEVICES, AND METHODS INCLUDING CATHETERS CONFIGURED TO RELEASE ULTRAVIOLET ENERGY ABSORBING AGENTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10 Nov. 2010, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

The present disclosure is directed to, among other things, an insertable device. In an embodiment, the insertable device includes a body structure having an outer surface and an inner surface defining one or more fluid-flow passageways. In an embodiment, a system or method is disclosed for operating the insertable device.

In an embodiment, the insertable device system includes a body structure having an outer surface and an inner surface defining one or more fluid-flow passageways; at least one independently addressable and actively controllable anti-microbial nanostructure projecting from at least one of the outer surface, or the inner surface of the body structure; and circuitry configured for determining the presence of at least one microorganism on at least one of the independently addressable and actively controllable anti-microbial nanostructure of the body structure.

In an embodiment, the insertable device system includes a body structure having an outer surface and an inner surface defining one or more fluid-flow passageways; at least one independently addressable and actively controllable anti-microbial nanostructure projecting from at least one of the outer surface, or the inner surface of the body structure; at least one sensor configured to detect one or more microorganisms present on the body structure; and means for determining the presence of at least one microorganism on at least one of the independently addressable and actively controllable anti-microbial nanostructure of the body structure.

In an embodiment, the insertable device system includes a computer-recordable medium bearing: a body structure having an outer surface and an inner surface defining one or more fluid-flow passageways; at least one independently addressable and actively controllable anti-microbial nanostructure; and one or more instructions for determining the presence of at least one microorganism on at least one of the at least one independently addressable and actively controllable anti-microbial nanostructure of the body structure.

In an embodiment, the insertable device system includes a body structure having an outer surface and an inner surface defining one or more fluid-flow passageways; a plurality of independently addressable anti-microbial regions including at least one actuatable anti-microbial property, the plurality of independently addressable anti-microbial regions being included in at least one of the outer surface, or the inner surface of the body structure; and circuitry configured for determining the presence of at least one microorganism proximate at least one of the independently addressable anti-microbial regions of the body structure.

In an embodiment, the insertable device includes a body structure having an outer surface and an inner surface defining one or more fluid-flow passageways, the body structure having a plurality of actuatable regions that are selectively actuatable between at least a first actuatable state and a second actuatable state; and one or more sensors configured to detect at least one anti-microbial component associated with a biological sample proximate the body structure.

In an embodiment, the insertable device includes an outer surface and an inner surface of the body structure, at least one surface including at least one anti-microbial nanostructure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3 illustrates a particular embodiment of a device in an embodiment of a system disclosed herein.

FIG. 8 illustrates a particular embodiment of a device in an embodiment of a system disclosed herein.

FIG. 9 illustrates a partial view of an embodiment of a method disclosed herein.

FIG. 10 illustrates a partial view of an embodiment of a method disclosed herein.

FIG. 11 illustrates a partial view of an embodiment of a method disclosed herein.

FIG. 12 illustrates a partial view of an embodiment of a method disclosed herein.

FIG. 13 illustrates a partial view of an embodiment of a method disclosed herein.

FIG. 14 illustrates a partial view of an embodiment of a method disclosed herein.

FIG. 15 illustrates a partial view of an embodiment of a method disclosed herein.

FIG. 16 illustrates a partial view of an embodiment of a method disclosed herein.

FIG. 17 illustrates a partial view of an embodiment of a method disclosed herein.

FIG. 18 illustrates a partial view of an embodiment of a method disclosed herein.

FIG. 19 illustrates a partial view of an embodiment of a method disclosed herein.

FIG. 20 illustrates a partial view of an embodiment of a method disclosed herein.

FIG. 21 illustrates a partial view of an embodiment of a method disclosed herein.

FIG. 22 illustrates a partial view of an embodiment of a method disclosed herein.

FIG. 23 illustrates a partial view of an embodiment of a method disclosed herein.

FIG. 24 illustrates a partial view of an embodiment of a method disclosed herein.

FIG. 25 illustrates a partial view of an embodiment of a method disclosed herein., FIG. 26 illustrates a partial view of an embodiment of a method disclosed herein.

FIG. 27 illustrates a partial view of an embodiment of a method disclosed herein.

FIG. 28 illustrates a partial view of an embodiment of a method disclosed herein.

FIG. 29 illustrates a partial view of an embodiment of a method disclosed herein.

FIG. 30 illustrates a partial view of an embodiment of a method disclosed herein.

DETAILED DESCRIPTION

Figures 1A, 1B:
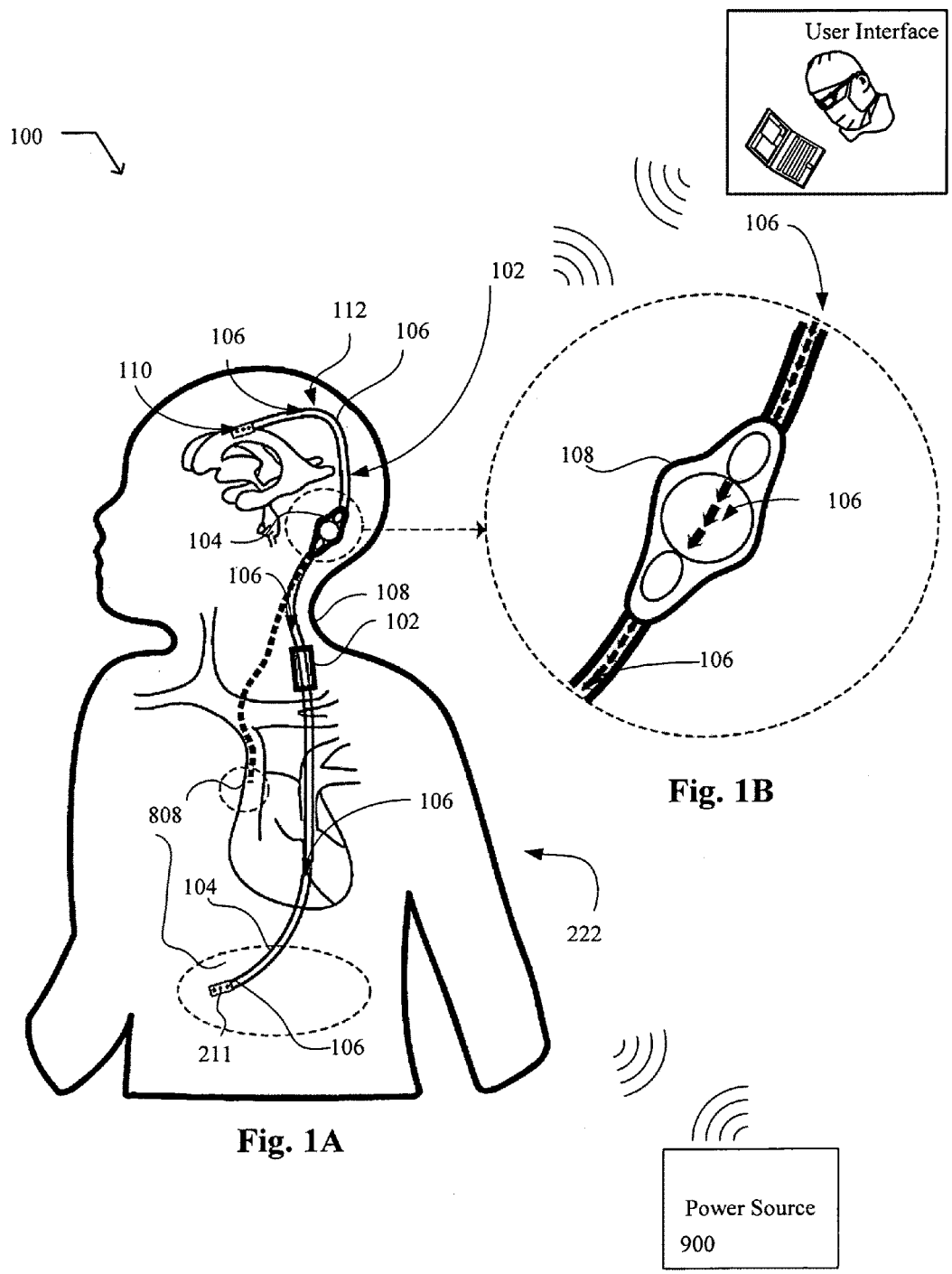
FIG. 1A illustrates a particular embodiment of a device disclosed herein.
FIG. 1B illustrates a close up view of a component of the device illustrated in FIG. 1A.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Insertable devices, such as implantable shunts (e.g., cardiac shunts, cerebral shunts, portacaval shunts, portosystemic shunts, pulmonary shunts, or the like), catheters (e.g., central venous catheters, multi-lumen catheters, peripherally inserted central catheters, Quinton catheters, Swan-Ganz catheters, tunneled catheters, or the like), or medical ports (e.g., arterial ports, low profile ports, multi-lumen ports, vascular ports, or the like) are useful for, among other things, managing movement of fluids; directly detecting (e.g., assessing, calculating, evaluating, determining, gauging, identifying, measuring, monitoring, quantifying, resolving, sensing, or the like) mechanical, physical, or biochemical information (e.g., the presence of a biomarker, intracranial pressure, blood pressure, a disease state, or the like) associated with a biological subject; draining or collecting body fluids; as well as for administering therapeutics, medications, pharmaceuticals, intravenous fluids, blood products, or delivering parenteral nutrition.

Infections, malfunctions (e.g., blocked or clogged fluid-flow passageways), and failures account for many of the complications associated with catheter devices and pose tremendous consequences for patients. For example, during an infection, an infectious agent (e.g., fungi, micro-organisms, parasites, pathogens (e.g., viral pathogens, bacterial pathogens, or the like), prions, viroids, viruses, or the like) generally interferes with the normal functioning of a biological subject, and causes, in some cases, chronic wounds, gangrene, loss of an infected tissue, loss of an infected limb, and occasionally death of the biological subject. Infections associated with catheter devices account for a significant number of nosocomial infections. Despite sterilization and aseptic procedures, infection remains a major impediment to medical implants and catheter devices, including artificial hearts or heart valves, subcutaneous sensors, contact lens, artificial joints, artificial prosthetics, breast implants, cochlear implants, dental implants, neural implants, orthopedic implants, ocular implants, prostheses, implantable electronic devices, implantable medical devices, catheters, contact lens, implantable biological fluid drainage system, mechanical heart valves, stents, subcutaneous sensors, shunts, vertebral spacers, and the like. Implant associated (including catheter device-associated) infections are often difficult to detect, problematic to cure, and expensive to manage. For example, in cases where the infection does not quickly subside, it sometimes becomes necessary to remove the catheter device. Implant device-associated infections can result from microorganism (e.g., bacteria) adhesion and possibly subsequent biofilm formation proximate an implantation site. For example, biofilm-forming microorganisms sometimes colonize catheter devices at least partially implanted into a biological subject. Once a biofilm-induced infection takes hold, it can prove difficult to treat, and can even be fatal for the biological subject.

The present disclosure includes, but is not limited to, systems, devices, and methods, of a catheter device configured to, for example, detect (e.g., assess, calculate, evaluate, determine, gauge, identify, measure, monitor, quantify, resolve, sense, or the like) an infectious agent (e.g., microorganism) present in, for example, a biological fluid. A non-limiting example includes systems, devices, and methods including a catheter device configured to, for example, detect an infectious agent present in, for example, a biological sample proximate a catheter device that is at least partially implanted into a biological subject.

An aspect includes systems, devices, methods, and Compositions for actively or passively detecting, treating, or preventing an infection, a fluid vessel abnormality (e.g., an obstruction), a biological fluid abnormality (e.g., cerebrospinal fluid abnormality, hematological abnormality, components concentration or level abnormality, flow abnormality, or the like), or the like. A non-limiting example includes systems, devices, and methods for actively detecting, treating, or preventing an infection or presence of at least one microorganism associated with a shunt or other catheter device. An aspect includes systems, devices, and methods for managing movement of fluids; directly detecting and monitoring functions or conditions (e.g., mechanical, physical, physiological, or biochemical functions or conditions) associated with a biological subject; draining or collecting body fluids; providing access to an interior of a biological subject; distending at least one passageway; as well as for administering therapeutics, medications, pharmaceuticals, intravenous fluids, or parenteral nutrition. A non-limiting example includes systems, devices, and methods for actively detecting, treating, or preventing fluid-flow obstructions in shunts or other catheter devices.

In certain aspects, at least one of the inner surface or the outer surface of the body structure of a catheter device disclosed herein includes at least one surface with reversibly switchable or actuatable properties. For example, a reversibly switchable surface generally includes a chemical switch (e.g., surface chemistry or surface charge that can be manipulated by the presence of a pathogen or other stimulus). For example, in an embodiment, the surface includes a nanolayer or microlayer of a material that switches from a first conformation (i.e. a first anti-microbial state) to a second conformation (i.e. a second anti-microbial state). In another example, when an external stimulus is applied (e.g., electrical, electrochemical, magnetic, optical, electro-optical, etc.), the surface is actuatable (e.g., by an electrical potential). See, for example, U.S. Patent App. Pub. No. 2006/0263033, which is incorporated herein by reference. In an embodiment, the presence of at least one microorganism acts as the external stimulus. In an embodiment, the external stimulus includes at least one of a chemical, electrical, or electro-chemical property. In an embodiment, the external stimulus includes at least one temporal gradient, spatial gradient, or concentration gradient.

For example, wettability of a surface can be switched or actuated. The wettability of a substrate can be determined using various technologies and methodologies including contact angle methods, the Goniometer method, the Whilemy method, or the Sessile drop technique. Wetting is a process by which a liquid interacts with a solid. Wettability (the degree of wetting) is determined by a force balance between adhesive and cohesive force and is often characterized by a contact angle. The contact angle is the angle made by the intersection of the liquid/solid interface and the liquid/air interface. Alternatively, it is the angle between a solid sample's surface and the tangent of a droplet's ovate shape at the edge of the droplet. Contact angle measurements provide a measure of interfacial energies and conveys direct information regarding the degree of hydrophilicity or hydrophobicity for a surface. For example, superhydrophilic surfaces have contact angles less than about 5 degrees, hydrophilic surfaces have contact angles less than about 90 degrees, hydrophobic surfaces have contact angles greater than about 90 degrees, and superhydrophobic surfaces have contact angles greater than about 150 degrees.

In an embodiment, the anti-microbial region includes at least one nanotube forest of vertically aligned carbon nanotubes. See, for example, Gjerde, et al., Nanotech. Vol. 17, pp. 4917-4922 (2006), which is incorporated herein by reference. For example, the nanotube forest, due to its roughness, not only exhibits very low static friction and dynamic friction, but it also acts as a springy and mechanically compliant surface, making it possible to lift up and manipulate delicate nanostructures such as organic nanofibers. Id.

In an embodiment, the surface of at least one of the inner surface or outer surface of the body structure includes a capillary-based switchable surface, which includes a surface tension force from several small liquid bridges, whose contacts are quickly made or broken with electronic controls, thus switching the surface. See, for example, Vogel and Steen, PNAS Early Edition on the web at pnas.org/cgi/doi/10.1073/pnas.0914720107), the content of which is incorporated herein by reference.

In an embodiment, at least one of the inner surface or outer surface of the body structure includes a wettablity switchable surface, including, for example a metal/polymer membrane with hydrophobic microposts. See Chen, et al. J. Micromech. Microeng. Vol. 17, pp. 489-495 (2007), which is incorporated herein by reference. For example, the water contact angles can be manipulated from 131 degrees to 152 degrees, depending on the fraction of a liquid/solid interface. Id. The process of surface wetting induced by morphology change (SWIM) allows a change in total surface area that contacts a water droplet, based on the number of microposts that are articulated at any given time, this allows for the change in wettability state. Id.

In an embodiment, the anti-microbial region includes at least one patterned surface configured to resist or enhance bioadhesion of microbes compared to the base surface. In an embodiment, the at least one anti-microbial region includes a surface with reversibly switchable properties (e.g., the surface switches from a first conformation state to a second conformation state when an external stimulus is applied). See, for example, U.S. Patent App. Pub. No. 2006/0263033, which is incorporated herein by reference.

In an embodiment, at least one sensor is operably coupled to the surface and is configured to detect at least one microbial component. For example, in particular instances the surface properties are switchable or actuatable between or among at least one of hydrophilicity, hydrophobicity, electrical charge, chemical composition, polarizability, transparence, conductivity, light absorption, osmotic potential, zeta potential, surface energy, coefficient of friction, or tackiness.

Infections account for one of the many complications associated with surgery and pose tremendous consequences for patients. During an infection, an infecting agent (e.g., fungi, micro-organisms, parasites, pathogens (e.g., viral pathogens, bacterial pathogens, and the like), prions, viroids, viruses, and the like) generally interferes with the normal functioning of a biological subject, and causes, in some cases, chronic wounds, gangrene, loss of an infected tissue, loss of an infected limb, and occasionally death of the biological subject.

Implant-associated infections account for a significant amount of nosocomial infections and despite sterilization and aseptic procedures, remain as a major impediment to medical implants including artificial hearts, artificial joints, artificial prosthetics, breast implants, catheters, contact lens, mechanical heart valves, subcutaneous sensors, vertebral spacers, and the like. Implant-associated infections are often difficult to detect, problematic to cure, and at times expensive to manage. For example, in cases where the infection does not quickly subside, it sometimes becomes necessary to remove the implant.

Implant-associated infections can result from bacterial adhesion and subsequent biofilm formation proximate an implantation site. For example, biofilm-forming microorganisms sometimes colonize implants. Once a biofilm-induced infection takes hold, it can prove difficult to treat.

As a non-limiting example, certain systems, devices, methods, and compositions described herein provide an actively controllable disinfecting implantable device configured to, for example, treat or prevent an infection (e.g., an implant-associated infection, hematogenous implant-associated infection, and the like), a hematological abnormality, and the like. One non-limiting approach for treating or preventing an infection, a hematological abnormality, and the like includes systems, devices, and methods for administrating a perioperative antibiotic prophylaxis to a patient. Another non-limiting approach includes systems, devices, methods, and compositions for actively forming an antimicrobial agent, in vivo. Another non-limiting approach includes systems, devices, methods, and compositions for impeding bacterial adherence to the implant surface. Another non-limiting approach includes systems, devices, methods, and compositions for actively impeding biofilm formation on an implant. Another non-limiting approach includes systems, devices, and methods including coating an implant with active agent compositions having, for example, anti-biofilm activity. Another non-limiting approach includes systems, devices, methods, and compositions for providing an implant with a scaffold-forming material. Another non-limiting approach includes systems, devices, and methods including coating an implant with one or more coatings having self-cleaning properties. Another non-limiting approach includes systems, devices, and methods including an implant with a self-cleaning coating having self-cleaning, and anti-bacterial activity. Another non-limiting approach includes systems, devices, and methods including an implant having one or more self-cleaning surfaces.

For example, in an embodiment the implantable device includes at least one actively controllable anti-microbial region. In an embodiment, the actively controllable anti-microbial region includes at least one actively-controllable excitation component, which may include at least one energy-emitting element (e.g., electric circuits, electrical conductors, electrodes, electrocautery electrodes, cavity resonators, conducting traces, ceramic patterned electrodes, electro-mechanical components, lasers, quantum dots, laser diodes, light-emitting diodes, arc flashlamps, continuous wave bulbs, ultrasonic emitting elements, ultrasonic transducers, thermal energy emitting elements, etc.).

In an embodiment, the medical device includes a power source. In an embodiment, the power source includes at least one piezoelectric material. In an embodiment, the power source includes at least one alternating-current nanogenerator. For example, a two-ends-bonded piezoelectric nanowire (e.g., zinc) is subjected to a periodic mechanical stretching and releasing, the mechanical-electric coupling effect of the nanowire, combined with the gate effect of the Schottky contact at the interface, results in an alternating flow of the charge in the external circuit. See, Li, et al., Adv. Mater. Vol. 22, pp. 1-4 (2010), which is incorporated herein by reference.

In an embodiment, at least one of the inner surface or the outer surface of the body structure includes at least one tunable static or dynamic contact angle anisotropy on gradient microscale patterned topography. See, Long, et al., Langmuir Abstract, vol. 25, no. 22, pp. 12982-12989 (2009), which is incorporated herein by reference. For example, translationally symmetric topographies are designed to induce anisotropy of static or dynamic contact angles fabricated out of a polymer (e.g., poly (dimethyl siloxane) elastomer). Id Microorganisms Associated with Catheter Use A catheter device is described herein for detecting and treating microorganisms in at least one of a plurality of anti-microbial regions of the body structure of the catheter. Examples of catheters include but are not limited to intravascular catheters, hemodialysis catheters, urinary catheters, peritoneal dialysis catheters, enteral feeding tubes, gastrostomy tubes, endotracheal tubes, tracheostomy tubes, and umbilical catheters. An intravascular catheter can be further designated by the type of vessel it occupies (e.g., peripheral venous, central venous, or arterial); its intended life span (e.g., temporary or short-term versus permanent of long-term); its site of insertion (e.g., subclavian, femoral, internal jugular, peripheral, and peripherally inserted central catheter (PICC)); its pathway from skin to vessel (e.g., tunneled versus nontunneled); its physical length (e.g., long versus short); or some specific characteristic of the catheter (e.g., presence or absence of a cuff, impregnation with heparin, antibiotics, or antiseptics, and the number of lumens). See, e.g., O'Grady, et al., *MMWR Recomm. Rep.*, 51(RR-10):1-32, 2002, which is incorporated herein by reference.

In some instances, a bloodstream infection can occur when bacteria or other microorganisms travel down a catheter and enter the blood and/or tissue. Catheter related bloodstream infections cause considerable morbidity, mortality, and healthcare costs. An estimated 82,000 catheter related bloodstream infections and up to 28,000 attributable deaths occur in intensive care units annually at an estimated cost of $45,000 per infection. Over 250,000 cases of central venous catheter-associated bloodstream infections have been estimated to occur annually in the hospital setting with an attributable mortality estimated at 12%-25%. See, e.g., Provonost, et al., *BMJ*, 340:c309, 2010; O'Grady, et al., *MMWR Recomm. Rep.*, 51(RR-10):1-32, 2002, each of which is incorporated herein by reference.

The most common microorganism associated with intravascular catheters is reportedly coagulase-negative staphylococci accounting for 37% of isolated causes of hospital acquired bloodstream infection. Other microorganisms associated with intravascular catheter biofilms and hospital acquired bloodstream infections include bacteria, e.g., *Staphylococcus epidermidis, Staphylococcus aureus, Pseudomonoas aeruginosa, Klebsiella pneumoniae, Enterobacteriaceae* and *Enterococcus faecalis* and *fungi*, e.g., *Candida albicans* and other *Candida* species. Microorgamisms commonly contaminating urinary catheters films include *S. epidermidis, Enterococcus faecalis, E. coli, Proteus mirabilis, P. aeruginosa, K. pneumoniae*, and other gram-negative organisms. Donlan, *Emerging Infectious Diseases*, 7:277-281, 2001; O'Grady, et al., *MMWR Recomm. Rep.*, 51(RR-10):1-32, 2002, each of which is incorporated herein by reference Of particular concern are emerging multi-drug resistant gram-negative bacteria for which there are increasingly fewer effective antibiotics. Gram negative bacteria accounted for 14% of catheter-associated bloodstream infections during the period spanning 1992-1999. An increasing percentage of ICU-related bacterial isolates contain Enterobacteriaceae that produce extended spectrum beta-lactamases, particularly *Klebsiella pneumonia*, which tend to be resistant to extended spectrum cephalosporins and broad spectrum antimicrobial agents. Examples of gram-negative bacteria associated with hospital acquired bacterial infections include but are not limited to *Pseudomonas aeruginosa, Escherichia coli, Klebsiella pneumoniae, Enterobacter cloacae, Acinetobacter spp., Serratia marcescens, Enterobacter aerogenes, Stenotrophomonas maltophilia, Proteus mirabilis, Klebsiella oxytoca*, and *Citrobacter freundii*. See, e.g., Lockhart et al., *J. Clin. Microbiol.*, 45:3352-3359, 2007, which is incorporated herein by reference. Antibiotics for use in treating gram-negative bacteria include but are not limited to carbapenems, exemplified by imipenem and meropenem. Multidrug resistance of gram-negative bacteria is defined as resistance to at least one extended-spectrum cephalosporin, one aminoglycoside, and ciprofloxacin and is increasing among isolates of *Acinetobacter spp., P. aeruginosa, K. pneumoniae*, and *E. cloacae*. Colistin and polymyxin B can be used to treat gram-negative bacterial infection. These drugs were largely abandoned sometime ago due to kidney and nerve damage, but because of their infrequent use, bacteria have not had an opportunity to develop resistance to them at present. See, e.g., Peleg & Hooper, *N. Engl. J. Med.*, 362:1804-1813, 2010, which is incorporated herein by reference.

The types of organisms that most commonly cause hospital-acquired blood stream infections change over time. During 1986-1989, for example, coagulase-negative staphylococci and *Staphylococcus aureus* were the most frequently reported causes of bloodstream infections, accounting for 27% and 16% of bloodstream infections, respectively. From 1992 to 1999, coagulase-negative staphylococci and enterococci were the most frequently isolated causes of hospital acquired bloodstream infections. Coagulase-negative staphylococci accounted for 37% and *S. aureus* accounted from 12.6% BSIs. By 1999, >50% of all *S. aureus* isolated from ICUs were resistant to oxacillin. In 1999, enterococci accounted for 13.5% of BSIs with vancomycin resistance escalating from 0.5% in 1989 to 25.9% in 1999. *Candida* spp. caused 8% of hospital-acquired BSIs reported during 1986-1989 and during 1992-1999. Resistance of *Candida* spp. to commonly used antifungal agents is increasing. For example, 10% of *C. albicans* bloodstream isolates from hospital patients were resistant to fluconazole. Additionally 48% of *Candida* BSIs were caused by nonalbicans species including *C. glabrata* and *C. krusei* which are more likely to exhibit fluconazole resistance. See, e.g., O'Grady, et al., *MMWR Recomm. Rep.*, 51(RR-10):1-32, 2002, which is incorporated herein by reference.

Pathogenesis

The most common route of infection for peripherally inserted, short-term catheters is migration of microorganisms associated with the patient's skin at the insertion site into the cutaneous catheter tract with subsequent colonization of the catheter tip. Contamination of the catheter hub contributes substantially to intraluminal colonization of long-term catheters by microorganisms. Occasionally, catheters might become hematogenously seeded from another focus of infection. Rarely, contamination of an infusate leads to catheter related bloodstream infections.

There are a number of important determinants of catheter-related infection including the material from which the device is made and the intrinsic virulence factors of the infecting microorganism. Catheters made of polyvinyl chloride or polyethylene appear to be less resistant to the adherence of microorganisms than are catheters made of Teflon, silicone elastomer, or polyurethane. Surface irregularities of some catheter materials can also enhance the microbial adherence of certain species (e.g., coagulase-negative staphylococci, *Acinetobacter calcoaceticus*, and *Pseudomonas aeruginosa*) and catheters made from these materials are especially vulnerable to microbial colonization and subsequent infection. In addition, some catheter materials are more thrombogenic than others, a characteristic that may predispose to catheter colonization and catheter-related infection. This association has led to emphasis on preventing catheter-related thrombus as an additional mechanism for reducing catheter-related bloodstream infections and inclusion of anticoagulant flush solutions in the treatment regimen. The adherence properties of a given microorganism also are important in the pathogenesis of catheter-related infection. In general, coagulase-negative staphylococci adhere to polymer surfaces more readily than do other pathogens and certain strains of coagulase-negative staphylococci produce an extracellular polysaccharide often referred to as "slime". This slime potentiates the pathogenicity of coagulase-negative staphylococci by allowing the bacteria to withstand host defense mechanisms (e.g., acting as a barrier to engulfment and killing by polymorphonuclear lymphocytes) or by making them less susceptible to antimicrobial agents (e.g., forming a matrix that binds antimicrobials before their contact with the organism cell wall). As another example, *S. aureus* can adhere to host proteins (e.g., fibronectin) commonly present on catheters. Certain *Candida* spp., in the presence of glucose-containing fluids, can produce slime similar to that of their bacterial counterparts, potentially explaining the increased proportion of bloodstream infections caused by fungal pathogens among patients receiving parenteral nutrition fluids. See, e.g., O'Grady, et al., *MMWR Recomm. Rep.*, 51(RR-10):1-32, 2002, which is incorporated herein by reference.

Sensors for Sensing Microorganisms on Catheter

The catheter device includes at least one sensor configured to detect the presence of at least one microorganism in at least one of a plurality of anti-microbial regions on the body structure of the device. The at least one sensor includes at least one of a plasmon sensor, pH sensor, temperature sensor, piezoelectric sensor, electrostrictive sensor, magnetostrictive sensor, biochemical sensor, optical sensor, or electronic sensor. Sensors can be incorporated directly onto the inner or outer surface of the catheter body structure. In an embodiment, the sensor is located in microchannels incorporated into the inner and/or outer surface of the catheter body structure, providing a localized measurement chamber. See, e.g., U.S. Patent Applications 2008/0214909; 2009/0297574; each of which is incorporated herein by reference.

In an aspect, the at least one sensor can be a plasmon sensor configured to detect at least one microorganism based on changes in the refractive index on the sensor surface in response to interaction of the microorganism with the sensor. In an aspect, the surface of the sensor is a glass support or other solid support coated with a thin film of metal, for example, gold. The sensor surface can include a matrix to which is immobilized one or more binding agents configured to recognize at least one microorganism. The binding agents can be antibodies or fragments thereof, oligonucleotide or peptide based aptamers, receptors or ligands, artificial binding substrates formed by molecular imprinting, or any other examples of molecules and or substrates that bind microorganisms. As a microorganism moves along the inner or outer surface of the catheter device, the microorganism interacts with binding agents on the surface of the sensor. The sensor is illuminated with a light source, e.g., a light emitting diode or optical fiber. Resonance occurs at a specific angle of incident light and is dependent on the concentration of microorganisms on the surface. See, e.g., Barlen, et al., *Sensors*, 7:1427-1446, 2007; Taylor, et al., "Surface plasmon resonance (SPR) sensors for the detection of bacterial pathogens," in *Principles of Bacterial Detection: Biosensors, Recognition Receptors and Microsystems*, ed. M. Zourob, S. Elwary, & A. Turner, pp. 83-108, 2008, Springer New York; and Kashyap & Nemova, *J. Sensors*, 2009: Article ID 645162, each of which is incorporated herein by reference.

The one or more sensors can be one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference.

In an aspect, the catheter device can include at least one impedance based sensor configured to detect a microorganism based on changes in electrical impedance. The sensor can include a measurement chamber, e.g., a microfluidics channel, incorporated into the inner or outer surface of the catheter device, with at least one surface functionalized with a binding agent, e.g., antibodies, specific for one or more components of a microorganism. Microorganisms entering the measurement chamber by diffusion and/or surface migration bind to the functionalized chamber surface. The cell membrane of the entrapped microorganism acts as an insulator at low alternating current frequency and produces a measurable change in the impedance within the chamber. Microorganisms may be detected based on volume using electrical impedance as commonly practiced using a Coulter counter. A MEMS resembling a miniaturized Coulter counter can be incorporated into the device described herein and can be constructed using thin platinum electrodes with a sensing zone of, for example, 20-100 microns (see, e.g., Zheng et al. (2006) Proceedings of 2006 International Conference on Microtechnologies in Medicine and Biology, IEEE, Okinawa, Japan, 9-12 May, 2006; Gao et al. (2003) Proceedings of the 25$^{th}$ Annual International Conference of the IEEE EMBS, Cancun, Mexico, Sep. 17-21, 2003), which is incorporated herein by reference.

In an aspect, the at least one sensor can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptors, e.g., ion channels, can be embedded into, the lipid bilayer and configured to open and close in response to binding of a specific microorganism. The open and closed states can be quantitatively measured as changes in impedance across the lipid bilayer. See, e.g., Yang, et al., IEEE SENSORS 2006, EXCO, Daegu, Korea/Oct. 22-25, 2006, which is incorporated herein by reference. Other examples of impedance-based sensors for detecting bacteria and fungi are reviewed in Heo & Hua, *Sensors*, 9:4483-4502, 2009, which is incorporated herein by reference.

In an aspect, the at least one sensor can include a parallel set of electrode configuration like interdigitated array (IDA) microelectrodes. An IDA sensor consists of a pair of microcomb array electrodes functionalized with a binding agent, e.g., microorganism selective antibody. A large number of parallel electrodes can be used to improve detection. An IDA sensor can be placed in a microfluidic channel using photolithographic techniques. Binding of a microorganism, e.g., bacteria, on the surface of the array of electrodes alters both current flow and capacitance between the neighboring electrodes, causing a measurable impedance change in a frequency-dependent manner. See, e.g., Heo & Hau, *Sensors*, 9:4483-4502, 2009, which is incorporated herein by reference.

In an aspect, the at least one sensor can include a microcantilever configured to detect changes in cantilever bending or vibrational frequency in response to binding of one or more microorganisms to the surface of the sensor. In an aspect the sensor can be bound to a microcantilever or a microbead as in an immunoaffinity binding array. In another aspect, a biochip can be formed that uses microcantilever bi-material formed from gold and silicon, as sensing elements. See, e.g. Vashist *J. Nanotech Online* 3:DO: 10.2240/azojono0115, 2007, which is incorporated herein by reference. The gold component of the microcantilever can be functionalized with one or more binding elements configured to bind one or more microorganisms. Aptamers or antibodies specific for one or more microorganisms can be used to functionalize the microcantilevers. See, e.g., U.S. Pat. No. 7,097,662, which is incorporated herein by reference. A number of microcantilever deflection detection methods can be used to measure microorganism binding including, among other things, piezoresistive deflection detection, optical deflection detection, capacitive deflection detection, interferometry deflection detection, optical diffraction grating deflection detection, and charge coupled device detection. In some aspects, the one or more microcantilever can be a nanocantilever with nanoscale components. The one or more microcantilevers and/or nanocantilevers can be arranged into arrays for detection of one or more target cells. Both microcantilevers and nanocantilevers can find utility in microelectromechnical systems (MEMS) and/or nanoelectromechnical systems (NEMS).

In an aspect, catheter device can include a field effect transistor (FET) based biosensor, in which a change in electrical signal is used to detect interaction of one or more microorganisms with one or more components of the sensor. See, e.g., U.S. Pat. No. 7,303,875, which is incorporated herein by reference. An example includes the use of carbon nanotubes functionalized with a microorganism-specific binding agent. See, e.g., Zelada-Guillén, et al., *Angew. Chem. Int. Ed.*, 48:7334-7337, 2009, which is incorporated herein by reference. Single walled carbon nanotubes can act as efficient ion-to-electron transducers in potentiometric analysis. The carbon nanotubes can be functionalized with a binding agent, e.g., an oligonucleotide aptamer, configured to selectively bind one or more microorganisms. The binding agent is modified with an amine group and covalently immobilized onto a layer of previously carboxylated single-walled carbon nanotubes. The aptamers are self-assembled on the carbon nanotubes through stacking interactions between the purine and pyrimidine bases of the oligonucleotide aptamers and the walls of the carbon nanotubes. Upon microorganism binding to the aptamer, the aptamers change conformation, separating the phosphate groups of the aptamer from the side-walls of the carbon nanotubes and inducing a charge change to the carbon nanotube and recorded potential. Carbon nanotubes can be used to form composites with silicone, polyurethane, and poly(vinyl) chloride, materials commonly used in production of medical catheters. See, e.g., Xanthos, "Polymers and Polymer Composites," in *Functional Fillers for Plastics*, ed. M. Xanthos, 2010, pp. 3-18, WILEY-VCH Verlag GMBH & Co. KGaA, Weinheim; U.S. Patent Applications 2009/0012610 and 2010/0104652, which is incorporated herein by reference.

In a further aspect, the catheter device can include at least one sensor that relies on optical imaging to sense one or more microorganisms. The microorganisms may be sensed using any of a number of imaging or optical methods including among other things light scattering, electrical impedance, infrared spectroscopy, acoustic imaging, thermal imaging, photothermal imaging, visible light absorption and refraction, and autofluorescence. See, e.g., U.S. Patent Application 2009/0093728; Doornbos et al. *Cytometry* 14:589-594, 1993; Gao et al. Proceedings of the 25$^{th}$ Annual International Conference of the IEEE EMBS, Cancun, Mexico, Sep. 17-21, 2003; Oberreuter et al. *Int. J. Syst. Evol. Microbiol.* 52:91-100, 2002; Baddour et al. Ultrasonics Symposium IEEE 2:1639-1644, 2002; Zharov et al. *J. Biochem.* 97:916-932, 2006; Zharov et al. *J. Biomed. Opt.* 11:054034-1-4, 2006; Koenig et al. *J. Fluoresc.* 4:17-40, 1994; which are each incorporated herein by reference In another aspect, the device can include at least one sensor configured to detect microorganisms based on autofluorescence. A microorganism can be detected by autofluorescence induced by electromagnetic energy. Naturally occurring autofluorescence in bacteria is derived from biomolecules containing fluorophores, such as porphyrins, amino acids tryptophan, tyrosine, and phenylalanine, and the coenzymes NADP, NADPH, and flavins. See, e.g., Koenig et al. *J. Fluoresc.* 4:17-40, 1994 which is incorporated herein by reference. Bacteria can be detected using fluorescence lifetimes measured at 280-540 nm after excitation at 250-450 nm (Bouchard et al. *J. Biomed. Opt.* 11:014011, 2006, which is incorporated herein by reference). For example, *Streptococcus pneumoniae*, can be detected using fluorescence spectroscopy at excitation wavelengths of 250 and 550 nm and emission wavelengths of 265 and 700 nm (Ammor *J. Fluoresc.* 17:455-459, 2007, which is incorporated herein by reference). Autofluorescence may also be used to detect members of the fungi family. *Candida albicans* and *Aspergillus niger* autofluoresce at wavelengths ranging from 515 nm to 560 nm when irradiated with electromagnetic energy at wavelengths of 465-495 nm. See, e.g., Mateus et al. *Antimicrob. Agents and Chemother.* 48:3358-3336, 2004; Sage et al. *American Biotechnology Laboratory* 24:20-23, 2006, each of which is incorporated herein by reference. Autofluorescence associated with the food vacuole of the malaria parasite *Plasmodium* spp. can used to detect infected red blood cells within the blood stream. See, e.g., Wissing et al. *J. Biol. Chem.* 277:37747-37755, 2002, which is incorporated herein by reference.

In an aspect, the catheter device includes at least one sensor configured to detect a microorganism based on changes in fluorescent signaling. The sensor can include a charged coupled device (CCD) or complementary metal-oxide-semiconductor (CMOS) sensor in combination with a binding agent that exhibits altered optical, e.g., fluorescence, properties in response to binding a microorganism. In an aspect, the sensor can include a one-chip CMOS detector and light emitting diode for exciting and measuring fluorescence associated with the sensor. See, e.g., Tamura, et al., *J. Neurosci. Methods,* 173:114-120, 2008, which is incorporated herein by reference.

In an aspect, the at least one sensor includes a binding molecule, e.g., an antibody or oligonucleotide aptamer, configured to exhibit Förster or fluorescence resonance energy transfer (FRET) in response to binding one or more microorganisms. FRET is a distance-dependent interaction between the electronic excited states of two fluorophore molecules in which excitation is transferred from a donor molecule to an acceptor molecule without emission of a photon. For use in a sensor, one or more binding molecules, e.g., antibodies or oligonucleotide aptamers, associated with the one or more sensors are configured with at least one donor molecule and at least one acceptor molecule. The interaction of a metabolic analyte with the binding molecule of the sensor results in a conformation change in the binding molecule, leading to changes in the distance between the donor and acceptor molecules and changes in measurable fluorescence.

A variety of donor and acceptor fluorophore pairs can be considered for FRET including, among other things, fluorescein and tetramethylrhodamine; IAEDANS and fluorescein; fluorescein and fluorescein; and BODIPY FL and BODIPY FL, and various Alexa Fluor pairings as described herein. The cyanine dyes Cy3, Cy5, Cy5.5 and Cy7, which emit in the red and far red wavelength range (>550 nm) as well as semiconductor quantum dots can also be used for FRET-based detection systems. Quenching dyes can also be used to quench the fluorescence of visible light-excited fluorophores, examples of which include DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the binding molecule including, among other things, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

Possible Microorganism Specific Biomolecules Recognized by Catheter Associated Sensors In an aspect, the catheter device includes at least one sensor configured to detect a microorganism. The at least one sensor can be configured to detect at least one component of at least one microorganism. The at least one component of a microorganism can include at least one of a lipid, peptide, polypeptide, glycolipid, proteoglycan, lipoprotein, glycoprotein, glycopeptide, metalloprotein, enzyme, carbohydrate, cytokine, microorganism cell membrane, microorganism cell receptor, or other microorganism component. For example, the sensor can be configured to detect at least one component of the outer membrane, cell wall, and/or cytoplasmic membrane of bacteria. Components of bacterial cell walls include peptidoglycan, a mesh-like polymer of N-acetyl glucosamine, N-acetyl muramic acid and amino acids, most commonly L-alanine, D-alanine, D-glutamic acid, and diaminopimelic acid. The cell wall of Gram-positive bacteria contains a thick layer of peptidoglycan that encircles the cell and further includes teichoic acid, a phosphodiester polymer of glycerol or ribitol joined by phosphate groups. In contrast, the cell wall of Gram-negative bacteria contains a thin layer of peptidoglycan separating the cytoplasmic membrane and the outer membrane. The cell wall of gram-negative bacteria further includes Braun's lipoprotein, which is covalently linked to the peptidoglycan and extends a hydrophobic anchor into the lipid bilayer of the outer membrane. Components of the outer membrane of Gram-negative bacteria include, but are not limited to, lipids, proteins, and lipopolysaccharides. Lipopolysaccharides are composed of Lipid A, a conserved core polysaccharide, and a highly variable O-polysaccharide. Proteins associated with the outer membrane include the OMP (outer membrane protein) porins, exemplified by OmpC, OmpF and PhoP of *E. coli*. The at least one sensor can be configured to detect components of the inner bacterial cytoplasmic membrane including, but are not limited to, the MPA1-C (also called polysaccharide copolymerase, PCP2a) family of proteins, the MPA2 family of proteins, and the ABC bacteriocin exporter accessory protein (BEA) family of proteins. Other examples of components of bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other components of bacteria have been described in Chung, et al., *J. Bacteriology* 183:1012-1021, 2001, which is incorporated herein by reference.

In an aspect, the catheter device includes at least one sensor configured to sense one or more components on the outer surface of a pathogenic fungus, examples of which include *Candida albicans, Candida glabrata*, and *Asperigillus* species. The cell wall of most fungi is composed of glycoproteins embedded within a polysaccharide matrix or scaffolding. Additionally, some fungal species produce a polysaccharide capsule that surrounds the cell wall (e.g., the glucuronoxylomannan capsule produced by *Cryptococcus neoformans*). In certain instances, carbohydrates are the first fungal components to contact the host tissue. Carbohydrate chains or glycans within the cell wall of fungi are composed of various combinations and derivatives of three monosaccharides: D-glucose, N-acetyl-D-glucosamine, and D-mannose. The cell envelope of *Candida albicans*, for example, contains highly branched polymers of glucose (glucan), linear polymers of N-acetyl-D-glucosamine (chitin), and mannose (mannan) incorporated into various glycoproteins. Sialic acid may also be a component of the fungal cell wall. See, e.g., Masuoka, *Clin. Microbiol. Rev.* 17:281-310, 2004, which is incorporated herein by reference.

In an aspect, the at least one sensor can be configured to sense one or more components secreted by a microorganism. Examples include various membrane-active peptides and exotoxins, in particular those produced by bacteria, for example, pneumolysins secreted by streptococci and alpha-toxin a major cytolysin secreted by *Staphylococcus aureus*. Other examples of toxins secreted by *S. aureus* include toxic shock syndrome toxin-1, enterotoxins, leukicidins, and phenyl-soluble modulins. Secretion of pore-forming exotoxins by bacteria is abundant and endotoxins, such as lipopolysaccharides (LPS). Examples of pore-forming toxins include but are not limited to perfringiolysin, hemolysin, listeriolysin, alpha toxin, pneumolysin, streptolysin O, and leukocidin. Examples of pyrogenic exotoxins include but are not limited to staphylococcal enterotoxins serotypes A-E, G, and H; group A streptococcal pyrogenic exotoxins A-c; staphylococcal exfoliatin toxin; and staphylococcal toxic shock syndrome toxin-1. Other toxins include exotoxin A (*Pseudomonas aeruginosa*). Examples of toxins secreted by other microorganisms include fungal toxins such as, for example, aflatoxin and gliotoxin secreted by *Aspergillus* species.

In an aspect, the catheter device can include at least one sensor configured to differentiate between microorganisms based on detecting distinguishing components specific for a given microorganism. For example, Gram-positive bacteria can be differentiated from Gram-negative bacteria based on detection of lipoteichoic acid, the latter of which is expressed on the Gram-positive bacteria *Listeria monocytogenes, Streptococcus pneumoniae, Staphylococcus aureus*, and *Staphylococcus epidermidis*. Gram-negative bacteria can be detected based on detection of lipopolysaccharides. In general, reagents, e.g., antibodies, that can distinguish between components of Gram-positive and Gram-negative bacteria can be developed using standard methods or are commercially available (from, e.g., Santa Cruz Biotechnology, Inc., Santa Cruz, Calif.; Novus Biologicals, LLC, Littleton, Colo.; GenWay Biotech, Inc., San Diego, Calif.). Fungi can be distinguished from bacteria based on the detection of glucan, chitin, mannan, or combinations thereof. For example, Sendid, et al., describe development of antibodies against glucan, chitin and mannan for detection of *Candida albicans* (in, *Clin. Vaccine Immunol.*, 15:1868-1877, 2008, which is incorporated herein by reference).

Binding Agents Specific for Recognition Targets

The at least one sensor can include at least one binding agent configured to bind a component of a microorganism. The at least one binding agent for selectively binding a component of a microorganism can include, but is not limited to, antibodies, antibody fragments, peptides, oligonucleotides, DNA, RNA, aptamers, protein nucleic acids, proteins, receptors, receptor ligands, lectins, an artificial binding substrate formed by molecular imprinting, or other examples of binding agents configured to bind microorganisms.

The at least one binding agent associated with the sensor(s) include, but is not limited to, antibodies configured to bind one or more components of a microorganism. Antibodies or fragments thereof for use as one or more binding agents can include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof can be generated using standard methods. See, e.g., Harlow & Lane (*Antibodies: A Laboratory Manual*, Cold Spring Harbor Laboratory Press; $1^{st}$ edition 1988), which is incorporated herein by reference.

Alternatively, an antibody or fragment thereof directed against one or more inflammatory mediators can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000), which is incorporated herein by reference. In some aspects, antibodies directed against one or more components of a microorganism may be available from a commercial source (from, e.g., Novus Biological, Littleton, Colo.; Sigma-Aldrich, St. Louis, Mo.; United States Biological, Swampscott, Mass.). Fenelon, et al., describe development of antibodies specific for three *Aspergillus* species commonly associated with human disease; *A. fumigatus, A. flavus*, and *A. niger* (m, *J. Clin. Microbiol.*, 37:1221-1223, 1999, which is incorporated herein by reference). Sendid, et al., describe development of antibodies against glucan, chitin and mannan for detection of *Candida albicans* (in, *Clin. Vaccine Immunol.*, 15:1868-1877, 2008, which is incorporated herein by reference)

The at least one binding agent associated with the sensor(s) includes but is not limited to, aptamers configured to bind one or more components of a microorganism. The aptamer can be an oligonucleotide RNA- or DNA-based aptamer. Aptamers are artificial oligonucleotides (DNA or RNA) which bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference. In general, SELEX may be used to generate aptamers against microorganisms including bacteria, fungi and parasites. For example, Cao, et al., describe using SELEX and whole bacteria to generate a panel of DNA aptamers configured to detect *Staphylococcus aureus* (in *Nucleic Acids Res.*, 37:4621-4628, 2009). For Gram positive bacteria, teichoic acids and peptidoglycan will serve as targets. For Gram negative bacteria, common lipopolysaccharide moieties such as 2-keto-3-deoxyoctanate (KDO antigen) will be targeted for aptamer development. Similarly, for fungi, cell wall chitin will be used to select highly specific FRET-aptamers from a randomized DNA library. Other examples are described in Shangguan, et al., *Proc. Natl. Acad. Sci. USA.* 103:11838-11843; Chen, et al., *Biochem. Biophys. Res. Commun.* 357:743-748, 2007; Ulrich, et al., *J. Biol. Chem.* 277:20756-20762, 2002; and Low, et al., *Biochem. Biophys. Res. Commun.*, 378:701-705, 2009, each of which is incorporated herein by reference.

In an aspect, the at least one binding agent associated with the sensor(s) include but is not limited to peptide-based aptamers configured to bind one or more components of a microorganism. Peptide-based aptamers are artificial proteins in which inserted peptides are expressed as part of the primary sequence of a structurally stable protein. See, e.g., Crawford, et al., *Brief. Funct. Genomic Proteomic* 2:72-79, 2003, which is incorporated herein by reference. Peptide-based aptamers can be generated by screening a target microorganism or parts thereof against yeast two-hybrid libraries, yeast expression libraries, bacterial expression libraries and/or retroviral libraries. Peptide-based aptamers can have binding affinities comparable to antibodies.

In an aspect, the at least one binding agent associated with the sensor(s) includes but is not limited to lectins configured to bind one or more components of a microorganism. While the term "lectin" was originally used to define agglutinins involved in the agglutination process, the term "lectin" is currently used more generally to include sugar-binding proteins. Lectins are able to recognize specific carbohydrate structures such that even oligosaccharides with identical sugar compositions can be distinguished or separated. Some lectins will bind only to structures with mannose or glucose residues, while others may recognize only galactose residues. Some lectins require that the particular sugar is in a terminal non-reducing position in the oligosaccharide, while others can bind to sugars within the oligosaccharide chain. As such, specific lectins can be used to distinguish various microorganisms based on the composition and pattern of cell surface carbohydrates. For example, Serra, et al., describe the use of lectins as binding agents in piezoelectric biosensors capable of detecting and quantifying *Staphylococcus aureus* (m, *Anal. Bioanal. Chem.*, 391:1853-1860, 2008).

Examples of lectins include, but are not limited to, algal lectins, e.g., b-prism lectin; animal lectins, e.g., tachylectin-2, C-type lectins, C-type lectin-like, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia* lectins, *chromobacterium* CV-IIL, *Pseudomonas* PA IIL, Ralsonia RS-ILL, ADP-ribosylating toxin, Ralstonia lectin, Clostridium hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., Aleuria aurantia lectin, integrin-like lectin, *Agaricus* lectin, Sclerotium lectin, Xerocomus lectin, Laetiporus lectin, *Marasmius* oreades agglutinin, agrocybe galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein (see, e.g., E. Bettler, R. Loris, A. Imberty "3D-Lectin database: A web site for images and structural information on lectins" 3rd Electronic Glycoscience Conference, The internet and World Wide Web, 6-17 Oct. 1997; on the worldwide web at cermay.cnrs.fr/lectines, Sahly, et al., *Infect. Immunity*, 78:1322-1332, 2008, the content of which is incorporated herein by reference.

The at least one binding agent associated with the sensor(s) includes but is not limited to, one or more artificial binding substrates formed by the process of molecular imprinting and configured to bind one or more components of a microorganism. In the process of molecular imprinting, a template, e.g., a whole microorganism or parts thereof, is combined with functional monomers which, upon cross-linking, form a polymer matrix that surrounds the template. See Alexander, et al., *J. Mol. Recog.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate can be mixed with a microorganism or parts thereof, in the presence of a photoinitiator and ultraviolet irradiation used to cross-link the monomers. The resulting polymer can be crushed or ground into smaller pieces and washed to remove the microorganism or parts thereof, leaving a particulate matrix material capable of binding the microorganism. For example, Cohen et al., describe using whole cell imprinting in-sol-gel imprinted films to generate a bacterial sensor (m, *Int. J. Mol. Sci.*, 11:1236-1252, 2010). Examples of other functional monomers, cross-linkers and initiators may be used to generate an artificial binding substrate are provided. See, e.g., U.S. Pat. No. 7,319,038; Alexander, et al., *J. Mol. Recognit.* 19:106-180, 2006, each of which is incorporated herein by reference. In a further aspect, hydrogels may be used for molecular imprinting. See, e.g., Byrne et al., "Molecular imprinting within hydrogels", *Advanced Drug Delivery Reviews*, 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, each of which is incorporated herein by reference.

Reservoirs

In an aspect, the catheter includes at least one anti-microbial agent reservoir configured to deliver one or more anti-microbial agents to one or more anti-microbial regions of the body structure of the catheter. The at least one anti-microbial agent reservoir can be positioned in one or more sites in at least one of the outer surface of the body structure, the inner surface of the body structure, embedded in the body structure itself, or combinations thereof. In an aspect, the at least one anti-microbial agent reservoir is in communication with one or more sensors. In an aspect, the reservoir is configured for controllable delivery of one or more anti-microbial agents in response to a signal from a sensor indicative of the presence of a microorganism. In an aspect, the catheter includes a single anti-microbial agent reservoir with multiple outlets for delivery of one or more anti-microbial agents to one or more anti-microbial regions. In an aspect, the catheter includes multiple anti-microbial agent reservoirs with one or more outlets for delivery of one or more anti-microbial agents to one or more anti-microbial regions. In an aspect, the catheter includes one or more anti-microbial agent reservoirs embedded in one or more pores in the catheter body structure. See, e.g., U.S. Pat. No. 7,575,593, which is incorporated herein by reference.

In an aspect, the at least one anti-microbial-agent reservoir includes at least one outlet with a release mechanism operably connected to one or more sensors for controllable delivery of an anti-microbial agent. The release mechanism can include but is not limited to a valve, a switch, a plug, a cap, or a membrane. In an aspect, the anti-microbial-agent reservoir includes a valve for controllable delivery of an anti-microbial agent. Various examples of micro valves or microelectromechanical systems (MEMS) valves for controlling fluid flow in micro devices have been described. See, e.g., Luckevich M. *Valve World*, May 2007, pp. 79-83; Givrad T K., et al., *Proceedings of BIOMed*2008, 3$^{rd}$ Frontiers in Biomedical Devices Conference. Jun. 18-20, 2008, Irvine, Calif., USA; U.S. Pat. Nos. 6,612,535; 7,124,773, each of which is incorporated herein by reference.

In an aspect, the at least one anti-microbial-agent reservoir can include at least one outlet covered with a removable membrane. The membrane can be responsive to a directly applied stimulus (e.g., an applied voltage or potential) or to a change in the local environment of the device (e.g., local pH change), or any of a number of other stimuli including among other things heat, light (e.g., laser), and magnetic field. See, e.g., U.S. Pat. No. 6,808,522; Grayson, R. et al., *Proceedings of IEEE* 92:6-21, 2004, which are each incorporated herein by reference. As an example, the at least one anti-microbial-agent reservoir can be an array of microreservoirs on a microchip in which each aliquot of one or more anti-microbial agents is contained in its own reservoir and capped by an environmentally sensitive material. In an aspect, the microreservoirs can be capped with a gold membrane which is weakened and ruptured by electrochemical dissolution in response to application of an anode voltage to the membrane in the presence of chloride ions, resulting in release of contents of the microreservoir as described in U.S. Pat. No. 5,797,898 and in Prescott, et al., *Nat. Biotech.*, 24:437-438, 2006, each of which is incorporated herein by reference.

Alternatively, the microreservoirs can be capped by a temperature sensitive material which can be ruptured in response to selective application of heat to one or more of the reservoirs as described in U.S. Pat. No. 6,669,683, which is incorporated herein by reference. For example, Elman, et al., describe a multi-layered temperature-responsive drug delivery system that includes a reservoir layer containing a drug solution; a membrane layer that hermetically seals the drug reservoir, and from where the drug is ejected; and an actuation layer, where bubbles are formed in response to localized heat application (in, *Biomedical Microdevices*, 11:625-631, 2009, which is incorporated herein by reference). The actuation layer is defined by micro-resistors, which once actuated, rapidly and locally heat a contained fluid to generate bubbles. The increase in pressure caused by the bubbles ruptures the membrane and jets the contained drug solution out of the device, allowing for rapid drug delivery.

In an embodiment, the system includes one or more computer-readable media (e.g., drives, interface sockets, Universal Serial Bus (USB) ports, memory card slots, input/output components (e.g., graphical user interface, display, keyboard, keypad, trackball, joystick, touch-screen, mouse, switch, dial, etc.)).

In an embodiment, the computer-readable media is configured to accept signal-bearing media. In an embodiment, a program for causing the system to execute any of the disclosed methods can be stored on, for example, a computer-readable recording medium, a signal-bearing medium, or the like. Examples of signal-bearing media include, among others, a recordable type medium such as magnetic tape, floppy disk, hard disk drive, Compact Disc (CD), Digital Video Disk (DVD), Blu-Ray Disc, digital tape, computer memory, etc., and transmission type medium (digital and/or analog). Other non-limiting examples of signal bearing media include, for example, DVD-ROM, DVD-RAM, DVD+RW, DVD-RW, DVD-R, DVD+R, CD-ROM, Super Audio CD, CD-R, CD+ R, CD+ RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, etc.

In an aspect, the at least one anti-microbial agent reservoir can be configured to include a release mechanism that is a natural and/or synthetic stimulus-responsive hydrogel or polymer which changes confirmation rapidly and reversibly in response to environmental stimuli such as, for example, temperature, pH, ionic strength, electrical potential, light, magnetic field or ultrasound. See, e.g., U.S. Pat. No. 5,226,902; and Stubbe, et al., *Pharmaceutical Res.*, 21:1732-1740, 2004, each of which is incorporated herein by reference. Examples of polymers are described in U.S. Pat. Nos. 5,830,207; 6,720,402; and 7,033,571, each of which is incorporated herein by reference. For example, a hydrogel or other polymer or other smart material may be used as an environmentally sensitive actuator to control flow of an agent out of an implantable device as described in U.S. Pat. Nos. 6,416,495; 6,571,125; and 6,755,621, each of which is incorporated herein by reference. As such, the at least one anti-microbial agent reservoir can incorporate a hydrogel or other polymer that modulates delivery of one or more anti-microbial agents in response to a trigger from a sensor.

The anti-microbial agent reservoirs can include one or more target-responsive microparticles attached to the catheter device in at least one of a plurality of regions and configured to release one or more anti-microbial agent upon interaction with a microorganism. The one or more target-responsive microparticles can include one or more binding elements incorporated into the microparticles and configured to bind at least one microorganism component. Examples of binding elements include but are not limited to antibodies, aptamers, oligonucleotides, protein nucleic acids, receptors, ligands, lectins, synthetic binding moieties, molecular imprinting, or combinations thereof. Binding of a microorganism to the microparticles changes the properties of the microparticle and allows for release of an encapsulated anti-microbial agent. For example, Yang et al. describe target-responsive microparticles which include a target-specific aptamer, two additional overlapping oligonucleotides linked to polymerized acrylamide, and an encapsulated material. Binding of a target to the target-specific aptamer disrupts the interaction of the overlapping oligonucleotides causing aggregates of polymerized acrylamide to separate from one another and allowing for release of the encapsulated material. See, e.g., Yang et al., *J. Am. Chem. Soc.*, 130:6320-6321, 2008; and Gu, et al., *Proc. Natl. Acad. Sci., USA*, 105:2586-2591, 2008, each of which is incorporated herein by reference. In another example, Miyata, et al., describe target-responsive hydrogels prepared by molecular imprinting in which ligands reactive with a target, such as, for example, lectins and/or antibodies, are conjugated with acrylate and polymerized with acrylamide to form a target-responsive hydrogel (*Proc. Natl. Acad. Sci., USA*, 103:1190-1193, 2006, which is incorporated herein by reference).

The one or more microparticles can include temperature-responsive microparticles configured to release an encapsulated anti-microbial agent in response to changes in temperature. In this instance, the change in temperature can include elevated endogenous temperature of the subject either globally due to a fever or locally due to inflammation, ischemia, or neoplastic tissue. The change in temperature can also include application of an energy source to the catheter to induce a localized increase in temperature. Temperature-responsive microparticles can include thermally sensitive lipid-based and/or polymer-based micelles. The micelles can be configured to encapsulate one or more anti-microbial agents and remain stable until a critical solution temperature (LCST) has been reached. For example, micelles fabricated from poly(N-isopropylacrylamide-co-N,N-dimethylacrylamide)-b-poly(D,L-lactide-co-glycolide) are stable at 37° C. but begin to release their contents at a LCST of 39° C. See, e.g., Liu, et al., *Mol. BioSyst.*, 1:158-165, 2005, which is incorporated herein by reference. Temperature-responsive micelles composed of N-(2-hydroxypropyl) methyl acrylamide (lactate) and optionally polyethylene glycol have also been described. See, e.g., U.S. Pat. No. 7,425,581, which is incorporated herein by reference. Examples of other polymers for use in generating temperature-responsive microparticles include but are not limited to poly(N-(3-ethoxypropyl)acrylamide), dimethylaminoethyl methacrylate, ethylene glycol dimethacrylate, and N-isopropyl acrylamide. See, e.g., U.S. Pat. No. 6,451,429, which is incorporated herein by reference.

Anti-Microbial Agents

Further non-limiting examples of anti-microbial agent include compounds, molecules, or treatments that elicit a biological response from any biological subject. Further non-limiting examples of anti-microbial agents include active agents (e.g., antimicrobial active agents), pharmaceuticals (e.g., a drug, a therapeutic compound, pharmaceutical salts, and the like) non-pharmaceuticals (e.g., a cosmetic substance, and the like), neutraceuticals, antioxidants, phytochemicals, homeopathic agents, and the like. Further non-limiting examples of anti-microbial agents include peroxidases (e.g., haloperoxidases such as chloroperoxidase, and the like), oxidoreductase (e.g., myeloperoxidase, eosinophil peroxidase, lactoperoxidase, and the like) oxidases, and the like.

Further non-limiting examples of anti-microbial agents include one or more pore-forming toxins. Non-limiting examples of pore-forming toxins include beta-pore-forming toxins, e.g., hemolysin, Panton-Valentine leukocidin S, aerolysin, Clostridial epsilon-toxin; binary toxins, e.g., anthrax, *C. perfringens* Iota toxin, *C. difficile* cytolethal toxins; cholesterol-dependent cytolysins; pneumolysin; small pore-forming toxins; and gramicidin A.

Further non-limiting examples of anti-microbial agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which have are available in a public database (see, e.g., Wang & Wang, *Nucleic Acids Res.* 32:D590-D592, 2004); on the worldwide web at asp.unmc.edu/AP/main-.php, which is incorporated herein by reference). More specific examples of antimicrobial peptides include, but are not limited to, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), androspin, moricin, ceratotoxin, and melittin from insects, cecropin P1 from *Ascaris* nematodes, magainin (2), dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of anti-microbial agents include antibacterial drugs. Non-limiting examples of antibacterial drugs include beta-lactam compounds, such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidime, ceftizoxime, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, enoxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectinomycin, trimethoprim, pyrimethamine, and trimethoprim-sulfamethoxazole.

Further non-limiting examples of anti-microbial agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

In an embodiment, the anti-microbial agents include, but are not limited to, oxidizing chemicals suitable to disrupt or destroy cell membranes. For example, some oxidizing chemicals may withdraw electrons from a cell membrane causing it to, for example, become destabilized. Destroying the integrity of cell membranes of, for example, a pathogen may lead to cell death.

Further non-limiting examples of anti-microbial agents include antiseptics and disinfectants. Non-limiting examples of antiseptics and disinfectants include acetic acid, acrisorcin, aluminum acetate, alcohols (e.g., ethanol, isopropanol, benzyl alcohol, phenylethyl alcohol), aldehydes (e.g., formaldehyde, glutaraldehyde), benzoic acid, boric acid, butylparaben, chlorhexidine gluconate, chlorine sodium hypochlorite, hexachlorophene, iodine, povidone-iodine, phenols, oxidizing agents (e.g., hydrogen peroxide), parabens (e.g., butylparaben, ethylparaben, methylparaben, propylparaben), phenylmercuric acetate, phenylmercuric nitrate, potassium permanganate, propylene oxide, pyrithione zinc, and quaternary ammonium (e.g., benzalkonium chloride, cetylpyridinum chloride, benzethonium chloride), nitrofurazone, selenium sulfide, silver nitrate, and silver sulfadiazine.

Non-limiting examples of carriers include any matrix that allows for transport of, for example, a disinfecting agent across any tissue, cell membranes, and the like of a biological subject, or that is suitable for use in contacting a biological subject, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, and the like. Further non-limiting examples of carriers include cyclic oligosaccharides, ethasomes, hydrogels, liposomes, micelle, microspheres, nisomes, non-ionic surfactant vesicles, organogels, phospholipid surfactant vesicles, phospholipid surfactant vesicles, transfersomes, virosomes. Further non-limiting examples of energy-sensitive carriers and the like include electrical energy-sensitive, light sensitive, pH-sensitive, ion-sensitive, sonic energy sensitive, ultrasonic energy sensitive carriers. Further non-limiting examples of energy-sensitive carriers and the like include cavitationally actuated drug delivery carriers, acoustically actuated drug delivery carries, and the like.

In an embodiment, the anti-microbial agent includes at least one active agent that selectively targets bacteria. For example, in an embodiment, the anti-microbial agent includes at least one bacteriophage that, for example, selectively targets bacteria. Bacteriophages generally comprise an outer protein hull enclosing genetic material. The genetic material can be ssRNA, dsRNA, ssDNA, or dsDNA. Bacteriophages are generally smaller than the bacteria they destroy, and range from about 20 nm to about 200 nm. Non-limiting examples of bacteriophages include T2, T4, T6, phiX-174, MS2, and the like. In an embodiment, the bacteriophage includes at least one engineered enzymatically active bacteriophage. For example, particular enzymatically active bacteriophage sets assist in dispersing biofilms. See U.S. Patent App. Pub. No. 20090155215, which is incorporated herein by reference.

Among antimicrobial agent compositions, examples include, but are not limited to, diluted solutions of NaCl, hypochlorous acid solutions (HAS), oxidative reduction potential aqueous compositions, STERILOX TX (PuriCore Inc.), STERILOX Solutions (PuriCore Inc.), MICROCYN (Nofil Corp.), superoxidized aqueous compositions, superoxidized water, superoxide dismutase compositions, physiologically balanced ionized acidic solutions, and the like. Further non-limiting examples of antimicrobial agent compositions may be found in, for example, the following documents (the contents of each of which is incorporated herein by reference): U.S. Pat. Nos. 7,276,255 (issued Oct. 2, 2007), 7,183,048 (issued Feb. 27, 2007), 6,506,416 (issued Jan. 14, 2003), 6,426,066 (issued Jul. 30, 2002), and 5,622,848 (Apr. 22, 1997); and U.S. Patent Nos. 2007/0196357 (published Aug. 23, 2007), 2007/0173755 (published Jul. 26, 2007), and 2005/0142157 (published Jun. 30, 2005).

In an aspect, the type of anti-microbial agent delivered and the spatial and temporal sequence of delivery is tailored to the catheter for the presence and/or development of drug resistant microorganisms. For example, the antibiotic nafcillin is a preferred first line of defense against methicillin-sensitive *Staphylococcus aureus* [MSSA]. Other antibiotics used to treat MSSA include but are not limited to cefazolin, clindamycin, and/or dicloxacillin. However, methicillin-resistant *Staphylococcus aureus* [MRSA] no longer responds to nafcillin and may require treatment with other anti-microbial agents, including among other things vancomycin, telavancin (a synthetic derivative of vancomycin), trimethoprim-sulfamethoxazole (for some strains of MRSA), minocycline, linezolid, quinupristin/dalfopristin, daptomycin, and/or tigecycline. See, e.g., Herchline, "Staphylococcal Infections," eMedicine, updated Jan. 8, 2010, accessed May 24, 2010 (emedicine.medscape.com), the content of which is incorporated herein by reference. In a recent study of 182 bacterial isolates from ICU patients infected with coagulase-negative *staphylococcus,* 95% were resistant to penicillin, 86% were resistant to oxacillin, 48% were resistant to erythromycin, 42% were resistant to clindamycin, 54% were resistant to gentamicin, 66% were resistant to ciprofloxacin, and 0% were resistant to vancomycin. In this same study, multiresistance was commonly seen: 21% of the isolates were resistant to six tested antibiotics, 34% to at least five tested antibiotics and 59% were resistant to at least four of the seven tested antibiotics. See, e.g., Agvald-Öhman, et al., Crit. Care, 8:R42—R47, 2004, which is incorporated herein by reference.

In an embodiment, the anti-microbial agent delivered from one or more anti-microbial regions or reservoirs includes at least one D-amino acid. For example, it has been reported that a factor including at least one of D-leucine, D-methionine, D-tyrosine, or D-tryptophan is capable of breaking down biofilms, and is capable of preventing biofilm formation. In particular, biofilm formation by *Staphlycoccus aureus* and *Pseudomonas aeruginosa* were inhibited. See, for example, Kolodkin-Gal, et al., SCIENCE Vol. 328, pp. 627-629 (2010), which is incorporated herein by reference.

Among the one or more coatings, functionalized surfaces, surface treatments, immuno-stimulating coatings, and the like, examples include, among other things, polymeric compositions that resist bacterial adhesion, antimicrobial coating, coatings that controllably release antimicrobial agents, quaternary ammonium silane coatings, chitosan coatings, and the like. Further non-limiting examples of coatings, functionalized surfaces, surface treatments, immuno-stimulating coatings, and the like may be found in, for example, the following documents (the content of each of which is incorporated herein by reference): U.S. Pat. Nos. 7,348,021 (issued Mar. 25, 2008), 7,217,425 (issued May 15, 2007), 7,151,139 (issued Dec. 19, 2006), and 7,143,709 (issued Dec. 5, 2006). In an embodiment, at least a portion of an inner or an outer surface of the implantable device includes one or more self-cleaning coating materials. Examples of self-cleaning coating (e.g., Lotus Effect) materials include, but are not limited to titanium dioxide, superhydrophobic materials, carbon nanotubes with nanoscopic paraffin coating, or the like. Further non-limiting examples of self-cleaning (e.g., non fouling) coating materials include antimicrobial, and nonfouling zwitterionic polymers, zwitterionic surface forming materials, zwitterionic polymers, poly(carboxybetaine methacrylate) (pCBMA), poly(carboxybetaine acrylic amide) (pCBAA), poly(oligo(ethylene glycol) methyl ether methacrylate) (pOEGMA), poly(N,N-dimethyl-N-(ethoxycarbonylmethyl)-N-[2'-(methacryloyloxy)ethyl]-ammonium bromide), cationic pC8NMA, switchable pCBMA-1 C2, pCBMA-2, and the like. See, e.g., WO 2008/083390 (published Jul. 10, 2008) (the contents of each of which is incorporated herein by reference).

In an embodiment, at least one of the inner surface or the outer surface of the body structure includes at least one high-aspect ratio polymer nanofibrillar structure (e.g., in the form of stooped or crispated nanohairs). See, for example, Kim, et al. Langmuir, vol. 25, no. 16, pp. 8879-8882 (2009), which is incorporated herein by reference. In an embodiment, the nanofibrillar surface can be controlled by oblique electron beam irradiation, such that the geometry of polymer nanohairs is tunable according to the tilting angle of the electron beam, the acceleration voltage, and the exposure time. Id.

In an embodiment, at least one of the inner surface or the outer surface of the body structure is switchable by exposure to ultraviolet light. For example, a fluorinated diarylethene molecule with two thiophene rings decorated with methoxy and methylated silane pendant groups undergo reversible photoisomerization between open and closed ring forms when irradiated with UV light. See, Greene, Materials Today, vol. 9, no. 11, p. 15 (2006), which is incorporated herein by reference.

In an embodiment, at least one of the inner surface or outer surface of the body structure includes graphene film configured to be superhydrophobic (contact angle of about 160 degrees) to superhydrophilic (contact angle of about 0 degrees), by manipulating the roughness of the surface.

In an embodiment, at least one anti-microbial region includes at least one self-cleaning coating, or other coating. In an embodiment, at least one anti-microbial region includes at least one surface structure composition or deposition. In an embodiment, the surface structure includes at least one substrate manufactured to include nanoscale topographic anti-microbial features.

Further non-limiting examples of coatings include superhydrophobic conducting polypyrrole films, coating, or components that are electrically switchable between an oxidized state and a neutral state, resulting in reversibly switchable superhydrophobic and superhydrophilic properties (see, e.g., Lahann et al., *A Reversibly Switching Surface*, 299 (5605): 371-374 (2003) 21:47-51 (2003), the contents of each of which is incorporated herein by reference); coatings including electrically isolatable fluid-support structures (see, e.g., U.S. Pat. No. 7,535,692 (issued May 19, 2009), the contents of each of which is incorporated herein by reference); coatings including a plurality of volume-tunable nanostructures (see, e.g., U.S. Patent Publication No. 2008/0095977 (published Apr. 24, 2008), the contents of each of which is incorporated herein by reference); coatings including re-entrant surface structures (see, e.g., Tuteja et al., *Robust Omniphobic Surfaces*, Epub 2008 Nov. 10, 105(47): 18200-5 (2008), the contents of each of which is incorporated herein by reference); coatings including superhydrophobic conducting polypyrrole materials, coatings including zwitterionic polymers (see, e.g., Cheng et al., *A Switchable Biocompatible Polymer Surface with Self-Sterilizing and Nonfouling Capabilities*, Angew. Chem. Int. Ed. 8831-8834 (2008), the contents of each of which is herein by reference); or the like.

Among active agents, examples include, but are not limited to, adjuvants, allergens, analgesics, anesthetics, antibacterial agents, antibiotics, antifungals, anti-inflammatory agents (e.g., nonsteroidal anti-inflammatory drugs), antimicrobials, antioxidants, antipyretics, anti-tumor agents, antivirals, bio-control agents, biologics or bio-therapeutics, chemotherapy agents, disinfecting agents, energy-actuatable active agents, immunogens, immunological adjuvants, immunological agents, immuno-modulators, immuno-response agents, immuno-stimulators (e.g., specific immuno-stimulators, non-specific immuno-stimulators, or the like), immuno-suppressants, non-pharmaceuticals (e.g., cosmetic substances, or the like), pharmaceuticals, protease inhibitors or enzyme inhibitors, receptor agonists, receptor antagonists, active agents, tolerogens, toll-like receptor agonists, toll-like receptor antagonists, vaccines, or combinations thereof.

Further non-limiting examples of active agents include nonsteroidal anti-inflammatory drugs such as acemetacin, aclofenac, aloxiprin, amtolmetin, aproxen, aspirin, azapropazone, benorilate, benoxaprofen, benzydamine hydrochloride, benzydamine hydrochloride, bromfenal, bufexamac, butibufen, carprofen, celecoxib, choline salicylate, clonixin, desoxysulindac, diflunisal, dipyone, droxicam, etodolac, etofenamate, etoricoxib, felbinac, fenbufen, fenoprofen, fentiazac, fepradinol, floctafenine, flufenamic acid, indomethacin, indoprofen, isoxicam, ketoralac, licofelone, lomoxicam, loxoprofen, magnesium salicylate, meclofenamic acid, meclofenamic acid, mefenamic acid, meloxicam, morniflumate, niflumic acid, nimesulide, oxaprozen, phenylbutazone, piketoprofen, piroxicam, pirprofen, priazolac, propyphenazone, proquazone, rofecoxib, salalate, salicylamide, salicylic acid, sodium salicylate, sodium thiosalicylate, sulindac, suprofen, tenidap, tenoxicam, tiaprofenic acid, tolmetin, tramadol, trolamine salicylate, zomepirac, or the like. Further non-limiting examples of active agents include energy (e.g., chemical energy, electrical resistance, laser energy, terahertz energy, microwave energy, optical energy, radio frequency energy, sonic energy, thermal energy, thermal resistance heating energy or ultrasonic energy, or the like)-actuatable active agents, and the like.

In an embodiment, the active agent includes at least one active agent that selectively targets bacteria. For example, in an embodiment, the active agent includes at least one bacteriophage that can, for example, selectively target bacteria. Bacteriophages generally comprise an outer protein hull enclosing genetic material. The genetic material can be ssRNA, dsRNA, ssDNA, or dsDNA. Bacteriophages are generally smaller than the bacteria they destroy generally ranging from about 20 nm to about 200 nm. Non-limiting examples of bacteriophages include T2, T4, T6, phiX-174, MS2, or the like). In an embodiment, the active agent includes at least one energy-actuatable agent that selectively targets bacteria. For example, in an embodiment, the active agent includes at least one triplet excited-state photosensitizer that can, for example, selectively target bacteria.

Further non-limiting examples of active agents include triplet excited-state photosensitizers, reactive oxygen species, reactive nitrogen species, any other inorganic or organic ion or molecules that include oxygen ions, free radicals, peroxides, or the like. Further non-limiting examples of active agents include compounds, molecules, or treatments that elicit a biological response from any biological subject. Further non-limiting examples of disinfecting agents include active agents (e.g., antimicrobial active agents), pharmaceuticals (e.g., a drug, a therapeutic compound, pharmaceutical salts, or the like) non-pharmaceuticals (e.g., a cosmetic substance, or the like), neutraceuticals, antioxidants, phytochemicals, homeopathic agents, and the like. Further non-limiting examples of disinfecting agents include peroxidases (e.g., haloperoxidases such as chloroperoxidase, or the like), oxidoreductase (e.g., myeloperoxidase, eosinophil peroxidase, lactoperoxidase, or the like) oxidases, and the like.

Further non-limiting examples of active agents include one or more pore-forming toxins. Non limiting examples of pore-forming toxins include beta-pore-forming toxins, e.g., hemolysin, Panton-Valentine leukocidin S, aerolysin, Clostridial epsilon-toxin; binary toxins, e.g., anthrax, *C. perfringens* Iota toxin, *C. difficile* cytolethal toxins; cholesterol-dependent cytolysins; pneumolysin; small pore-forming toxins; and gramicidin A.

Further non-limiting examples of active agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which are available in a public database (see, e.g., Wang & Wang, *Nucleic Acids Res.* 32:D590-D592, 2004); http://aps.unmc.edu/AP/main.php, which is incorporated herein by reference). More specific examples of antimicrobial peptides include, but are not limited to, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), andropin, moricin, ceratotoxin, and melittin from insects, cecropin P1 from *Ascaris* nematodes, magainin 2, dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactofericin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of active agents include antibacterial drugs. Non-limiting examples of antibacterial drugs include beta-lactam compounds such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxime, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole.

Further non-limiting examples of active agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

Further non-limiting examples of active agents include anti-parasite agents. Non-limiting examples of anti-parasite agents include antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and timidazole. Further non-limiting examples of active agents include ionic silver, (SilvaSorb®, Medline Industries, Inc), anti-microbial silver compositions (Arglaes®, Medline Industries, Inc), or the like. Further non-limiting examples of active agents include superoxide-forming compositions. Further non-limiting examples of active agents include oxazolidinones, gram-positive antibacterial agents, or the like. See, e.g., U.S. Pat. No. 7,322,965 (issued Jan. 29, 2008), which is incorporated herein by reference.

In an embodiment, the active agent includes one or more antimicrobial agents. In an embodiment, the antimicrobial agent is an antimicrobial peptide. Amino acid sequence information for a subset of these can be found as part of a public database (see, e.g., Wang & Wang, *Nucleic Acids Res.* 32:D590-D592, 2004); http://aps.unmc.edu/AP/main.php, which is incorporated herein by reference). Alternatively, a phage library of random peptides can be used to screen for peptides with antimicrobial properties against live bacteria, fungi and/or parasites. The DNA sequence corresponding to an antimicrobial peptide can be generated ex vivo using standard recombinant DNA and protein purification techniques.

In an embodiment, one or more of the active agent include chemicals suitable to disrupt or destroy cell membranes. For example, some oxidizing chemicals can withdraw electrons from a cell membrane causing it to, for example, become destabilized. Destroying the integrity of cell membranes of, for example, a pathogen can lead to cell death.

Non-limiting examples of energy-actuatable active agents include radiation absorbers, light energy absorbers, X-ray absorbers, photoactive agents, and the like. Non-limiting examples of photoactive agents include, but are not limited to photoactive antimicrobial agents (e.g., eudistomin, photoactive porphyrins, photoactive $TiO_2$, antibiotics, silver ions, antibodies, nitric oxide, or the like), photoactive antibacterial agents, photoactive antifungal agents, and the like. Further non-limiting examples of energy-actuatable agent includes energy-actuatable disinfecting agents, photoactive agents, or a metabolic precursor thereof. In an embodiment, the at least one energy-actuatable agent includes at least one X-ray absorber. In an embodiment, the at least one energy-actuatable agent includes at least one radiation absorber.

The at least one active agent reservoir can include, for example, among other things an acceptable carrier. In an embodiment, at least one active agent is carried by, encapsulated in, or forms part of, an energy-sensitive (e.g., energy-actuatable), carrier, vehicle, vesicle, pharmaceutical vehicle, pharmaceutical carrier, pharmaceutically acceptable vehicle, pharmaceutically acceptable carrier, or the like.

Non-limiting examples of carriers include any matrix that allows for transport of, for example, a disinfecting agent across any tissue, cell membranes, and the like of a biological subject, or that is suitable for use in contacting a biological subject, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, and the like. Further non-limiting examples of carriers include cyclic oligosaccharides, ethasomes, hydrogels, liposomes, micelle, microspheres, nisomes, non-ionic surfactant vesicles, organogels, phospholipid surfactant vesicles, phospholipid surfactant vesicles, transfersomes, virosomes. Further non-limiting examples of energy-sensitive carriers and the like include electrical energy-sensitive, light sensitive, pH-sensitive, ion-sensitive, sonic energy sensitive, ultrasonic energy sensitive carriers.

In an embodiment, one or more active agents are carried by energy-sensitive vesicles (e.g., energy-sensitive cyclic oligosaccharides, ethasomes, hydrogels, liposomes, micelles, microspheres, nisomes, non-ionic surfactant vesicles, organogels, phospholipid surfactant vesicles, transfersomes, virosomes, and the like). In an embodiment, at least one of the energy emitters is configured to provide energy of a character and for a time sufficient to liberate at least a portion of an active agent carried by the energy-sensitive vesicles.

Among tracer agents, examples include one or more in vivo clearance agents, magnetic resonance imaging agents, contrast agents, dye-peptide compositions, fluorescent dyes, or tissue specific imaging agents. In an embodiment, the one or more tracer agents include at least one fluorescent dye. In an embodiment, the one or more tracer agents include indocyanine green.

Formulations for Anti-Microbial Agents in Reservoirs

An anti-microbial agent delivered from one or more anti-microbial agent reservoirs can be administered alone or in combination with one or more pharmaceutically acceptable carriers, diluents, excipients, and/or vehicles such as, for example, buffers, surfactants, preservatives, solubilizing agents, isotonicity agents, and stablilizing agents as appropriate. In an embodiment, the anti-microbial agent can be carried by, encapsulated in, or forms part of, an energy-sensitive (e.g., energy-actuatable), carrier, vehicle, vesicle, pharmaceutically vehicle, pharmaceutically carrier, pharmaceutically acceptable vehicle, pharmaceutically acceptable carrier, or the like. A "pharmaceutically acceptable" carrier, for example, may be approved by a regulatory agency of the state and/or Federal government such as, for example, the United States Food and Drug Administration (US FDA) or listed in the U.S. Pharmacopeia or other generally recognized pharmacopeia for use in animals, and more particularly in humans. Conventional formulation techniques generally known to practitioners are described in Remington: The Science and Practice of Pharmacy, 20th Edition, Lippincott Williams & White, Baltimore, Md. (2000), which is incorporated herein by reference in its entirety.

Acceptable pharmaceutical carriers include, but are not limited to, the following: sugars, such as lactose, glucose and sucrose; starches, such as corn starch and potato starch; cellulose, and its derivatives, such as sodium carboxymethyl cellulose, ethyl cellulose, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions.

In an aspect, the anti-microbial agent is incorporated into the anti-microbial agent reservoir in a liquid form and diffuses or expels out of the reservoir once the release mechanism has been triggered. The anti-microbial agent can be formulated in a pharmaceutically acceptable liquid carrier. In an aspect, the liquid carrier or vehicle is a solvent or liquid dispersion medium comprising, for example, water, saline solution, ethanol, a polyol, vegetable oils, nontoxic glyceryl esters, and suitable mixtures thereof. The solubility of an anti-microbial agent can be enhanced using solubility enhancers such as, for example, water; diols, such as propylene glycol and glycerol; mono-alcohols, such as ethanol, propanol, and higher alcohols; DMSO (dimethylsulfoxide); dimethylformamide, N,N-dimethylacetamide; 2-pyrrolidone, N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones). In some instances, it may be preferable to include isotonic agents such as, for example, sugars, buffers, sodium chloride or combinations thereof.

In an aspect, the anti-microbial agent is incorporated into the reservoir in a non-soluble form, either as one or more dispersible particles or as an erodible form remaining in the opened reservoir. For example, the anti-microbial agent can be incorporated into the anti-microbial agent reservoir in solid form and formulated to slowly dissolve in a time dependent manner once in contact with the fluid environment of a patient's tissue. The anti-microbial agent can be formulated in a slow release, controlled release, or extended release biodegradable composition that dissolves or breaks down in a time dependent manner. Examples of slow release, controlled release, or extended release compositions include but are not limited to hydrogels, polymers, gelled and/or cross-linked water swellable polyolefins, polycarbonates, polyesters, polyamides, polyethers, polyepoxides and polyurethanes such as, for example, poly(acrylamide), poly (2-hydroxyethyl acrylate), poly(2-hydroxypropyl acrylate), poly(N-vinyl-2-pyrrolidone), poly(n-methylol acrylamide), poly(diacetone acrylamide), poly(2-hydroxyethyl methacrylate), poly(allyl alcohol). Other suitable polymers include but are not limited to cellulose ethers, methyl cellulose ethers, cellulose and hydroxylated cellulose, methyl cellulose and hydroxylated methyl cellulose, gums such as guar, locust, karaya, xanthan gelatin, and derivatives thereof.

As indicated in the Figures, in an embodiment, the device includes at least one reservoir. In an embodiment, the reservoir includes, but is not limited to, at least one of a metal, ceramic, glass, non-crystalline material, semiconductor, composite, or polymer. In an embodiment, the at least one reservoir includes at least one active agent. In an embodiment, the at least one active agent is in the form of a matrix including biodegradable material, or biocompatible material. In certain instances, the release rate of the at least one active agent can be regulated or controlled. In an embodiment, the release rate of the at least one active agent is continuous, for example, by diffusion out or through a material. In an embodiment, the at least one reservoir includes at least one biodegradable material. In an embodiment, degradation of the at least one reservoir results in release of the contents of the at least one reservoir, for example, by having at least a portion of the at least one reservoir selectively degrade. In an embodiment, the device includes multiple reservoirs. In an embodiment, one or more of the multiple reservoirs are selectively degraded in order to regulate release of the contests thereof.

One example of an active timed release device includes a reservoir having a cap consisting of a thin film of conductive material deposited over the reservoir and capable of dissolving or disintegrating upon electrical conductivity. See, for example, U.S. Patent App. Pub. No.: 20050149000, which is incorporated herein by reference.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

FIGS. 1A, 1B, 2A, and 2B show various embodiments of a system 100 (e.g., a catheter system, an implantable catheter system, an implantable system, an indwelling system, a partially implantable system, a fluid management system, or the like including an insertable device, partially implantable device, or implantable device) in which one or more methodologies or technologies can be implemented, such as, managing a transport of fluids, providing surgical access, delivering therapeutics, as well as actively detecting, treating, or preventing an infection (e.g., an implant-associated infection, a hematogenous associated infection, an infection present in tissue or biological fluid, a biofilm formation, a microbial colonization, or the like), a biological sample abnormality (e.g., a cerebral spinal fluid abnormality, a hematological abnormality, a tissue abnormality, or the like), or the like. In an embodiment, the system 100 has at least one component at least partially inserted into a biological subject 222.

In an embodiment, the system 100 is configured to, among other things, reduce an in vivo concentration of an infectious agent (e.g., microorganism) present in a biological fluid (e.g., bodily fluid, blood, amniotic fluid, ascites, bile, cerebrospinal fluid, interstitial fluid, pleural fluid, transcellular fluid, or the like) managed by the system 100, or a biological sample 808 proximate one or more components of the system 100. In an embodiment, the system 100 is configured to provide antimicrobial therapy.

The system 100 can include, among other things, at least one insertable device 102. In an embodiment, the insertable device 102 includes, among other things, a body structure 104 having an outer surface 106 and an inner surface 108 defining one or more fluid-flow passageways 110. In an embodiment, the system 100 is configured to reduce the concentration of an infectious agent in the immediate vicinity of an insertable device 102. For example, in an embodiment, the system 100 is configured to controllably deliver one or more anti-microbial agents to at least one of an inner surface 108 or an outer surface 106 of one or more fluid-flow passageways 110 of an insertable device 102.

The insertable device 102 can include, among other things, one or more catheters 112. In an embodiment, the insertable device 102 is positioned to facilitate the administration of therapeutics (e.g., anti-microbial agents or other therapeutic agents), nutraceuticals, intravenous fluids, blood products, parenteral nutrition, or the like. In an embodiment, the insertable device 102 is positioned to provide access for surgical instruments. In an embodiment, the insertable device 102 is positioned to provide vascular access. In an embodiment, the insertable device 102 is positioned to facilitate drainage.

Among catheters 112, examples include, but are not limited to, arterial catheters, dialysis catheters, drainage catheters, indwelling catheters, long term non-tunneled central venous catheters, long term tunneled central venous catheters, mechanical catheters, peripheral venous catheters, peripherally insertable central venous catheters, peritoneal catheters, pulmonary artery Swan-Ganz catheters, short-term central venous catheters, urinary catheters, ventricular catheters, and the like. In an embodiment, the body structure 104 includes one or more catheters 112 each having a proximal portion 114, a distal portion 116, and at least one fluid-flow passageway 110 extending therethrough. In an embodiment, one or more of the catheters 112 are configured for insertion into a body cavity, a duct, or a vessel of a subject. In an embodiment, the system 100 can include, among other things, one or more power sources 900.

In an embodiment, at least one of the anti-microbial regions 202 is selectively actuatable 202a. In an embodiment, at least one of the anti-microbial regions 202 is selectively actuatable between at least a first actuatable state and a second actuatable state. In an embodiment, at least one of the anti-microbial regions 202 is independently addressable 202b. In an embodiment, the insertable device 102 includes one or more ports 118 configured to provide access to, or from, an interior environment of at least one of the fluid-flow passageways 110.

In an embodiment, at least one of the anti-microbial regions 202 is configured to provide at least one anti-microbial property 204 of a character and for a time sufficient to inhibit microbial growth or microbial adherence to at least one of the anti-microbial regions 202 of the body structure 104. In an embodiment, at least one of the anti-microbial regions 202 is configured to provide at least one anti-microbial property 204 of a character and for a time sufficient to inhibit at least one of microbial aggregation on the surface of the body structure 104. In an embodiment, at least one of the anti-microbial regions 202 is configured to provide at least one anti-microbial property 204 of a character and for a time sufficient to inhibit adherence of at least one extracellular matrix component to the surface of the body structure 104. In an embodiment, the extracellular matrix component includes at least one of a protein, or glycosaminoglycan. In an embodiment, the at least one anti-microbial property 204 includes at least one of nano-scale or micro-scale roughness.

In an embodiment, the anti-microbial agent includes at least one of an anti-fungal agent, anti-parasitic agent, energy emitter, photoactive material, thermal plasmonic structure, thermal ridge, nanostructure, microstructure, surface undulation, protease, amino acid, surfactant, electricity, optical energy, plasmonic energy, bacteriophage, photoactive material, or antibiotic. In an embodiment, the bacteriophage includes an engineered enzymatically active bacteriophage. In an embodiment, the anti-microbial agent includes at least two different bacteriophage sets.

In an embodiment, the antibiotic includes at least one of azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, sulfadizine, sulfacetamide, sulfadiazine, sulfamethoxazole, sulfasalazine, sulfisoxazole, trimethoprim-sulfamethoxazole, sulfamethizole, linezolid, quinopristin+dalfopristin, bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, coliistin, cycloserine, capreomycin, ethionamide, pyrazinamide, para-aminosalicyclic acid, erythromycin ethylsuccinate+sulfisoxazole, penicillin, beta-lactamase inhibitor, methicillin, cefaclor, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate, Amphotericin B, Carbol-Fuchsin, Ciclopirox, Clotrimzole, Econazole, Haloprogin, Ketoconazole, Mafenide, Miconazole, Naftifine, Nystatin, Oxiconazole Silver, Sulfadiazine, Sulconazole, Terbinatine, Tioconazole, Tolnaftate, Undecylenic acid, flucytosine, miconazole, cephabam, beta-lactam, or cephalosporin. In an embodiment, the anti-microbial agent includes at least one of a macrolide, lincosamine, quinolone, fluoroquinolone, carbepenem, monobactam, aminoglycoside, glycopeptide, enzyme, tetracycline, sulfonamide, rifampin, oxazolidonone, streptogramin, or a synthetic moiety thereof. In an embodiment, the anti-microbial agent includes at least one surfactant or amino acid. In an embodiment, the amino acid includes at least one D-amino acid. In an embodiment, the anti-microbial agent includes at least one of a ceramic, super-oxide forming compound, enzyme, or polymer. In an embodiment, the anti-microbial agent includes at least one metal, or salt thereof. In an embodiment, the enzyme includes at least one of DNAse, protease, glucosidase, or endopeptidase. In an embodiment, the ceramic includes zeolite, optionally with silver ions exchanged onto internal acidic sites of the zeolite. In an embodiment, the anti-microbial agent includes polytetrafluoroethylene. In an embodiment, the anti-microbial agent includes at least one of Group B Streptococci phage lysin, aminoglycoside, carbapenem, cephlasporin, fluoroquinolone, glycylcycline, macrolide, monobactam, penicillin, polypeptide, sulfonamide, tetracycline, metronidazole, rifampin, pyrazinamide, nitrofurantoin, quinupristin-dalfopristin, spectinomycin, telithromycin, vancomycin, linezolid, isoniazid, fosfomycin, ethambutol, daptomycin, clindamycin, or chloramphenicol. In an embodiment at least one of the anti-microbial regions 202 includes at least one of silver, copper, zirconium, diamond, rubidium, platinum, gold, nickel, lead, cobalt, potassium, zinc, bismuth, tin, cadmium, chromium, aluminum, calcium, mercury, thallium, gallium, strontium, barium, lithium, magnesium, oxides, hydroxides, or salts thereof.

In an embodiment, an insertable device 102 includes a body structure 104 having an outer surface 106 and an inner surface 108 defining one or more fluid-flow passageways 110; one or more anti-microbial regions 202 including at least one D-amino acid coating on at least one of the outer surface 106, inner surface 108, or embedded in the body structure 104. In an embodiment, the D-amino acid includes at least one of D-leucine, D-methionine, D-tyrosine, or D-tryptophan. In an embodiment, an insertable device 102 includes a body structure 104 having an outer surface 106 and an inner surface 108 defining one or more fluid-flow passageways 110; one or more selectively actuatable anti-microbial regions 202a including at least one anti-microbial reservoir 208 including at least one D-amino acid, the anti-microbial reservoir 208 configured to deliver at least one D-amino acid to at least one of the outer surface 106 inner surface 108, or internal body structure 104.

In an embodiment, at least one of the anti-microbial regions 202 includes at least one of black silica, or hydrogenated diamond. In an embodiment, at least one of the anti-microbial regions includes at least one electroactive polymer. In an embodiment, at least one of the anti-microbial regions includes at least one of polyvinyl chloride, polyester, polyethylene, polypropylene, ethylene, or polyolefin; or homopolymers or copolymers thereof.

In an embodiment, at least one of the anti-microbial regions 202 includes an anti-microbial property 204 selective for at least one of a single phylum of microorganism, single genus of microorganism, single strain of microorganism, or single microorganism. In an embodiment, the at least one anti-microbial property 204 is selected based on expected microorganism presence or actual microorganism presence proximate the body structure 104. In an embodiment, at least one anti-microbial property 204 is selected based on expected microorganism response to at least one other anti-microbial region 202 of the body structure 104.

In an embodiment, the body structure 104 of the insertable device 102 includes at least one porous material 209. In an embodiment, at least one of the anti-microbial regions 202 includes at least one porous material 209. In an embodiment, the at least one porous material 209 is configured to capture at least one microorganism proximate to at least one of the inner surface 108 or the outer surface 106 of the body structure 104. In an embodiment, the at least one porous material 209 is further configured to retain a captured microorganism. In an embodiment, the porous material 209 includes hydrophobic polycations bound thereto. In an embodiment, the hydrophobic polycations are covalently bound to the porous material 209. In an embodiment, the hydrophobic polycations include at least one of N-alkylated poly 14-vinylpyridine, hexyl-poly 14-vinylpyridine, or N-hexylated-methylated high molecular weight polyethylenimine. In an embodiment, the porous material 209 includes at least one of cotton, wool, nylon, or polyester.

In an embodiment, the insertable device 102 includes one or more catheters 112 configured for directly detecting or monitoring mechanical, physical, or biochemical functions associated with a biological subject; draining or collecting body fluids; providing access to an interior of a biological subject; or distending at least one fluid-flow passageway 110; as well as for administering therapeutics, nutraceuticals, intravenous fluids, nutrition, or the like. In an embodiment, the insertable device 102 includes one or more at least partially implantable catheters 112. In an embodiment, the insertable device 102 includes one or more ports 118 configured to provide access to, or from, an interior environment of at least one of the fluid-flow passageways 110. In an embodiment, the insertable device 102 includes one or more biocompatible materials, biodegradable materials, polymeric materials, thermoplastics, silicone materials (e.g., polydimethysiloxanes), polyvinyl chloride materials, silk, biodegradable polymer, hydrogel, latex rubber materials, or the like.

In an embodiment, an at least partially implantable fluid management system includes: a catheter assembly having a body structure 104 including at least an outer surface 106 and an inner surface 108 defining one or more fluid-flow passageways 110; and a plurality of selectively actuatable anti-microbial regions 202a configured to deliver at least one anti-microbial agent to at least a portion of one or more of the outer surface 106, the inner surface 108, or embedded in the internal body structure 104.

Further non-limiting examples of catheters 112, shunts, medical ports, insertable devices, implantable devices, implantable or insertable device assemblies, or components thereof, may be found in, for example the following documents (the contents of each of which is incorporated herein by reference): U.S. Pat. Nos. 7,524,298 (issued Apr. 28, 2009), 7,390,310 (issued Jun. 24, 2008), 7,334,594 (issued Feb. 26, 2008), 7,309,330 (issued Dec. 18, 2007), 7,226,441 (issued Jun. 5, 2007), 7,118,548 (issued Oct. 10, 2006), 6,932,787 (issued Aug. 23, 2005), 6,913,589 (issued Jul. 5, 2005), 6,743,190 (issued Jun. 1, 2004), 6,585,677 (issued Jul. 1, 2003); and U.S. Patent Publication Nos. 2009/0118661 (published May 7, 2009), 2009/0054824 (published Feb. 26, 2009), 2009/0054827 (published Feb. 26, 2009), 2008/0039768 (published Feb. 14, 2008), and 2006/0004317 (published Jan. 5, 2006).

In an embodiment, the one or more anti-microbial regions 202 can take a variety of shapes, configurations, or geometries, including, but not limited to, cylindrical, conical, planar, parabolic, regular or irregular forms. In an embodiment, a plurality of anti-microbial regions 202 are configured as bands on at least one of the outer surface 106, the inner surface 108, or embedded in the body structure 104 of the device 102. The one or more anti-microbial regions 202 can also form a variety of patterns 109 (e.g., spatial or temporal patterns), such as, repeating pattern, non-repeating pattern, graduating pattern, blocking pattern, or partially repeating pattern. In an embodiment, the at least one spatial pattern or temporal pattern is derived from information relating to the type of microorganism expected to be present proximate the body structure 104. In an embodiment, the at least one spatial pattern or temporal pattern is based at least in part on information relating to at least one of the type of microorganism previously detected on at least one anti-microbial region of the body structure 104. In an embodiment, the blocking pattern is configured such that it forms the sole pathway to another pattern on the body structure 104. In an embodiment, multiple anti-microbial regions 202 are formed from a single substrate or structure. Non-limiting examples of anti-microbial regions 202 include at least one anti-microbial surface property 204 (e.g., anti-microbial protruding elements 206 (e.g., anti-microbial nanostructures 206a, etc.), anti-microbial polymers, anti-microbial metals, anti-microbial agents, etc., anti-microbial reservoir 208 including at least one anti-microbial agent, or the like). In an embodiment, the one or more anti-microbial regions 202 include at least one structure, agent, or other anti-microbial surface property 204 suitable for directing at least one microorganism toward or away from a particular location of the insertable device 102. In an embodiment, the anti-microbial agent is formulated to be released or activated over time.

In an embodiment, at least one of the anti-microbial regions 202 is actuatable 202a. In an embodiment, the actuatable anti-microbial region 202a is configured to release at least one anti-microbial agent based at least in part on at least one detected microbial component associated with the biological sample 808. In an embodiment, at least one of the anti-microbial regions 202 is actuatable by the presence of at least one microorganism (e.g., bacteria, fungi, etc.). In an embodiment, the at least one microorganism includes at least one of *Staphylococcus, Pseudomonas*, or *Escherichia* bacteria. In an embodiment, the at least one microorganism includes at least one of *Candida*, or *Saccharomyces*.

In an embodiment, the actuatable anti-microbial region 202a is configured for reversible activation. In an embodiment, the at least one actuatable anti-microbial region 202a is configured for irreversible activation. In an embodiment, the actuatable anti-microbial region 202a is actuatable by at least partial degradation of the body structure 104.

In an embodiment, the insertable device 102 further comprises at least one light source 211. In an embodiment, the at least one light source 211 is coupled to at least one anti-microbial region 202. In an embodiment, the at least one light source 211 includes at least one of a light-emitting diode, ultraviolet light source, or infrared light source.

In an embodiment, the system 100 comprises a body structure 104 having an outer surface 106 and an inner surface 108 defining one or more fluid-flow passageways 110; at least one independently addressable and actively controllable anti-microbial nanostructure 206a projecting from at least one of the outer surface 106, or the inner surface 108 of the body structure 104; at least one sensor 302 configured to detect one or more microorganisms present proximate the body structure 104; and means for determining the presence of at least one microorganism proximate at least one of the independently addressable and actively controllable anti-microbial nanostructure 206a of the body structure 104. In an embodiment, the system 100 further includes one or more instructions for determining the presence of at least one microorganism proximate at least one of the independently addressable anti-microbial regions 202b of the body structure 104.

Figures 2A, 2B:
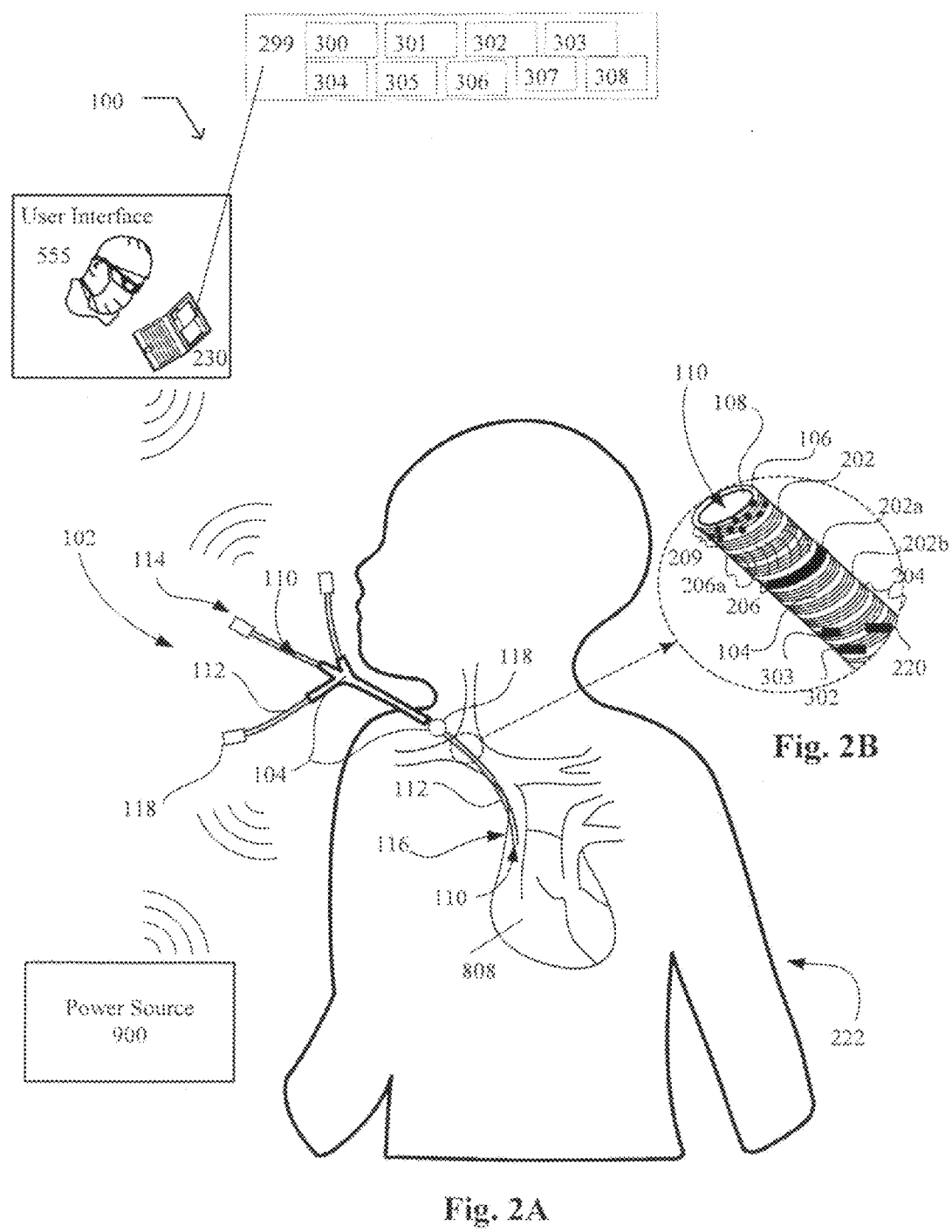
FIG. 2A illustrates a particular embodiment of a device disclosed herein.
FIG. 2B illustrates a close up of the device illustrated in FIG. 2A.
Figure 4A:
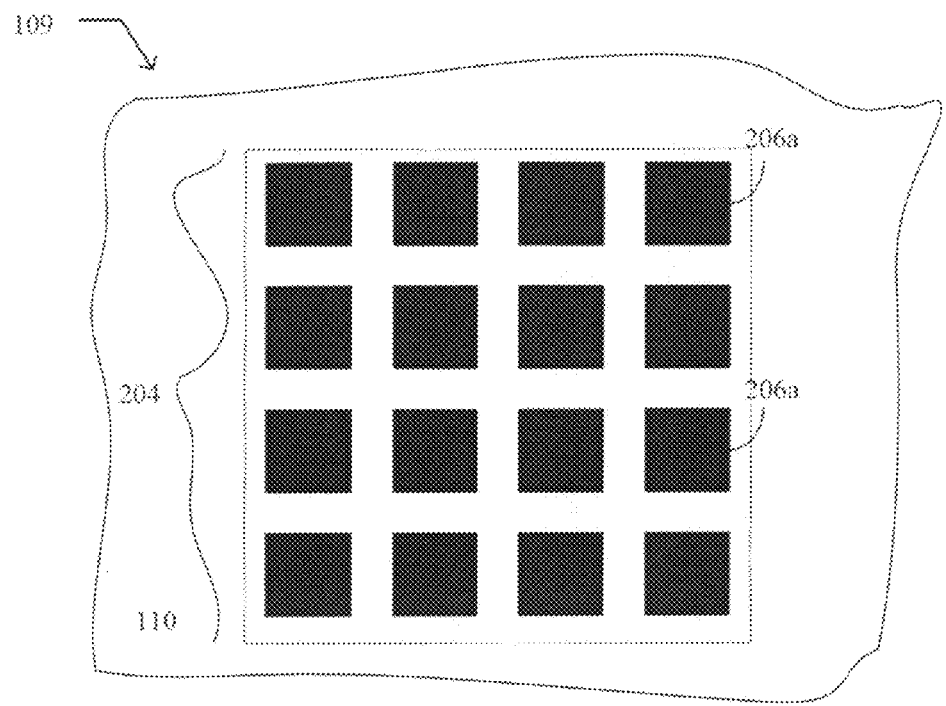
FIG. 4A illustrates a close up of a particular embodiment of a component of a device disclosed herein.
Figure 4B:
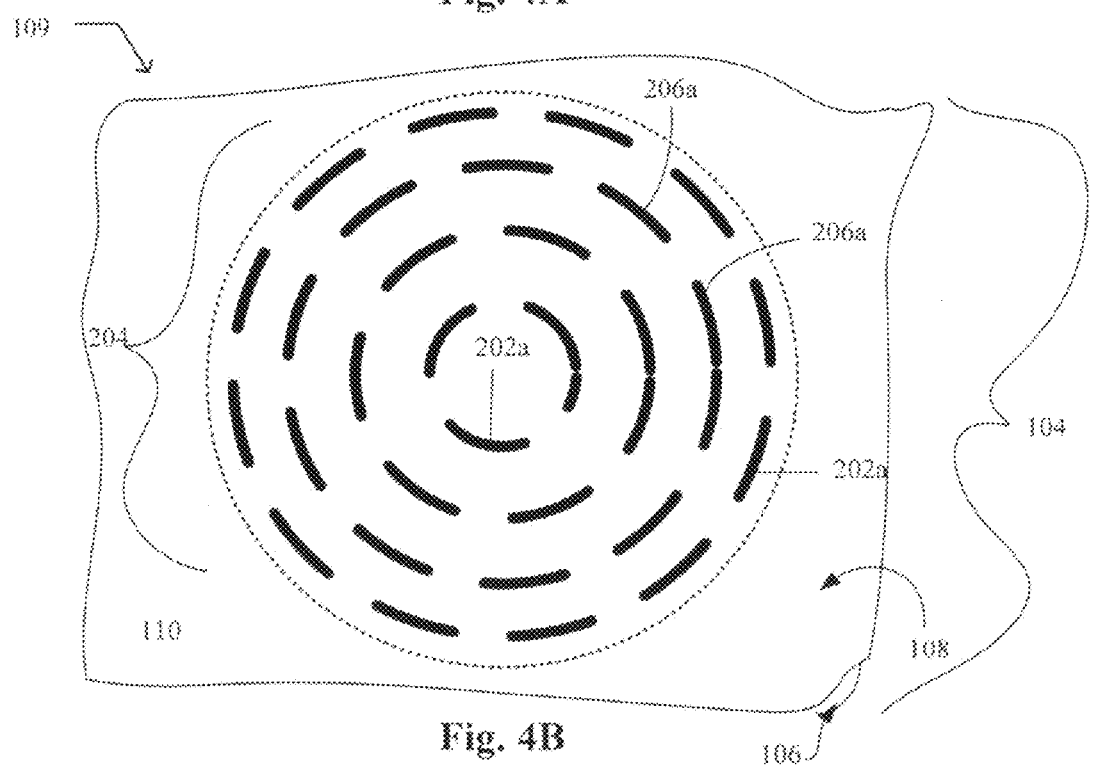
FIG. 4B illustrates a close up of a particular embodiment of a component of a device disclosed herein.

Referring to FIGS. 2A and 2B, the system 100 can include, among other things, at least one sensor 302. In an embodiment, the sensor 302 includes at least one of a plasmon sensor, pH sensor, temperature sensor, piezoelectric sensor, electrostrictive sensor, magnetostrictive sensor, biochemical sensor, optical sensor, optical density sensor, refractive index sensor, biomass sensor, electrochemical sensor, fluid-flow sensor, or electronic sensor.

In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) associated with a biological subject 222. In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) a microbial component. In an embodiment, the microbial component includes at least one a lipid, peptide, lipopolysaccharide, flagellin, lipoteichoic acid, peptidoglycan, nucleic acid (e.g., DNA, double stranded RNA, etc), unmethylated CpG motifs, polypeptide, protein, glycolipid, proteoglycan, lipoprotein, glycoprotein, glycosaminoglycan, polysaccharide, glycopeptides, metalloprotein, enzyme, carbohydrate, cytokine, microbial cell membrane, microbial cell receptor, pathogen-associated molecular pattern, or other microbial component.

In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) of a microbial component proximate the body structure 104. In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) of the presence of at least one microorganism within at least one of the fluid-flow passageways 110. In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) the presence of at least one microorganism proximate at least one of the anti-microbial regions 202. In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) the presence of at least one microorganism proximate one or more fluid-flow passageways 110. In an embodiment, the sensor 302 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) of the presence of at least one microorganism within the one or more fluid-flow passageways 110 based on one or more flow characteristics.

In an embodiment, the sensor 302 is configured to perform a real-time comparison of a measurand associated with a biological sample 808 proximate the insertable device 102 to stored reference data and to generate a response 299 based on the comparison. In an embodiment, the sensor 302 is configured to perform a comparison of a real-time detection associated with at least one anti-microbial region 202 of at least one of the outer surface 106, or the inner surface 108 of the body structure 104, to the microbial marker information and to generate a response 299 based at least in part on the comparison. In an embodiment, the sensor 302 is configured to perform a comparison of a cumulative detection associated with at least one anti-microbial region 202 of at least one of the outer surface 106 or the inner surface 108 of the body structure 104 to the microbial marker information to generate a response 299 based at least in part on the comparison. For example, the response 299 can include, among other things, activating an authorization protocol, activating an authentication protocol, activating a software update protocol 333, activating a data transfer protocol 303, or activating an anti-microbial region diagnostic protocol 334. In an embodiment, the response 299 includes one or more of a response 299 signal, control signal, or change in delivery of at least one anti-microbial agent. In an embodiment, the response 299 includes one or more of sending information associated with at least one of an authentication protocol, an authorization protocol, an anti-microbial delivery protocol, an activation protocol, an encryption protocol, or a decryption protocol.

In an embodiment, the sensor 302 is operably coupled to one or more computing devices 230. In an embodiment, at least one computing device 230 is operably coupled to the sensor 302 and configured to process an output associated with one or more sensor measurands. In an embodiment, at least one computing device 230 is configured to concurrently or sequentially operate multiple sensors 302. In an embodiment, the sensor 302 includes a computing device 230 configured to process sensor measurand information and configured to cause the storing of the measurand information in a data storage medium. In an embodiment, the sensor 302 includes an identification code and is configured to implement instructions addressed to the sensor 302 according to the component identification code.

In an embodiment, the sensor 302 includes one or more surface plasmon resonance sensors. For example, in an embodiment, the sensor 302 includes one or more localized surface plasmon resonance sensors. In an embodiment, the sensor 302 includes a light transmissive support and a reflective metal layer. In an embodiment, the sensor 302 includes a wavelength-tunable surface plasmon resonance sensor. In an embodiment, the sensor 302 includes a surface plasmon resonance microarray sensor having a wavelength-tunable metal-coated grating. In an embodiment, the sensor 302 includes a surface plasmon resonance microarray sensor having an array of micro-regions configured to capture target molecules.

In an embodiment, the sensor 302 includes one or more electrochemical transducers, optical transducers, piezoelectric transducers, or thermal transducers. For example, in an embodiment, the sensor 302 includes one or more transducers configured to detect acoustic waves associated with changes in a biological mass present proximate a surface of the body structure 104.

In an embodiment, the sensor 302 includes one or more thermal detectors, photovoltaic detectors, or photomultiplier detectors. In an embodiment, the sensor 302 includes one or more charge-coupled devices, complementary metal-oxide-semiconductor devices, photodiode image sensor devices, whispering gallery mode (WGM) micro cavity devices, photoelectric device, wavelength-tunable surface plasmon resonance sensor, surface plasmon resonance microarray sensor having a wavelength-tunable metal-coating grating, or scintillation detector devices. In an embodiment, the sensor 302 includes one or more ultrasonic transducers.

In an embodiment, the sensor 302 includes at least one of an imaging spectrometer, a photo-acoustic imaging spectrometer, a thermo-acoustic imaging spectrometer, and a photo-acoustic/thermo-acoustic tomographic imaging spectrometer. In an embodiment, the sensor 302 includes at least one of a thermal detector, a photovoltaic detector, or a photomultiplier detector.

In an embodiment, the sensor 302 includes one or more density sensors. In an embodiment, the sensor 302 includes one or more optical density sensors. In an embodiment, the sensor 302 includes one or more refractive index sensors. In an embodiment, the sensor 302 includes one or more fiber optic refractive index sensors.

In an embodiment, the sensor 302 includes one or more biosensors 303 (e.g., acoustic biosensors, amperometric biosensors, calorimetric biosensors, optical biosensors, or potentiometric biosensors). In an embodiment, the sensor 302 includes one or more fluid-flow sensors. In an embodiment, the sensor 302 includes one or more differential electrodes, biomass sensors, immunosensors, or the like. In an embodiment, the sensor 302 includes one or more one-, two-, or three-dimensional photodiode arrays.

In an embodiment, the system 100 includes one or more sensors 302. In an embodiment, the insertable device 102 includes one or more of the sensors 302. Non-limiting examples of sensors 302 include acoustic wave sensors, aptamer-based sensors, biosensors, blood volume pulse sensors, cantilevers, conductance sensors, fluorescence sensors, force sensors, heat sensors (e.g., thermistors, thermocouples, or the like), high resolution temperature sensors, differential calorimeter sensors, optical sensors, goniometry sensors, potentiometer sensors, resistance sensors, respiration sensors, sound sensors (e.g., ultrasound), Surface Plasmon Band Gap sensor (SPRBG), physiological sensors, and the like. Further non-limiting examples of sensors 302 include affinity sensors, bioprobes, biostatistics sensors, enzymatic sensors, in-situ sensors (e.g., in-situ chemical sensor), ion sensors, light sensors (e.g., visible, infrared, or the like), microbiological sensors, microhotplate sensors, micronscale moisture sensors, nanosensors, optical chemical sensors, single particle sensors, and the like.

Further non-limiting examples of sensors 302 include chemical sensors, cavitand-based supramolecular sensors, nucleic acid sensors, deoxyribonucleic acid sensors (e.g., electrochemical DNA sensors, or the like), supramolecular sensors, and the like. In an embodiment, at least one of the sensors 302 is configured to detect or measure the presence or concentration of specific target chemicals (e.g., blood components, biological sample component, cerebral spinal fluid component, infectious agents, infection indication chemicals, inflammation indication chemicals, diseased tissue indication chemicals, biological agents, molecules, ions, or the like).

Further non-limiting examples of sensors 302 include chemical transducers, ion sensitive field effect transistors (ISFETs), ISFET pH sensors, membrane-ISFET devices (MEMFET), microelectronic ion-sensitive devices, potentiometric ion sensors, quadruple-function ChemFET (chemical-sensitive field-effect transistor) integrated-circuit sensors, sensors with ion-sensitivity and selectivity to different ionic species, and the like. Further non-limiting examples of the one or more sensors 302 can be found in the following documents (the contents of each of which is incorporated herein by reference): U.S. Pat. Nos. 7,396,676 (issued Jul. 8, 2008) and 6,831,748 (issued Dec. 14, 2004).

In an embodiment, the one or more sensors 302 include one or more acoustic transducers, electrochemical transducers, photochemical transducer, optical transducers, piezoelectrical transducers, or thermal transducers. For example, in an embodiment, the one or more sensors 302 include one or more acoustic transducers. In an embodiment, the one or more sensors 302 include one or more thermal detectors, photovoltaic detectors, or photomultiplier detectors. In an embodiment, the one or more sensors 302 include one or more charge coupled devices, complementary metal-oxide-semiconductor devices, photodiode image sensor devices, whispering gallery mode micro cavity devices, or scintillation detector devices. In an embodiment, the one or more sensors 302 include one or more complementary metal-oxide-semiconductor image sensors.

In an embodiment, the one or more sensors 302 include one or more conductivity sensor. In an embodiment, the one or more sensors 302 include one or more spectrometers. In an embodiment, the one or more sensors include one or more Bayer sensors. In an embodiment, the one or more sensors include one or more Foveon sensors. In an embodiment, the one or more sensors 302 include one or more density sensors. In an embodiment, the one or more density sensors include one or more optical density sensors. In an embodiment, the one or more density sensors include one or more refractive index sensors. In an embodiment, the one or more refractive index sensors include one or more fiber optic refractive index sensors.

In an embodiment, the one or more sensors 302 include one or more surface plasmon resonance sensors. In an embodiment, the one or more sensors 302 are configured to detect target molecules. For example, surface-plasmon-resonance-based-sensors detect target molecules suspended in a fluid, for example, by reflecting light off thin metal films in contact with the fluid. Adsorbing molecules cause changes in the local index of refraction, resulting in changes in the resonance conditions of the surface plasmon waves.

In an embodiment, the one or more sensors 302 include one or more localized surface plasmon resonance sensors. In an embodiment, detection of target molecules includes monitoring shifts in the resonance conditions of the surface plasmon waves due to changes in the local index of refraction associates with adsorption of target molecules. In an embodiment, the one or more sensors 302 include one or more functionalized cantilevers. In an embodiment, the one or more sensors 302 include a light transmissive support and a reflective metal layer. In an embodiment, the one or more sensors 302 include a biological molecule capture layer. In an embodiment, the biological molecule capture layer includes an array of different binding molecules that specifically bind one or more target molecules. In an embodiment, the one or more sensors 302 include a surface plasmon resonance microarray sensor having an array of micro-regions configured to capture target molecules.

In an embodiment, the one or more sensors 302 include one or more acoustic biosensors, amperometric biosensors, calorimetric biosensors, optical biosensors, or potentiometric biosensors. In an embodiment, the one or more sensors 302 include one or more fluid flow sensors. In an embodiment, the one or more sensors 302 include one or more differential electrodes. In an embodiment, the one or more sensors 302 include one or more biomass sensors. In an embodiment, the one or more sensors 302 include one or more immunosensors.

In an embodiment, the sensor 302 is operably coupled to a microorganism colonization biomarker array. In an embodiment, the sensor 302 includes a biological molecule capture layer. In an embodiment, the sensor 302 includes a biological molecule capture layer having an array of different binding molecules that specifically bind one or more target molecules. In an embodiment, the sensor 302 includes one or more computing devices 230 operably coupled to one or more sensors. For example, in an embodiment, the sensor 302 includes a computing device 230 operably coupled to one or more surface plasmon resonance microarray sensors.

In an embodiment, the sensor 302 is configured to detect at least one attribute associated with a biological subject 222. In an embodiment, the at least one attribute includes at least one of physiological condition, genetic profile, proteomic profile, genetic characteristic, proteomic characteristic, response to previous treatment, weight, height, medical diagnosis, familial background, results of one or more medical tests, ethnic background, body mass index, age, presence or absence of at least one disease or condition, species, ethnicity, race, allergies, gender, presence or absence of at least one biological or chemical agent in the subject, pregnancy status, lactation status, medical history, or blood condition.

In an embodiment, the at least one characteristic associated with a biological sample 808 proximate the insertable device 102 includes at least one of a transmittance, an energy frequency change, a frequency shift, an energy phase change, or a phase shift. In an embodiment, the at least one characteristic includes at least one of a fluorescence, an intrinsic fluorescence, a tissue fluorescence, or a naturally occurring fluorophore fluorescence. In an embodiment, the at least one characteristic includes at least one of an electrical conductivity, and electrical polarizability, or an electrical permittivity. In an embodiment, the at least one characteristic associated with a biological sample 808 proximate the insertable device 102 includes at least one of a thermal conductivity, a thermal diffusivity, a tissue temperature, or a regional temperature.

In an embodiment, the at least one characteristic associated with a biological sample 808 proximate the insertable device 102 includes information related to metabolism or biological response to an anti-microbial agent or other anti-microbial surface property 204.

In an embodiment, the at least one characteristic associated with a biological sample 808 proximate the insertable device 102 includes at least one parameter associated with a doppler optical coherence tomograph. (See, e.g., Li et al., *Feasibility of Interstitial Doppler Optical Coherence Tomography for In vivo Detection of Microvascular Changes During Photodynamic Therapy*, Lasers in Surgery and Medicine 38(8):754-61. (2006), which is incorporated herein by reference; see, also U.S. Pat. No. 7,365,859 (issued Apr. 29, 2008), which is incorporated herein by reference).

In an embodiment, the at least one characteristic associated with a biological sample 808 proximate the insertable device 102 includes spectral signature information associated with an implant device. For example, in an embodiment, the at least one characteristic associated with a biological sample 808 proximate the insertable device 102 includes implant device spectral signature information associated with at least one of a bio-implants, (e.g., bioactive implants, facial implants, buttock implants, breast implants, cochlear implants, dental implants, neural implants, orthopedic implants, ocular implants) prostheses, implantable electronic device, implantable medical devices, and the like. Further non-limiting examples of implant devices include replacements implants (e.g., artificial joint implants, or the like such as knee, shoulder, wrists elbow, or hip replacements implants, or the like), subcutaneous drug delivery devices (e.g., implantable pills, drug-eluting stents, or the like), shunts (e.g., cardiac shunts, lumbar-peritoneal shunts, cerebrospinal fluid shunts, cerebral shunts, pulmonary shunts, portosystemic shunts, portacaval shunts, or the like), stents (e.g., coronary stents, peripheral vascular stents, prostatic stents, ureteral stents, vascular stents, or the like), urological catheters, central lines, surgical drains, biological fluid flow controlling implants, and the like. Further non-limiting examples of implant device include artificial hearts, endoscopes, valves (e.g., heart valves), surgical drains, stomach partition clip, artificial prosthetics, catheters, contact lens, mechanical heart valves, subcutaneous sensors, urinary catheters, vascular catheters, and the like.

In an embodiment, the at least one characteristic includes at least one parameter associated with a medical state (e.g., medical condition, disease state, disease attributes, etc.). Inflammation is a complex biological response to insults that can arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids such as prostaglandins and leukotrienes act on blood vessels at the site of infection to localize blood flow, concentrate plasma proteins, and increase capillary permeability.

Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens. Certain cytokines, interleukins and TNF, induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells.

Oxygen radicals, cytotoxic factors, and growth factors can also be released to fight pathogen infection or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution does not occur as expected. Prolonged inflammation, known as chronic inflammation, leads to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

Non-limiting suitable techniques for optically measuring a diseased state may be found in, for example, U.S. Pat. No. 7,167,734 (issued Jan. 23, 2007), which is incorporated herein by reference. In an embodiment, the at least one characteristic of a biological sample 808 proximate the insertable device 102 includes at least one of an electromagnetic energy absorption parameter, an electromagnetic energy emission parameter, an electromagnetic energy scattering parameter, an electromagnetic energy reflectance parameter, or electromagnetic energy depolarization parameter. In an embodiment, the at least one characteristic includes at least one of an absorption coefficient, an extinction coefficient, and a scattering coefficient.

In an embodiment, the at least one characteristic of a biological sample 808 proximate the insertable device 102 includes at least one parameter associated with an infection marker (e.g., an infectious agent marker), an inflammation marker, an infective stress marker, a systemic inflammatory response syndrome marker, or a sepsis marker. Non-limiting examples of infection makers, inflammation markers, and the like may be found in, for example, Imam et al., *Radiotracers for Imaging of Infection and Inflammation—A Review*, World J. Nucl. Med. 40-55 (2006), which is incorporated herein by reference. Non-limiting characteristics associated with an infection marker, an inflammation marker, an infective stress marker, a systemic inflammatory response syndrome marker, or a sepsis marker include at least one of an inflammation indication parameter, an infection indication parameter, a diseased state indication parameter, or a diseased tissue indication parameter.

In an embodiment, the at least one characteristic of a biological sample 808 proximate the insertable device 102 includes at least one of tissue water content, oxy-hemoglobin concentration, deoxyhemoglobin concentration, oxygenated hemoglobin absorption parameter, deoxygenated hemoglobin absorption parameter, tissue light scattering parameter, tissue light absorption parameter, hematological parameter, or pH level.

In an embodiment, the at least one characteristic includes a physiological characteristic of the biological subject 222. Physiological characteristics such as, for example pH can be used to assess blood flow, a cell metabolic state (e.g., anaerobic metabolism, or the like), the presence of an infectious agent, a disease state, and the like. Among physiological characteristics examples include, but are not limited to, at least one of a temperature, a regional or local temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, a respiratory rate, a vital statistic, and the like.

In an embodiment, the at least one characteristic includes at least one of a temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, and a respiratory rate. In an embodiment, the at least one characteristic includes at least one hematological parameter. In an embodiment, the hematological parameter is associated with a hematological abnormality.

In an embodiment, the at least one characteristic of the biological sample 808 proximate the insertable device 102 includes at least one hematological parameter. Non-limiting examples of hematological parameters include an albumin level, a blood urea level, a blood glucose level, a globulin level, a hemoglobin level, erythrocyte count, a leukocyte count, or the like. In an embodiment, the infection marker includes at least one parameter associated with a red blood cell count, a lymphocyte level, a leukocyte count, a myeloid count, an erythrocyte sedimentation rate, or a C-reactive protein level. In an embodiment, the at least one characteristic includes at least one parameter associated with a cytokine plasma level or an acute phase protein plasma level. In an embodiment, the at least one characteristic includes at least one parameter associated with a leukocyte level.

In an embodiment, the at least one characteristic of a biological sample 808 proximate the insertable device 102 includes a spectral parameter associated with a biofilm-specific tag. In an embodiment, the at least one characteristic includes at least one of an optical density, opacity, refractivity, absorbance, fluorescence, or transmittance. In an embodiment, the at least one characteristic includes at least one of an inflammation indication parameter, infection indication parameter, diseased state indication parameter, or diseased tissue indication parameter. In an embodiment, the at least one characteristic includes at least one of an electromagnetic energy absorption parameter, electromagnetic energy emission parameter, electromagnetic energy scattering parameter, electromagnetic energy reflectance parameter, or electromagnetic energy depolarization parameter. In an embodiment, the at least one characteristic includes at least one of an absorption coefficient, extinction coefficient, scattering coefficient, or fluorescence coefficient. In an embodiment, the at least one characteristic includes at least one of parameter associated with at least one of a biomarker, infection marker, inflammation marker, infective stress marker, or sepsis marker.

In an embodiment, the at least one characteristic includes at least one of an electromagnetic energy phase shift parameter, an electromagnetic energy dephasing parameter, and an electromagnetic energy depolarization parameter. In an embodiment, the at least one characteristic includes at least one of an absorbance, a reflectivity, and a transmittance. In an embodiment, the at least one characteristic includes at least one of a refraction and a scattering.

In an embodiment, the sensor 302 is configured to determine at least one characteristic associated with one or more biological markers or biological components (e.g., cerebrospinal fluid components, blood components, or the like). In an embodiment, the sensor 302 is configured to determine at least one characteristic associated with a biological sample proximate the insertable device 102. In an embodiment, the sensor 302 is configured to determine a spatial dependence associated with the least one characteristicassociated with a biological sample. In an embodiment, the sensor 302 is configured to determine a temporal dependence associated with the least one characteristic associated with a biological sample. In an embodiment, the sensor 302 is configured to concurrently or sequentially determine at least one spatial dependence associated with the least one characteristic associated with a biological sample, and at least one temporal dependence associated with the least one characteristic associated with a biological sample.

In an embodiment, the sensor 302 is configured to determine at least one spectral parameter associated with one or more imaging probes (e.g., chromophores, fluorescent agents, fluorescent marker, fluorophores, molecular imaging probes, quantum dots, radio-frequency identification transponders (RFIDs), x-ray contrast agents, or the like). In an embodiment, the sensor 302 is configured to determine at least one characteristic associated with one or more imaging probes attached, targeted to, conjugated, bound, or associated with at least one inflammation markers. See, e.g., the following documents (the contents of each of which is incorporated herein by reference): Jaffer et al., Arterioscler. Thromb. Vasc. Biol. 2002; 22; 1929-1935 (2002); Kalchenko et al., J. of Biomed. Opt. 11(5):050507 (2006).

In an embodiment, the one or more imaging probes include at least one carbocyanine dye label. In an embodiment, the sensor 302 is configured to determine at least one characteristic associated with one or more imaging probes attached, targeted to, conjugated, bound, or associated with at least one biomarker or biological sample component (e.g. biological tissue component, or biological fluid component, etc.).

In an embodiment, the one or more imaging probes include at least one of a fluorescent agen, quantum dot, radio-frequency identification transponder, x-ray contrast agent, or molecular imaging probe.

Further non-limiting examples of imaging probes include fluorescein (FITC), indocyanine green (ICG), and rhodamine B. Non-limiting examples of other fluorescent dyes for use in fluorescence imaging include a number of red and near infrared emitting fluorophores (600-1200 nm) including cyariine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, Alexa Fluor 750 (Molecular Probes-Invitrogen, Carlsbad, Calif., USA; see, also, U.S. Patent Pub. No. 2005/0171434 (published Aug. 4, 2005) (the contents of each of which is incorporated herein by reference), and the like.

Further non-limiting examples of imaging probes include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS, ADS 821-NS (American Dye Source, Montreal, Calif.), NIAD-4 (ICx Technologies, Arlington, Va.), and the like. Further non-limiting examples of fluorophores include BODIPY-FL, europium, green, yellow and red fluorescent proteins, luciferase, and the like. Quantum dots of various emission/excitation properties can be used as imaging probes. See, e.g., Jaiswal, et al. Nature Biotech. 21:47-51 (2003) (the contents of each of which is incorporated herein by reference). Further non-limiting examples of imaging probes include those including antibodies specific for leukocytes, anti-fibrin antibodies, monoclonal anti-diethylene triamine pentaacetic acid (DTPA), DTPA labeled with Technetium-99m ($^{99m}$TC), and the like.

Further non-limiting examples of biomarkers include high-sensitivity C-reactive protein (hs-CRP), cardiac troponin T (cTnT), cardiac troponin I (cTnI), N-terminal-pro B-type natriuretic peptide (NT-proBNP), D-dimer, P-selectin, E-selectin, thrombin, interleukin-10, fibrin monomers, phospholipid microparticles, creatine kinase, interleukin-6, tumor necrosis factor-alpha, myeloperoxidase, intracellular adhesion molecule-1 (ICAM1), vascular adhesion molecule (VCAM), matrix metalloproteinase-9 (MMP9), ischemia modified albumin (IMA), free fatty acids, choline, soluble CD40 ligand, insulin-like growth factor, (see, e.g., Giannitsis, et al. *Risk stratification in pulmonary embolism based on biomarkers and echocardiography*. Circ. 112:1520-1521 (2005), Barnes, et al., *Novel biomarkers associated with deep venous throbosis: A comprehensive review*. Biomarker Insights 2:93-100 (2008); Kamphuisen, *Can anticoagulant treatment be tailored with biomarkers in patients with venous thromboembolism?* J. Throm. Haemost. 4:1206-1207 (2006); Rosalki, et al., *Cardiac biomarkers for detection of myocardial infarction: Perspectives from past to present. Clin. Chem.* 50:2205-2212 (2004); Apple, et al., *Future biomarkers for detection of ischemia and risk stratification*

*in acute coronary syndrome*, Clin. Chem. 51:810-824 (2005), each of which is incorporated herein by reference).

In an embodiment, the sensor 302 is configured to detect a spectral response 299 (e.g., an emitted energy, a remitted energy, an energy absorption profile, energy emission profile, or the like) associated with a biomarker. Among biomarker examples include, but are not limited to, one or more substances that are measurable indicators of a biological state and can be used as indicators of normal disease state, pathological disease state, and/or risk of progressing to a pathological disease state. In some instances, a biomarker can be a normal blood component that is increased or decreased in the pathological state. A biomarker can also be a substance that is not normally detected in biological sample 808 (e.g. a biological fluid, or tissue), but is released into circulation because of the pathological state. In some instances, a biomarker can be used to predict the risk of developing a pathological state. For example, plasma measurement of lipoprotein-associated phospholipase A2 (Lp-PLA2) is approved by the U.S. Food & Drug Administration (FDA) for predicting the risk of first time stroke.

In other instances, the biomarker can be used to diagnose an acute pathological state. For example, elevated plasma levels of S-100b, B-type neurotrophic growth factor (BNGF), von Willebrand factor (vWF), matrix metalloproteinase-9 (MMP-9), and monocyte chemoattractant protein-1 (MCP-1) are highly correlated with the diagnosis of stroke (see, e.g., Reynolds, et al., *Early biomarkers of stroke*. Clin. Chem. 49:1733-1739 (2003), which is incorporated herein by reference).

In an embodiment, the sensor 302 is configured to detect at least one characteristic associated with one or more biological sample components. In an embodiment, the at least one characteristic includes at least one of absorption coefficient information, extinction coefficient information, or scattering coefficient information associated with the at least one molecular probe. In an embodiment, the at least one characteristic includes spectral information indicative of at least one of rate of change, accumulation rate, aggregation rate, or rate of change associated with at least one physical parameter associated with a biological sample component.

In an embodiment, the sensor 302 is configured to detect spectral information associated with a real-time change in one or more parameters associated with a biological sample 808 (e.g., biological tissue or fluid). For example, in an embodiment, the sensor 302 is configured to detect at least one of an emitted energy and a remitted energy associated with a real-time change in one or more parameters associated with a biological sample 808 within one or more anti-microbial regions of an insertable device 102. In an embodiment, the sensor 302 includes one or more transducers configured to detect sound waves associated with changes in a biological sample 808 present proximate at least one of the outer surface 106 or the inner surface 108 of the body structure 104.

In an embodiment, the sensor 302 is configured to detect at least one of an emitted energy and a remitted energy. In an embodiment, the sensor 302 is configured to detect at least one of an emitted energy and a remitted energy associated with a biological subject 222. In an embodiment, the sensor 302 is configured to detect an optical energy absorption profile of a target sample, a portion of a tissue, or portion of a biological sample 808 (e.g., biological tissue or fluid) within the biological subject 222. In an embodiment, the sensor 302 is configured to detect an excitation radiation and an emission radiation associated with a portion of a target sample, a portion of a tissue, or portion of a biological sample 808 within the biological subject 222. In an embodiment, the sensor 302 is configured to detect at least one of an energy absorption profile and an energy reflection profile of a region within a biological subject 222.

In an embodiment, the sensor 302 is configured to detect a spectral response 299 from a biological sample 808 of a biological subject 222. Blood is a tissue composed of, among other components, formed elements (e.g., blood cells such as erythrocytes, leukocytes, thrombocytes, or the like) suspend in a matrix (plasma). The heart, blood vessels (e.g., arteries, arterioles, capillaries, veins, venules, or the like), and blood components, make up the cardiovascular system. The cardiovascular system, among other things, moves oxygen and other gases, as well as other biochemical agents to and from cells and tissues, maintains homeostasis by stabilizing body temperature and pH, and helps fight diseases.

In an embodiment, the sensor 302 is configured to detect at least one of an emitted energy and a remitted energy associated with a portion of a cardiovascular system. In an embodiment, the sensor 302 is configured to detect at least one of an emitted energy and a remitted energy associated with one or more blood components within a biological subject 222. In an embodiment, the sensor 302 is configured to detect at least one of an emitted energy and a remitted energy associated with one or more formed elements within a biological subject 222. In an embodiment, the sensor 302 is configured to detect spectral information associated with one or more of one or more blood components. In an embodiment, the sensor 302 is configured to detect at least one of an emitted energy and a remitted energy associated with a real-time change in one or more parameters associated with at least one blood component within a biological subject 222. In an embodiment, the sensor 302 is configured to detect an energy absorption of one or more blood components.

Non-limiting examples of detectable blood components include erythrocytes, leukocytes (e.g., basophils, granulocytes, eosinophils, monocytes, macrophages, lymphocytes, neutrophils, or the like), thrombocytes, acetoacetate, acetone, acetylcholine, adenosine triphosphate, adrenocorticotrophic hormone, alanine, albumin, aldosterone, aluminum, amyloid proteins (non-immunoglobulin), antibodies, apolipoproteins, ascorbic acid, aspartic acid, bicarbonate, bile acids, bilirubin, biotin, blood urea, nitrogen, bradykinin, bromide, cadmium, calciferol, calcitonin (ct), calcium, carbon dioxide, carboxyhemoglobin (as HbcO), cell-related plasma proteins, cholecystokinin (pancreozymin), cholesterol, citric acid, citrulline, complement components, coagulation factors, coagulation proteins, complement components, c-peptide, c-reactive protein, creatine, creatinine, cyanide, 11-deoxycortisol, deoxyribonucleic acid, dihydrotestosterone, diphosphoglycerate (phosphate), or the like.

Further non-limiting examples of detectable blood components include dopamine, enzymes, epidermal growth factor, epinephrine, ergothioneine, erythrocytes, erythropoietin, folic acid, fructose, furosemide glucuronide, galactoglycoprotein, galactose (children), gamma-globulin, gastric inhibitory peptide, gastrin, globulin, α-1-globulin, α-2-globulin, α-globulins, β-globulins, glucagon, glucosamine, glucose, immunoglobulins (antibodies), lipase p, lipids, lipoprotein (sr 12-20), lithium, low-molecular weight proteins, lysine, lysozyme (muramidase), α-2-macroglobulin, γ-mobility (non-immunoglobulin), pancreatic polypeptide, pantothenic acid, para-aminobenzoic acid, parathyroid hormone, pentose, phosphorated, phenol, phenylalanine, phosphatase, acid, prostatic, phospholipid, phosphorus, prealbumin, thyroxine-binding, proinsulin, prolactin (female), prolactin (male), proline, prostaglandins, prostate specific antigen, protein, protoporphyrin, pseudoglobulin I, pseudoglobulin II, purine, pyridoxine, pyrimidine nucleotide, pyruvic acid, CCL5 (RANTES), relaxin, retinol, retinol-binding protein, riboflavin, ribonucleic acid, secretin, serine, serotonin (5-hydroxytryptamine), silicon, sodium, solids, somatotropin (growth hormone), sphingomyelin, succinic acid, sugar, sulfates, inorganic, sulfur, taurine, testosterone (female), testosterone (male), triglycerides, triiodothyronine, tryptophan, tyrosine, urea, uric acid, water, miscellaneous trace components, and the like.

Non-limiting examples of α-globulins examples include α1-acid glycoprotein, α1-antichymotrypsin, α1-antitrypsin, α1B-glycoprotein, α1-fetoprotein, α1-microglobulin, α1T-glycoprotein, α2HS-glycoprotein, α2-macroglobulin, 3.1 S Leucine-rich α2-glycoprotein, 3.8 S histidine-rich α2-glycoprotein, 4 S α2, α1-α1-glycoprotein, 8 S α3-glycoprotein, 9.5 S α1-glycoprotein (serum amyloid P protein), Corticosteroid-binding globulin, ceruloplasmin, GC globulin, haptoglobin (e.g., Type 1-1, Type 2-1, or Type 2-2), inter-α-trypsin inhibitor, pregnancy-associated α2-glycoprotein, serum cholinesterase, thyroxine-binding globulin, transcortin, vitamin D-binding protein, Zn-α2-glycoprotein, and the like. Among β-Globulins, examples include, but are not limited to, hemopexin, transferrin, β2-microglobulin, β2-glycoprotein I, β2-glycoprotein II, (C3 proactivator), β2-glycoprotein III, C-reactive protein, fibronectin, pregnancy-specific β1-glycoprotein, ovotransferrin, and the like. Among immunoglobulins examples include, but are not limited to, immunoglobulin G (e.g., IgG, $IgG_1$, $IgG_2$, $IgG_3$, $IgG_4$), immunoglobulin A (e.g., IgA, $IgA_1$, $IgA_2$), immunoglobulin M, immunoglobulin D, immunoglobulin E, κ Bence Jones protein, γ Bence Jones protein, J Chain, and the like.

Among apolipoproteins examples include, but are not limited to, apolipoprotein A-I (HDL), apolipoprotein A-II (HDL), apolipoprotein C—I (VLDL), apolipoprotein C-II, apolipoprotein C-III (VLDL), apolipoprotein E, and the like. Among γ-mobility (non-immunoglobulin) examples include, but are not limited to, 0.6 S γ2-globulin, 2 S γ2-globulin, basic Protein B2, post-γ-globulin (γ-trace), and the like. Among low-molecular weight proteins examples include, but are not limited to, lysozyme, basic protein B1, basic protein B2, 0.6 S γ2-globulin, 2 S γ2-globulin, post γ-globulin, and the like.

Among complement components examples include, but are not limited to, C1 esterase inhibitor, C1q component, C1r component, C1s component, C2 component, C3 component, C3a component, C3b-inactivator, C4 binding protein, C4 component, C4a component, C4-binding protein, C5 component, C5a component, C6 component, C7 component, C8 component, C9 component, factor B, factor B (C3 proactivator), factor D, factor D (C3 proactivator convertase), factor H, factor H ($β_1H$), properdin, and the like. Among coagulation proteins examples include, but are not limited to, antithrombin III, prothrombin, antihemophilic factor (factor VIII), plasminogen, fibrin-stabilizing factor (factor XIII), fibrinogen, thrombin, and the like.

Among cell-related plasma proteins examples include, but are not limited to, fibronectin, β-thromboglobulin, platelet factor-4, serum Basic Protease Inhibitor, and the like. Among amyloid proteins (Non-Immunoglobulin) examples include, but are not limited to, amyloid-Related apoprotein (apoSAA1), AA (FMF) (ASF), AA (TH) (AS), serum amyloid P component (9.5 S 7α1-glycoprotein), and the like.

Among miscellaneous trace components examples include, but are not limited to, varcinoembryonic antigen, angiotensinogen, and the like.

In an embodiment, the sensor 302 is configured to detect a spectral response 299 associated with a real-time change in one or more parameters associated with at least one biological sample 808 component (e.g., a cerebrospinal fluid component). Non-limiting examples of detectable cerebrospinal fluid components include adenosine deaminase, albumin, calcium, chloride, C-reactive protein, creatine kinase, creatinine, cystatin C, cytokines, glucose, hydrogencarbonate, immunoglobulin G, interleukins, lactate, lactate dehydrogenase, lipids, lymphocytes, monocytes, mononuclear cells, myelin basic protein, neuron-specific enolase, potassium, proteins, S-100 protein, small molecules, sodium, $β_2$-microglobulin, and the like.

In an embodiment, the sensor 302 is in optical communication along an optical path with at least one of the energy emitters 220. In an embodiment, one or more of the energy emitters 220 are configured to direct an in vivo generated pulsed energy stimulus along an optical path for a duration sufficient to interact with one or more regions within the biological subject 222 and for a duration sufficient for a portion of the in vivo generated pulsed energy stimulus to reach a portion of the sensor 302 that is in optical communication along the optical path. In an embodiment, one or more of the energy emitters 220 are configured to direct optical energy along an optical path for a duration sufficient to interact with one or more regions within the biological subject 222 and with at least a portion of the optical energy sensor 302. In an embodiment, one or more of the energy emitters 220 are configured to emit a pulsed optical energy stimulus along an optical path for a duration sufficient to interact with a sample received within the one or more fluid-flow passageways 110; such that a portion of the pulsed optical energy stimulus is directed to a portion of the sensor 302 that is in optical communication along the optical path.

As indicated in FIG. 3, in an embodiment, the at least one anti-microbial region 202 including at least one anti-microbial agent is configured to release the anti-microbial agent over time. In an embodiment, the anti-microbial agent includes a microbial tactic agent. In an embodiment, the microbial tactic agent includes at least one chemotactic agent. In an embodiment, the at least one microbial tactic agent includes at least one attractant or repellant surface property. In an embodiment, the repellant surface property is located proximate to a protected site 310. In an embodiment, the repellant surface property encircles a protected site 310. In an embodiment, the protected site 310 or the destructive site 305 includes at least one of a port 118, or sensor 302.

In an embodiment, the insertable device 102 comprises a body structure 104 having an outer surface 106 and an inner surface 108 defining one or more fluid-flow passageways 110; a plurality of anti-microbial regions 202 arranged in at least one pattern 109 (e.g., spatial pattern or temporal pattern), one or more of the anti-microbial regions 202 included on at least one of the outer surface 106 or the inner surface 108, or embedded in the body structure 104.

In an embodiment, the system 100 is configured to compare an input associated with at least one characteristic associated with a biological sample 808 proximate the insertable device 102 (e.g., received within one or more fluid-flow passageways 110, proximate (e.g., on or near) a surface of the body structure 104, or the like) to a database 258 of stored reference values, and to generate a response 299 based in part on the comparison. In an embodiment, the response 299 includes at least one of a visual representation, audio representation (e.g., alarm, audio waveform representation of a tissue region, or the like), haptic representation, or tactile representation (e.g., tactile diagram, tactile display, tactile graph, tactile interactive depiction, tactile model (e.g., multidimensional model of an infected tissue region, or the like), tactile pattern (e.g., refreshable Braille display), tactile-audio display, tactile-audio graph, or the like). In an embodiment, the response 299 includes generating at least one of a visual, audio, haptic, or tactile representation of biological sample 808 spectral information (e.g., biological fluid spectral information, tissue spectral information, fat spectral information, muscle spectral information, bone spectral information, blood component spectral information, biomarker spectral information, infectious agent spectral information, and the like). In an embodiment, the response 299 includes generating at least one of a visual, audio, haptic, or tactile representation of at least one physical or biochemical characteristic associated with a biological subject 222.

In an embodiment, the response 299 includes initiating one or more treatment protocols. In an embodiment, the response 299 includes activating one or more sterilization protocols. In an embodiment, the response 299 includes initiating at least one treatment regimen. In an embodiment, the response 299 includes delivering an energy stimulus. In an embodiment, the response 299 includes delivering an active agent (e.g., anti-microbial agent). In an embodiment, the response 299 includes concurrently or sequentially delivering an energy stimulus and an active agent (e.g., anti-microbial agent).

In an embodiment, the response 299 includes at least one of a response signal, a control signal, a change to a sterilizing stimulus parameter (e.g., an electrical sterilizing stimulus, electromagnetic sterilizing stimulus, acoustic sterilizing stimulus, or thermal sterilizing stimulus), or the like. In an embodiment, the response 299 includes at least one of a change in an excitation intensity, change in an excitation frequency, change in an excitation pulse frequency, change in an excitation pulse ratio, change in an excitation pulse intensity, change in an excitation pulse duration time, change in an excitation pulse repetition rate, or the like.

In an embodiment, the response 299 includes at least one of activating an authorization protocol 300, activating an authentication protocol 301, activating a software update protocol 333, activating a data transfer protocol 303, or activating an infection sterilization diagnostic protocol 304. In an embodiment, the response 299 includes sending information associated with at least one of an authentication protocol 301, authorization protocol 300, delivery protocol 305, activation protocol 306, encryption protocol 307, or 308 decryption protocol.

In an embodiment, the system 100 is configured to compare an input associated with a biological subject 222 to a database 258 of stored reference values, and to generate a response 299 based in part on the comparison. In an embodiment, the system 100 is configured to compare an output of one or more of the plurality of logic components and to determine at least one parameter associated with a cluster centroid deviation derived from the comparison. In an embodiment, the system 100 is configured to compare a measurand associated with the biological subject 222 to a threshold value associated with a spectral model and to generate a response 299 based on the comparison. In an embodiment, the system 100 is configured to generate the response 299 based on the comparison of a measurand that modulates with a detected heart beat of the biological subject 222 to a target value associated with a spectral model.

In an embodiment, the system 100 is configured to compare the measurand associated with the biological subject 222 to the threshold value associated with a spectral model and to generate a real-time estimation of an infection state based on the comparison. In an embodiment, the system 100 is configured to compare an input associated with at least one characteristic associated with, for example, a biological sample proximate an insertable device 102 to a database 258 of stored reference values, and to generate a response 299 based in part on the comparison.

Figure 7:
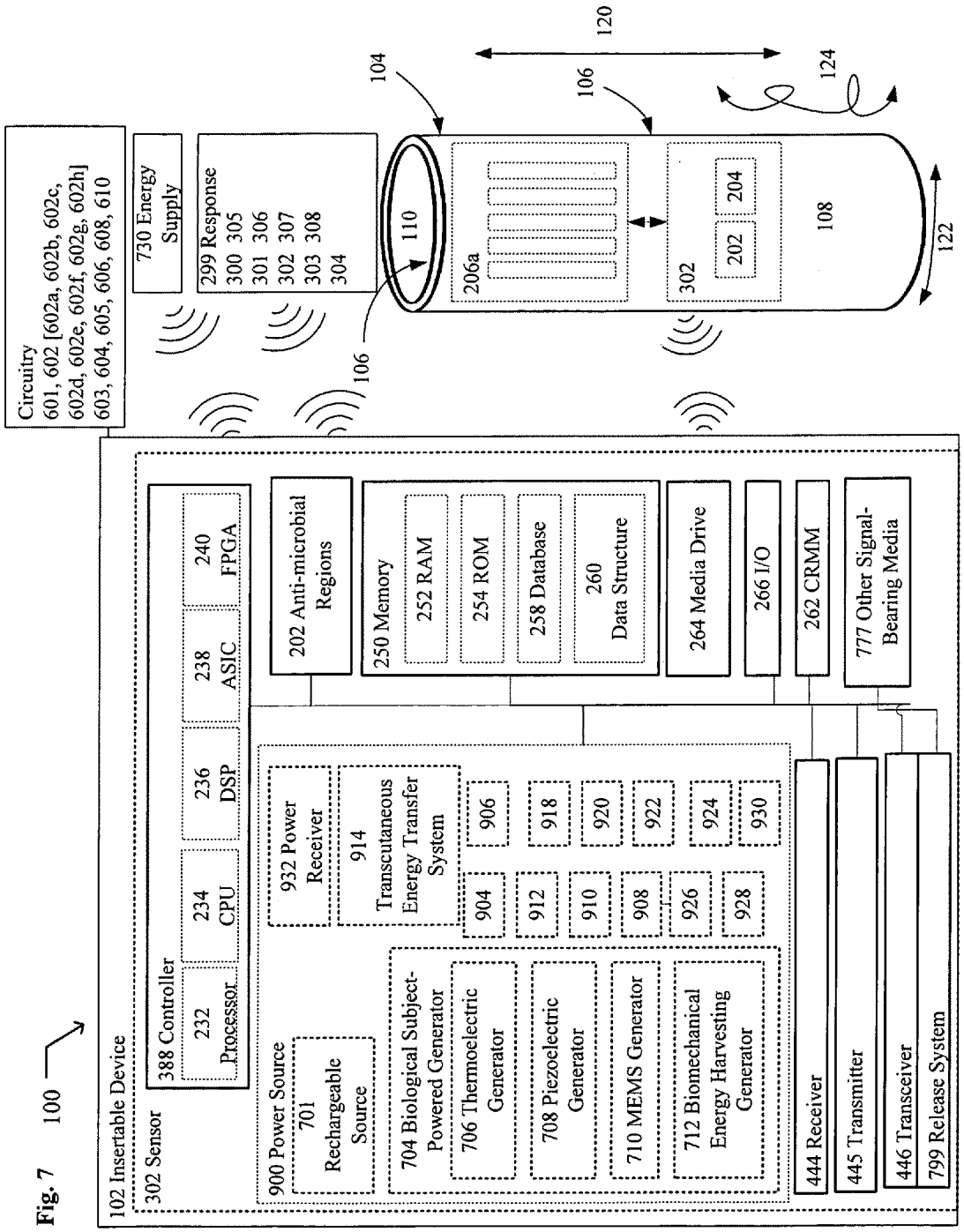
FIG. 7 illustrates a particular embodiment of a device in an embodiment of a system disclosed herein.

As described in FIG. 7, the system 100 can include, among other things, one or more data structures (e.g., physical data structures) 260. In an embodiment, a data structure 260 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. The system 100 can include, among other things, at least one of inflammation indication parameter data, infection indication parameter data, diseased tissue indication parameter data, or the like configured as a data structure 260. In an embodiment, a data structure 260 includes information associated with least one parameter associated with a cytokine plasma concentration or an acute phase protein plasma concentration. In an embodiment, a data structure 260 includes information associated with a disease state of a biological subject 222. In an embodiment, a data structure 260 includes measurement data. In an embodiment, the computing device 230 includes a processor 232 configured to execute instructions, and a memory 250 that stores instructions configured to cause the processor 232 to generate a second response from information encoded in a data structure 260.

In an embodiment, an insertable device 102 includes: a body structure 104 having an outer surface 106 and an inner surface 108 defining one or more fluid-flow passageways 110; at least one anti-microbial region 202 configured to deliver at least one anti-microbial agent to one or more areas of at least one of the outer surface 106, the inner surface 108 or embedded in the internal body structure 104; a sensor 302 configured to detect at least one microbial component proximate at least one of the outer surface 106 or the inner surface 108 of the body structure 104; and one or more computer-readable memory media 262 having microbial marker information configured as a data structure 260, the data structure 260 including a characteristic information section having characteristic microbial information representative of the presence of at least one microorganism proximate at least one of the outer surface 106 or the inner surface 108 of the body structure 104, or the interior of the fluid-flow passageway 110.

In an embodiment, the at least one sensor 302 is operably associated with at least one of the anti-microbial regions 202. In an embodiment, the at least one sensor 302 is configured to detect the presence of at least one microorganism proximate at least one of the inner surface 108 or the outer surface 106 of the one or more fluid-flow passageways 110. In an embodiment, the at least one sensor 302 is configured to detect the presence of at least one microorganism within the one or more fluid-flow passageways 110 based on one or more flow characteristics. In an embodiment, the at least one sensor 302 is configured to detect a location associated with the presence of at least one microorganism. In an embodiment, the at least one sensor 302 is configured to detect at least one microbial component. In an embodiment, the at least one sensor 302 includes a microbial component capture layer. In an embodiment, the microbial capture layer includes an array of different binding molecules that specifically bind one or more components of at least one microorganism.

The system 100 can include, among other things, one or more computer-readable memory media (CRMM) 262 having biofilm marker information configured as a data structure 260. In an embodiment, the data structure 260 includes a characteristic information section having characteristic microbial component information representative of the presence of at least one microorganism proximate at least one of the outer surface 106 or the inner surface 108 of the body structure 104. In an embodiment, the data structure 260 includes infection marker information. In an embodiment, the data structure 260 includes biofilm marker information. In an embodiment, the data structure 260 includes biological mass information associated with the presence of at least one microorganism proximate at least one of the inner surface 108 or the outer surface 106 of the body structure 104. In an embodiment, the data structure 260 includes a characteristic information section having characteristic microbial metabolic information associated with the presence of at least one microorganism proximate at least one of the inner surface 108, or the outer surface 106 of the body structure 104. In an embodiment, the data structure 260 includes a characteristic information section having characteristic cell surface information associated with the presence of at least one microorganism proximate at least one of the inner surface 108, or the outer surface 106 of the body structure 104.

In an embodiment, the data structure 260 includes a characteristic information component including metabolite information associated with a microorganism presence. In an embodiment, the data structure 260 includes a characteristic information component including temporal metabolite information or spatial metabolite information associated with a microorganism presence. In an embodiment, the data structure 260 includes a characteristic information component including oxygen concentration gradient information associated with a microorganism presence. In an embodiment, the data structure 260 includes a characteristic information component including pH information associated with a microorganism presence. In an embodiment, the data structure 260 includes a characteristic information component including nutrient information associated with a microorganism presence. In an embodiment, the data structure 260 includes a characteristic information component including spectral information associate with a biofilm-specific tag.

In an embodiment, the data structure 260 includes a characteristic information component including optical density information. In an embodiment, the data structure 260 includes a characteristic information component including opacity information. In an embodiment, the data structure 260 includes a characteristic information component including refractivity information. In an embodiment, the data structure 260 includes a characteristic information component including characteristic infection marker spectral information. In an embodiment, the data structure 260 includes a characteristic information component including characteristic infective stress marker spectral information. In an embodiment, the data structure 260 includes a characteristic information component including characteristic sepsis maker spectral information.

In an embodiment, the data structure 260 includes at least one of psychosis state marker information, psychosis trait marker information, or psychosis indication information. In an embodiment, the data structure 260 includes at least one of psychosis state indication information, psychosis trait indication information, or predisposition for a psychosis indication information. In an embodiment, the data structure 260 includes at least one of infection indication information, inflammation indication information, diseased state indication information, or diseased tissue indication information.

In an embodiment, a data structure 260 includes biological sample spectral information. In an embodiment, the data structure 260 includes one or more heuristically determined parameters associated with at least one in vivo or in vitro determined metric. For example, information associated with a biological sample 808 can be determined by one or more in vivo or in vitro technologies or methodologies including, for example, high-resolution proton magnetic resonance spectroscopy, nanoprobe nuclear magnetic resonance spectroscopy, in vivo micro-dialysis, flow cytometry, or the like. Non-limiting examples of heuristics include a heuristic protocol, heuristic algorithm, threshold information, a threshold level, a target parameter, or the like. The system 100 can include, among other things, a means 276 for generating one or more heuristically determined parameters associated with at least one in vivo or in vitro determined metric including one or more data structures 260. The system 100 can include, among other things, a means 460 for generating a response 299 based on a comparison, of a detected at least one of an emitted energy and a remitted energy to at least one heuristically determined parameter, including one or more data structures 260.

In an embodiment, a data structure 260 includes one or more heuristics. In an embodiment, the one or more heuristics include a heuristic for determining a rate of change associated with at least one physical parameter associated with a biological sample 808. For example, in an embodiment, the one or more heuristics include a heuristic for determining the presence of an infectious agent. In an embodiment, the one or more heuristics include a heuristic for determining at least one dimension of an infected tissue region. In an embodiment, the one or more heuristics include a heuristic for determining a location of an infection. In an embodiment, the one or more heuristics include a heuristic for determining a rate of change associated with a biochemical marker within the one or more fluid-flow passageways 110.

In an embodiment, the one or more heuristics include a heuristic for determining a biochemical marker aggregation rate. In an embodiment, the one or more heuristics include a heuristic for determining a type of biochemical marker. In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, a data structure 260 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, ahematological parameter, a pH level, or the like. The system 100 can include, among other things, at least one of inflammation indication parameter data, infection indication parameter data, diseased tissue indication parameter data, or the like configured as a data structure 260. In an embodiment, a data structure 260 includes information associated with least one parameter associated with a cytokine plasma concentration or an acute phase protein plasma concentration. In an embodiment, a data structure 260 includes information associated with a disease state of a biological subject 222. In an embodiment, a data structure 260 includes measurement data.

The system 100 can include, among other things, one or more computer-readable media drives 264, interface sockets, Universal Serial Bus (USB) ports, memory card slots, and the like, and one or more input/output components 266 such as, for example, a graphical user interface 268, a display, a keyboard 270, a keypad, a trackball, a joystick, a touch-screen, a mouse, a switch, a dial, and the like, and any other peripheral device. In an embodiment, the system 100 includes one or more user input/output components 266 that operably couple to at least one computing device 230 to control (electrical, electromechanical, software-implemented, firmware-implemented, or other control, or combinations thereof) at least one parameter associated with the energy delivery associated with one or more of the anti-microbial regions 202.

In an embodiment, the system 100 includes one or more instructions that when executed on at least one computing device 230 cause the computing device 230 to generate at least one output to a user. In an embodiment, the at least one computing device 230 is remote to the insertable device. In an embodiment, the at least one output includes at least one of a treatment protocol, identification of a detected microorganism, status of the insertable device 102, or location of a detected microorganism. In an embodiment, the user includes at least one entity 555. In an embodiment, the at least one entity 555 includes at least one person or computer. In an embodiment, the at least one output includes output to a user readable display. In an embodiment, the user readable display is operably coupled to the insertable device 102. In an embodiment, the at least one output is in real-time. In an embodiment, the at least, one output is associated with historical information. In an embodiment, the user readable display includes a human readable display. In an embodiment, the user readable display includes one or more active displays. In an embodiment, the user readable display includes one or more passive displays. In an embodiment, the user readable display includes one or more of a numeric format, graphical format, or audio format.

In an embodiment, the attractant surface property is located distal to a protected site 310. In an embodiment, the attractant surface property is configured to direct one or more microorganisms away from a protected site 310. In an embodiment, the attractant surface property is configured to direct one or more microorganisms toward a destructive site 305. In an embodiment, the at least one microbial tactic agent includes at least one chemoattractant or chemorepellant. In an embodiment, the chemoattractant includes at least one of a carbohydrate, glycopeptides, proteoglycan, glycolipid, enzyme, lipopolysaccharide, lipid, peptide, polypeptide, protein, organic, or inorganic molecule. In an embodiment, the at least one chemoattractant includes at least one of glucose, formyl peptide, or chemokine. In an embodiment, the at least one chemorepellent includes at least one of a carbohydrate, glycopeptides, proteoglycan, glycolipid, lipopolysaccharide, enzyme, lipid, peptide, polypeptide, protein, organic, or inorganic molecule. In an embodiment, the at least one chemorepellent includes at least one of a hormone, oxide, peroxide, alcohol, or aldehyde. In an embodiment, the at least one chemorepellent includes at least one of an inorganic salt, amino acid, or chemokine. In an embodiment, the at least one microbial destructive site 305 includes at least one anti-microbial agent.

In an embodiment, the insertable device 102 includes at least one microbial destructive site 305. In an embodiment, at least one of the anti-microbial regions 202 includes at least one gradient 312 (such as a temporal gradient, spatial gradient, or chemical gradient). In an embodiment, at least one of the anti-microbial regions 202 includes at least one gradient 312 of self-assembled monolayers including at least one alkanethiol. In an embodiment, the at least one alkanethiol includes $HS(CH_2)_{11}(OCH_2CH_2)_3OH$.

In an embodiment, the insertable device 102 includes one or more power sources 900. In an embodiment, the power source 900 is electromagnetically, magnetically, acoustically, optically, ultrasonically, inductively, electrically, or capacitively coupled to the body structure 104. In an embodiment, the power source 900 is coupled to at least one of the anti-microbial regions 202, a computing device 230, or a sensor 302. Non-limiting examples of power sources 900 include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources 900 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, and the like. In an embodiment, the power source 900 includes at least one rechargeable power source 701. In an embodiment, the power source 900 is carried by the catheter device 102. In an embodiment, the catheter device 102 can include, among other things, at least one of a battery, a capacitor, and a mechanical energy store (e.g., a spring, a flywheel, or the like). In an embodiment, the power source 900 comprises at least one rechargeable power source 701. In an embodiment, the insertable device 102 is configured to receive power from an ex vivo power source. In an embodiment, the power receiver 701 is configured to receive power from an in vivo power source (e.g., thermoelectric generator, piezoelectric generator, electromechanical systems generator, alternating current nanogenerator, biomechanical-energy harvesting generator, etc.).

The system 100 can include, among other things, a plurality of selectively actuatable anti-microbial regions 202a. For example, in an embodiment, the catheter device 102 includes a plurality of selectively actuatable anti-microbial regions 202a that define one or more portions of the body structure 104. In an embodiment, at least a portion of the outer surface 106 of the body structure 104 includes one or more of the plurality of selectively actuatable anti-microbial regions 202a. In an embodiment, at least a portion of the inner surface 108 of the body structure 104 includes one or more of the plurality of selectively actuatable anti-microbial regions 202a.

In an embodiment, the insertable device 102 comprises a body structure 104 having an outer surface 106 and an inner surface 108 defining one or more fluid-flow passageways 110, the body structure 104 having a plurality of actuatable anti-microbial regions 202a that are selectively actuatable between at least a first actuatable state and a second actuatable state; and one or more sensors 302 configured to detect at least one microbial component in a biological sample 808 proximate at least one of the outer surface 106 or the inner surface 108 of the body structure 104. In an embodiment, the one or more sensors 302 are configured to detect one or more microorganisms present proximate to the body structure 104.

In an embodiment, the insertable device 102 comprises a body structure 104 defining one or more fluid-flow passageways 110; the body structure 104 including one or more selectively actuatable anti-microbial regions 202a including at least one anti-microbial agent, the one or more selectively actuatable anti-microbial regions 202a configured to direct at least one anti-microbial agent to one or more areas of at least one of the outer surface 106 of the body structure 104, the inner surface 108 of the body structure 104, or embedded in the internal body structure 104; and one or more sensors 302 configured to detect at least one microbial component proximate one or more areas of the body structure 104.

In an embodiment, an insertable device 102 comprises a body structure 104 having an outer surface 106 and an inner surface 108 defining one or more fluid-flow passageways 110; at least one actively controllable anti-microbial nanostructure 206a projecting from at least one of the outer surface 106, or the inner surface 108, and at least one sensor 302 configured to detect one or more microorganisms present proximate the body structure 104.

In an embodiment, an anti-microbial region 202 is configured to provide at least one of an energy stimulus 350 (e.g., electromagnetic energy stimulus 350a, electrical energy stimulus 350b, acoustic energy stimulus 350c, or thermal energy stimulus 350d). In an embodiment, the plurality of selectively actuatable anti-microbial regions 202a are configured to deliver at least one of a spatially collimated energy stimulus 350e; spatially focused energy stimulus 350f; temporally patterned energy stimulus 350g; or spaced-apart patterned energy stimulus 350h.

As shown in FIG. 8, the system 100 can include, among other things, one or more databases 258. In an embodiment, a database 258 includes spectral information configured a physical data structure 790. In an embodiment, a database 258 includes at least one of inflammation indication parameter data 776a, infection indication parameter data 776b, diseased tissue indication parameter data 776c, or the like. In an embodiment, a database 258 includes at least one of absorption coefficient data 776d, extinction coefficient data 776e, scattering coefficient data 776f, or the like. In an embodiment, a database 258 includes at least one of stored reference data 776g (e.g., infection marker data, inflammation marker data, infective stress marker data, systemic inflammatory response syndrome data, sepsis marker data, or the like).

In an embodiment, a database 258 includes information associated with a disease state of a biological subject 222. In an embodiment, a database 258 includes measurement data. In an embodiment, a database 258 includes at least one of psychosis state indication information, psychosis trait indication information, or predisposition for a psychosis indication information. In an embodiment, a database 258 includes at least one of infection indication information, inflammation indication information, diseased state indication information, or diseased tissue indication information. In an embodiment, a database 258 includes at least one of cryptographic protocol information, regulatory compliance protocol information (e.g., FDA regulatory compliance protocol information, or the like), regulatory use protocol information, authentication protocol information, authorization protocol information, delivery regimen protocol information, activation protocol information, encryption protocol information, decryption protocol information, treatment protocol information, or the like. In an embodiment, a database 258 includes at least one of energy stimulus control delivery information, energy emitter 220 control information, power control information, anti-microbial region 202 control information, or the like. In an embodiment, a database 258 includes at least one spatial or temporal information associated with anti-microbial region activation, anti-microbial agent delivery, anti-microbial protruding element actuation, or other anti-microbial surface property 204 employed.

In an embodiment, the system 100 is configured to compare an input associated with at least one characteristic associated with a biological subject 222 to a database 258 of stored reference values, and to generate a response 299 based in part on the comparison. In an embodiment, the system 100 is configured to compare an input associated with at least one physiological characteristic associated with a biological subject 222 to a database 258 of stored reference values, and to generate a response 299 based in part on the comparison.

In an embodiment, the at least one characteristic associated with a biological subject 222 includes real-time detected information associated with a biological sample 808 (e.g., tissue, biological fluid, infections agent, biomarker, or the like) proximate an insertable device 102. In an embodiment, the at least one characteristic associated with a biological subject 222 includes a measurand detected at a plurality of time intervals. In an embodiment, the at least one characteristic associated with a biological subject 222 includes real-time detected information associated with a biological sample 808 (e.g., a biological fluid) received within one or more fluid-flow passageways 110.

Referring again to FIG. 3, the system 100 can include, among other things, a plurality of actuatable anti-microbial regions 202a that are selectively actuatable between at least a first anti-microbial state and a second anti-microbial state. For example, in an embodiment, an insertable device 102 includes a body structure 104 having an outer surface 106 and an inner surface 108 defining one or more fluid-flow passageways 110; and one or more actuatable anti-microbial regions 202a configured to direct at least one anti-microbial agent to one or more anti-microbial regions 202 proximate at least one of the outer surface 106 or inner surface 108 of the body structure 104. In an embodiment, the one or more actuatable anti-microbial regions 202a are configured to alter at least one anti-microbial property 204 in response 299 to detection of at least one microorganism. In an embodiment, the one or more actuatable anti-microbial regions 202a are selectively actuatable between at least a first anti-microbial state and a second anti-microbial state. In an embodiment, a plurality of actuatable anti-microbial regions 202a are configured to actuate between the at least first anti-microbial state and the second anti-microbial state in response 299 to a detected microorganism. In another example, the anti-microbial nanostructure 206a is actively controllable. In an embodiment, the at least one actively controllable anti-microbial nanostructure 206a is configured for cyclical activation. In an embodiment, the cyclical activation includes cyclical activation of a spaced-apart distribution or a temporally patterned distribution. In an embodiment, the at least one actively controllable anti-microbial nanostructure 206a is configured for patterned activation (e.g., spatial or temporal pattern). In an embodiment, the at least one actively controllable anti-microbial nanostructure 206a is configured to be randomly or nonrandomly activated. In another example, the system 100 includes an actively controllable circuit configured to deliver in vivo an external stimulus to one or more anti-microbial regions 202 of the body structure 104 for a character and time sufficient to actuate from the first anti-microbial state to the second anti-microbial state. In an embodiment, one or more actuatable anti-microbial regions are configured to actuate at least one of electrochemically, electromagnetically, photochemically, acoustically, magnetically, or electro-optically between the first actuatable state and second actuatable state. In an embodiment, the one or more actuatable anti-microbial regions 202a are controllably actuatable between an active state and a passive state. In an embodiment, the one or more actuatable anti-microbial regions 202a are controllably actuatable between an active state and a passive state based at least in part on detected information from one or more sensors 302. In an embodiment, one or more actuatable anti-microbial regions 202a are selectively actuatable between at least one first actuatable state and a second actuatable state via at least one switch 118.

With continued reference to FIG. 3, the system 100 can include, among other things, at least one computing device 230 including one or more processors (e.g., a microprocessors), central processing units (CPUs) 234, a digital signal processors (DSPs) 236, an application-specific integrated circuits (ASICs) 238, a field programmable gate arrays (FPGAs) 240, or other controllers 388, or the like, or any combinations thereof, and can include discrete digital or analog circuit elements or electronics, or combinations thereof. The system 100 can include, among other things, one or more field programmable gate arrays having a plurality of programmable logic components. The system 100 can include, among other things, one or more an application specific integrated circuits having a plurality of predefined logic components.

In an embodiment, the processor 232 is configured to control activation or actuation of at least one anti-microbial region 202. In an embodiment, the processor 232 is configured to be responsive to at least one sensor 302 of the system 100. In an embodiment the computing device 230 comprises at least one controller 388. In an embodiment, at least one computing device 230 is operably coupled to one or more anti-microbial regions 202. In an embodiment, one or more of the anti-microbial regions 202 are configured for selective actuation via one or more computing devices 230. In an embodiment, the controller 388 is configured to actuate one or more independently addressable anti-microbial regions 202b. In an embodiment, the controller 388 is configured to actuate at least one or more independently addressable anti-microbial regions 202b in response to detected information from at least one sensor 302. In an embodiment, the controller 388 is configured to actuate one or more independently addressable anti-microbial regions 202b in response to at least one of a scheduled program, external command, history of a previous presence of a microorganism, expected presence of microorganisms, expected presence of a particular microorganism, or history of a previous actuation. In an embodiment, the system 100 includes actuating means (e.g., switch, etc.) for concurrently or sequentially actuating two or more of the plurality of independently addressable anti-microbial regions 202b determined to have a microorganism present proximate to the same.

Figure 6:
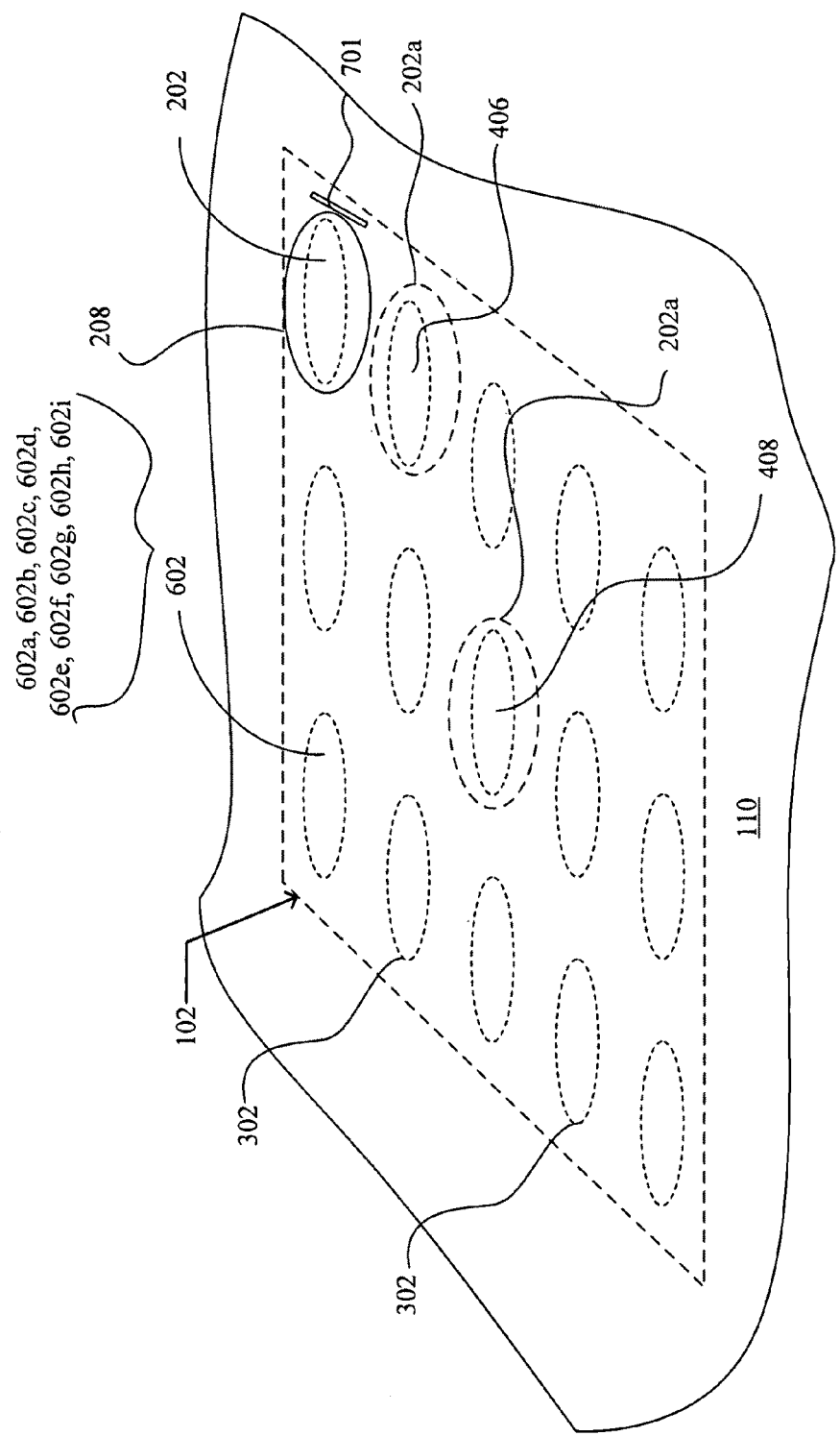
FIG. 6 illustrates a particular embodiment of a component of a device disclosed herein.

The system 100 can include, among other things, a plurality of independently addressable anti-microbial regions 202b. In an embodiment, the plurality of independently addressable anti-microbial regions 202b is disposed along a longitudinal axis of the insertable device 102. In an embodiment, the independently addressable anti-microbial regions 202b are configured to direct an anti-microbial property 204 to one or more regions proximate at least one of the outer surface 106 or the inner surface 108 of the body structure 104. In an embodiment, the plurality of independently addressable anti-microbial regions 202b includes at least one actuatable anti-microbial property 204. In an embodiment, the system 100 further includes circuitry 602 (as shown in FIG. 6), configured for determining the presence of at least one microorganism proximate at least one of a plurality of independently addressable anti-microbial regions 202b of the body structure 104. In an embodiment, the at least one actuatable anti-microbial property 204 is configured to be actuated by at least one of a program, or the presence of at least one microorganism.

In an embodiment, the system 100 includes actuating means 272 for concurrently or sequentially actuating two or more of the anti-microbial regions 202. In an embodiment, the actuating means 272 includes one or more switches 218. In an embodiment, the one or more switches 218 are operably coupled to one or more computing devices 230. In an embodiment, the one or more switches 218 are configured to increase or decrease the release of at least one anti-microbial agent from the one or more selectively actuatable anti-microbial regions 202a.

In an embodiment, the one or more switches 218 include at least one acoustically active material 218g. In an embodiment, the one or more switches 218 include at least one of an electro-mechanical switch 218a, electrochemical switch 218b, electrical switch 218c, electro-optic switch 218d, acousto-optic switch 218e, or optical switch 218f.

In an embodiment, the actuating means 272 includes at least one computing device 230 operably coupled to one or more switches 218. In an embodiment, the actuating means 272 includes at least one optical antifuse. In an embodiment, the actuating means 272 includes a movable component having an optical energy reflecting substrate. In an embodiment, the movable component is actuated by an electromagnetic energy stimulus generated by one or more energy emitters 220, and configured to guide an optical energy along at least one of the anti-microbial regions 202 when actuated. In an embodiment, the actuating means 272 is configured to concurrently or sequentially actuate two or more of the independently addressable energy or selectively actuatable anti-microbial regions 202a.

Figure 5A:
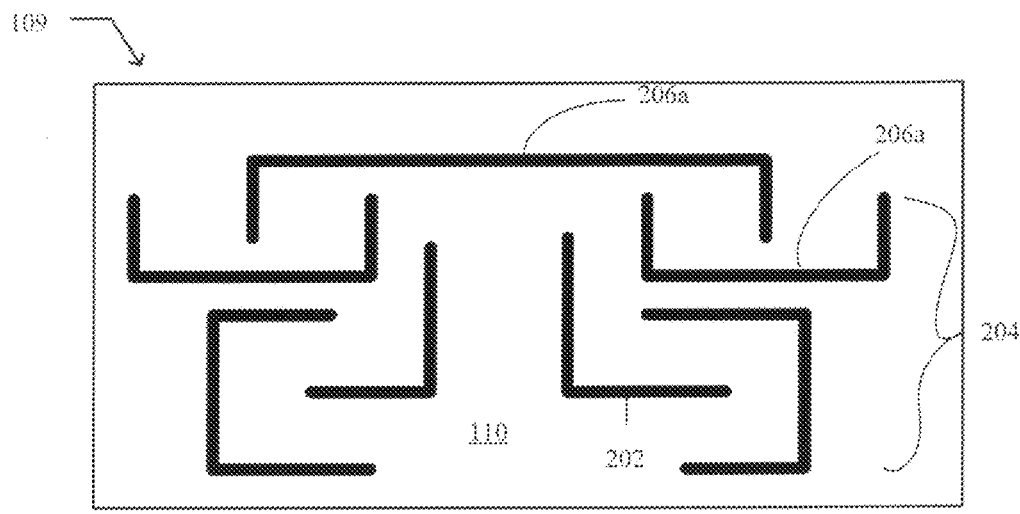
FIG. 5A illustrates a close up of a particular embodiment of a component of a device disclosed herein.
Figure 5B:
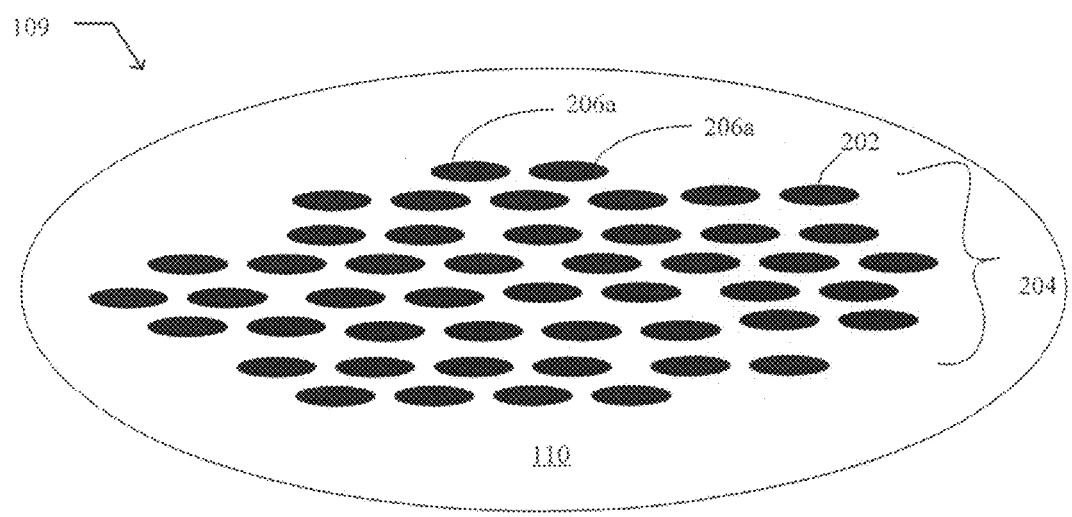
FIG. 5B illustrates a close up of a particular embodiment of a component of a device disclosed herein.

Anti-microbial regions 202 forming part of the insertable device 102, can take a variety of forms, configurations, and geometrical patterns including for example, but not limited to, a one-, two-, or three-dimensional arrays, a pattern 109 comprising concentric geometrical shapes, a pattern comprising rectangles, squares, circles, triangles, polygons, any regular or irregular shapes, or the like, or any combination thereof (as shown in FIGS. 5A and 5B).

In an embodiment, at least one of the actuatable anti-microbial regions 202a includes at least one anti-microbial reservoir 208 actuatable by the presence of at least one microorganism proximate at least one of the actuatable anti-microbial regions 202a. In an embodiment, the one or more actuatable anti-microbial regions 202a are configured to deliver at least one anti-microbial agent in a spatially patterned distribution. In an embodiment, the one or more actuatable anti-microbial regions 202a are configured to deliver at least one anti-microbial agent in a temporally patterned distribution.

In an embodiment, the actively controllable anti-microbial nanostructure 206a is movable. In an embodiment, the movable anti-microbial nanostructure 206a includes at least one micro-electromechanical structure. In an embodiment, the movable anti-microbial nanostructure 206a includes at least one electroactive polymer. In an embodiment, the movable anti-microbial nanostructure 206a is configured to deflect one or more microorganisms. In an embodiment, the movable anti-microbial nanostructure 206a is configured to extend or contract. In an embodiment, the movable anti-microbial nanostructure 206a is configured to increase or decrease the spacing between two or more nanostructures 206a. In an embodiment, the movable anti-microbial nanostructure 206a is configured to move in at least one of rotation, torsion, compression, axial, radial, or lateral movement.

In an embodiment, the distance between at least two anti-microbial nanostructures 206a is less than or equal to about 0.01 µm, about 0.05 µm, about 1.0 µm, about 2.0 µm, about 3.0 µm, about 4.0 µm, about 5.0 µm, about 6.0 µm, about 7.0 µm, about 8.0 µm, about 9.0 µm, about 10.0 µm, about 11.0 µm, about 12.0 µm, about 13.0 µm, about 14.0 µm, about 15.0 µm, about 16.0 µm, about 17.0 µm, about 18.0 µm, about 19.0 µm, about 20.0 µm.

In an embodiment, the actively controllable anti-microbial nanostructure 206a includes at least one of silver, copper, rubidium, platinum, gold, nickel, lead, cobalt, potassium, zinc, bismuth, tin, cadmium, chromium, aluminum, calcium, mercury, thallium, gallium, strontium, barium, lithium, magnesium, oxides, hydroxides, or salts thereof. In an embodiment, the at least one actively controllable anti-microbial nanostructure 206a includes at least one of graphene, black silica, hydrogenated diamond, zirconium, or diamond. In an embodiment, the at least one actively controllable anti-microbial nanostructure 206a includes at least one of polyvinyl chloride, polyester, polyethylene, polypropylene, ethylene, polyolefin, acrylic, polycarbonate, or silicone, or homopolymers or copolymers thereof. In an embodiment, the at least one actively controllable anti-microbial nanostructure 206a includes at least one of polytetrafluoroethylene or polydimethylsiloxane elastomer.

In an embodiment, the at least one actively controllable anti-microbial nanostructure 206a includes a plurality of nanostructures 206a configured in at least one spatial pattern. In an embodiment, the at least one spatial or temporal pattern 109 includes at least one of a repeating pattern, non-repeating pattern, or partially repeating pattern. In an embodiment, the at least one spatial pattern is derived from information relating to the type of microorganism expected to be present proximate the body structure 104.

In an embodiment, the spacing between at least two actively controllable anti-microbial nanostructures 206a includes a space of at least about 1 µm, at least about 5 µm, at least about 10 µm, at least about 15 µm, at least about 20 µm, at least about 25 at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 95 µm, at least about 100 µm, at least about 110 µm, at least about 120 µm, at least about 130 µm, at least about 150 µm, at least about 160 µm, at least about 170 µm, at least about 180 µm, at least about 190 µm, at least about 200 µm, or any space therebetween or greater than.

In an embodiment, the diameter of the at least one actively controllable anti-microbial nanostructure 206a is at least about 0.5 nm, at least about 1 nm, at least about 5 nm, at least about 10 nm, at least about 15 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 110 nm, at least about 120 nm, at least about 130 nm, at least about 150 nm, at least about 160 nm, at least about 170 nm, at least about 180 nm, at least about 190 nm, at least about 200 nm, or any value therebetween or greater.

In an embodiment, the spacing between components of an anti-microbial region 202 is such that a single microorganism can fit (or complete an electrical circuit) therein.

In an embodiment, the depth of the at least one actively controllable anti-microbial nanostructure 206a is at least about 0.25 µm, at least about 0.5 µm, at least about 1 µm, at least about 5 µm, at least about 10 µm, at least about 15 µm, at least about 20 µm, at least about 25 µm, at least about 30 µm, at least about 35 µm, at least about 40 µm, at least about 45 µm, at least about 50 µm, at least about 55 µm, at least about 60 µm, at least about 65 µm, at least about 70 µm, at least about 75 µm, at least about 80 µm, at least about 85 µm, at least about 90 µm, at least about 95 µm, at least about 100 µm, at least about 110 µm, at least about 120 µm, at least about 130 µm, at least about 150 µm, at least about 160 µm, at least about 170 µm, at least about 180 µm, at least about 190 µm, at least about 200 µm, or any value therebetween or greater.

In an embodiment, the actively controllable anti-microbial nanostructure 206a includes at least one electrically actuatable contact. In an embodiment, the actively controllable anti-microbial nanostructure 206a includes at least two electrically actuatable contacts. In an embodiment, the at least two electrically actuatable contacts are differentially chargeable. In an embodiment, the at least two electrically actuatable contacts are arranged in a static charge pattern. In an embodiment, the at least two electrically actuatable contacts are arranged in a dynamic charge pattern. In an embodiment, the at least one electrically actuatable contact can be locally charged based on detection of at least one microbe present proximate the at least one electrically actuatable contact. In an embodiment, the at least two electrically actuatable contacts are spaced such that the presence of a microbe conducts current via the at least two electrically actuatable contacts. In an embodiment, the at least one anti-microbial nanostructure 206a includes at least one photoactive material. In an embodiment, the photoactive material includes at least one photocatalyst. In an embodiment, the photoactive material includes titanium dioxide.

In an embodiment, the plurality of actuatable anti-microbial regions 202a are actively controllable, via one or more computing device 230, between the at least first anti-microbial state and the second anti-microbial state.

The system 100 can include, among other things, one or more actively controllable reflective or transmissive components configured to outwardly transmit or internally reflect an energy stimulus propagated therethrough. In an embodiment, an insertable device 102 includes one or more actively controllable reflective or transmissive components configured to outwardly transmit or internally reflect an energy stimulus propagated therethrough.

In an embodiment, one or more actuatable anti-microbial regions 202a are selectively actuatable between at least a first transmissive state and a second transmissive state via at least one acoustically active material. In an embodiment, one or more of plurality of actuatable anti-microbial regions 202a are selectively actuatable between at least a first transmissive state and a second transmissive state via at least one electro-mechanical switch. In an embodiment, one or more of plurality of actuatable anti-microbial regions 202a are selectively actuatable between at least a first transmissive state and a second transmissive state via at least one electro-optic switch. In an embodiment, one or more of the actuatable anti-microbial regions 202a are selectively actuatable between at least a first transmissive state and a second transmissive state via at least one acousto-optic switch. In an embodiment, one or more of the actuatable anti-microbial regions 202a are selectively actuatable between at least a first transmissive state and a second transmissive state via at least one optical switch.

The system 100 can include, among other things, a computing device 230 operably coupled to one or more of the actuatable anti-microbial regions 202a. In an embodiment, the controller 388 is configured to cause a change between an at least first anti-microbial state and a second anti-microbial state based on detected information from the one or more sensors 302. In an embodiment, the controller 388 is programmable.

In an embodiment, the insertable device 102 includes one or more computing devices 230 operably coupled to one or more of the actuatable anti-microbial regions 202a. In an embodiment, at least one of the computing devices 230 is configured to cause a change between the at least a first anti-microbial state and a second anti-microbial state based on detected information from the one or more sensors 302. In an embodiment, at least one computing device 230 is configured to actuate one or more of the actuatable anti-microbial regions 202a between the at least first anti-microbial state and the second anti-microbial state based on a comparison of a detected characteristic associated with the biological sample 808 proximate at least one of the outer surface 106 or the inner surface 108 of the body structure 104. For example, in an embodiment, the one or more sensors 302 are configured to detect at least one characteristic associated with one or more anti-microbial regions 202 proximate at least one of the outer surface 106 or the inner surface 108 of the body structure 104; and at least one controller 388 operably coupled to one or more of the spaced-apart release ports 118a and configured to actuate one or more of the spaced-apart release ports 118a between an anti-microbial agent discharge state and an anti-microbial agent retention state based on a comparison of a detected characteristic to stored reference data.

For example, in an embodiment the anti-microbial region 202 affects adhesion of, for example, bacteria, or other microorganisms, and biofilm formation by changing at least one of a functional, structural, and chemical characteristic of a surface on an insertable device 102. For example, adhesion may be affected by changing surface morphology. It may also be possible to modulate the adhesion and biofilm formation by modulating at least one of the functional, structural, or chemical characteristics of a surface on an insertable device 102. By modulating at least one of a functional, structural, or chemical characteristic of a surface on an insertable device 102, the transport properties of a fluid exposed to the surface on an insertable device 102 may also be affected.

In an embodiment, at least one of the fluid-flow passageways 110 includes one or more surface anti-microbial regions that are energetically actuatable between a substantially hydrophobic state and a substantially hydrophilic state. In an embodiment, the one or more fluid-flow passageways 110 includes a surface region that is energetically actuatable between at least a first hydrophilic state and a second hydrophilic state. In an embodiment, at least one of the fluid-flow passageways 110 includes a surface region that is energetically actuatable between a hydrophobic state and a hydrophilic state. In an embodiment, at least one of the fluid-flow passageways 110 includes a surface region having a material that is switchable between a zwitterionic state and a non-zwitterionic state.

In an embodiment, the one or more fluid-flow passageways 110 includes at least one of an anti-microbial coating. In an embodiment, at least one of the fluid-flow passageways 110 includes an anti-microbial coating. In an embodiment, at least one of the fluid-flow passageways 110 includes a surface region that is energetically actuatable between an anti-microbial state. In an embodiment, at least one anti-microbial coating is configured for time-release of at least one anti-microbial agent. In an embodiment, the coating includes at least one of an anti-microbial agent, electroactive polymer, petroleum jelly, silver gel, surfactant, alcohol gel, or other coating. In an embodiment, the coating includes at least one expandable material. In an embodiment the expandable material is actively controllable. In an embodiment, the expandable material is configured to physically dislocate at least one microorganism on at least one of the inner surface 108 or outer surface 106 of the body structure 104. In an embodiment, the at least one expandable material is configured to expand in at least one longitudinal or transverse motion.

In an embodiment, an insertable device 102 includes a body structure 104 having an outer surface 106 and an inner surface 108 defining one or more fluid-flow passageways 110; one or more anti-microbial regions 202 including at least one anti-microbial coating actuatable by the presence of at least one microorganism, and configured to actively elute at least one anti-microbial agent proximate to at least one of the outer surface 106 or the inner surface 108 of the body structure 104.

In an embodiment, an insertable device 102 includes a body structure 104 having an outer surface 106 and an inner surface 108 defining one or more fluid-flow passageways 110; one or more anti-microbial regions 202 including at least one anti-microbial reservoir 208 including at least one anti-microbial agent, the at least one anti-microbial reservoir 208 configured to deliver at least one anti-microbial agent proximate to at least one of the outer surface 106 or the inner surface 108 of the body structure 104.

In an embodiment, the body structure 104 includes one or more anti-microbial protruding elements 206 (e.g., nanostructure, microstructure, nanoscale pillar, nanoscale ridge, high aspect ratio nanofibrillar structure, nanoscale projection, nanoscale irregularity, nanoscale elongation, nanoscale valley, nanoscale trough, nanoscale spike (e.g., blunt tip spike, sharp tip spike, etc.), or the like) on at least one surface. In an embodiment, the at least one anti-microbial nanostructure 206a includes at least one surface portion that is energetically unstable. In an embodiment, the at least one anti-microbial nanostructure 206a includes at least a portion of a surface that is hydrophilic. In an embodiment, the at least one anti-microbial nanostructure 206a includes at least a portion of a surface that is hydrophobic.

In an embodiment, the anti-microbial protruding element 206 is produced by femtosecond laser pulses against a substrate. In an embodiment, the substrate includes at least one of a hydrophobic, superhydrophobic, or ultrahydrophobic substrate. In an embodiment, the substrate includes one or more of a metal, ceramic, glass, non-crystalline material, semiconductor, composite, or polymer. In an embodiment, the polymer includes a diarylethene. In an embodiment, the polymer includes at least one electrically conductive polymer. In an embodiment, the at least one electrically conductive polymer includes at least one dopant. In an embodiment, the at least one dopant includes at least one low surface energy dopant. In an embodiment, the at least one dopant includes perfluorooctanesulfonate. In an embodiment, the at least one electrically conductive polymer includes the at least one electrically conductive polymer includes at least one of polythiophene, poly(p-phenylene), poly(aniline), polyacetylene, poly(pyrrole), poly (N-methylpyrrole), poly (thiophene), poly(alkyl thiophene), poly(furan), poly(pyridine), poly(fluorene), poly(3-hexylthiophene), polynaphthalene, poly(p-phenylene sulfide), poly(azulene), polyacene, polyquinone,polystyrene sulfonate, polyethylenedioxythiophene, poly(p-phenylene), poly(p-phenylene vinylene), polysulfone, poly(pyridine), poly(quinoxaline), polyanthraquinone, poly(n-vinylcarbazole), poly(acene), or poly(heteroaromatic vinylene).

In an embodiment, the liquid-solid contact angle of the substrate is greater than about 0 degrees, greater than about 5 degrees, greater than about 10 degrees, greater than about 20 degrees, greater than about 30 degrees, greater than about 40 degrees, greater than about 50 degrees, greater than about 60 degrees, greater than about 70 degrees, greater than about 80 degrees, greater than about 90 degrees, greater than about 100 degrees, greater than about 105 degrees, greater than about 110 degrees, greater than about 120 degrees, greater than about 130 degrees, greater than about 140 degrees, greater than about 150 degrees, greater than about 160 degrees, greater than about 170 degrees, about 180 degrees, or any value therebetween.

In an embodiment, a plurality of nanostructures 206a includes at least two nanostructures 206a oriented parallel to each other. In an embodiment, a plurality of nanostructures 206a includes at least two nanostructures 206a oriented perpendicular to each other. In an embodiment, a plurality of nanostructures 206a includes at least two nanostructures 206a with at least one topographical pattern. In an embodiment, the plurality of anti-microbial nanostructures 206a includes at least two different anti-microbial nanostructures 206a. In an embodiment, the at least two different anti-microbial nanostructures 206a include at least one different spatial property or temporal property (e.g. wettability).

The wettability, or other surface properties can be controlled by altering the density of the protruding elements. See e.g., Spori et al., *Cassie-State Wetting Investigated by Means of a Hole-to-Pillar Density Gradient*, Langmuir, 2010, 26 (12), pp 9465-9473. In an embodiment, the anti-microbial nanostructure 206a is actuatable. In an embodiment, the at least one anti-microbial nanostructure 206a includes at least one of a rough surface or patterned surface. In an embodiment, the rough surface includes an engineered roughness index of from about 1 to about 100, wherein the roughness index includes the ratio of the actual surface area to the geometric surface area. In an embodiment, the at least one anti-microbial nanostructure 206a is configured to be actuated by at least partial degradation of at least one component of the body structure 104.

In an embodiment, the at least one anti-microbial nanostructure 206a is configured to modulate at least one of microbial movement, microbial attachment, microbial growth, or microbial persistence proximate at least one surface of the body structure 104. In an embodiment, the at least one anti-microbial nanostructure 206a is configured to increase at least one of microbial movement, microbial attachment, microbial growth, or microbial persistence proximate at least one surface of the body structure 104. In an embodiment, the at least one anti-microbial nanostructure 206a is configured to decrease at least one of microbial movement, microbial attachment, microbial growth, or microbial persistence proximate at least one surface of the body structure 104.

In an embodiment, the insertable device 102 includes at least one switchable surface 404. In an embodiment, the switchable surface 404 is configured to alter the liquid-solid contact angle of the at least one actuatable anti-microbial nanostructure 206a. In an embodiment, the at least one switchable surface 404 includes poly(dimethylsiloxane). In an embodiment, the switchable surface 404 is reversibly switchable. In an embodiment, the switchable surface 404 is configured to alter at least one of the electrical charge, chemical composition, polarizability, transparency, conductivity, light absorption, osmotic potential, zeta potential, surface energy, coefficient of friction, or affinity for at least one microbial component. In an embodiment, the at least one switchable surface 404 is configured to switch from a first conformation state to a second conformation state in response 299 to an external stimulus. In an embodiment, the at least one switchable surface 404 is switchable from a first state to a second state. In an embodiment, the second state inhibits anti-microbial presence proximate at least one surface of the insertable device 102.

In an embodiment, the external stimulus includes at least one microorganism. In an embodiment, the external stimulus includes at least one physical or chemical change proximate the switchable surface 404. In an embodiment, the at least one external stimulus includes at least one of a change in applied voltage, change in temperature, change in pH, exposure to ultraviolet light, disruption to ultraviolet light, electromagnetic radiation, magnetic field, removal of a magnetic field, change in capacitance, change in electrostatic charge, removal of electrostatic charge, exposure to a ligand, exposure to a solvent, or exposure to an ion. In an embodiment, the first conformation state and the second conformation state differ in degree of hydrophobicity. In an embodiment, the second conformation state has a greater liquid-solid contact angle than the first conformation state.

In an embodiment, the at least one anti-microbial nanostructure 206a is configured to be activated by at least one physical or chemical change on the switchable surface 404. In an embodiment, the at least one anti-microbial nanostructure 206a is configured to be activated by at least one of a change in applied voltage, change in temperature, change in pH, exposure to ultraviolet light, disruption to ultraviolet light, electromagnetic radiation, magnetic field, removal of a magnetic field, change in capacitance, change in electrostatic charge, removal of electrostatic charge, exposure to a ligand, exposure to a solvent, or exposure to an ion. In an embodiment, the first conformation state and the second conformation state differ in degree of hydrophobicity. In an embodiment, the second conformation state has a greater liquid-solid contact angle than the first conformation state.

In an embodiment, the insertable device 102 includes at least one photonic crystal. In an embodiment, the photonic crystal includes at least one biopolymer. In an embodiment, the photonic crystal includes at least one nanopatterned surface. In an embodiment, the at least one photonic crystal includes at least one embedded material. In an embodiment, th at least one embedded material includes at least one of a biological cell, enzyme, nucleic acid, detection material, small molecule, protein, peptide, polypeptide, amino acid, carbohydrate, lipid, therapeutic agent, electronic component, or other material. In an embodiment, the at least one detection material includes at least one of a contrast agent, or electronic identification device. In an embodiment, the at least one detection material includes at least one of a radioactive substance, luminescent substance, or odorous substance. In an embodiment, the detection material includes at least one of a diamagnetic particle, ferromagnetic particle, paramagnetic particle, super paramagnetic particle, particle with altered isotope, or other magnetic particle.

For example, in an embodiment, an insertable device 102 comprises a body structure 104 having an outer surface 106 and an inner surface 108 defining one or more fluid-flow passageways 110; wherein at least one of the outer surface 106 or the inner surface 108 of the body structure 104 includes at least one anti-microbial nanostructure 206a. In an embodiment, an insertable device 102 comprises a body structure 104 including at least one anti-microbial nanostructure 206a. In an embodiment, an insertable device 102 comprises a body structure 104 having an outer surface 106 and an inner surface 108 defining one or more fluid-flow passageways 110; wherein at least one of the outer surface 106, or the inner surface 108 of the body structure 104 includes at least one actuatable anti-microbial nanostructure 206a. In an embodiment, an insertable device 102 comprises a body structure 104 including at least one actuatable anti-microbial nanostructure 206a.

In an embodiment, the one or more anti-microbial regions 202 are configured to photochemically actuate between the first wettability state and the second wettability state in the presence of an ultraviolent energy. In an embodiment, the one or more anti-microbial regions 202 are configured to actuate between the first wettability state and the second wettability state in the presence of an applied potential. In an embodiment, the one or more anti-microbial regions 202 are UV-manipulatable between the first wettability and the second wettability.

In an embodiment, the one or more anti-microbial regions 202 are configured to photochemically actuate between a substantially hydrophobic state and a substantially hydrophilic state. In an embodiment, the one or more anti-microbial regions 202 are configured to electrically actuate between a substantially hydrophobic state and a substantially hydrophilic state. In an embodiment, the one or more anti-microbial regions 202 include at least one ZnO nanorod film, coating, or material that is UV-manipulatable between a superhydrophobic state and superhydrophilic state.

In an embodiment, the one or more anti-microbial regions 202 are energetically controllably actuatable between a substantially hydrophobic state and a substantially hydrophilic state. In an embodiment, the one or more anti-microbial regions 202 are energetically controllably actuatable between at least a first hydrophilic state and a second hydrophilic state. In an embodiment, the one or more anti-microbial regions 202 are energetically controllably actuatable between a hydrophobic state and a hydrophilic state. In an embodiment, the one or more anti-microbial regions 202 include a material that is switchable between a zwitterionic state and a non-zwitterionic state.

Controllable-wettability-components 804 can be made using a variety of methodologies and technologies including, for example, spray pyrolysis, electro-deposition, electro-deposition onto laser-drilled polymer molds, laser cutting and electro-polishing, laser micromachining, photolithography, surface micro-machining, soft lithography, x-ray lithography, LIGA techniques (e.g., X-ray lithography, electroplating, and molding), conductive paint silk screen techniques, conventional pattering techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, or the like), complementary-symmetry/metal-oxide semiconductor (CMOS) technology, deep x-ray exposure techniques, and the like. Further examples of methodologies and technologies for making controllable wettability components can found in the following documents (the contents of each of which is incorporated herein by reference): Feng et al., *Reversible Super-hydrophobicity to Super-hydrophilicity Transition of Aligned ZnO Nanorod Films*, J. Am. Chem. Soc., 126, 62-63 (2004), Lin et al., Electrically Tunable Wettability of Liquid Crystal/Polymer Composite Films, Optics Express 16(22): 17591-598 (2008), Spori et al., *Cassie-State Wetting Investigated by Means of a Hole-to-Pillar Density Gradient*, Langmuir, 2010, 26 (12), pp 9465-9473Wang et al., *Photoresponsive Surfaces with Controllable Wettability*, Journal of Photochemistry and Photobiology C: Photochemistry Reviews, 8(1): 18-29 (2007), U.S. Pat. No. 6,914,279 (issued Jul. 5, 2005), and U.S. Patent Publication No. 2008/0223717 (published Sep. 18, 2008).

The wettability of a substrate can be determined using various technologies and methodologies including contact angle methods, the Goniometer method, the Whilemy method, the Sessile drop technique, or the like. Wetting is a process by which a liquid interacts with a solid. Wettability (the degree of wetting) is determined by a force balance between adhesive and cohesive force and is often characterized by a contact angle. The contact angle is the angle made by the intersection of the liquid/solid interface and the liquid/air interface. Alternatively, it is the angle between a solid sample's surface and the tangent of a droplet's ovate shape at the edge of the droplet. Contact angle measurements provide a measure of interfacial energies and conveys direct information regarding how hydrophilic or hydrophobic a surface is. For example, superhydrophilic surfaces have contact angles less than about 5°, hydrophilic surfaces have contact angles less than about 90°, hydrophobic surfaces have contact angles greater than about 90°, and superhydrophobic surfaces have contact angles greater than about 150°.

In an embodiment, the insertable device 102 includes a body structure 104 including one or more controllable-wettability-components 804 having switchable wetting properties. In an embodiment, the insertable device 102 includes a body structure 104 including one or more controllable-wettability-components 804 that are energetically actuatable between at least a first wettability and a second wettability. In an embodiment, the one or more controllable-wettability-components 804 are acoustically, chemically, electro-chemically, electrically, optically, thermally, or photo-chemically actuatable between at least, a first wettability and a second wettability.

In an embodiment, the one or more controllable-wettability-components 804 include at least one acousto-responsive material.

In an embodiment, the one or more controllable-wettability-components 804 include at least one photo-responsive material. Non-limiting examples of photo-responsive materials include $SnO$, $SnO_2$, $TiO_2$, $W_2O_3$, $ZnO$, $ZnO$, and the like. In an embodiment, the one or more controllablewettability-components 804 include at least one film, coating, or material including SnO, SnO$_2$, TiO$_2$, W$_2$O$_3$, ZnO, ZnO, or the like. In an embodiment, the one or more controllable-wettability-components 804 are UV-manipulatable between at least a first wettability and a second wettability. In an embodiment, the one or more controllable-wettability-components 804 include one or more ZnO nanorod films, coatings, or materials that are UV-manipulatable between a superhydrophobic state and superhydrophilic state. In an embodiment, the one or more controllable-wettability-components 804 include at least one electrochemically active material. Non-limiting examples of electrochemically active materials include electrochemically active polymers (e.g., polyaniline, polyethylenethioxythiophene, conjugated polymer poly(3-hexylthiophene), or the like), and the like.

In an embodiment, the one or more controllable-wettability-components 804 include one or more superhydrophobic conducting polypyrrole films, coatings, or components that are electrically switchable between an oxidized state and a neutral state, resulting in reversibly switchable superhydrophobic and superhydrophilic properties. (See, e.g., Lahann et al., *A Reversibly Switching Surface*, 299 (5605): 371-374 (2003) 21:47-51 (2003), the contents of each of which is incorporated herein by reference). In an embodiment, the one or more controllable-wettability-components 804 include one or more electrically isolatable fluid-support structures. See, e.g., U.S. Pat. No. 7,535,692 (issued May 19, 2009), the contents of each of which is incorporated herein by reference).

In an embodiment, the one or more controllable-wettability-components 804 include a plurality of volume-tunable nanostructures 206*a*. See, e.g., U.S. Patent Publication No. 2008/0095977 (published Apr. 24, 2008), the contents of each of which is incorporated herein by reference). In an embodiment, the one or more controllable-wettability-components 804 include one or more tunable (electrically tunable) superhydrophobic conducting polypyrrole films, coatings, or components. See, e.g., Krupenki et al, *Electrically Tunable Superhydrophobic Nanostructured Surfaces*, Bell Labs Technical Journal 10 (3): 161-170 (2009), the contents of each of which is incorporated herein by reference). In an embodiment, the one or more controllable-wettability-components 804 include one or more electrically tunable crystal/polymer composites. In an embodiment, the one or more controllable-wettability-components 804 include a switchable surface 404. See e.g., Gras et al., *Intelligent Control of Surface Hydrophobicity*, ChemPhysChem 8(14): 2036-2050 (2007).

In an embodiment, the insertable device 102 includes one or more coatings (e.g., optically active coatings, reflective coating, opaque coatings, transmissive coatings, etc.). In an embodiment, at least a portion of the body structure 104 includes a surface having a coating, coatings configured to treat or reduce the concentration of an infectious agent in the immediate vicinity of the insertable device 102.

Non-limiting examples of coatings include anti-biofilm activity coatings, coatings having self-cleaning properties, coatings having self-cleaning or anti-bacterial activity, and the like.

Further non-limiting examples coatings include polymeric compositions that resist bacterial adhesion, antimicrobial coatings, coatings that controllably release antimicrobial agents, quaternary ammonium silane coatings, chitosan coatings, and the like. Further non-limiting examples of coatings may be found in, for example, the following documents (the contents of each of which is incorporated herein by reference): U.S. Pat. Nos. 7,348,021 (issued Mar. 25, 2008), 7,217,425 (issued May 15, 2007), 7,151,139 (issued Dec. 19, 2006), and 7,143,709 (issued Dec. 5, 2006).

In an embodiment, at least a portion of an inner or an outer surface of the insertable device 102 includes one or more self-cleaning coating materials. Non limiting examples of self-cleaning coating (e.g., *Lotus* Effect) materials include superhydrophobic materials, carbon nanotubes with nanoscopic paraffin coating, or the like. Further non-limiting examples of self-cleaning (e.g., non fouling) coating materials include antimicrobial, and nonfouling zwitterionic polymers, zwitterionic surface forming materials, zwitterionic polymers, poly(carboxybetaine methacrylate) (pCBMA), poly(carboxybetaine acrylic amide) (pCBAA), poly(oligo(ethylene glycol) methyl ether methacrylate) (pO-EGMA), poly(N,N-dimethyl-N-(ethoxycarbonylmethyl)-N-[2'-(methacryloyloxy)ethyl]-ammonium bromide), cationic pC8NMA, switchable pCBMA-1 C2, pCBMA-2, and the like. See, e.g., WO 2008/083390 (published Jul. 10, 2008) (the contents of each of which is incorporated herein by reference).

Further non-limiting examples of coatings include superhydrophobic conducting polypyrrole coatings that are electrically switchable between an oxidized state and a neutral state, resulting in reversibly switchable superhydrophobic and superhydrophilic properties (see, e.g., Lahann et al., *A Reversibly Switching Surface*, 299 (5605): 371-374 (2003) 21:47-51 (2003), the contents of each of which is incorporated herein by reference); coatings including electrically isolatable fluid-support structures (see, e.g., U.S. Pat. No. 7,535,692 (issued May 19, 2009), the contents of each of which is incorporated herein by reference); coatings including a plurality of volume-tunnable nanostructures (see, e.g., U.S. Patent Publication No. 2008/0095977 (published Apr. 24, 2008), the contents of each of which is incorporated herein by reference); coatings including re-entrant surface structures (see, e.g., Tuteja et al., *Robust Omniphobic Surfaces*, Epub 2008 Nov. 10, 105(47):18200-5 (2008), the contents of each of which is incorporated herein by reference); coatings including superhydrophobic conducting polypyrrole materials, coatings including zwitterionic polymers (see, e.g., Cheng et al., *A Switchable Biocompatible Polymer Surface with Self-Sterilizing and Nonfouling Capabilities*, Angew. Chem. Int. Ed. 8831-8834 (2008), the contents of each of which is incorporated herein by reference); or the like.

Further non-limiting examples of coating include reflective coatings, beam-splitter coatings, broadband multilayer coatings, composite coatings, dielectric coatings, dielectric reflective coatings (e.g., dielectric high reflective coatings), grating waveguide coatings (e.g., high reflectivity grating waveguide coatings), IR reflective coatings, metallic reflective coatings (e.g., metallic high reflective coatings), multi-layer coatings, narrow or broad band coatings, optical coatings, partial reflective coatings, polymeric coatings, single layer coatings, UV reflective coatings, UV-IR reflective coatings, and the like, and combinations thereof. For example, in an embodiment, the insertable device 102 includes at least one of an outer internally reflective or an inner internally reflective coating on the body structure 104. For example, in an embodiment, at least a portion of an inner surface 108 or an outer surface 106 of the insertable device 102 includes a coating configured to internally reflect at least a portion of an emitted energy stimulus within an interior of at least one of the fluid-flow passageways 110. In an embodiment, at least a portion of the body structure 104 includes at least one of an outer internally reflective coating and an inner internally reflective coating.

The system 100 can include, among other things, one or more reflective materials. In an embodiment, the insertable device 102 includes a reflective material. For example, in an embodiment, at least a portion of the body structure 104 includes a reflective material. Non limiting examples of reflective materials include aluminum, aluminum oxide, barium sulfate, chromium, copper, fluorine, germanium, gold, hafnium dioxide, high refractive index materials, low refractive index materials, magnesium fluoride, nickel, nickel-chromium platinum, quartz, rhodium, sapphire, silicon dioxide, silver, tantalum pentoxide, thorium fluorides, titanium, titanium dioxide, titanium oxide, tungsten, yttrium oxide, zinc oxide, zinc sulfide, zirconium, zirconium oxide, and the like, as well as compounds, composites, and mixtures thereof.

For example, in an embodiment, at least a portion of the insertable device 102 includes one or more coatings including at least one reflective material. In an embodiment, the reflective material includes at least one of aluminum, barium sulfate, gold, silver, titanium dioxide, and zinc oxide. In an embodiment, the reflective material includes an ultraviolet energy reflective material. In an embodiment, the ultraviolet energy reflective material comprises a metallic film. In an embodiment, the ultraviolet energy reflective material comprises enhanced aluminum. In an embodiment, the ultraviolet energy reflective material comprises enhanced aluminum overcoated with at least one of magnesium fluoride, silicon dioxide, or silicon monoxide. In an embodiment, the ultraviolet energy reflective material comprises enhanced aluminum overcoated with high phosphorous nickel. In an embodiment, the ultraviolet energy reflective material comprises barium sulfate.

In an embodiment, at least a portion of the body structure 104 includes an optical material that permits the transmission of at least a portion of an emitted energy stimulus from an interior of at least one of the fluid-flow passageways 110 to an exterior of at least one of the fluid-flow passageways 110. In an embodiment, at least a portion of the body structure 104 includes an optical material that internally reflects at least a portion of an emitted energy stimulus present within an interior of at least one of the fluid-flow passageways 110. In an embodiment, at least a portion of the body structure 104 includes an optical material that internally reflects at least a portion of an emitted energy stimulus within an interior of at least one of the fluid-flow passageways 110, without substantially permitting the transmission of the emitted energy stimulus through an exterior of the body structure 104. In an embodiment, at least a portion of the body structure 104 includes an optical material that internally directs at least a portion of an emitted energy stimulus along a substantially longitudinal direction of at least one of the fluid-flow passageways 110. In an embodiment, wherein at least a portion of the body structure 104 includes an optical material that internally directs at least a portion of an emitted energy stimulus along a substantially lateral direction of at least one of the fluid-flow passageways 110.

In an embodiment, an insertable device 102 comprises a body structure 104 having an outer surface 106 and an inner surface 108 defining one or more fluid-flow passageways 110; at least one actuatable anti-microbial region 202a including at least one anti-microbial reservoir 208 including at least one anti-microbial agent, the at least one actuatable anti-microbial reservoir 208 actuatable by the presence of at least one microorganism and configured to actively elute at least one anti-microbial agent proximate to at least one of the outer surface 106 or the inner surface 108 of the body structure 104.

In an embodiment, an insertable device 102 comprises a body structure 104 having an outer surface 106 and an inner surface 108 defining one or more fluid-flow passageways 110; one or more anti-microbial regions 202 of the body structure 104 including at least one anti-microbial agent reservoir 208, the reservoir 208 configured to release one or more anti-microbial agents to the one or more anti-microbial regions 202 of the body structure 104. In an embodiment, a system 100 comprises an insertable device 102 including a body structure 104 having an outer surface 106 and an inner surface 108 defining one or more fluid-flow passageways 110; and one or more anti-microbial regions 202 proximate at least one of an outer surface 106, an inner surface 108, or embedded in the internal body structure 104; the body structure 104 including at least one anti-microbial agent reservoir 208 operably coupled to the one or more anti-microbial regions 202; and circuitry 604 configured for operating the at least one anti-microbial agent reservoir 208.

In an embodiment, the system 100 comprises circuitry 605 configured for operating at least one sensor 302 operably coupled to at least one of the anti-microbial regions 202. In an embodiment, the system 100 comprises circuitry 605 configured for operating at least one sensor 302 operably coupled to at least one of the at least one anti-microbial agent reservoir 208. In an embodiment, the at least one sensor 302 is configured to detect information related to at least one microbial component. In an embodiment, the system 100 further comprises circuitry 606 configured for operating one or more central processing units 234.

In an embodiment, a system 100 includes means for operating an insertable device 102, the insertable device 102 including a body structure 104 having an outer surface 106 and an inner surface 108 defining one or more fluid-flow passageways 110; and one or more anti-microbial regions 202 proximate at least one of an outer surface 106, an inner surface 108 or embedded in the internal body structure 104; the body structure 104 including at least one anti-microbial agent reservoir 208 operably coupled to the one or more anti-microbial regions 202; and means 604 (as shown in FIG. 7) for operating the at least one anti-microbial agent reservoir 208. In an embodiment, the system 100 further comprises means 605 for operating one or more sensor transmitters 445 or sensor receivers 444.

In an embodiment, the system 100 includes one or more computing devices 230 operably coupled to one or more sensors 302. In an embodiment, at least one computing device 230 is configured to process an output associated with one or more sensors 302. In an embodiment, the system 100 includes one or more computing devices 230 configured to concurrently or sequentially operate multiple sensors 302. In an embodiment, the system 100 is configured to compare an input associated with at least one characteristic associated with a biological sample proximate an insertable device 102 to a data structure 260 including reference values, and to generate a response 299 based in part on the comparison. In an embodiment, the system 100 is configured to compare an input associated with at least one physiological characteristic associated with a biological subject 222 to a data structure 260 including reference values, and to generate a response 299 based in part on the comparison. In an embodiment, the system 100 is configured to compare an input associated with at least one characteristic associated with a biological sample 808 proximate an insertable device 102 to a data structure 260 including reference values, and to generate a response 299 based in part on the comparison.

In an embodiment, at least one computing device 230 is configured to perform a comparison of at least one detected characteristic to stored reference data, and to generate a response 299 based at least in part on the comparison. For example, in an embodiment, at least one computing device 230 is configured to perform a comparison of at least one characteristic associated with the biological sample 808 to stored reference data, and to initiate a treatment protocol based at least in part on the comparison. In an embodiment, at least one computing device 230 is configured to perform a comparison of a detected at least one of the emitted optical energy or the remitted optical energy from the region proximate the body structure 104 to reference spectral information, and to cause an emission of an energy stimulus from one or more energy emitters 220 to at least one of the outer surface 106 and the inner surface 108 of the body structure 104. In an embodiment, one or more computing devices 230 are communicatively coupled to one or more sensors 302 and configured to actuate a determination of the at least one characteristic associated with a biological specimen proximate a surface of the insertable device 102.

In an embodiment, a computing device 230 is configured to compare a measurand associated with the biological subject 222 to a threshold value associated with a tissue spectral model and to generate a response 299 based on the comparison. In an embodiment, a computing device 230 is configured to compare an input associated with at least one characteristic associated with, for example, a biological sample proximate an insertable device 102 to a database 258 of stored reference values, and to generate a response 299 based in part on the comparison.

The response 299 can include, among other things, at least one of a response signal, an absorption parameter, an extinction parameter, a scattering parameter, a comparison code, a comparison plot, a diagnostic code, a treatment code, an alarm response, and a test code based on the comparison of a detected optical energy absorption profile to characteristic spectral signature information. In an embodiment, the response 299 includes at least one of a display, a visual representation (e.g., a visual depiction representative of the detected (e.g., assessed, calculated, evaluated, determined, gauged, measured, monitored, quantified, resolved, sensed, or the like) information) component, a visual display of at least one spectral parameter, and the like. In an embodiment, the response 299 includes a visual representation indicative of a parameter associated with an infection present in a region of a biological sample proximate one or more sensors 302. In an embodiment, the response 299 includes a generating a representation (e.g., depiction, rendering, modeling, or the like) of at least one physical parameter associated with a biological specimen.

In an embodiment, at least one computing device 230 is configured to perform a comparison of the at least one characteristic associated with the microbial component from an anti-microbial region 202 proximate at least one of the outer surface 106 or the inner surface 108 of the body structure 104 to stored reference data, and to initiate a treatment protocol based at least in part on the comparison, or deliver at least one anti-microbial agent to at least one of the outer surface 106 or the inner surface 108 of the body structure 104.

In an embodiment, the computing device 230 is configured to perform a comparison of a real-time measurand associated with a region proximate the insertable device 102 to infection marker or biomarker information configured as a physical data structure 260 and to generate a response 299 based at least in part on the comparison. In an embodiment, one or more computing devices 230 are operably coupled to at least one of the selectively actuatable anti-microbial regions 202a, and configured to actuate at least one of the selectively actuatable anti-microbial regions 202a in response 299 to detected information from the one or more sensors 302.

Referring to FIGS. 4A, 4B, 5A, and 5B, in an embodiment, the plurality of selectively actuatable anti-microbial regions 202a are configured to provide a spatial or temporal patterned 109 anti-microbial surface property 204. In an embodiment, the plurality of selectively actuatable anti-microbial regions 202a are configured to deliver an anti-microbial agent of a dose sufficient (e.g., of character and for a duration sufficient, of sufficient strength or duration, etc.) to provide a spatial or temporal patterned 109 anti-microbial surface of the body structure 104.

In an embodiment, the insertable device 102 comprises a body structure 104 having an outer surface 106, and an inner surface 108 defining one or more fluid-flow passageways 110; wherein at least one of the outer surface 106, or the inner surface 108 of the body structure 104 includes at least one anti-microbial nanostructure 206a.

In an embodiment, the insertable device 102 comprises a body structure 104 including at least one anti-microbial nanostructure 206a. In an embodiment, the insertable device 102 comprises a body structure 104 having an outer surface 106 and an inner surface 108 defining one or more fluid-flow passageways 110; wherein at least one of the outer surface 106, or the inner surface 108 of the body structure 104 includes at least one actuatable anti-microbial nanostructure 206a.

In an embodiment, the insertable device 102 comprises a body structure 104 including at least one actuatable anti-microbial nanostructure 206a.

As indicated in FIG. 7, in an embodiment, a catheter system 100 comprises a body structure 104 having an outer surface 106 and an inner surface 108 defining one or more fluid-flow passageways 110; and a plurality of selectively actuatable anti-microbial regions 202a configured to direct at least one anti-microbial agent to one or more areas of at least one of the outer surface 106 of the body structure 104, the inner surface 108 of the body structure 104, or embedded in the internal body structure; and circuitry 602 configured for determining the presence of at least one microorganism proximate to one or more areas of the body structure 104. In an embodiment, the circuitry 602 configured for determining the presence of at least one microorganism includes at least one sensor 302 operably coupled to a microorganism biomarker array. In an embodiment, the circuitry 602 configured for determining the presence of at least one microorganism includes at least one of an electrochemical transducer 602a, optical transducer 602b, biochemical transducer 602c, ultrasonic transducer 602d, piezoelectric transducer 602e, or thermal transducer 602f. In an embodiment, the circuitry 602 configured for determining the presence of at least one microorganism includes at least one thermal detector 602g, photovoltaic detector 602h or photomultiplier detector 602i.

In an embodiment, the transcutaneous energy transfer system 914 is electromagnetically, magnetically, acoustically, optically, inductively, electrically, or capacitively coupleable to an in vivo power supply. In an embodiment, the transcutaneous energy transfer system 914 includes at least one electromagnetically coupleable power supply 916, magnetically coupleable power supply 918, acoustically coupleable power supply 920, optically coupleable power supply 922, inductively coupleable power supply 924, electrically coupleable power supply 926, or capacitively coupleable power supply 928. In an embodiment, the energy transcutaneous transfer system 914 is configured to wirelessly receive power from a remote power supply 930. For example, in an embodiment the power source 900 includes at least one biological-subject powered generator 704. In an embodiment, the power source 900 includes a thermoelectric generator 706. In an embodiment, the power source 900 includes a piezoelectric generator 708. In an embodiment, the power source 900 includes a MEMS generator 710. In an embodiment, the power source 900 includes a biomechanical energy harvesting generator 712.

In an embodiment, the power source 900 is configured to wirelessly receive power from a remote power supply 930. In an embodiment, the catheter device 102 includes one or more power receivers 932 configured to receive power from an in vivo or ex vivo power source. In an embodiment; the power source 900 is configured to wirelessly receive power via at least one of an electrical conductor or an electromagnetic waveguide. In an embodiment, the power source 900 includes one or more power receivers 932 configured to receive power from an in vivo or ex vivo power source. In an embodiment, the in vivo power source includes at least one of a thermoelectric generator, a piezoelectric generator, a microelectromechanical systems generator, or a biomechanical-energy harvesting generator.

In an embodiment, the catheter device 102 includes one or more generators configured to harvest mechanical energy from for example, acoustic waves, mechanical vibration, blood flow, and the like. For example, in an embodiment, the power source 900 includes at least one of a biological-subject (e.g., human)-powered generator 904, a thermoelectric generator 906, piezoelectric generator 908, electromechanical generator 910 (e.g., a microelectromechanical systems (MEMS) generator, or the like), biomechanical-energy harvesting generator 912, and the like.

In an embodiment, the biological-subject-powered generator 904 is configured to harvest thermal energy generated by the biological subject. In an embodiment, the biological-subject-powered generator 904 is configured to harvest energy generated by the biological subject using at least one of a thermoelectric generator 906, piezoelectric generator 908, electromechanical generator 910 (e.g., a microelectromechanical systems (MEMS) generator, or the like), biomechanical-energy harvesting generator 912, and the like. For example, in an embodiment, the biological-subject-powered generator 904 includes one or more thermoelectric generators 906 configured to convert heat dissipated by the biological subject into electricity. In an embodiment, the biological-subject-powered generator 904 is configured to harvest energy generated by any physical motion or movement (e.g., walking) by biological subject. For example, in an embodiment, the biological-subject-powered generator 904 is configured to harvest energy generated by the movement of a joint within the biological subject. In an embodiment, the biological-subject-powered generator 904 is configured to harvest energy generated by the movement of a fluid (e.g., biological fluid) within the biological subject.

The system 100, can include, among other things, a transcutaneous energy transfer system 914. In an embodiment, the catheter device 102 includes a transcutaneous energy transfer system 914. For example, in an embodiment, the catheter device 102 includes one or more power receivers 932 configured to receive power from at least one of an in vivo or an ex vivo power source. In an embodiment, the transcutaneous energy transfer system 914 is electromagnetically, magnetically, acoustically, optically, inductively, electrically, or capacitively coupled to at least one of the anti-microbial regions 202 (e.g., selectively actuatable anti-microbial regions 202a), computing device 230, or sensor 302.

In an embodiment, the transcutaneous energy transfer system 914 is configured to transfer power from at least one of an in vivo or an ex vivo power source to the catheter device 102. In an embodiment, the transcutaneous energy transfer system 914 is configured to transfer power to the catheter device 102 and to recharge a power source 900a within the catheter device 102.

In an embodiment, the circuitry 602 configured to determine the microorganism presence includes at least one sensor 302. In an embodiment, the circuitry 602 configured to determine the microorganism presence includes at least one sensor 302 having a component identification code and configured to implement instructions addressed to the sensor 302 according to the component identification code. In an embodiment, the circuitry 602 configured to determine the microorganism presence includes at least one sensor 302 operably coupled to a microorganism colonization biomarker array.

In an embodiment, the circuitry 602 configured to determine the microorganism presence includes biofilm marker information configured as a physical data structure. In an embodiment, the physical data structure includes a characteristic information section having characteristic microbial colonization spectral information representative of the presence of a microbial colonization proximate the insertable device 102.

The system 100 can include, among other things, circuitry 604 configured to obtain information. In an embodiment, the circuitry 604 configured to obtain information includes circuitry 604 configured to obtain information associated with a delivery of the optical energy. In an embodiment, the circuitry 604 configured to obtain information includes circuitry 604 configured to obtain at least one of a command stream, a software stream, and a data stream.

The system 100 can include, among other things, circuitry 606 configured to store information. In an embodiment, the circuitry 606 configured to store information includes one or more data structures.

The system 100 can include, among other things, circuitry 608 configured to provide information. In an embodiment, the circuitry 608 configured to provide information includes circuitry 608 configured to provide having infection marker information. In an embodiment, the circuitry 608 configured to provide information includes circuitry 608 configured to provide status information. In an embodiment, the circuitry 608 configured to provide information includes circuitry 608 configured to provide information regarding the detection of at least one of the emitted optical energy or the remitted optical energy. In an embodiment, the circuitry 608 configured to provide information includes circuitry 608 configured to detect at least one delivered anti-microbial agent, or other anti-microbial protruding elements 206 actuated.

The system 100 can include, among other things, circuitry 610 configured to perform a comparison of the determined at least one characteristic associated with the biological sample 808 proximate the insertable device 102 to stored reference data following the delivery of the anti-microbial surface property 204. The insertable device 102 can include, among other things, circuitry 602 configured to generate a response 299 based at least in part on the comparison. The circuitry 602 configured to perform a comparison can include, among other things, one or computing devices 230 configured to perform a comparison of the at least one characteristic associated with the biological sample 808 proximate the insertable device 102 stored reference data following delivery of the anti-microbial agent, and to generate a response 299 based at least in part on the comparison.

In an embodiment, the insertable device 102 includes one or more anti-microbial regions 202a that form part of a surface along a longitudinal direction 120 of a fluid-flow passageway 110. In an embodiment, the insertable device 102 includes one or more anti-microbial regions 202a that form part of a surface along a lateral direction 122 of a fluid-flow passageway 110. In an embodiment, the insertable device 102 includes one or more anti-microbial regions 202a that form part of a surface along a helical direction 124 of a fluid-flow passageway 110. In an embodiment, the one or more anti-microbial regions 202a are configured to laterally, 122 internally direct, longitudinally 120 internally direct, or helically 124 internally direct at least a portion of at least one anti-microbial property 204 within an interior of at least one of the fluid-flow passageways 110. In an embodiment, the one or more anti-microbial regions 202a are configured to direct at least a portion of at least one anti-microbial property 204 in peristaltic movement along one or more fluid-flow passageways 110. In an embodiment, at least one anti-microbial nanostructure 206a extends substantially longitudinally 120 along at least one of the fluid-flow passageways 110. In an embodiment, at least one of the anti-microbial nanostructures 206a extends substantially laterally 122 within at least one of the fluid-flow passageways 110. In an embodiment, at least one of the anti-microbial nanostructures 206a extends substantially helically 124 along at least one of the fluid-flow passageways 110.

In an embodiment, at least one of the anti-microbial regions 202a extends substantially longitudinally 120 along at least one of the fluid-flow passageways 110. In an embodiment, at least one of the anti-microbial regions 202a extends substantially laterally 122 within at least one of the fluid-flow passageways 110. In an embodiment, at least one of the anti-microbial regions 202a extends substantially helically 124 within at least one of the fluid-flow passageways 110. In an embodiment, at least one of the anti-microbial regions 202a extends substantially laterally 122 along a first portion of the body structure 104 and a different one of the one or more anti-microbial regions 202a extends substantially laterally 122 along a second portion of the body structure 104. In an embodiment, at least one of the anti-microbial regions 202a extends substantially helically 124 along a first portion of the body structure 104 and a different one of the anti-microbial regions 202a extends substantially helically along a second portion of the body structure 104. In an embodiment, at least one of the anti-microbial regions 202a extends substantially longitudinally 120 along a first portion of the body structure 104 and a different one of the anti-microbial regions 202a extends substantially longitudinally 120 along a second portion of the body structure 104.

In an embodiment, one or more anti-microbial regions 202a are configured to direct at least one first anti-microbial property 204 or anti-microbial agent along a substantially lateral 122 direction in one or more anti-microbial regions 202 of at least one of the fluid-flow passageways 110 and configured to direct at least one second anti-microbial property 204 along a substantially longitudinal 120 direction in one or more anti-microbial regions 202 of at least one of the fluid-flow passageways 110. In an embodiment, one or more anti-microbial regions 202 are configured to direct at least a portion of a first anti-microbial property 204 along a substantially lateral 122 direction in a first region of at least one of the fluid-flow passageways 110 and configured to direct at least a portion of a second anti-microbial property 204 along a substantially lateral 122 direction in a second region of the one or more fluid-flow passageways 110, the second region different from the first region. In an embodiment, the one or more anti-microbial regions 202a are configured to direct at least a portion of a first anti-microbial property 204 along a substantially longitudinal 120 direction in a first region of at least one of the fluid-flow passageways 110 and configured to direct at least a portion of a second anti-microbial property 204 along a substantially longitudinal 120 direction in a second region of the one or more fluid-flow passageways 110, the second region different from the first region. In an embodiment, the one or more anti-microbial regions 202a are configured to externally direct at least a portion of an anti-microbial property 204. In an embodiment, the one or more anti-microbial regions 202a are configured to direct at least a portion of a first anti-microbial property 204 along a substantially helical 124 direction in a first region of at least one of the fluid-flow passageways 110 and configured to direct at least a portion of a second anti-microbial property 204 along a substantially helical 124 direction in a second region of the one or more fluid-flow passageways 110, the second region different from the first region.

In an embodiment, a plurality of anti-microbial regions 202, are disposed along the one or more fluid-flow passageways 110. In an embodiment, a plurality of anti-microbial regions 202 are configured to form at least a portion of at least one of the inner surface 108 or outer surface 106 of the body structure 104. In an embodiment, at least one of the anti-microbial regions 202 on the inner surface 108 of the body structure 104 is different than at least one of the anti-microbial regions 202 on the outer surface 106 or embedded in the body structure 104. In an embodiment at least one of the anti-microbial regions 202 on the outer surface 106 of the body structure 104 is different than at least one of the anti-microbial regions 202 on the inner surface 108 or embedded in the body structure 104. In an embodiment, at least one of the anti-microbial regions 202 embedded in the body structure 104 is different than at least one of the anti-microbial regions 202 on the outer surface 106 or the inner surface 108 of the body structure 104.

The system 100 includes, among other things, circuitry 601 configured for obtaining information. In an embodiment, the circuitry 601 configured for obtaining information includes circuitry 601 configured for obtaining information associated with delivery of at least one anti-microbial agent. In an embodiment, the circuitry 601 configured for obtaining information includes circuitry 601 configured for obtaining at least one of a command stream, software stream, or data stream.

The system 100 includes, among other things, circuitry 603 configured for providing information. In an embodiment, the circuitry 603 configured for providing information includes circuitry 603 configured for providing microbial marker information. In an embodiment, the circuitry 603 configured for providing information includes circuitry 603 configured for providing status information. In an embodiment, the circuitry 603 configured for providing information includes circuitry 603 configured for providing information regarding the detection of at least one microbial component proximate to at least one of the outer surface 106 or the inner surface 108 of the body structure 104. In an embodiment, the circuitry 601 configured for obtaining information further includes circuitry 603 configured for providing information.

The transcutaneous energy transfer system 914 can include, among other things, an inductive power supply. In an embodiment, the inductive power supply includes a primary winding operable to produce a varying magnetic field. The catheter device 102 can include, among other things, a secondary winding electrically coupled to one or more energy emitters 220 for providing a voltage to biological sample proximate the catheter device 102 in response 299 to the varying magnetic field of the inductive power supply. In an embodiment, the transcutaneous energy transfer system 914 includes a secondary coil configured to provide an output voltage ranging from about 10 volts to about 25 volts. In an embodiment, the transcutaneous energy transfer system 914 is configured to manage a duty cycle associated with emitting an effective amount of the sterilizing energy stimulus from one or more energy emitters 220. In an embodiment, the transcutaneous energy transfer system 914 is configured to transfer power to the catheter device 102 and to recharge a power source 900 within the catheter device 102.

In an embodiment, the insertable device 102 is, for example, wirelessly coupled to a computing device 230 that communicates with the insertable device 102 via wireless communication. Non-limiting examples of wireless communication include optical connections, ultraviolet connections, infrared, BLUETOOTH®, Internet connections, radio, network connections, and the like.

The system 100 can include, among other things, one or more memories 250 that, for example, store instructions or data, for example, volatile memory (e.g., Random Access Memory (RAM) 252, Dynamic Random Access Memory (DRAM), or the like), non-volatile memory (e.g., Read-Only Memory (ROM) 254, Electrically Erasable Programmable Read-Only Memory (EEPROM), Compact Disc Read-Only Memory (CD-ROM), or the like), persistent memory, or the like. Further non-limiting examples of one or more memories 250 include Erasable Programmable Read-Only Memory (EPROM), flash memory, and the like. Various components of the insertable device 102 (e.g., memories 250, processors 232, or the like) can be operably coupled to each other via one or more instruction 775, data 776, or power buses 256.

Referring to FIG. 6, the system 100 can include, among other things, circuitry 602 configured to determine a microorganism presence in one or more anti-microbial regions 202 in proximity to the insertable device 102, for example, proximate at least one of the outer surface 106 or the inner surface 108 of the body structure 104. Circuitry 602 can include one or more components operably coupled (e.g., communicatively coupled, electromagnetically, magnetically, acoustically, optically, inductively, electrically, capacitively coupleable, or the like) to each other. In an embodiment, circuitry 602 includes one or more remotely located components. In an embodiment, remotely located components are operably coupled via wireless communication. In an embodiment, remotely located components are operably coupled via one or more receivers 444, transmitters 445, transceivers 446, and the like.

In an embodiment, the system 100 includes control circuitry 602 operably coupled to the one or more anti-microbial regions 202. In an embodiment, the system 100 includes control circuitry 602 operably coupled to the active agent assemblies 800 (e.g., anti-microbial regions 202). In an embodiment, the control circuitry 602 is configured to control delivery of at least one active agent (including an anti-microbial agent) from one or more anti-microbial regions 202. In an embodiment, the control circuitry 602 is configured to control delivery of at least one active agent (including an anti-microbial agent) from at least one active agent reservoir (e.g., anti-microbial agent reservoir 208). In an embodiment, the at least one anti-microbial agent reservoir 208 includes an electricity storage device 701. In an embodiment, the at least one electricity storage device 701 is rechargeable and electricity can be reloaded into the storage device 701. In an embodiment, at least one computing device 230 is operably coupled to one or more selectively actuatable anti-microbial region 202a and configured to control at least one of a delivery regimen, spatial distribution, or temporal distribution associated with the delivery of the active agent. In an embodiment, the one or more computing devices 230 are configured to actuate at least one selectively actuatable anti-microbial regions 202a in response to a scheduled program, an external command, a history of a previous microbial presence, a signal, data point, or a history of a previous actuation. In an embodiment, the one or more computing devices 230 are configured to control delivery of at least one anti-microbial agent from an anti-microbial reservoir 208 of the anti-microbial region 202.

In an embodiment, the system 100 includes at least one computing device 230 communicably coupled to one or more anti-microbial regions 202, and optionally configured to control at least one parameter associated with selectively actuating one or more anti-microbial regions 202.

In an embodiment, the plurality of selectively actuatable anti-microbial regions 202a are configured to provide a spatial or temporal patterned 109 anti-microbial surface property 204 at least a first region 406 and a second region 408 different from the first region 406. For example, in an embodiment, the second region 408 includes at least one of a spectral power distribution ($SPD_n$), an irradiance ($I_n$), or a peak power ($P_n$) different from the first region 406. In an embodiment, the second region 408 includes at least one of an illumination intensity, peak emission wavelength, or pulse frequency different from the first region 406. In an embodiment, the second region 408 includes at least one of an intensity, phase, or polarization different from the first region 406. In an embodiment, the second region 408 includes at least one of a frequency, repetition rate, or bandwidth different from the first region 406. In an embodiment, the second region 408 includes at least one of an energy-emitting pattern, ON-pulse duration, or OFF-pulse duration different from the first region 406. In an embodiment, the second region 408 includes at least one of an emission intensity, emission phase, emission polarization, or emission wavelength different from the first region 406. In an embodiment, the second region has at least one different anti-microbial property 204 (e.g., structure, agent, reservoir, etc.) different from the first region 406. For example, in an embodiment, the second region 408 includes at least one of an anti-microbial protruding element 206 (e.g., nanostructure 206a, or other element) different than the first region 406. In an embodiment, the second region 408 includes at least one of an anti-microbial agent that is different than the first region 406.

The system 100 can include, among other things, one or more modules optionally operable for communication with one or more input/output components 266, that are configured to relay user output and/or input. In an embodiment, a module includes one or more instances of electrical, electromechanical, software-implemented, firmware-implemented, or other control devices. For example, in an embodiment, the insertable device 102, includes a controller 388 operably coupled to the sensor 302. In an embodiment, the at least one controller 388 is configured to be responsive to the detected presence of at least one microorganism by the at least one sensor 302. Such devices include one or more instances of memory 250, computing devices 230, ports, valves, fuses, antifuses, antennas, power, or other supplies; logic modules or other signaling modules; gauges or other such active or passive detection components; program instructions, or piezoelectric transducers, shape memory elements, micro-electro-mechanical system (MEMS) elements, or other actuators. In an embodiment, the controller 388 is configured to activate at least one independently addressable and actively controllable anti-microbial nanostructure 202a in response 299 to detected information from at least one sensor 302. In an embodiment, the controller 388 is configured to activate at least one independently addressable and actively controllable anti-microbial nanostructure 206a in response 299 to at least one of a scheduled program, external command, history of a previous presence of a microorganism, or history of a previous activation. In an embodiment, the system 100 further comprises circuitry 602 configured for determining the presence of at least one microorganism proximate the body structure 104 subsequent to a first round of activation of at least one independently addressable and actively controllable anti-microbial nanostructure 206a. In an embodiment, the system 100 further comprises circuitry 602 configured for altering the type of response 299 of an independently addressable and actively controllable anti-microbial nanostructure 202a based on the determination of the presence of at least one microorganism proximate the body structure 104 subsequent to a first round of activation. In an embodiment, the system 100 further comprises electrically activating means (e.g., switches 118, etc.) for concurrently or sequentially electrically activating two or more of the at least one independently addressable and actively controllable anti-microbial nanostructure 202a determined to have at least one microorganism present thereon.

The computer-readable media drive 264 or memory slot can be configured to accept signal-bearing medium 777 (e.g., computer-readable memory media, computer-readable recording media, or the like). In an embodiment, a program for causing the system 100 to execute any of the disclosed methods can be stored on, for example, a computer-readable recording medium (CRMM) 262, or other signal-bearing medium 777. Non-limiting examples of signal-bearing media 777 include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter 445, receiver 444, transmission logic, reception logic, etc.), etc.). Further non-limiting examples of signal-bearing media 777 include, but are not limited to, DVD-ROM, DVD-RAM, DVD+RW, DVD-RW, DVD-R, DVD+R, CD-ROM, Super Audio CD, CD-R, CD$^+$R, CD$^+$ RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like.

For example, in an embodiment, the system 100 includes a signal-bearing medium 777 bearing: one or more instructions for operating an insertable device 102, the insertable device 102 including a body structure 104 having an outer surface 106 and an inner surface 108 defining one or more fluid-flow passageways 110; and one or more anti-microbial regions 202 proximate at least one of an outer surface 106, an inner surface 108, or embedded in the internal body structure 104; the body structure 104 including at least one anti-microbial agent reservoir 208 operably coupled to the one or more anti-microbial regions 202; and one or more instructions for operating the at least one anti-microbial agent reservoir 208. In an embodiment, the system 100 further comprises one or more instructions for operating one or more sensor receivers 444 or sensor transmitters 445. In an embodiment, the signal-bearing medium 777 includes a computer-readable medium. In an embodiment, the signal-bearing medium 777 includes a recordable medium or a communications medium.

In an embodiment, the system 100 includes a signal-bearing medium 777 bearing: a body structure 104 having an outer surface 106 and an inner surface 108 defining one or more fluid-flow passageways 110; at least one independently addressable and actively controllable anti-microbial nanostructure 206a; and one or more instructions for controlling the at least one independently addressable and actively controllable anti-microbial nanostructure 206a of the body structure 104.

In an embodiment, an insertable device system 100, comprises a body structure 104 having an outer surface 106 and an inner surface 108 defining one or more fluid-flow passageways 110; at least one independently addressable and actively controllable anti-microbial nanostructure 206a projecting from at least one of the outer surface 106, or the inner surface 108 of the body structure 104; and circuitry configured 602 for determining the presence of at least one microorganism on at least one of the independently addressable and actively controllable anti-microbial nanostructure 206a of the body structure 104.

In an embodiment, the system 100 includes at least one receiver 444 configured to acquire information based at least in part on a detected microbial component (e.g. microbial marker information). In an embodiment, the at least one receiver 444 is configured to acquire instructions. In an embodiment, the at least one receiver 444 is configured to acquire information based at least in part on whether a detected microbial component from one or more regions proximate at least one of the outer surface 106 or the inner surface 108 of the body structure 104 satisfies a target condition. In an embodiment, the at least one receiver 444 is configured to acquire information associated with delivery of at least one anti-microbial agent. In an embodiment, the at least one receiver 444 is configured to receive one or more signals (e.g., acoustic signal, electromagnetic signal, optical signal, infrared signal, radio signal, radio frequency signal, microwave signal, ultrasonic signal, or biochemical signal). In an embodiment, the at least one receiver 444 is configured to receive one or more signals according to one or more schedules. In an embodiment, the at least one receiver 444 is configured to receive one or more signals in response 299 to detection of at least one microbial component. In an embodiment, the at least one receiver 444 is configured to receive one or more signals in response 299 to one or more queries. In an embodiment, the at least one receiver 444 is configured to acquire data, or acquire software. In an embodiment, the at least one receiver 444 is configured to receive stored reference data. In an embodiment, the at least one receiver 444 is configured to receive data from one or more distal sensors 302. In an embodiment, the at least one receiver 444 is configured to receive stored reference data.

In an embodiment, the system 100 includes at least one transmitter 445 configured to send information based at least in part on historical action taken with regard to at least one anti-microbial region 202. In an embodiment, the historical action taken includes at least one of activation or response 299 to at least one microorganism. In an embodiment, the at least one transmitter 445 is configured to send a request for transmission of at least one of data, command, authorization, update, or code. In an embodiment, the system 100 includes circuitry 601 configured for obtaining information; and circuitry 603 configured for providing information. In an embodiment, the at least one transmitter 445 is configured to transmit one or more signals (e.g., acoustic signal, electromagnetic signal, optical signal, infrared signal, radio signal, radio frequency signal, microwave signal, ultrasonic signal, or biochemical signal). In an embodiment, the at least one transmitter 445 is configured to transmit one or more signals according to one or more schedules. In an embodiment, the at least one transmitter 445 is configured to transmit one or more signals in response 299 to detection of at least one microbial component. In an embodiment, the at least one transmitter 445 is configured to transmit in response 299 to the status of at least one of the level of anti-microbial agent in the reservoir 208, or release of the at least one anti-microbial agent from the reservoir 208. In an embodiment, the at least one transmitter 445 is configured to transmit one or more signals in response 299 to one or more queries. In an embodiment, the at least one transmitter 445 is configured to transmit one or more encrypted signals.

In an embodiment, the system 100 comprises: a signal-bearing medium 777 bearing: a body structure 104 having an outer surface 106 and an inner surface 108 defining one or more fluid-flow passageways 110; at least one independently addressable and actively controllable anti-microbial nanostructure 206a; and one or more instructions for determining the presence of at least one microorganism on at least one of the independently addressable and actively controllable anti-microbial nanostructure 206a of the body structure 104.

In an embodiment, the system 100 includes signal-bearing media 777 in the form of one or more logic devices (e.g., programmable logic devices, complex programmable logic device, field-programmable gate arrays, application specific integrated circuits, or the like) comprising, for example, a data structure 260 including one or more look-up tables. The system 100 can include, among other things, signal-bearing media 777 having sample information (e.g., biological sample 808 information, reference information, characteristic spectral information, or the like) configured as a data structure 260. In an embodiment, the data structure 260 includes at least one of psychosis state indication information, psychosis trait indication information, or predisposition for a psychosis indication information. In an embodiment, the data structure 260 includes at least one of infection indication information, inflammation indication information, diseased state indication information, or diseased tissue indication information.

Many of the disclosed embodiments can be electrical, electromechanical, software-implemented, firmware-implemented, or other otherwise implemented, or combinations thereof. Many of the disclosed embodiments can be software or otherwise in memory, such as one or more executable instruction sequences or supplemental information as described herein. For example, in an embodiment, the insertable device 102 can include, among other things, one or more computing devices 230 configured to perform a comparison of the at least one characteristic associated with the biological subject 222 to stored reference data, and to generate a response 299 based at least in part on the comparison.

As indicated in FIG. 8, in an embodiment, the system 100 includes a cryptographic logic component 221. In an embodiment, the cryptographic logic component 221 is configured to implement at least one cryptographic process or cryptographic logic. In an embodiment, the cryptographic logic component 221 is configured to implement one or more processes associated with at least one of a cryptographic protocol, decryption protocol, or encryption protocol. In an embodiment, the cryptographic logic component 221 is configured to implement one or more processes associated with at least one of a regulatory compliance protocol, regulatory use protocol, or authentication protocol. In an embodiment, the cryptographic logic component 221 is configured to implement one or more processes associated with at least one of an authorization protocol, activation protocol, or treatment regimen protocol. In an embodiment, the cryptographic logic component 221 is configured to generate information associated with at least one of an authentication protocol, authorization protocol, delivery of at least one anti-microbial agent protocol, activation protocol, encryption protocol, or decryption protocol. In an embodiment, the cryptographic logic component 221 is configured to generate information associated with at least one of an authorization instruction, authentication instruction, prescription dosing instruction, anti-microbial agent administration instruction, or prescribed regimen instruction. In an embodiment the cryptographic logic component 221 is configured to generate information associated with at least one of an instruction stream, encrypted data stream, authentication data stream, or authorization data stream. In an embodiment, the cryptographic logic component 221 is configured to generate information associated with at least one of an activation code, error code, command code, or authorization code. In an embodiment, the cryptographic logic component 221 is configured to generate information associated with at least one of a cryptographic protocol, decryption protocol, encryption protocol, regulatory compliance protocol, or regulatory use protocol.

In an embodiment, the insertable device 102 includes at least one outer internally reflective coating 708 on a body structure 104 defining the one or more fluid-flow passageways 110. In an embodiment, the insertable device 102 includes at least one inner internally reflective coating 709 on a body structure 104 defining the one or more fluid-flow passageways 110.

In an embodiment, the system 100 is configured to initiate one or more medical protocols 399 (e.g. clinical trial protocol, diagnostic protocol, treatment protocol, etc.). In an embodiment, the system 100 is configured to initiate at least one medical protocol 399 based on a detected spectral event. In an embodiment, the system 100 is configured to initiate at least one medical protocol 399 based on a detected biomarker event. In an embodiment, the system 100 is configured to initiate at least one medical protocol 399 based on a detected infection. In an embodiment, the system 100 is configured to initiate at least one medical protocol 399 based on a detected a fluid vessel abnormalities (e.g., an obstruction), a detected biological sample 808 abnormality (e.g., cerebrospinal fluid abnormalities, hematological abnormalities, components concentration or level abnormalities, flow abnormalities, or the like), a detected biological parameter, or the like.

In an embodiment, the system 100 can include, among other things, one or more active agent assemblies 800

(including but not limited to, anti-microbial reservoirs 208). In an embodiment, the insertable device 102 includes at least one active agent assembly 800 including one or more anti-microbial reservoir 208. In an embodiment, the at least one anti-microbial reservoir 208 is actuatable by the presence of at least one microorganism. In an embodiment, the anti-microbial reservoir 208 is configured for at least one of active or passive delivery of the at least one anti-microbial agent. In an embodiment, the at least one anti-microbial reservoir 208 is configured for time-release of at least one anti-microbial agent.

In an embodiment, an insertable device 102 includes a body structure 104 having an outer surface 106 and an inner surface 108 defining one or more fluid-flow passageways 110; one or more anti-microbial regions 202 of the body structure 104 including at least one selectively actuatable anti-microbial agent reservoir 208 configured to be actuatable by the presence of at least one microorganism, and configured to actively deliver one or more anti-microbial agents to the one or more anti-microbial regions 202 of the body structure 104.

In an embodiment, the active agent assembly 800 is configured to deliver one or more active agents from the at least one active agent reservoir (e.g., anti-microbial agent reservoir 208) to one or more anti-microbial regions proximate the body structure 104. For example, in an embodiment, the insertable device 102 includes one or more active agent assemblies 800 configured to deliver at least one active agent from the at least one anti-microbial reservoir 208 to at least one of a region proximate an outer surface 108 and a region proximate an inner surface 110 of the insertable device 102.

In an embodiment, the anti-microbial reservoir 208 includes at least one active agent composition. Non-limiting examples of active agents include adjuvants, allergens, analgesics, anesthetics, antibacterial agents, antibiotics, antifungals, anti-inflammatory agents (e.g., nonsteroidal anti-inflammatory drugs), antimicrobials, anti-parasitic, antioxidants, antipyretics, anti-tumor agents, antivirals, bio-control agents, biologics or bio-therapeutics, chemotherapy agents, disinfecting agents, energy-actuatable active agents, anti-clotting factor, vaccine, small molecule, nutraceutical, vitamin, mineral, anti-microbial agent, immunogens, immunological adjuvants, immunological agents, immuno-modulators, immuno-response agents, immuno-stimulators (e.g., specific immuno-stimulators, non-specific immuno-stimulators, or the like), immuno-suppressants, non-pharmaceuticals (e.g., cosmetic substances, or the like), pharmaceuticals, protease inhibitors or enzyme inhibitors, receptor agonists, receptor antagonists, therapeutic agents, tolerogens, toll-like receptor agonists, toll-like receptor antagonists, vaccines, or combinations thereof.

Further non-limiting examples of active agents include nonsteroidal anti-inflammatory drugs such as acemetacin, aclofenac, aloxiprin, amtolmetin, aproxen, aspirin, azapropazone, benorilate, benoxaprofen, benzydamine hydrochloride, benzydamine hydrochloride, bromfenal, bufexamac, butibufen, carprofen, celecoxib, choline salicylate, clonixin, desoxysulindac, diflunisal, dipyone, droxicam, etodolac, etofenamate, etoricoxib, felbinac, fenbufen, fenoprofen, fentiazac, fepradinol, floctafenine, flufenamic acid, indomethacin, indoprofen, isoxicam, ketoralac, licofelone, lomoxicam, loxoprofen, magnesium salicylate, meclofenamic acid, meclofenamic acid, mefenamic acid, meloxicam, morniflumate, niflumic acid, nimesulide, oxaprozen, phenylbutazone, piketoprofen, piroxicam, pirprofen, priazolac, propyphenazone, proquazone, rofecoxib, salalate, salicylamide, salicylic acid, sodium salicylate, sodium thiosalicylate, sulindac, suprofen, tenidap, tenoxicam, tiaprofenic acid, tolmetin, tramadol, trolamine salicylate, zomepirac, or the like.

Further non-limiting examples of active agents include energy-actuatable active agents (e.g., chemical energy, electrical resistance, laser energy, terahertz energy, microwave energy, optical energy, radio frequency energy, acoustic energy, thermal energy, thermal resistance heating energy, or ultrasonic energy actuatable active agents, or the like) and the like.

In an embodiment, the active agent includes at least one active agent that selectively targets bacteria. For example, in an embodiment, the active agent includes at least one bacteriophage that can, for example, selectively target bacteria. Bacteriophages generally comprise an outer protein hull enclosing genetic material. The genetic material can be ssRNA, dsRNA, ssDNA, or dsDNA. Bacteriophages are generally smaller than the bacteria they destroy generally ranging from about 20 nm to about 200 nm. Non-limiting examples of bacteriophages include T2, T4, T6, phiX-174, MS2, or the like). In an embodiment, the active agent includes at least one energy-actuatable agent that selectively targets bacteria. For example, in an embodiment, the active agent includes at least one triplet excited-state photosensitizer that can, for example, selectively target bacteria.

Further non-limiting examples of active agents include triplet excited-state photosensitizers, reactive oxygen species, reactive nitrogen species, any other inorganic or organic ion or molecules that include oxygen ions, free radicals, peroxides, or the like. Further non-limiting examples of active agents include compounds, molecules, or treatments that elicit a biological response from any biological subject 222. Further non-limiting examples of disinfecting agents include therapeutic agents (e.g., antimicrobial therapeutic agents), pharmaceuticals (e.g., a drug, a therapeutic compound, pharmaceutical salts, or the like) non-pharmaceuticals (e.g., a cosmetic substance, or the like), neutraceuticals, antioxidants, phytochemicals, homeopathic agents, and the like. Further non-limiting examples of disinfecting agents include peroxidases (e.g., haloperoxidases such as chloroperoxidase, or the like), oxidoreductase (e.g., myeloperoxidase, eosinophil peroxidase, lactoperoxidase, or the like) oxidases, and the like.

Further non-limiting examples of active agents include one or more pore-forming toxins. Non limiting examples of pore-forming toxins include beta-pore-forming toxins, e.g., hemolysin, Panton-Valentine leukocidin S, aerolysin, Clostridial epsilon-toxin; binary toxins, e.g., anthrax, *C. perfringens* lota toxin, *C. difficile* cytolethal toxins; cholesterol-dependent cytolysins; pneumolysin; small pore-forming toxins; and gramicidin A.

Further non-limiting examples of active agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which are available in a public database (see, e.g., Wang & Wang, *Nucleic Acids Res.* 32:D590-D592, 2004); http://aps.unmc.edu/AP/main.php, the contents of each of which is incorporated herein by reference).

More specific examples of antimicrobial peptides include, among others, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), andropin, moricin, ceratotoxin, and melittin from insects, cecropin P1 from *Ascaris* nematodes, magainin 2, dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of active agents include antibacterial drugs. Non-limiting examples of antibacterial drugs include beta-lactam compounds such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, chloramphenicol, quinupristin-dalfopristin, linezolid, spectrinomycin, trimethoprim, pyrimethamine, and trimethoprim-sulfamethoxazole.

Further non-limiting examples of active agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

Further non-limiting examples of active agents include anti-parasite agents. Non-limiting examples of anti-parasite agents include antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and tinidazole. Further non-limiting examples of active agents include ionic silver, (SilvaSorb®, Medline Industries, Inc), anti-microbial silver compositions (Arglaes®, Medline Industries, Inc), or the like. Further non-limiting examples of active agents include superoxide-forming compositions. Further non-limiting examples of active agents include oxazolidinones, gram-positive antibacterial agents, or the like. See, e.g., U.S. Pat. No. 7,322,965 (issued Jan. 29, 2008), which is incorporated herein by reference.

In an embodiment, the active agent includes one or more antimicrobial agents. In an embodiment, the antimicrobial agent is an antimicrobial peptide. Amino acid sequence information for a subset of these can be found as part of a public database (see, e.g., Wang & Wang, *Nucleic Acids Res.* 32:D590-D592, 2004); http://aps.unmc.edu/AP/main.php, which is incorporated herein by reference). Alternatively, a phage library of random peptides can be used to screen for peptides with antimicrobial properties against live bacteria, fungi and/or parasites. The DNA sequence corresponding to an antimicrobial peptide can be generated ex vivo using standard recombinant DNA and protein purification techniques.

In an embodiment, one or more of the active agent include chemicals suitable to disrupt or destroy cell membranes. For example, some oxidizing chemicals can withdraw electrons from a cell membrane causing it to, for example, become destabilized. Destroying the integrity of cell membranes of, for example, a pathogen can lead to cell death.

In an embodiment, the insertable device 102 includes one or more active agent assemblies 800 configured to deliver at least one active agent from the at least one reservoir 208 to at least one of a region proximate an outer surface 106 or an inner surface 108 of the insertable device 102. In an embodiment, at least one of the active agent assemblies 800 is configured to deliver one or more active agents in a spatially or temporally patterned distribution. In an embodiment, at least one of the active agent assemblies 800 is configured to deliver one or more active agents in a temporally patterned distribution. In an embodiment, the insertable device 102 includes a plurality of spaced-apart-release-ports 118a adapted to deliver one or more active agents in a spatially patterned distribution. In an embodiment, the insertable device 102 includes a plurality of spaced apart controllable-release ports 118a adapted to deliver one or more active agents in a spatially patterned distribution.

In an embodiment, the insertable device 102 includes a release system 799.

In an embodiment, the insertable device 102 includes at least one computing device 230 operably coupled to one or more of the plurality of spaced-apart-release-ports 118a and configured to actuate one or more of the plurality of spaced-apart-release-ports between an active agent discharge state and an active agent retention state. In an embodiment, a computing device 230 is operable to actuate one or more of the plurality of spaced-apart-release-ports 118a between an active agent discharge state and an active agent retention state based on a comparison of a detected characteristic to stored reference data.

In an embodiment, the computing device 230 is operably coupled to the active agent assembly and configured to actively control one or more of the plurality of spaced-apart-release-ports 118a. In an embodiment, at least one computing device 230 is operably coupled to one or more of the spaced-apart controllable-release ports 118a and configured to control at least one of a port release rate, a port release amount, and a port release pattern associated with a delivery of the one or more active agents. In an embodiment, at least one processor 232 is operably coupled to the active agent assembly 800 (e.g., an anti-microbial reservoir 208) and configured to control at least one of a port release rate, a port release amount, and a port release pattern associated with the delivery of the one or more active agents from the at least one active agent reservoir 208 to an interior of the one or more fluid-flow passageways 110.

In an embodiment, a computing device 230 is operably coupled to the active agent assembly 800 and configured to control at least one of an active agent delivery rate, an active agent delivery amount, an active agent delivery composition, a port release rate, a port release amount, and a port release pattern.

In an embodiment, at least one computing device 230 is operably coupled to one or more of the plurality of spaced-apart-release-ports 118a and configured to actuate one or more of the plurality of spaced-apart-release-ports 118a between an active agent discharge state and an active agent retention state. In an embodiment, the insertable device 102 includes one or more active agent assemblies 800 including one or more active agent reservoir 208 configured to deliver at least one active agent from the at least one active agent (e.g., anti-microbial agent) reservoir 208 to at least one of a region proximate an outer surface 108 and a region proximate an inner surface 110 of the insertable device 102.

In an embodiment, the insertable device 102 includes one or more active agent assemblies 800 configured to deliver one or more disinfecting agents. In an embodiment, the insertable device 102 includes one or more active agent assemblies 800 configured to deliver at least one energy-actuatable agent from at least one reservoir 208 to, for example, an interior of one or more fluid-flow passageways 110. Non-limiting examples of energy-actuatable active agents include radiation absorbers, light energy absorbers, X-ray absorbers, photoactive agents, and the like. Non-limiting examples of photoactive agents include, but are not limited to photoactive antimicrobial agents (e.g., eudistomin, photoactive porphyrins, photoactive $TiO_2$, antibiotics, silver ions, antibodies, nitric oxide, or the like), photoactive antibacterial agents, photoactive antifungal agents, and the like. Further non-limiting examples of energy-actuatable agent includes energy-actuatable disinfecting agents, photoactive agents, or a metabolic precursor thereof. In an embodiment, the at least one energy-actuatable agent includes at least one X-ray absorber. In an embodiment, the at least one energy-actuatable agent includes at least one radiation absorber.

In an embodiment, the active agent assembly 800 is configured to deliver at least one energy-actuatable disinfecting agent from at least one reservoir 208 to a biological sample 808 proximate the insertable device 102. In an embodiment, the insertable device 102 includes one or more active agent assemblies 800 configured to deliver at least one energy-actuatable disinfecting agent from the at least one active agent reservoir 208 to a biological sample 808 proximate at least one surface of the insertable device 102. In an embodiment, at least one of the active agent assemblies 800 is configured to deliver at least one energy-actuatable disinfecting agent in a spatially patterned distribution. In an embodiment, the active agent assembly 800 is configured to deliver at least one energy-actuatable steroid to biological sample 808 proximate the at least one outer surface 108 of the insertable device 102.

The at least one active agent reservoir 208 can include, among other things, an acceptable carrier. In an embodiment, at least one active agent is carried by, encapsulated in, or forms part of, an energy-sensitive (e.g., energy-actuatable), carrier, vehicle, vesicle, pharmaceutical vehicle, pharmaceutical carrier, pharmaceutically acceptable vehicle, pharmaceutically acceptable carrier, or the like.

Non-limiting examples of carriers include any matrix that allows for transport of a disinfecting agent across any tissue, cell membranes, and the like of a biological subject 222, or that is suitable for use in contacting a biological subject 222, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, and the like. Further non-limiting examples of carriers include cyclic oligosaccharides, ethasomes, hydrogels, liposomes, micelle, microspheres, nisomes, non-ionic surfactant vesicles, organogels, phospholipid surfactant vesicles, phospholipid surfactant vesicles, transfersomes, virosomes. Further non-limiting examples of energy-sensitive carriers and the like include electrical energy-sensitive, light sensitive, pH-sensitive, ion-sensitive, acoustic energy sensitive, ultrasonic energy sensitive carriers.

In an embodiment, one or more active agents are carried by energy-sensitive vesicles (e.g., energy-sensitive cyclic oligosaccharides, ethasomes, hydrogels, liposomes, micelles, microspheres, nisomes, non-ionic surfactant vesicles, organogels, phospholipid surfactant vesicles, transfersomes, virosomes, and the like). In an embodiment, at least one of the energy emitters 220 is configured to provide energy of a dose sufficient to liberate at least a portion of an active agent carried by the energy-sensitive vesicles.

In an embodiment, the insertable device 102 includes one or more biological sample compartment 708. In an embodiment, the insertable device 102 includes one or more active agent assemblies 800 configured to receive one or more biological samples 808. In an embodiment, the biological sample compartment 708 is placed under the scalp of a user. In an embodiment, the biological sample compartment 708 is configured to allow for the removal of biological sample with a syringe. In an embodiment, the biological sample compartment 708 includes a sensor 302 configured to detect, for example, bacteria, cancer cells, blood, or proteins of a fluid sample received within. In an embodiment, the sensor 302 is operably coupled to the at least one biological sample compartment 708 (e.g., operably coupled to at least one selectively actuatable anti-microbial agent reservoir 208). In an embodiment, the biological sample compartment 708 is configured to allow the injection or introduction of antibiotics for cerebrospinal fluid infection or chemotherapy medication. In an embodiment, the biological sample compartment 708 includes circuitry configured to detect at least one physical quantity, environmental attribute, or physiologic characteristic associated with, for example, a shunting process. In an embodiment, the sensor 302 is configured to detect at least one microorganism proximate at least one anti-microbial nanostructure 206a. In an embodiment, the sensor 302 is configured to detect at least one microorganism proximate at least one anti-microbial region 202a. In an embodiment, the at least one sensor 302 is operably associated with at least one anti-microbial nanostructure 206a within at least one of the fluid-flow passageways 110. In an embodiment, the at least one sensor 302 is configured to detect at least one microorganism in one or more fluid-flow passageways 110 based at least in part on one or more flow characteristics.

In an embodiment, a plurality of the selectively actuatable anti-microbial regions 202a form at least one spatial or temporal pattern extending over at least a portion of the body structure 104. In an embodiment, the selectively actuatable anti-microbial region 202a (optionally including an anti-microbial reservoir 208) are capable of at least one of independent or dependent actuation.

In an embodiment, the insertable device 102 includes one or more active agent assemblies 800 configured to deliver at least one tracer agent from at least one reservoir 208. In an embodiment, the insertable device 102 includes one or more active agent assemblies 800 including one or more tracer agent reservoir 208 configured to deliver at least one tracer agent. In an embodiment, the one or more active agent assemblies 800 are configured to deliver one or more tracer agents. Non-limiting examples of tracer agents include one or more in vivo clearance agents, magnetic resonance imaging agents, contrast agents, dye-peptide compositions, fluorescent dyes, or tissue specific imaging agents. In an embodiment, the one or more tracer agents include at least one fluorescent dye. In an embodiment, the one or more tracer agents include indocyanine green.

In an embodiment, active agent assembly 800 is further configured to concurrently or sequentially deliver one or more tracer agents and one or more energy-actuatable disinfecting agents. In an embodiment, the active agent assembly 800 is further configured to deliver one or more tracer agents for indicating the presence or concentration of one or more energy-actuatable disinfecting agents in at least a region proximate the insertable device 102. In an embodiment, the active agent assembly 800 is further configured to deliver one or more tracer agents for indicating the response of the one or more energy-actuatable disinfecting agents to energy emitted from the one or more energy-emitting emitters 302.

In an embodiment, one or more fluid-flow passageways 110 include a photoactive agent. In an embodiment, one or more fluid-flow passageways 110 include a photoactive coating material. In an embodiment, one or more fluid-flow passageways 110 include a photoactive agent configured to emit ultraviolet light energy in the presence of an energy stimulus. In an embodiment, the one or more fluid-flow passageways 110 include a photoactive agent configured to emit ultraviolet light energy in the presence of an electrical potential. In an embodiment, the one or more fluid-flow passageways 110 include a photoactive agent having one or more photoabsorption bands in the visible region of the electromagnetic spectrum.

Various methods for reducing, inhibiting, or eliminating growth or adherence of at least one microorganism are disclosed herein, each of which can utilize additional steps disclosed, for example in FIGS. 9-28, or throughout the specification. For example, as depicted in FIG. 9, a method 1500 includes activating 1501 at least one anti-microbial region of a plurality of anti-microbial regions of at least one of an outer surface, an inner surface, or embedded in a body structure of an insertable device, the body structure defining one or more fluid-flow passageways, based on an automatically detected biomarker associated with at least one microorganism. In an embodiment, 1510 wherein activating the at least one anti-microbial region includes activating a spatially or temporally patterned anti-microbial region in at least one of the plurality of anti-microbial regions of the body surface. In an embodiment 1520 wherein activating the at least one anti-microbial region is based at least in part on one or more of a detected fluorescence, detected impedance, detected optical reflectance, detected thermal transfer, or detected microbial component. In an embodiment 1530 wherein activating the at least one anti-microbial region is initiated at least one of prior to, during, or subsequent to insertion of the insertable device into a biological subject. In an embodiment 1540 wherein activating the at least one anti-microbial region is based at least in part on one or more of current biomarker information, previous biomarker information, or previous activation events. In an embodiment 1550 the method is implemented by at least one computing device. In an embodiment 1555 the method further comprises generating at least one output to a user. In an embodiment 1560 wherein the at least one output includes at least one of a treatment protocol, identification of a detected microorganism, status of the insertable device, or location of a detected microorganism. In an embodiment 1570 wherein the at least one output occurs in real-time. In an embodiment 1580 wherein the at least one output is associated with historical information. In an embodiment 1590 the user includes at least one entity. In an embodiment 1591 the at least one entity includes at least one person or computer. In an embodiment 1592, the at least one output includes output to a user readable display. In an embodiment 1593 the user readable display includes a human readable display. In an embodiment 1594 the user readable display includes at leat one of a passive display or active display. In an embodiment 1599 the user readable display is coupled to the insertable device.

As depicted in FIG. 10, a method 1600 includes 1610 actuating at least one anti-microbial region of a plurality of anti-microbial regions configured to direct at least one anti-microbial agent to one or more areas of at least one of an outer surface, an inner surface, or internally embedded in a body structure of an insertable device, the body structure defining one or more fluid-flow passageways, in response to an in vivo detected microbial component associated with a biological sample proximate to one or more areas of the body structure.

As depicted in FIG. 11, a method 1700 includes 1705 automatically comparing one or more characteristics communicated from an inserted insertable device to stored reference data, the one or more characteristics including at least one of information associated with microbial marker information; and information associated with at least one microbial component detected proximate to at least one of an outer surface or inner surface of the insertable device, or information associated with a fluid received within one or more fluid-flow passageways of the inserted insertable device; and initiating a treatment protocol based at leastin part on the comparison. In an embodiment 1710 automatically comparing the one or more characteristics communicated from an inserted insertable device to stored reference data includes comparing, via circuitry forming part of the inserted insertable device, one or more characteristics communicated from the inserted insertable device to stored reference data. In an embodiment 1720 initiating the treatment protocol includes generating a spatially patterned distribution of at least one anti-microbial agent released from at least one anti-microbial region of the device. In an embodiment 1730 initiating the treatment protocol includes delivering a dose of at least one anti-microbial agent based at least in part on the comparison. In an embodiment 1740 initiating the treatment protocol includes concurrently or sequentially delivering two or more anti-microbial agents to at least one of the outer surface, or the inner surface of the body structure of the insertable device, based at least in part on the comparison. In an embodiment 1750 initiating the treatment protocol includes activating at least one of an authorization protocol, authentication protocol, or anti-microbial agent delivery protocol based at least in part on the comparison.

As depicted in FIG. 12, a method 1800 includes activating at least one activatable anti-microbial region including at least one anti-microbial reservoir configured to actively elute at least one anti-microbial agent proximate at least one of the outer surface or the inner surface of the body structure of the device, based at least in part on detecting the presence of at least one microorganism proximate to one or more areas of the body structure.

As depicted in FIG. 13, a method 1900 includes 1905 selectively releasing at least one anti-microbial agent from an anti-microbial agent reservoir operably coupled to one or more anti-microbial regions proximate at least one of an outer surface, inner surface, or embedded in the internal body structure of an insertable device, the insertable device including a body structure having an outer surface and an inner surface defining one or more fluid-flow passageways, in response to an automatically detected signal associated with the at least one microbial component proximate at least one of the outer surface or inner surface of the insertable device, or present in the fluid-flow passageway. In an embodiment 1910, selectively releasing at least one anti-microbial agent from an anti-microbial agent reservoir operably coupled to one or more anti-microbial regions includes concurrently or sequentially releasing at least one first anti-microbial agent from an anti-microbial agent reservoir operably coupled to a first anti-microbial region, and releasing at least one second anti-microbial agent from an anti-microbial agent reservoir operably coupled to a second anti-microbial agent reservoir.

In an embodiment 1920, releasing the at least one anti-microbial agent includes releasing the anti-microbial agent at a dose sufficient to modulate an activity of the detected microorganism in response to the automatically detected signal associated with at least one microbial component. In an embodiment 1930, the method further comprises initiating a treatment protocol in response to the automatically detected signal associated with at least one microbial component proximate at least one of the outer surface or inner surface of the insertable device. In an embodiment 1940 initiating the treatment protocol includes activating at least one of an authorization protocol, authentication protocol, or anti-microbial agent delivery protocol, based at least in part on the automatically detected signal associated with at least one microbial component.

As depicted in FIG. 14, a method 2000, includes 2005 a method implemented by at least one computing device. In an embodiment 2010, the method further comprises generating at least one output to a user. In an embodiment 2020, the at least one output includes at least one output to a user readable display. In an embodiment 2030 the at least one output includes at least one of a treatment protocol, identification of a detected microorganism, status of the insertable device, or location of a detected microorganism. In an embodiment 2040 the user includes at least one entity. In an embodiment 2050 the at least one entity includes at least one person or computer. In an embodiment 2060 the at least one output includes at least one output to a user readable display. In an embodiment 2070 the user readable display includes a human readable display. In an embodiment 2080 the user readable display includes one or more active displays. In an embodiment 2090, the user readable display includes one or more passive displays. In an embodiment 2094 the at least one output occurs in real-time. In an embodiment 2095 the user readable display includes one or more of a numeric format, graphical format, or audio format. In an embodiment 2096 the signal includes at least one of a fluorescent signal, impedance signal, optical signal, thermal signal, biochemical signal, or electrochemical signal. In an embodiment 2097, selectively releasing the at least one anti-microbial agent is initiated at least one of prior to, during, or subsequent to insertion of the insertable device into a biological subject. In an embodiment 2098 the at least one output is associated with historical information. In an embodiment 2099 the user readable display is coupled to the insertable device.

As depicted in FIG. 15, a method 2100 includes 2110 selectively actuating one or more anti-microbial regions so as to partially release at least one anti-microbial agent through at least one of an outer surface or an inner surface of the catheter assembly in response to real-time, detected information associated with the presence of a microbial component proximate one or more regions of at least one of an outer surface or inner surface of the catheter assembly.

As depicted in FIG. 16, a method 2200 includes 2210 activating via control circuitry at least one actively controllable anti-microbial nanostructure of at least one of the outer surface or the inner surface in a body structure of an insertable device. In an embodiment 2215 the body structure defines one or more fluid-flow passageways, based on at least one of an automatically detected biomarker, temporal randomness, or a heuristically determined parameter associated with at least one microorganism. In an embodiment 2220 wherein activating the at least one actively controllable anti-microbial nanostructure includes electrically activating a spatially patterned anti-microbial nanostructure. In an embodiment 2230 activating the at least one actively controllable anti-microbial nanostructure includes electrically activating a temporally patterned anti-microbial nanostructure. In an embodiment 2240 the actuation is based at least in part on detection of at least one microorganism. In an embodiment 2250 the actuation is based at least in part on a schedule. In an embodiment 2260 the actuation is based at least in part on a command from an implant. In an embodiment 2270 the actuation is based at least in part on a command from one or more sensors. In an embodiment 2280 the actuation is based at least in part on an external command.

As depicted in FIG. 17, a method 2300 includes 2305 activating the at least one actively controllable anti-microbial nanostructure includes activating a spatially patterned anti-microbial nanostructure based on at least one characteristic. In an embodiment 2310, the at least one characteristic includes at least one detected characteristic including one or more of a detected fluorescence, detected impedance, detected optical reflectance, detected thermal transfer, detected change in conductance, detected change in index of refraction, detected pH, or detected microbial component of at least one microorganism. In an embodiment 2320 activating the at least one actively controllable anti-microbial nanostructure is initiated at least one of prior to, during, or subsequent to insertion of the insertable device into a biological subject. In an embodiment 2330, the method includes electrically activating a computing device to execute the method. In an embodiment 2340 the method further comprises generating at least one output to a user. In an embodiment 2350 generating at least one output to the user includes electrically activating at least one of a treatment protocol, identification of a detected microorganism, status of the insertable device, or location of a detected microorganism. In an embodiment 2360 generating at least one output to the user includes generating at least one output to at least one entity. In an embodiment 2365 the at least one entity includes at least one person or computer. In an embodiment 2370 the at least one output includes at least one output to a user readable display. In an embodiment 2380 the user readable display includes one or more active displays. In an embodiment 2390 the user readable display includes one or more passive displays. In an embodiment 2395 the user readable display includes one or more of a numeric format, graphical format, or audio format.

As depicted in FIG. 18, a method 2400 includes 2405 the heuristically determined parameter includes at least one of a threshold level or target parameter. In an embodiment 2410 the heuristically determined parameter includes at least one heuristic protocol determined parameter or heuristic algorithm determined parameter.

As depicted in FIG. 19, a method 2500 includes 2505 activating via control circuitry at least one independently addressable and actively controllable anti-microbial nanostructure projecting from at least one of the outer surface or the inner surface of a body structure of an insertable device, the body structure defining one or more fluid-flow passageways, based on at least one of an automatically detected biomarker or a heuristically determined parameter associated with at least one microorganism. In an embodiment 2506 activating the at least one actively controllable anti-microbial nanostructure includes activating a spatially patterned anti-microbial nanostructure. In an embodiment 2507 activating the at least one actively controllable anti-microbial nanostructure includes activating a temporally patterned anti-microbial nanostructure.

As depicted in FIG. 20, a method 2600 includes 2605 actuating at least one anti-microbial region between a first anti-microbial state and a second anti-microbial state, the at least one anti-microbial region included in at least one of the outer surface or the inner surface of a body structure of an insertable device, the body structure defining one or more fluid-flow passageways, based at least in part on an automatically detected biomarker or a heuristically determined parameter associated with at least one microorganism. In an embodiment 2610, actuating includes reversibly actuating between the first actuatable anti-microbial state and the second actuatable anti-microbial state in response to a detected presence of at least one microbial component. In an embodiment 2620, the first actuatable anti-microbial state includes a first adsorption affinity, and the second actuatable anti-microbial state includes a second adsorption affinity. In an embodiment 2630, actuating between the at least one of the first actuatable anti-microbial state or the second actuatable anti-microbial state includes at least one of a change in at least one of hydrophilicity, hydrophobicity, electrical charge, chemical composition, polarizability, transparence, conductivity, light absorption, osmotic potential, zeta potential, surface energy, coefficient of friction, or tackiness. In an embodiment 2640, actuating the at least one actively controllable anti-microbial nanostructure includes actuating a spatially patterned anti-microbial nanostructure based on at least one of detected fluorescence, detected impedance, detected optical reflectance, detected thermal transfer, detected change in conductance, detected change in index of refraction, detected pH, or detected microbial component. In an embodiment 2650, the actuation is based at least in part on a schedule, command from an implant, command from one or more sensors, or external command. In an embodiment 2660, the method further comprises generating at least one output to a user.

As depicted in FIG. 21, a method 2700 includes 2705 actuating at least one independently addressable and actuatable anti-microbial region, the at least one independently addressable and actuatable anti-microbial region included in at least one of the outer surface or the inner surface of a body structure of an insertable device, the body structure defining one or more fluid-flow passageways, based at least in part on an automatically detected biomarker or a heuristically determined parameter associated with at least one microorganism.

As depicted in FIG. 22, a method 2800 includes 2805 actuating one or more anti-microbial regions of an insertable device between at least a first actuatable anti-microbial state and a second actuatable anti-microbial state in response to a detected presence of at least one microbial component proximate at least one of the one or more anti-microbial regions of an insertable device. In an embodiment 2810, actuating includes reversibly actuating between the first actuatable anti-microbial state and the second actuatable anti-microbial state in response to a detected presence of at least one microbial component. In an embodiment 2820 the first actuatable anti-microbial state includes a first adsorption affinity, and the second actuatable anti-microbial state includes a second adsorption affinity. In an embodiment 2830, actuating between the at least one of the first actuatable anti-microbial state or the second actuatable anti-microbial state includes at least one of a change in at least one of hydrophilicity, hydrophobocity, electrical charge, chemical composition, polarizability, transparence, conductivity, light absorption, osmotic potential, zeta potential, surface energy, coefficient of friction, or tackiness.

As depicted in FIG. 23, a method 2900 includes actuating at least one anti-microbial region of a plurality of anti-microbial regions configured to direct at least one anti-microbial agent to one or more areas of at least one of an outer surface, an inner surface, or internally embedded in a body structure of an insertable device, the body structure defining one or more fluid-flow passageways, in response to an in vivo detected microbial component associated with a biological sample proximate to one or more areas of the body structure. In an embodiment 2905, actuating the at least one anti-microbial region including actuating at least one spatially patterned or temporally patterned anti-microbial region in at least one of the plurality of anti-microbial regions of the body surface. In an embodiment 2906, actuating the at least one anti-microbial region is based at least in part on at least one of a detected fluorescence, detected impedance, detected optical reflectance, detected thermal transfer, or detected microbial component. In an embodiment 2907, actuating the at least one anti-microbial region is initiated at least one of prior to, during, or subsequent to insertion of the insertable device into a biological subject. In an embodiment 2908 actuating the at least one anti-microbial region is based at least in part on one or more of current biomarker information, previous biomarker information, or previous actuation events.

As depicted in FIG. 24, a method 3000 includes 3010 activating the at least one actively controllable anti-microbial nanostructure is based at least in part on detection of at least one microorganism. In an embodiment 3020, activating the at least one actively controllable anti-microbial nanostructure is based at least in part on a schedule. In an embodiment 3030, activating the at least one actively controllable anti-microbial nanostructure is based at least on part on a command from an implant. In an embodiment 3040, activating the at least one actively controllable anti-microbial nanostructure is based at least in part on a command from one or more sensors. In an embodiment 3050, activating the at least one actively controllable anti-microbial nanostructure is based at least in part on an external command. In an embodiment 3060, activating the at least one actively controllable anti-microbial nanostructure includes activating a spatially patterned anti-microbial nanostructure based on a detected fluorescence. In an embodiment 3070, activating the at least one actively controllable anti-microbial nanostructure includes activating a spatially patterned anti-microbial nanostructure based on a detected impedance. In an embodiment 3080 activating the at least one actively controllable anti-microbial nanostructure includes activating a spatially patterned anti-microbial nanostructure based on a detected optical reflectance.

As depicted in FIG. 25, a method 3100 includes 3110 activating the at least one actively controllable anti-microbial nanostructure includes activating a spatially patterned anti-microbial nanostructure based on a detected thermal transfer. In an embodiment 3120 activating the at least one actively controllable anti-microbial nanostructure includes activating a spatially patterned anti-microbial nanostructure based on a detected change in conductance. In an embodiment 3130, activating the at least one actively controllable anti-microbial nanostructure includes activating a spatially patterned anti-microbial nanostructure based on a detected change in index of refraction. In an embodiment 3140, activating the at least one actively controllable anti-microbial nanostructure includes activating a spatially patterned anti-microbial nanostructure based on a detected pH. In an embodiment 3150, activating the at least one actively controllable anti-microbial nanostructure includes activating a spatially patterned anti-microbial nanostructure based on a detected microbial component of at least one microorganism. In an embodiment 3160, activating the at least one actively controllable anti-microbial nanostructure includes electrically activating a computing device to execute the method. In an embodiment 3170, activating the at least one actively controllable anti-microbial nanostructure is initiated at least one of prior to, during, or subsequent to insertion of the insertable device into a biological subject.

As depicted in FIG. 26, a method 3200 includes 3210 actuating the one or more anti-microbial regions based at least in part on detection of at least one microorganism. In an embodiment 3220 actuating the one or more anti-microbial regions is based at least in part on a schedule. In an embodiment 3230 actuating the one or more anti-microbial regions is based at least in part on a command from an implant. In an embodiment 3240 actuating the one or more anti-microbial regions is based at least in part on a command from one or more sensors. In an embodiment 3250, actuating the one or more anti-microbial regions is based at least in part on an external command. In an embodiment 3260, actuating the one or more anti-microbial regions includes actuating a spatially patterned anti-microbial region based on a detected fluorescence. In an embodiment 3270, actuating the one or more anti-microbial regions includes activating a spatially patterned anti-microbial region based on a detected impedance. In an embodiment 3280 actuating the one or more anti-microbial regions includes actuating a spatially patterned anti-microbial region based on a detected optical reflectance.

As depicted in FIG. 27, a method 3300 includes 3310 actuating the one or more anti-microbial regions includes actuating a spatially patterned anti-microbial region based on a detected thermal transfer. In an embodiment 3320 actuating the one or more anti-microbial regions includes actuating a spatially patterned anti-microbial region based on a detected change in conductance. In an embodiment 3330 actuating the one or more anti-microbial regions includes actuating a spatially patterned anti-microbial region based on a detected change in index of refraction. In an embodiment 3340 actuating the one or more anti-microbial regions includes actuating a spatially patterned anti-microbial region based on a detected pH. In an embodiment 3350 actuating the one or more anti-microbial regions includes actuating a spatially patterned anti-microbial region based on a detected microbial component of at least one microorganism. In an embodiment 3360 actuating the one or more anti-microbial regions includes electrically activating a computing device to execute the method. In an embodiment 3370 actuating the one or more anti-microbial regions is initiated at least one of prior to, during, or subsequent to insertion of the insertable device into a biological subject.

As depicted in FIG. 28, a method 3400 includes 3401 actuating at least one actuatable anti-microbial region including at least one anti-microbial reservoir configured to actively elute at least one anti-microbial agent proximate at least one of the outer surface or the inner surface of the body structure of the device, based at least in part on detecting the presence of at least one microorganism proximate to one or more areas of the body structure.

As depicted in FIG. 29, a method 3500 includes 3510 at least one anti-microbial region including one or more of an anti-microbial agent, or anti-microbial nanostructure. In an embodiment 3520 the anti-microbial agent includes at least one surfactant or amino acid. In an embodiment 3530 the amino acid includes at least one D-amino acid. In an embodiment 3540 the anti-microbial agent includes at least one of an anti-fungal agent, anti-parasitic agent, bacteriophage, or antibiotic. In an embodiment 3550 the anti-microbial agent includes at least one enzymatically active bacteriophage. In an embodiment 3560, the antibiotic includes at least one of azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, sulfadizine, sulfacetamide, sulfadiazine, sulfamethoxazole, sulfasalazine, sulfisoxazole, trimethoprim-sulfamethoxazole, sulfamethizole, linezolid, quinopristin+dalfopristin, bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, coliistin, cycloserine, capreomycin, ethionamide, pyrazinamide, para-aminosalicyclic acid, erythromycin ethylsuccinate+sulfisoxazole, penicillin, beta-lactamase inhibitor, methicillin, cefaclor, cefamandole nafate, cefazolin, cefixime, cefinetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate, Amphotericin B, Carbol-Fuchsin, Ciclopirox, Clotrimzole, Econazole, Haloprogin, Ketoconazole, Mafenide, Miconazole, Naftifine, Nystatin, Oxiconazole Silver, Sulfadiazine, Sulconazole, Terbinatine, Tioconazole, Tolnaftate, Undecylenic acid, flucytosine, miconazole or cephalosporin.

As depicted in FIG. 30, a method 3600 includes 3610 an anti-microbial agent including at least one of a macrolide, lincosamine, quinolone, fluoroquinolone, carbepenem, monobactam, aminoglycoside, glycopeptide, enzyme, tetracycline, sulfonamide, rifampin, oxazolidonone, streptogramin, or a synthetic moiety thereof. In an embodiment 3620, the anti-microbial agent includes at least one of a metal, ceramic, super-oxide forming compound, or polymer. In an embodiment 3630, the anti-microbial agent includes at least one of polyvinyl chloride, polyester, polyethylene, polypropylene, ethylene, polyolefin, homopolymers or copolymers thereof. In an embodiment 3640, the anti-microbial agent includes polytetrafluoroethylene. In an embodiment 3650, at least one of the plurality of anti-microbial regions includes at least one of silver, copper, zirconium, diamond, rubidium, platinum, gold, nickel, lead, cobalt, potassium, zinc, bismuth, tin, cadmium, chromium, aluminum, calcium, mercury, thallium, gallium, strontium, barium, lithium, magnesium, oxides, hydroxides, or salts thereof. In an embodiment 3660, the at least one of the plurality of anti-microbial regions includes at least one of an electroactive polymer, hydrogenated diamond, or black silica.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including among other things," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An insertable device system, comprising:
   a body structure having an outer surface and an inner surface defining one or more fluid-flow passageways;
   at least one independently addressable and actively controllable anti-microbial nanostructure including a nanofiber of a surface switchable between a zwitterionic state and a non-zwitterionic state and projecting from at least one of the outer surface or the inner surface of the body structure; and
   circuitry operably coupled to the nanofiber and configured to activate the nanofiber based on at least one signal from a sensor configured to determine the presence of at least one microorganism on at least one of the independently addressable and actively controllable anti-microbial nanostructure of the body structure.

2. The insertable device system of claim 1, further including a controller operably coupled to the at least one sensor, the controller configured to actuate at least one of the independently addressable and actively controllable anti-microbial nanostructure in response to at least one of a scheduled program, external command, history of a previous presence of a microorganism, or history of a previous activation.

3. The insertable device system of claim 1, further including circuitry configured for determining the presence of at least one microorganism on the body structure subsequent to a first round of activation of the at least one independently addressable and actively controllable anti-microbial nanostructure.

4. The insertable device system of claim 3, wherein the circuitry configured for determining the presence of at least one microorganism includes at least one sensor including an identification code.

5. The insertable device system of claim 4, wherein the at least one sensor is configured to implement instructions addressed to the at least one identification code.

6. The insertable device system of claim 3, wherein the circuitry configured for determining the presence of at least one microorganism includes at least one sensor operably coupled to a microorganism biomarker array.

7. The insertable device system of claim 3, wherein the circuitry configured for determining the presence of at least one microorganism includes at least one of an electrochemical transducer, optical transducer, biochemical transducer, ultrasonic transducer, piezoelectric transducer, or thermal transducer.

8. The insertable device system of claim 3, wherein the circuitry configured for determining the presence of at least one microorganism includes at least one thermal detector, photovoltaic detector, or photomultiplier detector.

9. The insertable device system of claim 3, wherein the circuitry configured for determining the presence of at least one microorganism includes at least one of a density sensor, refractive index sensor, surface plasmon resonance sensor, biomass sensor, electrochemical sensor, fluid-flow sensor, or biochemical sensor.

10. The insertable device system of claim 3, wherein the circuitry configured for determining the presence of at least one microorganism includes a microbial component capture layer.

11. The insertable device system of claim 10, wherein the microbial component capture layer includes an array of different binding molecules that specifically bind one or more components on at least one microorganism.

12. The insertable device system of claim 1, further including circuitry configured for altering the type of response of the independently addressable and actively controllable anti-microbial nanostructure based on the determination of the presence of at least one microorganism on the body structure subsequent to a first round of activation.

13. The insertable device system of claim 1, further including electrically activating means for concurrently or sequentially electrically activating two or more of the at least one independently addressable and actively controllable anti-microbial nanostructure determined to have at least one microorganism present thereon.

14. The insertable device system of claim 1, further including at least one computing device.

15. The insertable device system of claim 14, wherein the at least one computing device is remote to the insertable device.

16. The insertable device system of claim 14, further including one or more instructions that when executed on the at least one computing device cause the at least one computing device to generate at least one output to a user.

17. The insertable device system of claim 16, wherein the at least one output includes at least one of a treatment protocol, identification of a detected microorganism, status of the insertable device, or location of a detected microorganism.

18. The insertable device system of claim 16, wherein the user includes at least one entity.

19. The insertable device system of claim 18, wherein the at least one entity includes at least one person or computer.

20. The insertable device system of claim 16, wherein the at least one output includes output to a user readable display.

21. The insertable device system of claim 20, wherein the user readable display includes a human readable display.

22. The insertable device system of claim 20, wherein the user readable display includes one or more active displays.

23. The insertable device system of claim 20, wherein the user readable display includes one or more passive displays.

24. The insertable device system of claim 20, wherein the user readable display includes one or more of a numeric format, graphical format, or audio format.

25. An insertable device system, comprising:
a body structure having an outer surface and an inner surface defining one or more fluid-flow passageways;
at least one independently addressable and actively controllable anti-microbial nanostructure including a nanofiber of a surface switchable between a zwitterionic state and a non-zwitterionic state and projecting from at least one of the outer surface or the inner surface of the body structure;
at least one sensor configured to detect one or more microorganisms present on the body structure; and
means for determining the presence of at least one microorganism on at least one of the independently addressable and actively controllable anti-microbial nanostructure of the body structure.

26. An insertable device system, comprising:
a computer-recordable medium bearing:
a body structure having an outer surface and an inner surface defining one or more fluid-flow passageways;
at least one independently addressable and actively controllable anti-microbial nanostructure including a nanofiber of a surface switchable between a zwitterionic state and a non-zwitterionic state and; and
one or more instructions for determining the presence of at least one microorganism on at least one of the at least one independently addressable and actively controllable anti-microbial nanostructure of the body structure.

27. The insertable device system of claim 26, wherein the at least one independently addressable and actively controllable anti-microbial nanostructure is configured to be actuated by the presence of at least one microorganism.

28. An insertable device system, comprising:
a computer-recordable medium bearing:
a body structure having an outer surface and an inner surface defining one or more fluid-flow passageways;
at least one independently addressable and actively controllable anti-microbial nanostructure including a nanofiber of a surface switchable between a zwitterionic state and a non-zwitterionic state; and
one or more instructions for controlling the at least one independently addressable and actively controllable anti-microbial nanostructure of the body structure.

29. A method of reducing microbial growth of at least a portion of an insertable device, comprising:
activating via control circuitry at least one independently addressable and actively controllable anti-microbial nanostructure including a nanofiber of a surface switchable between a zwitterionic state and a non-zwitterionic state and projecting from at least one of the outer surface or the inner surface of a body structure of an insertable device, the body structure defining one or more fluid-flow passageways, based on at least one of an automatically detected biomarker or a heuristically determined parameter associated with at least one microorganism.

30. The method of claim 29, wherein activating the at least one actively controllable anti-microbial nanostructure includes activating a spatially patterned anti-microbial nanostructure.

31. The method of claim 29, wherein activating the at least one actively controllable anti-microbial nanostructure includes activating a temporally patterned anti-microbial nanostructure.

32. The method of dam 29, wherein activating the at least one actively controllable anti-microbial nanostructure includes activating a spatially patterned anti-microbial nanostructure based on at least one of detected fluorescence, detected impedance, detected optical reflectance, detected thermal transfer, detected change in conductance, or detected change in index of refraction.

33. The method of claim 29, wherein activating the at least one actively controllable anti-microbial nanostructure includes activating a spatially patterned anti-microbial nanostructure based on a detected pH.

34. The method of claim 29, wherein activating the at least one actively controllable anti-microbial nanostructure includes activating a spatially patterned anti-microbial nanostructure based on a detected microbial component of at least one microorganism.

35. The method of claim 29, wherein activating the at least one actively controllable anti-microbial nanostructure is initiated at least one of prior to, during, or subsequent to insertion of the insertable device into a biological subject.

36. The method of claim 29, wherein the method includes electrically activating a computing device to execute the method.

37. The method of claim 29, further including generating at least one output to a user.

38. The method of claim 37, wherein generating at least one output to the user includes electrically activating at least one of a treatment protocol, identification of a detected microorganism, status of the insertable device, or location of a detected microorganism.

39. The method of claim 37, wherein generating at least one output to the user includes generating at least one output to at least one entity.

40. The method of claim 37, wherein the at least one entity includes at least one person or computer.

41. The method of claim 37, wherein the at least one output includes at least one output to a user readable display.

42. The method of claim 41, wherein the user readable display includes a human readable display.

43. The method of claim 41, wherein the user readable display includes one or more active displays.

44. The method of claim 41, wherein the user readable display includes one or more passive displays.

45. The method of claim 41, wherein the user readable display includes one or more of a numeric format, graphical format, or audio format.

* * * * *

UNITED STATES PATENT AND TRADEMARK OFFICE
CERTIFICATE OF CORRECTION

PATENT NO. : 9,474,831 B2
APPLICATION NO. : 12/931926
DATED : October 25, 2016
INVENTOR(S) : Edward S. Boyden et al.

Page 1 of 1

It is certified that error appears in the above-identified patent and that said Letters Patent is hereby corrected as shown below:

In the Claims

Column 111, Claim 26, Line 62:
"state and a non-zwitterionic state and; and"
Should be:
--state and a non-zwitterionic state and;--

Column 112, Claim 32, Line 38:
"The method of dam 29,"
Should be:
--The method of claim 29,--

Signed and Sealed this
Fourth Day of July, 2017

Joseph Matal
*Performing the Functions and Duties of the
Under Secretary of Commerce for Intellectual Property and
Director of the United States Patent and Trademark Office*